(12) United States Patent
Fruehauf et al.

(10) Patent No.: US 9,012,213 B2
(45) Date of Patent: Apr. 21, 2015

(54) BACTERIA MEDIATED GENE SILENCING

(75) Inventors: Johannes Fruehauf, Newton, MA (US); Moreshwar Bhanudas Vaze, Bedford, MA (US); Floyd Stephen Laroux, Jr., Brookline, MA (US); Noel Joy Sauer, Attleboro, MA (US)

(73) Assignee: Marina Biotech, Inc., Bothell, WA (US)

( * ) Notice: Subject to any disclaimer, the term of this patent is extended or adjusted under 35 U.S.C. 154(b) by 585 days.

(21) Appl. No.: 12/632,985

(22) Filed: Dec. 8, 2009

(65) Prior Publication Data
US 2010/0092438 A1   Apr. 15, 2010

Related U.S. Application Data

(63) Continuation of application No. 12/157,969, filed on Jun. 13, 2008, now abandoned.

(60) Provisional application No. 60/934,751, filed on Jun. 15, 2007, provisional application No. 61/010,028, filed on Jan. 4, 2008.

(51) Int. Cl.
  C12N 15/63     (2006.01)
  C07H 21/02     (2006.01)
  C07H 21/04     (2006.01)
  C12N 1/20      (2006.01)
  C12N 15/85     (2006.01)
  C12N 15/11     (2006.01)
  C12N 15/113    (2010.01)

(52) U.S. Cl.
  CPC .......... C12N 15/113 (2013.01); C12N 15/111 (2013.01); C12N 15/1131 (2013.01); C12N 15/1135 (2013.01); C12N 2310/111 (2013.01); C12N 2310/14 (2013.01); C12N 2320/32 (2013.01)

(58) Field of Classification Search
None
See application file for complete search history.

(56) References Cited

U.S. PATENT DOCUMENTS 6,500,419 B1   12/2002   Hone et al. .......... 424/93.2

FOREIGN PATENT DOCUMENTS

| WO | wo 99/18221      | 4/1999  |
| WO | WO 02/097114 A2  | 12/2002 |
| WO | WO-2006/007569 A2 | 1/2006 |
| WO | WO 2006/021894 A2 | 3/2006 |
| WO | WO 2006/066048   | 6/2006  |
| WO | WO 2006/066048 A2 | 6/2006 |
| WO | WO 2008/012695 A2 | 1/2008 |
| WO | WO-2008/156661 A2 | 12/2008 |

OTHER PUBLICATIONS

Fruehauf, "Treatment of Gastrointestinal Targets Using RNA Interference" ORAL Presentation, *RNAi World Congress:* Boston (Apr. 30-May 2, 2008).

Kong, et al., "RNA Interference as Novel and Powerful Tool in Immunopharmacological Research" *International Immunopharmacology*, 7(4):417-426 (2007).

Zhang, et al., "Engineering Mucosal RNA Interference in Vivo" *Molecular Therapy*, 14(3):336-342 (2006).

Butz et al., "siRNA targeting of the viral E6 oncogene efficiently kills human papillomavirus-positive cancer cells", *Oncogene*, 22(38):5938-5945 (2003).

Gu et al., "Inhibition of cervical cancer cell growth in vitro and in vivo with lentiviral-vector delivered short hairpin RNA targeting human papillomavirus E6 andE7 oncogenes", *Cancer Gene Ther.*, 13(11):1023-1032 (2006).

Keates et al., "Cequent Pharmaceuticals, Inc.: the biological pitcher for RNAi therapeutics", *Pharmacogenomics*, 8(7):867-871 (2007).

Macron, D., "Cequent reports delay in lead program, but unveils new drug-development efforts", *RNAI NEWS*, 6(19):1-3 (2008).

Al-Marin et al., "*Yersinia enterocolitica* as a Vehicle for a Naked DNA Vaccine Encoding *Brucella abortus* Bacterioferritin or P39 Antigen", *Infect. Immun.*, 70(4):1915-1923 (2002).

Bitko et al., "Inhibition of respiratory viruses by nasally administered siRNA", *Nat. Med.*, 11(1):50-55 (2005).

Bridge et al., "Induction of an interferon response by RNAi vectors in mammalian cells", *Nat. Genet.*, 34(3):263-264 (2003).

Brummelkamp et al., "A System for Stable Expression of Short Interfering RNAs in Mammalian Cells", *Science*, 296:550-553 (2002).

Brummelkamp et al., "Stable suppression of tumorigenicity by virus-mediated RNA interference", *Cancer Cell*, 2:243-247 (2002).

Caplen et al., "Specific inhibition of gene expression by small double-stranded RNAs in invertebrate and vertebrate systems", *Proc. Natl. Acad. Sci. U.S.A.*, 98(17):9742-9747 (2001).

Courvalin et al., "Gene transfer from bacteria to mammalian cells", *C. R. Acad. Sci. Paris, Sciences de la vie/Life sciences*, 318:1207-1212 (1995).

Darji et al., "Oral Somatic Transgene Vaccination Using Attenuated *S. typhimurium*", *Cell*, 91:765-775 (1997).

Dillon et al., "RNAi as an Experimental and Therapeutic Tool to Study and Regulate Physiological and Disease Processes", *Annu. Rev. Physiol.*, 67:147-173 (2005).

Dykxhoorn et al., "The Silent Revolution: RNA Interference as Basic Biology, Research Tool, and Therapeutic", *Annu. Rev. Med.*, 56:401-423 (2005).

Elbashir et al., "Duplexes of 21-nucleotide RNAs mediate RNA interference in cultured mammalian cells", *Nature*, 411:494-498 (2001).

(Continued)

*Primary Examiner* — Amy Bowman
(74) *Attorney, Agent, or Firm* — Eckman Basu LLP

(57) ABSTRACT

Methods are described for the delivery of one or more small interfering RNAs (siRNAs) to a eukaryotic cell using a bacterium or BTP. Methods are also described for using this bacterium to regulate gene expression in eukaryotic cells using RNA interference, and methods for treating viral diseases and disorders. The bacterium or BTP includes one or more siRNAs or one or more DNA molecules encoding one or more siRNAs. Vectors are also described for use with the bacteria of the invention for causing RNA interference in eukaryotic cells.

23 Claims, 18 Drawing Sheets

(56) References Cited

OTHER PUBLICATIONS

Elbashir et al., "RNA interference is mediated by 21- and 22-nucleotide RNAs", *Genes Dev.*, 15(2):188-200 (2001).
Fire et al., "Potent and specific genetic interference by double-stranded RNA in *Caenorhabditis elegans*", *Nature*, 391:806-811 (1998).
Grillot-Courvalin, et al., "Functional gene transfer from intracellular bacteria to mammalian cells", *Nat. Biotechnol.*, 16:862-866 (1998).
Grimm et al., "Fatality in mice due to oversaturation of cellular microRNA/short hairpin RNA pathways", *Nature*, 441:537-541 (2006).
Hacein-Bey-Abina et al., "A Serious Adverse Event after Successful Gene Therapy for X-Linked Severe Combined Immunodeficiency", *N. Engl. J. Med.*, 348(3):255-256 (2003).
Harborth et al., "Sequence, Chemical, and Structural Variation of Small Interfering RNAs and Short Hairpin RNAs and the Effect on Mammalian Gene Silencing", *Antisense Nucl. Acid Drug Dev.*, 13(2):83-105 (2003).
Hense et al., "Eukaryotic expression plasmid transfer from the intracellular bacterium *Listeria monocytogenes* to host cells", *Cell. Microbiol.*, 3(9):599-609 (2001).
Hoiseth et al., "Aromatic-dependent *Salmonella typhimurium* are non-virulent and effective as live vaccines", *Nature*, 291:238-239 (1981).
Holle et al., "Bcl-2 targeting siRNA expressed by a T7 vector system inhibits human tumor cell growth in vitro", *Int. J. Oncol.*, 24(3):615-621 (2004).
Isberg et al,, "Identification of invasion: a protein that allows enteric bacteria to penetrate cultured mammalian cells", *Cell*, 50:769-778 (1987).
Jana et al., "RNA interference: potential therapeutic targets", *Appl. Microbial. Biotechnol.*, 65:649-657 (2004).
Keates et al., "Cequent Pharmaceuticals, Inc.: the biological pitcher for RNAi therapeutics", *Phannacogenomics*, 8(7):867-871 (2007).
Lenz, G., "The RNA interference revolution", *Braz. J. Med. Biol. Res.*, 38(12):1749-1757 (2005).
Lewis et al., "Efficient delivery of siRNA for inhibition of gene expression in postnatal mice", *Nat. Genet.*, 32:107-108 (2002).
Li et al., "Delivery of RNA Interference", *Cell Cycle*, 5(18):2103-2109 (2006).
Li et al, "Inhibition of HIV-1 Infection by Lentiviral Vectors Expressing Pol Ill-Promoted Anti-HIV RNAs", *Mol. Ther.*, 8(2):196-206 (2003).
Liu et al., "Hydrodynamics-based transfection in animals by systemic administration of plasmid DNA", *Gene Ther.*, 6:1258-1266 (1999).
Marshall, E., "Gene Therapy Death Prompts Review of Adenovirus Vector", *Science*, 286(5448): 2244-2245 (1999).
Mathew et al., "Cytosolic delivery of antisense oligonucleotides by listeriolysin O-containing liposomes", *Gene Ther.*, 10:1105-1115 (2003).
McCaffrey et al., "Inhibition of hepatitis B virus in mice by RNA interference", *Nat. Biotechnol.*, 21(6):639-644 (2003).
McCaffrey et al., "RNA interference in adult mice", *Nature*, 418:38-39 (2002).
Miliotis, M., "Acridine Orange Stain for Determining Intracellular Enteropathogens in HeLa Cells", *J. Clin. Microbiol.*, 29(4):830-831 (1991).
Milligan et al., "Oligoribonucleotide synthesis using T7 RNA polymerase and synthetic DNA templates", *Nucl. Acids Res.*, 15(21):8783-8798 (1987).
Milligan et al., "Synthesis of Small RNAs Using 17 RNA Polymerase", *Meth. Enzymol.*, 180:51-62 (1989).
Miyagishi et al., "Strategies for Generation of siRNA Expression Library Directed Against the Human Genome", *Oligonucleotides*, 13:325-334 (2003).
Morrissey et al., "Activity of Stabilized Short Interfering RNA in a Mouse Model of Hepatitis B Virus Replication", *Hepatology*, 41(6):1349-1356 (2005).

Morrissey et al., "Potent and persistent in vivo anti-HBV activity of chemically modified siRNAs", *Nat. Biotechnol.*, 23(8):1002-1007 (2005).
Ocker et al., "Variants of bcl-2 specific siRNA for silencing antiapoptotic bcl-2 in pancreatic cancer", *Gut*, 54:1298-1308 (2005).
Paddison et al., "Short hairpin RNAs (shRNAs) induce sequence-specific silencing in mammalian cells", *Genes Dev.*, 16:948-958 (2002).
Paddison et al., "Stable suppression of gene expression by RNAi in mammalian cells", *Proc. Natl. Acad. Sci. U. S. A.*, 99(3):1443-1448 (2002).
Palffy et al., "Bacteria in gene therapy: bactofection versus alternative gene therapy", *Gene Ther.*, 13(2);101-105 (2006).
Palliser et al., "An siRNA-based microbicide protects mice from lethal herpes simplex virus 2 infection", *Nature*, 439:89-94(2006).
Pawelek et al., "Bacteria as tumour-targeting vectors", *Lancet Oncol.*, 4:548-556 (2003).
Pawelek et al., "Tumor-targeted *Salmonella* as a Novel Anticancer Vector", *Cancer Res.*, 57:4537-4544 (1997).
Peer et al., "Selective gene silencing in activated leukocytes by targeting siRNAs to the integrin lymphocyte function-associated antigen-1", *Proc. Natl. Acad. Sci. U. S. A.*, 104(10):4095-4100 (2007).
Peer et al., "Systemic Leukocyte-Directed siRNA Delivery Revealing Cyclin D1 as an Anti-Inflammatory Target", *Science*, 319(5863):627-630 (2008).
Pilgrim et al., "Bactofection of mammalian cells by Listeria monocytogenes: improvement and mechanism of DNA delivery", *Gene Ther.*, 10:2036-2045 (2003).
Russmann H, "Bacterial type III translocation: a unique mechanism for cytosolic display of heterologous antigens by attenuated *Salmonella*", *Int. J. Med. Microbiol.*, 293:107-112 (2003).
Santel et al., "A novel siRNA-lipoplex technology for RNA interference in the mouse vascular endothelium", *Gene Ther.*, 13:1222-1234 (2006).
Santel et al., "RNA interference in the mouse vascular endothelium by systemic administration of siRNA-lipoplexes for cancer therapy", *Gene Ther.*, 13:1360-1370 (2006).
Schoen et al., "Bacterial delivery of functional messenger RNA to mammalian cells", *Cell. Microbiol.*, 7(5):709-724 (2005).
Sharp et al., "RNA to the rescue?", *Nature*, 425:10-12 (2003).
Sizemore et al., "Attenuated Shigella as a DNA Delivery Vehicle for DNA-Mediated Immunization", *Science*, 270:299-302 (1995).
Song et al., "Antibody mediated in vivo delivery of small interfering RNAs via cell-surface receptors", *Nat. Biotech.*, 23(6):709-717 (2005).
Song et al., "RNA interference targeting Fas protects mice from fulminant hepatitis", *Nat. Med.*, 9(3):347-351 (2003).
Sorensen et al., "Gene Silencing by Systemic Delivery of Synthetic siRNAs in Adult Mice", *J. Mol. Biol.*, 327:761-766 (2003).
Soutschek et al., "Therapeutic silencing of an endogenous gene by systemic administration of modified siRNAs", *Nature*, 432:173-178 (2004).
Spankuch et al., "Cancer Inhibition in Nude Mice After Systemic Application of U6 Promoter-Driven Short Hairpin RNAs Against PLK1", *J. Natl. Cancer Inst.*, 96(11):862-872 (2004).
Timmons et al., "Ingestion of bacterially expressed dsRNAs can produce specific and potent genetic interference in *Caenorhabditis elegans*", *Gene*, 263:103-112 (2001).
Timmons et al., "Specific interference by ingested dsRNA", *Nature*, 395:854 (1998).
Toso et al., "Phase. I Study of the Intravenous Administration of Attenuated *Salmonella typhimurium* to Patients With Metastatic Melanoma", *J. Clin. Oncol.*, 20(1):142-152 (2002).
Weiss et al., "Transfer of eukaryotic expression plasmids to mammalian host cells by bacterial carriers", *Curr. Opin. Biotechnol.*, 12:467-472 (2001).
Xia et al., "siRNA-mediated gene silencing in vitro and in vivo", *Nat. Biotechnol.*, 20:1006-1010 (2002).
Xiang et al., "Short hairpin RNA-expressing bacteria elicit RNA interference in mammals", *Nat. Biotechnol.*, 24(6):697-702 (2006).

(56) References Cited

OTHER PUBLICATIONS

Young et al., "The Invasin Protein of *Yersinia enterocolitica*: Internalization of Invasin-bearing Bacteria by Eukaryotic Cells is Associated with Reorganization of the Cytoskeleton", *J. Cell Biol.*, 116(1):197-207 (1992).
Yu et al., "RNA interference by expression of short-interfering RNAs and hairpin RNAs in mammalian cells", *Proc. Natl. Acad. Sci. U. S. A.*, 99(9):6047-6052 (2002).
Zamore et al., "siRNAs knock down hepatitis", *Nat. Med.*, 9(3):266-267 (2003).
Zhang et al., "Hydroporation as the mechanism of hydrodynamic delivery", *Gene Ther.*, 11:675-682 (2004).
Zhang et al., "Intratumoral Delivery and Suppression of Prostate Tumor Growth by Attenuated *Salmonella enterica serovar typhimurium* Carrying Plasmid-Based Small Interfering RNAs", *Cancer Res.*, 67(12):5859-5864 (2007).
Zhao et al., "High-throughput screening of effective siRNAs from RNAi libraries delivered via bacterial invasion", *Nat. Meth.*, 2(12):967-973 (2005).
Zhao et al., "Tumor-targeting bacterial therapy with amino acid auxotrophs of GFP-expressing *Salmonella typhimurium*", *Proc. Natl. Acad. Sci . U. S. A.*, 102(3):755-760 (2005).
Zimmermann et al., "RNAi-mediated gene silencing in non-human primates", *Nature*, 441:111-114 (2006).
Abraham et al., "IL-23 and Autoimmunity: New Insights into the Pathogenesis of Inflammatory Bowel Disease", *Annu. Rev. Med.*, Oct. 31, 2008.
Ahrens et al., "Intestinal Macrophage/Epithelial Cell-Derived CCL11/Eotaxin-1 Mediates Eosinophil Recruitment and Function in Pediatric Ulcerative Colitis", *J. Immunol.*, Nov. 15;181(l0):7390-9 (2008).
Alphen et al., "Influence of osmolarity of the growth medium on the outer membrane protein pattern of *Escherichia coli*", *J. Bacteriol.*, Aug.;131(2):623-30 (1977).
Bader et al., "Recognition of antimicrobial peptides by a bacterial sensor kinase", *Cell*, Aug. 12;122(3):461-72 (2005).
Bhatia et al., "Treatment with bindarit, an inhibitor of MCP-1 synthesis, protects mice against trinitrobenzene sulfonic acid-induced colitis", *Inflamm. Res.*, Oct.;57(10):464-71 (2008).
Blankenhorn et al., "Acid- and base-induced proteins during aerobic and anaerobic growth of *Escherichia coli* revealed by two-dimensional gel electrophoresis",*J Bacteriol.*, Apr.;181(7):2209-16 (1999).
Bouma et al., "The immunological and genetic basis of inflammatory bowel disease",*Nat. Rev. Immunol.*, Jul.;3(7):521-33 (2003).
Calin-Jageman et al., "Mutational analysis of an RNA internal loop as a reactivity epitope for *Escherichia coli* ribonuclease III substrates", *Biochemistry*, May 6;42(17):5025-34 (2003).
Cromie et al., "An RNA Sensor for Intracellular Mg2+", *Cell*, Apr. 125, 71-84 (2006).
Datsenko et al., "One-step inactivation of chromosomal genes in *Escherichia coli* K12 using PCR products", *Proc. Natl. Acad. Sci. USA*, Jun. 6;97(12):6640-5 (2000).
De Boer et al., "The tac promoter: a functional hybrid derived from the trp and lac promoters",*Proc. Natl. Acad. Sci. USA*, Jan. ;80(1):21-5 (1983).
Devine et al., "Cationic peptides: distribution and mechanisms of resistance", *Curr. Pharm.Des.*, 8(9):703-14 (2002).
Dietrich et al., "Delivery of antigen-encoding plasmid DNA into the cytosol of macrophages by attenuated suicide *Listeria monocytogenes*",*Nature Biotechnol.*, Feb.;16(2):181-5 (1998).
Dinarello et al., "IL-32, a novel cytokine with a possible role in disease",*Ann. Rheum. Dis.*, Nov.;65 Suppl 3:iii61-4 (2006).
Eguchi et al., "Transcriptional regulation of drug efflux genes by EvgAS, a two-component system in *Escherichia coli*", *Microbiology*, Oct.;149(Pt 10):2819-28 (2003).
Estrem et al.., "Identification of an UP element consensus sequence for bacterial promoters",*Proc. Natl. Acad Sci. USA*, Aug. 18;95(17):9761-6 (1998).
Fantini et al., "IL-21 comes of age as a regulator of effector T cells in the gut", *Mucosal. Immunol.*, Mar.;1(2):110-5 (2008).

Fantini et al., "IL-21 regulates experimental colitis by modulating the balance between Treg and Th17 cells", *Eur. J. Immunol.*, Nov.;37(I I):3155-63 (2007).
Fantini et al., "New players in the cytokine orchestra of inflammatory bowel disease",*Inflamm. Bowel. Dis.*, Nov.;13(11):1419-23 (2007).
Feng et al., "Dual regulation by phospho-OmpR of ssrA/B gene expression in *Salmonella pathogenicity* island 2", *Mol. Microbiol*, May;48(4):1131-43 (2003).
Fina et al., "Regulation of gut inflammation and th17 cell response by interleukin-21", *Gastroenterology*, Apr.;134(4):1038-48 (2008).
Groisman, E., "The pleiotropic two-component regulatory system PhoP-PhoQ", *J. Bacteriol*, Mar.;183(6):1835-42 (2001).
Gu et al., "Inhibition of cervical cancer cell growth in vitro and in vivo with lentiviral-vector delivered short hairpin RNA targeting human papillomavirus E6 and E7 oncogenes",*Cancer Gene Ther.*,Nov.;13 (1 I) :1023-32 (2006).
Gu et al., "siRNA and shRNA as anticancer agents in a cervical cancer model", *Methods Mol. Biol.*, 442:159-72, (2008).
Heidrich et al., "Involvement of N-acetylmuramyl-L-alanine amidases in cell separation and antibiotic-induced autolysis of *Escherichia coli*",*Mol. Microbiol.*, Jul.;41(1):167-78 (2001).
Heller et al., "Interleukin-13 is the key effector Th2 cytokine in ulcerative colitis that affects epithelial tight junctions, apoptosis, and cell restitution", *Gastroenterology*, Aug.;129(2):550-64 (2005).
Hernandez-Chico et al., "Gene ompR and regulation of microcin 17 and colicin e2 syntheses",*J. Bacteriol.*, Nov.;152(2):897-900 (1982).
Hjalt et al., "Bulged-out nucleotides protect an antisense RNA from RNase III cleavage", *Nucleic Acids Res.*, Feb. 25;23(4):571-9 (1995).
Hou et al., "Study of Claudin Function by RNA Interference", *J. Biol. Chem.*, Nov. 24;281(47):36117-23 (2006).
Huang et al., "Phosphorylation stimulates the cooperative DNA-binding properties of the transcription factor OmpR", *Proc. Natl. Acad. Sci. USA*, Apr. 1;94(7):2828-32 (1997).
Inokuchi et al., "Domains involved in osmoregulation of the ompF gene in *Escherichia coli*",*J. Bacteriol.*, Nov.;164(2):585-90 (1985).
Jack et al., "Bacteriocins of Gram-Positive Bacteria",*Microbiol Rev.*, Jun. p. 171-200 (1995).
Jain et al., "Use of lambda phage S and R gene products in an inducible lysis system for Vibrio cholerae- and *Salmonella enterica* serovar typhimuriu-based DNA vaccine delivery systems", *Infect. Immun.*, Feb.;68(2):986-9 (2000).
Katchar et al., "MIP-3_neutralizing monoclonal antibody protects against TNBS-induced colonic injury and inflammation in mice", *Am. J. Physiol. Gastrointest.*, 292: G1263-01271 (2007).
Kato et al., "Molecular characterization of the PhoP-PhoQ two-component system in *Escherichia coli* K-12: identification of extracellular Mg2+-responsive promoters", *J. Bacteriol.*, Sep.;181(17):5516-20 (1999).
Kawada et al., "Role of mammalian chitinases in inflammatory conditions", *Keio J. Med.*, Mar.;56(1):21-7 (2007).
Kim et al., "Interleukin-32: A Cytokine and Inducer of TNF", *Immunity*, Jan, vol. 22, 131-142 (2005).
Kloos et al., "Inducible cell lysis system for the study of naturaltransformation and environmental fate of DNA released by cell death", *J. Bacteriol.*, Dec.;176(23):7352-61 (1994).
Lazzaroni et al., "Excretion of alkaline phosphatase by *Escherichia coli* K-12 pho constitutive mutants transformed with plasmids carryirg the alkaline phosphatase structural gene", *J. Bacteriol*, Dec.;164(3):1376-80 (1985).
Lesnik et al., "Prediction of rho-independent transcriptional terminators in *Escherichia coli*",*Nucleic Acids Res.*, Sep. 1;29(17):3583-94 (2001).
Li et al., "Differential expression and regulation of IL-23 and IL-12 subunits and receptors in adult mouse microglia", *J. Neural. Sci*, Nov. 15;215(1-2):95-103 (2003).
Li et al., "Delivery of RNA interference.", *Cell Cycle.* 5(18):2103-2109 (2006).
Lisser et al., "Compilation of *E. coli* mRNA promoter sequences",*Nucleic Acids Res.*, Apr. 11;21(7):1507-16 (1993).
Maeda et al., "Evidence for multiple OmpR-binding sites in the upstream activation sequence of the ompC promoter in *Escherichia coli*: a single OmpR-binding site is capable of activating the promoter", *J Bacteriol.*, Jan.;172(1):501-3 (1990).

(56) References Cited

OTHER PUBLICATIONS

Martin-Orozco et al., "Visualization of vacuolar acidification-induced transcription of genes of pathogens inside macrophages", *Mol. Biol. Cell.*, Jan.;17(1):498-510 (2006).
Meng et al., "UP element-dependent transcription at the *Escherichia coli* rrnB P1 promoter: positional requirements and role of the RNA polymerase alpha subunit linker" ,*Nucleic Acids Res.*, Oct. 15;29(20):4166-78 (2001).
Meselson et al., "DNA Restriction Enzyme from *E. Coli*",*Nature*, Mar. vol. 217 (1968).
Minagawa et al., "Identification and molecular characterization of the Mg2+ stimulon of *Escherichia coli*", *J. Bacterial.*, Jul. ;185(13):3696-702 (2003).
Mitsuyama et al., "Interleukin-6 trans-signaling in inflammatory bowel disease", *Cytokine Growth Factor Rev.*, Dec.;17(6):451-61 (2006).
Mizoguchi, "Chitinase 3—Like-1 Exacerbates Intestinal Inflammation by Enhancing Bacterial Adhesion and Invasion in Colonic Epithelial Cells", *Gastroenterology*, 130:398-411 (2006).
Nicholson, "Function, mechanism and regulation of bacterial ribonucleases",*FEMS Microbial. Rev.*, Jun.;23(3):371-90, (1999).
Nguyen et al., "RNAi therapeutics: an update on delivery.", *Curr Opin Mol Ther.* 10(2):158-167 (2008).
Nguyen and Fruehauf "Bacterial vectors for RNAi delivery." *Pathobiotechnology*, Chapter 9: 121-125, Ed. Sleator, Llandes Bioscience, (2008).
Normanly et al., "Changing the identity of a transfer RNA",*Nature*, May 15-21;321(6067):213-9 (1986).
Oshima et al., "Transcriptome analysis of all two-component regulatory system mutants of *Escherichia coli* K-12", *Mol. Microbial.*, Oct.;46(1):281-91 (2002).
Pertzev et al., "Characterization of RNA sequence determinants and antideterminants of processing reactivity for a minimal substrate of *Escherichia coli* ribonuclease III",*Nucleic Acids Res.*, Aug 8;34(13):3708-21 (2006).
Putral et al., "RNA interference against human papillomavirus oncogenes in cervical cancer cells results in increased sensitivity to cisplatin",*Mol. Pharmacol.*, Nov.;68(5):1311-9 (2005).
Rodionov et al., "Regulation of lysine biosynthesis and transport genes in bacteria: yet another RNA riboswitch?", *Nucleic Acid Res.*, Dec. 1;31(23):6748-57 (2003).
Šeputiene et al., "Transcriptional analysis of the acid-inducible asr gene in enterobacteria", *Res. Microbiol.*, Sep.;155(7):535-42 (2004).
Shultzaberger et al., "Anatomy of *Escherichia coli* sigma70 promoters", *Nucleic Acids Res.*, 35(3):771-88 (2007).
Sivakumar et al., "Interleukin 18 is a primary mediator of the inflammation associated with dextran sulphate sodium induced colitis: blocking interleukin 18 attenuates intestinal damage",*Gut*, Jun.;50(6):812-20 (2002).
Small et al., "Acid and base resistance in *Escherichia coli* and *Shigella flexneri*: role of rpoS and growth pH", *J. Bacterial.*, Mar.;176(6):1729-37 (1994).
Soncini et al., "Two-component regulatory systems can interact to process multiple environntntal signals", *J. Bacteriol.*, Dec.;178(23):6796-801 (1996).
Srividhya et al., "Sub classification and targeted characterization of prophage-encoded two-component cell lysis cassette", *J. Biosci.*, Aug. 32(5), 979-990 (2007).
Staudinger et al., "mRNA expression profiles for *Escherichia coli* ingested by normal and phagocyte oxidase-deficient human neutrophils", *J. Clin. Invest.*, Oct.;110(8):1151-63 (2002).
Sudarsan et al., "An mRNA structure in bacteria that controls gene expression by birrling lysine", *Genes Dev.*, Nov 1;17(21):2688-97 (2003).
Sudarsan et al., "Thiamine pyrophosphate riboswitches are targets for the antimicrobial compound pyrithiamine", *Chem. Biol.*, Dec.; 12(12):1325-35 (2005).
Suziedeliene et al., "The acid-inducible asr gene in *Escherichia coli*: transcriptional control by the phoBR operon", *J. Bacterial.*, Apr.;181(7):2084-93 (1999).
Targan et al., "Defects in mucosal immunity leading to ulcerative colitis",*Immunal Rev.*, Aug. ;206:296-305 (2005).
Taylor et al., "Identification of OmpR: a positive regulatory protein controlling expression of the major outer membrane matrix porin proteins of *Escherichia coli* K-12", *J. Bacterial.*, Jul.; 147(1):255-8 (1981).
Taylor et al., "Mutations that define the promoter of ompF, a gene specifying a major outer membrane porin protein", *J. Bacterial.*, Jun.;162(3):1054-60 (1985).
Ten Hove et al., "Blockade of endogenous IL-18 ameliorates TNBS-induced colitis by decreasing local TNF-alpha production in mice", *Gastroenterology*, Dec.;121(6):1372-9 (2001).
Teramoto et al., "Increased lymphocyte trafficking to colonic microvessels is dependent on MAdCAM 1 and C-C chemokin mLARC/CCL 20 in DSS-induced mice colities", *British Soc. for Immunol., Clin and Ex. Immunol.*, 139:421-428 (2005).
Thouvenot et al., "The strong efficiency of the *Escherichia coli* gapA P1 promoter depends on a complex combination of functional determinants",*Biochem. J.*, Oct. 15;383(Pt 2):371-82 (2004).
Tominaga, "Characterization of six flagellin genes in the H3, H53 and H54 standard strains of *Escherichia coli*", *Genes Genet. Syst.*, Feb.;79(1):1-8 (2004).
Watanabe et al., "Interleukin 7 transgenic mice develop chronic colitis with decreased interleukin 7 protein accumulation in the colonic mucosa", *J. Exp. Med.*, Feb. 2;187(3):389-402 (1998).
Weber et al., "Claudin-I and claudin-2 expression is elevated in inflammatory bowel disease and may contribute to early neoplastic transformation": *Lab. Invest.*, Oct.;88(10):1110-20 (2008).
Weckmann et al., "Critical link between TRIAL and CCL20 for the activation of TH2 cells and the expression of allergic airway disease", *Nature*, 1308-1315 (2007).
Winkler et al., "Thiamine derivatives bind messenger RNAs directly to regulate bacterial gene expression", *Nature*, Oct. 31;419(6910):952-6 (2002).
Wosten et al., "A signal transduction system that responds to extracellular iron", *Cell*, Sep. 29;103(1):113-25 (2000).
Wurtzel et al., "Osmoregulation of gene expression. I. DNA sequence of the ompR gene of the ompB operon of *Escherichia coli* and characterization of its gene product",*J. Biol. Chem.*, Nov. 25;257(22): 13685-91 (1982).
Yamazaki et al., "Mucosal T cells expressing high levels of IL-7 receptor are potential targets for treatment of chronic colitis", *J. Immunol.*, Aug. 1 ;171(3):1556-63 (2003).
Young, "Bacteriophage Lysis: Mechanism and Regulation",*Microbiol. Rev.*, Sep. p. 430-481 (1992).
Zeissig et al., "Changes in expression and distribution of claudin 2,5 and 8 lead to discontinuous tight junctions and barrier dysfunction in active Crohn's disease", *Gut*, Jan. ;56(1):61-72 (2007).
Zhang, K., et al., "Regulation of ribonuclease III processing by double-helical sequence antideterminants", *Proc.Natl. Acad. Sci., USA*, Dec. 9;94(25):13437-41 (1997).
Zwir et al., "Dissecting the PhoP regulatory network of *Escherichia coli* and *Salmonella* enteric",*Proc. Natl. Acad, Sci. USA*, Feb. 22;102(8):2862-7 (2005).
Young, Transcription Termination in the *Escherichia coli* Ribosomal RNA Operon rrnC, The Journal of Biological Chemistry, 1979, vol. 254, No. 24, pp. 12725-12731.
Jones et al., A novel *Escherichia coli* lipoprotein expression vector, Gene, 1995, 165, pp. 145 and 146.
Jiang et al., Selective silencing of viral gene expression in HPV-positive human cervical carcinoma cells treated with siRNA, a primer of RNA interference, Oncogene, 2002, 21, pp. 6041-6048.
Vassaux et al., Bacterial gene therapy strategies, Journal of Pathology, 2006, 208, pp. 290-298.
Bogosian and Kane. "Nucleotide sequence of the EcoRl fragment from PLJ3 bearing two tandem lacUV5 promoters." *Nucleic Acids Research.* 15.17(1987):7185.
Wanner et al. "Physiological Regulation of a Decontrolled *lac* Operon." *Journal of Bacteriology.* 130.1(1977):212-222.

SEQUENCE LISTING

<160> NUMBER OF SEQ ID NOS: 563

<210> SEQ ID NO 1
<211> LENGTH: 18
<212> TYPE: DNA
<213> ORGANISM: Escherichia coli

<400> SEQUENCE: 1
taatacgact cactatag                                                      18

<210> SEQ ID NO 2
<211> LENGTH: 53
<212> TYPE: DNA
<213> ORGANISM: Escherichia coli

<400> SEQUENCE: 2
taaccaggct ttacacttta tgcttccggc tcgtataatg tgtggaagga tcc               53

<210> SEQ ID NO 3
<211> LENGTH: 47
<212> TYPE: DNA
<213> ORGANISM: Escherichia coli

<400> SEQUENCE: 3
taaccaggct ttacacttta tgcttccggc tcgtataatg tgtggaa                      47

<210> SEQ ID NO 4
<211> LENGTH: 53
<212> TYPE: DNA
<213> ORGANISM: Escherichia coli

<400> SEQUENCE: 4
taaaattcaa aaatttattt gctttcagga aaattttttct gtataataga ttc              53

<210> SEQ ID NO 5
<211> LENGTH: 32
<212> TYPE: DNA
<213> ORGANISM: Escherichia coli

<400> SEQUENCE: 5
taattgatac tttatgcttt tttctgtata at                                       32

<210> SEQ ID NO 6
<211> LENGTH: 100
<212> TYPE: DNA
<213> ORGANISM: Escherichia coli

<400> SEQUENCE: 6
aagctttcag tcgcgtaatg cttaggcaca ggattgattt gtcgcaatga ttgacacgat        60
tccgcttgac actgcgtaag ttttgtgtta taatggatcc                              100

<210> SEQ ID NO 7
<211> LENGTH: 100
<212> TYPE: DNA
<213> ORGANISM: Escherichia coli

<400> SEQUENCE: 7

```
aagcttaagg agagacaact taaagagact taaagatta atttaaaatt tatcaaaaag    60
agtattgact taaagtctaa cctataggat acttggatcc                       100

<210> SEQ ID NO 8
<211> LENGTH: 77
<212> TYPE: DNA
<213> ORGANISM: Escherichia coli

<400> SEQUENCE: 8
aagctttgtg tggaattgtg agcggataac aattccacac attgacactt tatgcttccg    60
gctcgtataa tggatcc                                                   77

<210> SEQ ID NO 9
<211> LENGTH: 75
<212> TYPE: DNA
<213> ORGANISM: Escherichia coli

<400> SEQUENCE: 9
aagcttggaa aatttttttt aaaaaagtca tgtgtggaat tgtgagcgga taacaattcc    60
acatataatg gatcc                                                     75

<210> SEQ ID NO 10
<211> LENGTH: 1285
<212> TYPE: DNA
<213> ORGANISM: Escherichia coli

<400> SEQUENCE: 10
gacttcatat acccaagctt taaaaaaaaa atccttagct ttcgctaagg atctccgtca    60
agccgtcaat tgtctgattc gttaccaatt atgacaactt gacggctaca tcattcactt   120
tttcttcaca accggcacga aactcgctcg gctggcccc ggtgcatttt ttaaatactc    180
gcgagaaata gagttgatcg tcaaaaccaa cattgcgacc gacggtggcg ataggcatcc   240
gggtagtgct caaaagcagc ttcgcctgac taatgcgttg gtcctcgcgc agcttaaga   300 cgctaatccc taactgctgg cggaaaagat gtgacagacg cgacggcgac aagcaaacat   360
gctgtgcgac gctggcgata tcaaaattgc tgtctgccag gtgatcgctg atgtactgac   420
aagcctcgcg tacccgatta tccatcggtg gatggagcga ctcgttaatc gcttccatgc   480
gccgcagtaa caattgctca agcagattta tcgccagcag ctccgaatag cgcccttccc   540
cttgcccggc gttaatgatt tgcccaaaca ggtcgctgaa atgcggctgg tgcgcttcat   600
ccgggcgaaa gaaacccgta ttggcaaata ttgacggcca gttaagccat tcatgccagt   660
aggcgcgcgg acgaaagtaa acccactggt gataccattc gcgagcctcc ggatgacgac   720
cgtagtgatg aatctctcct ggcgggaaca gcaaaatatc acccgtcgg cagacaaatt    780 ctcgtccctg atttttcacc accccctgac cgcgaatggt gagattgaga atataacctt   840
tcattcccag cggtcggtcg ataaaaaaat cgagataacc gttggcctca atcggcgtta   900
aacccgccac cagatgggcg ttaaacgagt atcccggcag caggggatca ttttgcgctt   960
cagccatact tttcatactc ccaccattca gagaagaaac caattgtcca tattgcatca  1020
gacattgccg tcactgcgtc ttttactggc tcttctcgct aacccaaccg gtaaccccgc  1080
ttattaaaag cattctgtaa caaagcggga ccaaagccat gacaaaaacg cgtaacaaaa  1140
gtgtctataa tcacggcaga aaagtccaca ttgattattt gcacggcgtc acactttgct  1200
atgccatagc atttttatcc ataagattag cggatcctac ctgacgcttt ttatcgcaac  1260
```

```
tctctactgt agatctatct gcgat                                         1285

<210> SEQ ID NO 11
<211> LENGTH: 59
<212> TYPE: DNA
<213> ORGANISM: Escherichia coli

<400> SEQUENCE: 11
taaaattcaa aaatttattt gctttcagga aaattttct gtataataga ttcggatcc     59

<210> SEQ ID NO 12
<211> LENGTH: 38
<212> TYPE: DNA
<213> ORGANISM: Escherichia coli

<400> SEQUENCE: 12
taattgatac tttatgcttt tttctgtata atggatcc                           38

<210> SEQ ID NO 13
<211> LENGTH: 47
<212> TYPE: DNA
<213> ORGANISM: Escherichia coli

<400> SEQUENCE: 13
tagcataacc ccttggggcc tctaaacggg tcttgagggg ttttttg                 47

<210> SEQ ID NO 14
<211> LENGTH: 49
<212> TYPE: DNA
<213> ORGANISM: Escherichia coli

<400> SEQUENCE: 14
ttgtcacgtg agcggataac aatttcacac aggaaacaga attcttaat               49

<210> SEQ ID NO 15
<211> LENGTH: 43
<212> TYPE: DNA
<213> ORGANISM: Escherichia coli

<400> SEQUENCE: 15
ttgtcacaaa ccccgccacc ggcggggttt ttttctgctt aat                     43

<210> SEQ ID NO 16
<211> LENGTH: 65
<212> TYPE: DNA
<213> ORGANISM: Escherichia coli

<400> SEQUENCE: 16
ttgtcacaat tctatggtgt atgcatttat tgcatacat tcaatcaatt ggatcctgca    60
ttaat                                                               65

<210> SEQ ID NO 17
<211> LENGTH: 42
<212> TYPE: DNA
<213> ORGANISM: Escherichia coli

<400> SEQUENCE: 17
gtgagcggat aacaatttca cacaggaaac agaattctta at                      42

<210> SEQ ID NO 18
<211> LENGTH: 36
<212> TYPE: DNA
<213> ORGANISM: Escherichia coli
```

<400> SEQUENCE: 18 aaacccgcc accggcgggg ttttttctg cttaat                                36

<210> SEQ ID NO 19
<211> LENGTH: 58
<212> TYPE: DNA
<213> ORGANISM: Escherichia coli

<400> SEQUENCE: 19
aattctatgg tgtatgcatt tatttgcata cattcaatca attggatcct gcattaat    58

<210> SEQ ID NO 20
<211> LENGTH: 86
<212> TYPE: DNA
<213> ORGANISM: Escherichia coli

<400> SEQUENCE: 20
aattcggggc tatagctcag ctgggagagc gcttgcatct aatgcaagag gtcagcggtt    60
cgatcccgct tagctccacc actgca                                         86

<210> SEQ ID NO 21
<211> LENGTH: 83
<212> TYPE: DNA
<213> ORGANISM: Escherichia coli

<400> SEQUENCE: 21
aattcgcccg gatagctcag tcggtagagc aggggattct aaatcccgt gtccttggtt     60 cgattccgag tccgggcact gca                                            83

<210> SEQ ID NO 22
<211> LENGTH: 876
<212> TYPE: DNA
<213> ORGANISM: Escherichia coli

<400> SEQUENCE: 22
atgaccagta gctatctgca ttagccggag taggatccgg tcattttctc aataggaccc    60
gtggcgcttc actggtacgg cctgatgtat ctggtgggtt tcattttgc aatgtggctg    120 gcaacacgac gggcgaatcg tccgggcagc ggctggacca aaaatgaagt tgaaaactta   180
ctctatgcgg gcttcctcgg cgtcttcctc gggggacgta ttggttatgt tctgttctac   240
aatttcccgc agtttatggc cgatccgctg tatctgttcc gtgtctggga cggcggcatg   300
tctttccacg gcggcctgat ggcgttatc gtggtgatga ttatcttcgc ccgccgtact    360
aaacgttcct tcttccaggt ctctgatttt atcgcaccac tcattccgtt tggtcttggt   420
gccgggcgtc tgggcaactt tattaacggt gaattgtggg gccgcgttga cccgaacttc   480
ccgtttgcca tgctgttccc tggctcccgt acagaagata ttttgctgct gcaaaccaac   540
ccgcagtggc aatccattt cgacacttac ggtgtgctgc cgcgccaccc atcacagctt    600
tacgagctgc tgctggaagg tgtggtgctg tttattatcc tcaacctgta tattcgtaaa   660
ccacgcccaa tggagctgt ctcaggtttg ttcctgattg gttacggcgc gtttcgcatc    720
attgttgagt ttttccgcca gcccgacgcg cagtttaccg tgcctgggt gcagtacatc    780 agcatggggc aaattctttc catcccgatg attgtcgcgg gtgtgatcat gatggtctgg   840
gcatatcgtc gcagcccaca gcaacacgtt tcctga                             876

<210> SEQ ID NO 23

<211> LENGTH: 1260
<212> TYPE: DNA
<213> ORGANISM: Escherichia coli

<400> SEQUENCE: 23

| | | | | | |
|---|---|---|---|---|---|
| atggataaat | ttcgtgttca | ggggccaacg | aagctccagg | gcgaagtcac | aatttccggc | 60 |
| gctaaaaatt | agtagctgcc | tatccttttt | gccgcactac | tggcggaaga | accggtagag | 120 |
| atccagaacg | tcccgaaact | gaaagacgtc | gatacatcaa | tgaagctgct | aagccagctg | 180 |
| ggtgcgaaag | tagaacgtaa | tggttctgtg | catattgatg | cccgcgacgt | taatgtattc | 240 |
| tgcgcacctt | acgatctggt | taaaaccatg | cgtgcttcta | tctgggcgct | ggggccgctg | 300 |
| gtagcgcgct | ttggtcaggg | gcaagtttca | ctacctggcg | gttgtacgat | cggtgcgcgt | 360 |
| ccggttgatc | tacacatttc | tggcctcgaa | caattaggcg | cgaccatcaa | actggaagaa | 420 |
| ggttacgtta | aagcttccgt | cgatggtcgt | ttgaaaggtg | cacatatcgt | gatggataaa | 480 |
| gtcagcgttg | gcgcaacggt | gaccatcatg | tgtgctgcaa | ccctggcgga | aggcaccacg | 540 |
| attattgaaa | acgcagcgcg | tgaaccggaa | atcgtcgata | ccgcgaactt | cctgattacg | 600 |
| ctgggtgcga | aaattagcgg | tcagggcacc | gatcgtatcg | tcatcgaagg | tgtggaacgt | 660 |
| ttaggcggcg | gtgtctatcg | cgttctgccg | gatcgtatcg | aaaccggtac | tttcctggtg | 720 |
| gcggcggcga | tttctcgcgg | caaaattatc | tgccgtaacg | cgcagccaga | tactctcgac | 780 |
| gccgtgctgg | cgaaactgcg | tgacgctgga | cggacatcg | aagtcggcga | agactggatt | 840 |
| agcctggata | tgcatggcaa | acgtccgaag | gctgttaacg | tacgtaccgc | gccgcatccg | 900 |
| gcattcccga | ccgatatgca | ggcccagttc | acgctgttga | acctggtggc | agaagggacc | 960 |
| gggtttatca | ccgaaacggt | ctttgaaaac | cgctttatgc | atgtgccaga | gctgagccgt | 1020 |
| atgggcgcgc | acgccgaaat | cgaaagcaat | accgttattt | gtcacggtgt | tgaaaaactt | 1080 |
| tctggcgcac | aggttatggc | aaccgatctg | cgtgcatcag | caagcctggt | gctggctggc | 1140 |
| tgtattgcgg | aagggacgac | ggtggttgat | cgtatttatc | acatcgatcg | tggctacgaa | 1200 |
| cgcattgaag | acaaactgcg | cgctttaggt | gcaaatattg | agcgtgtgaa | aggcgaataa | 1260 |

<210> SEQ ID NO 24
<211> LENGTH: 1297
<212> TYPE: DNA
<213> ORGANISM: Escherichia coli

<400> SEQUENCE: 24

| | | | | | |
|---|---|---|---|---|---|
| gccaggcgac | tgtcttcaat | attacagccg | caactactga | catgacgggt | gatggtgttc | 60 |
| acaattccag | ggcgatcggc | acccaacgca | gtgatcacca | gataatgttg | cgatgacagt | 120 |
| gtcaaactgg | ttattccttt | aagggggtgag | ttgttcttaa | ggaaagcata | aaaaaaacat | 180 |
| gcatacaaca | atcagaacgg | ttctgtctgc | ttgcttttaa | tgccatacca | aacgtaccat | 240 |
| tgagacactt | gtttgcacag | aggatggccc | atgttcacgg | gaagtattgt | cgcgattgtt | 300 |
| actccgatgg | atgaaaaagg | taatgtctgt | cgggctagct | tgaaaaaact | gattgattat | 360 |
| catgtcgcca | gcggtacttc | ggcgatcgtt | tctgttggca | ccactggcga | gtccgctacc | 420 |
| ttaaatcatg | acgaacatgc | tgatgtgtgt | atgatgacgc | tggatctggc | tgatgggcgc | 480 |
| attccggtaa | ttgccgggac | cggcgctaac | gctactgcgg | aagccattag | cctgacgcag | 540 |
| cgcttcaatg | acagtggtat | cgtcggctgc | ctgacggtaa | ccccttacta | caatcgtccg | 600 |
| tcgcaagaag | gtttgtatca | gcatttcaaa | gccatcgctg | agcatactga | cctgccgcaa | 660 |
| attctgtata | atgtgccgtc | ccgtactggc | tgcgatctgc | tcccggaaac | ggtgggccgt | 720 |

| | |
|---|---|
| ctggcgaaag taaaaaatat tatcggaatc aaagaggcaa cagggaactt aacgcgtgta | 780 |
| aaccagatca aagagctggt ttcagatgat tttgttctgc tgagcggcga tgatgcgagc | 840 |
| gcgctggact tcatgcaatt gggcggtcat ggggttattt ccgttacggc taacgtcgca | 900 |
| gcgcgtgata tggcccagat gtgcaaactg gcagcagaag gcattttgc cgaggcacgc | 960 |
| gttattaatc agcgtctgat gccattacac aacaaactat tgtcgaacc caatccaatc | 1020 |
| ccggtgaaat gggcatgtaa ggaactgggt cttgtggcga ccgatacgct gcgcctgcca | 1080 |
| atgacaccaa tcaccgacag tggtcgtgag acggtcagag cggcgcttaa gcatgccggt | 1140 |
| ttgctgtaaa gtttagggag atttgatggc ttactctgtt caaaagtcgc gcctggcaaa | 1200 |
| ggttgcgggt gtttcgcttg ttttattact cgctgcctgt agttctgact cacgctataa | 1260 |
| gcgtcaggtc agtggtgatg aagcctacct ggaagcg | 1297 |

```
<210> SEQ ID NO 25
<211> LENGTH: 99
<212> TYPE: DNA
<213> ORGANISM: Escherichia coli

<400> SEQUENCE: 25
```

| | |
|---|---|
| catggcgccg cttctttgag cgaacgatca aaaataagtg gcgccccatc aaaaaaatat | 60 |
| tctcaacata aaaactttg tgtaatactt gtaacgctg | 99 |

```
<210> SEQ ID NO 26
<211> LENGTH: 63
<212> TYPE: DNA
<213> ORGANISM: Escherichia coli

<400> SEQUENCE: 26
```

| | |
|---|---|
| catggcgccc catcaaaaaa atattctcaa cataaaaaac tttgtgtaat acttgtaacg | 60 |
| ctg | 63 |

```
<210> SEQ ID NO 27
<211> LENGTH: 32
<212> TYPE: DNA
<213> ORGANISM: Escherichia coli

<400> SEQUENCE: 27
```

| | |
|---|---|
| gatccttagc gaaagctaag gatttttttt ac | 32 |

```
<210> SEQ ID NO 28
<211> LENGTH: 32
<212> TYPE: DNA
<213> ORGANISM: Escherichia coli

<400> SEQUENCE: 28
```

| | |
|---|---|
| gatccttagc gaaagctaag gatttttttt tt | 32 |

```
<210> SEQ ID NO 29
<211> LENGTH: 720
<212> TYPE: DNA
<213> ORGANISM: Escherichia coli

<400> SEQUENCE: 29
```

| | |
|---|---|
| atgcaagaga actacaagat tctggtggtc gatgacgaca tgcgcctgcg tgcgctgctg | 60 |
| gaacgttatc tcaccgaaca aggcttccag gttcgaagcg tcgctaatgc agaacagatg | 120 |
| gatcgcctgc tgactcgtga atctttccat cttatggtac tggatttaat gttacctggt | 180 |

```
gaagatggct tgtcgatttg ccgacgtctt cgtagtcaga gcaacccgat gccgatcatt    240
atggtgacgg cgaaagggga agaagtggac cgtatcgtag gcctggagat tggcgctgac    300
gactacattc caaaaccgtt taacccgcgt gaactgctgg cccgtatccg tgcggtgctg    360
cgtcgtcagg cgaacgaact gccaggcgca ccgtcacagg aagaggcggt aattgctttc    420
ggtaagttca aacttaacct cggtacgcgc gaaatgttcc gcgaagacga gccgatgccg    480
ctcaccagcg gtgagtttgc ggtactgaag gcactggtca gccatccgcg tgagccgctc    540
tcccgcgata agctgatgaa ccttgcccgt ggtcgtgaat attccgcaat ggaacgctcc    600
atcgacgtgc agatttcgcg tctgcgccgc atggtggaag aagatccagc gcatccgcgt    660
tacattcaga ccgtctgggg tctgggctac gtctttgtac cggacggctc taaagcatga    720
```

<210> SEQ ID NO 30
<211> LENGTH: 672
<212> TYPE: DNA
<213> ORGANISM: Escherichia coli

<400> SEQUENCE: 30

```
atgcgcgtac tggttgttga agacaatgcg ttgttacgtc accaccttaa agttcagatt    60
caggatgctg gtcatcaggt cgatgacgca gaagatgcca agaagccga ttattatctc    120 aatgaacata taccggatat tgcgattgtc gatctcggat tgccagacga ggacggtctg    180
tcactgattc gccgctggcg tagcaacgat gtttcactgc cgattctggt attaaccgcc    240
cgtgaaagct ggcaggacaa agtcgaagta ttaagtgccg gtgctgatga ttatgtgact    300
aaaccgtttc atattgaaga ggtgatggcg cgaatgcagg cattaatgcg gcgtaatagc    360
ggtctggctt cacaggtcat ttcgctcccc ccgtttcagg ttgatctctc tcgccgtgaa    420
ttatctatta atgacgaagt gatcaaactg accgcgttcg aatacactat tatggaaacg    480
ttgatacgca ataatggcaa agtggtcagc aaagattcgt taatgctcca actctatccg    540
gatgcggagc tgcggaaaag ccataccatt gatgtactga tgggacgtct gcgcaaaaaa    600
attcaggcac aatatcccca agaagtgatt accaccgttc gcggccaggg ctatctgttc    660
gaattgcgct ga                                                         672
```

<210> SEQ ID NO 31
<211> LENGTH: 390
<212> TYPE: DNA
<213> ORGANISM: Escherichia coli

<400> SEQUENCE: 31

```
gatcatcctg ttacggaata ttacattgca acatttacgc gcaaaaacta atccgcattc    60
ttattgcgga ttagtttttt cttagctaat agcacaattt tcatactatt ttttggcatt    120
ctggatgtct gaaagaagat tttgtgccag gtcgataaag tttccatcag aaacaaaatt    180
tccgtttagt taatttaaat ataaggaaat catataaata gattaaaatt gctgtaaata    240
tcatcacgtc tctatggaaa tatgacggtg ttcacaaagt tccttaaatt ttacttttgg    300
ttacatattt tttctttttg aaaccaaatc tttatctttg tagcactttc acggtagcga    360
aacgttagtt tgaatggaaa gatgcctgca                                      390
```

<210> SEQ ID NO 32
<211> LENGTH: 198
<212> TYPE: DNA
<213> ORGANISM: Escherichia coli

<400> SEQUENCE: 32

```
tttaaaaaag ttccgtaaaa ttcatatttt gaaacatcta tgtagataac tgtaacatct    60
taaaagtttt agtatcatat tcgtgttgga ttattctgta ttttgcgga gaatggactt    120 gccgactggt taatgagggt taaccagtaa gcagtggcat aaaaaagcaa taaaggcata   180
taacagaggg ttaataac                                                 198

<210> SEQ ID NO 33
<211> LENGTH: 200
<212> TYPE: DNA
<213> ORGANISM: Escherichia coli

<400> SEQUENCE: 33
agtgattcca ttttttaccc ttctgttttt ttgaccttaa gtctccgcat cttagcacat    60
cgttcatcca gagcgtgatt tctgccgagc gtgatcagat cggcatttct ttaatctttt   120
gtttgcatat ttttaacaca aaatacacac ttcgactcat ctggtacgac cagatcacct   180
tgcggattca ggagactgac                                               200

<210> SEQ ID NO 34
<211> LENGTH: 200
<212> TYPE: DNA
<213> ORGANISM: Escherichia coli

<400> SEQUENCE: 34
gagctatcac gatggttgat gagctgaaat aaacctcgta tcagtgccgg atggcgatgc    60
tgtccggcct gcttattaag attatccgct tttatttttt tcactttacc tccctcccc   120 gctggtttat ttaatgttta cccccataac cacataatcg cgttcactca ttttaataat   180
taagacaggg agaaataaaa                                               200

<210> SEQ ID NO 35
<211> LENGTH: 238
<212> TYPE: DNA
<213> ORGANISM: Escherichia coli

<400> SEQUENCE: 35
gcttcaacac gctcgcgggt gagctggctc acgccgcttt cgttattcag cacccgggaa    60
actgtagatt tccccacgcc gcttaagcgc gcgatatctt tgatggtcag ccgattttgc   120
atcctgttgt cctgtaacgt gttgtttaat tatttgagcc taacgttacc cgtgcattca   180
gcaatgggta agtctggtt tatcgttggt ttagttgtca gcaggtatta tatcgcca     238

<210> SEQ ID NO 36
<211> LENGTH: 73
<212> TYPE: DNA
<213> ORGANISM: Escherichia coli

<400> SEQUENCE: 36
gagctgttga caattaatca tcgaactagt taactagtac gcaagttcac gtaaaaggg     60 tatctagaat tct                                                       73

<210> SEQ ID NO 37
<211> LENGTH: 1353
<212> TYPE: DNA
<213> ORGANISM: Escherichia coli

<400> SEQUENCE: 37
atgaggcgat tgcgcttctc gccacgaagt tcatttgccc gtacgttatt gctcatcgtc    60
```

| | |
|---|---|
| accttgctgt tcgccagcct ggtgacgact tatctggtgg tgctgaactt cgcgattttg | 120 |
| ccgagcctcc agcagtttaa taaagtcctc gcgtacgaag tgcgtatgtt gatgaccgac | 180 |
| aaactgcaac tggaggacgg cacgcagttg gttgtgcctc ccgcttttccg tcgggagatc | 240 |
| taccgtgagc tggggatctc tctctactcc aacgaggctg ccgaagaggc aggtctgcgt | 300 |
| tgggcgcaac actatgaatt cttaagccat cagatggcgc agcaactggg cggcccgacg | 360 |
| gaagtgcgcg ttgaggtcaa caaaagttcg cctgtcgtct ggctgaaaac ctggctgtcg | 420 |
| cccaatatct gggtacgcgt gccgctgacc gaaattcatc agggcgattt ctctccgctg | 480 |
| ttccgctata cgctggcgat tatgctattg gcgataggcg gggcgtggct gtttattcgt | 540 |
| atccagaacc gaccgttggt cgatctcgaa cacgcagcct gcaggttgg taaagggatt | 600 |
| attccgccgc cgctgcgtga gtatggcgct tcggaggtgc gttccgttac ccgtgcctt | 660 |
| aaccatatgg cggctggtgt taagcaactg gcggatgacc gcacgctgct gatggcgggg | 720 |
| gtaagtcacg acttgcgcac gccgctgacg cgtattcgcc tggcgactga gatgatgagc | 780 |
| gagcaggatg gctatctggc agaatcgatc aataaagata tcgaagagtg caacgccatc | 840 |
| attgagcagt ttatcgacta cctgcgcacc gggcaggaga tgccgatgga aatggcggat | 900 |
| cttaatgcag tactcggtga ggtgattgct gccgaaagtg gctatgagcg ggaaattgaa | 960 |
| accgcgcttt accccggcag cattgaagtg aaaatgcacc cgctgtcgat caaacgcgcg | 1020 |
| gtggcgaata tggtggtcaa cgccgcccgt tatggcaatg gctggatcaa agtcagcagc | 1080 |
| ggaacggagc cgaatcgcgc ctggttccag gtggaagatg acggtccggg aattgcgccg | 1140 |
| gaacaacgta agcacctgtt ccagccgttt gtccgcggcg acagtgcgcg caccattagc | 1200 |
| ggcacgggat tagggctggc aattgtgcag cgtatcgtgg ataaccataa cgggatgctg | 1260 |
| gagcttggca ccagcgagcg gggcgggctt tccattcgcg cctggctgcc agtgccggta | 1320 |
| acgcgggcgc agggcacgac aaaagaaggg taa | 1353 |

<210> SEQ ID NO 38
<211> LENGTH: 1461
<212> TYPE: DNA
<213> ORGANISM: Escherichia coli

<400> SEQUENCE: 38

| | |
|---|---|
| atgaaaaaat tactgcgtct ttttttcccg ctctcgctgc gggtacgttt tctgttggca | 60 |
| acggcagcgg tagtactggt gctttcgctt gcctacggaa tggtcgcgct gatcggttat | 120 |
| agcgtcagtt tcgataaaac tacgtttcgg ctgttacgtg gcgagagcaa tctgttctat | 180 |
| acccttgcga agtgggaaaa caataagttg catgtcgagt tacccgaaaa tatcgacaag | 240 |
| caaagcccca ccatgacgct aatttatgat gagaacgggc agcttttatg ggcgcaacgt | 300 |
| gacgtgccct ggctgatgaa gatgatccag cctgactggc tgaaatcgaa tggttttcat | 360 |
| gaaattgaag cggatgttaa cgataccagc ctcttgctga gtggagatca ttcgatacag | 420 |
| caacagttgc aggaagtgcg ggaagatgat gacgacgcgc agatgaccca ctcggtggca | 480 |
| gtaaacgtct acccggcaac atcgcggatg ccaaaattaa ccattgtggt ggtggatacc | 540 |
| attccggtgg agctaaaaag ttcctatatg gtctggagct ggtttatcta tgtgctctca | 600 |
| gccaatctgc tgttagtgat cccgctgctg tgggtcgccg cctggtggag tttacgcccc | 660 |
| atcgaagccc tggcaaaaga agtccgcgaa ctgaagaac ataaccgcga attgctcaat | 720 |
| ccagccacaa cgcgagaact gaccagtctg gtacgaaacc tgaaccgatt gttaaaaagt | 780 |
| gaacgcgaac gttacgacaa ataccgtacg acgctcaccg acctgaccca tagtctgaaa | 840 |

| | |
|---|---|
| acgccactgg cggtgctgca aagtacgctg cgttctctgc gtagtgaaaa gatgagcgtc | 900 |
| agtgatgctg agccggtaat gctggagcaa atcagccgca tttcacagca aattggctac | 960 |
| tacctgcatc gtgccagtat gcgcggcggg acattgctca gccgcgagct gcatccggtc | 1020 |
| gccccactgc tggacaatct cacctcagcg ctgaacaaag tgtatcaacg caaaggggtc | 1080 |
| aatatctctc tcgatatttc gccagagatc agctttgtcg gtgagcagaa cgattttgtc | 1140 |
| gaggtgatgg gcaacgtgct ggataatgcc tgtaaatatt gcctcgagtt tgtcgaaatt | 1200 |
| tctgcaaggc aaaccgacga gcatctctat attgtggtcg aggatgatgg ccccggtatt | 1260 |
| ccattaagca agcgagaggt cattttcgac cgtggtcaac gggttgatac tttacgccct | 1320 |
| gggcaaggtg tagggctggc ggtagcccgc gaaatcaccg agcaatatga gggtaaaatc | 1380 |
| gtcgccggag agagcatgct gggcggtgcg cggatggagg tgattttttgg tcgccagcat | 1440 |
| tctgcgccga aagatgaata a | 1461 |

<210> SEQ ID NO 39
<211> LENGTH: 490
<212> TYPE: DNA
<213> ORGANISM: Homo sapiens

<400> SEQUENCE: 39

| | |
|---|---|
| ctatagaaga cctgggacag aggactgctg tctgccctct ctggtcaccc tgcctagcta | 60 |
| gaggatctgt gaccccagcc atgaggaccc tcgccatcct tgctgccatt ctcctggtgg | 120 |
| ccctgcaggc ccaggctgag ccactccagg caagagctga tgaggttgct gcagccccgg | 180 |
| agcagattgc agcggacatc ccagaagtgg ttgtttccct tgcatgggac gaaagcttgg | 240 |
| ctccaaagca tccaggctca aggaaaaaca tggcctgcta ttgcagaata ccagcgtgca | 300 |
| ttgcaggaga acgtcgctat ggaacctgca tctaccaggg aagactctgg gcattctgct | 360 |
| gctgagcttg cagaaaaaga aaaatgagct caaaatttgc tttgagagct acagggaatt | 420 |
| gctattactc ctgtaccttc tgctcaattt cctttcctca tcccaaataa atgccttggt | 480 |
| acaagaaaag | 490 |

<210> SEQ ID NO 40
<211> LENGTH: 487
<212> TYPE: DNA
<213> ORGANISM: Homo sapiens

<400> SEQUENCE: 40

| | |
|---|---|
| ccttgctata gaagacctgg gacagaggac tgctgtctgc cctctctggt caccctgcct | 60 |
| agctagagga tctgtgaccc cagccatgag gaccctcgcc atccttgctg ccattctcct | 120 |
| ggtggccctg caggcccagg ctgagccact ccaggcaaga gctgatgagg ttgctgcagc | 180 |
| cccggagcag attgcagcgg acatcccaga agtggttgtt tcccttgcat gggacgaaag | 240 |
| cttggctcca aagcatccag gctcaaggaa aaacatggac tgctattgca gaataccagc | 300 |
| gtgcattgca ggagaacgtc gctatggaac ctgcatctac cagggaagac tctgggcatt | 360 |
| ctgctgctga gcttgcagaa aagaaaaat gagctcaaaa tttgctttga gagctacagg | 420 |
| gaattgctat tactcctgta ccttctgctc aatttccttt cctcatctca aataaatgcc | 480 |
| ttgttac | 487 |

<210> SEQ ID NO 41
<211> LENGTH: 542
<212> TYPE: DNA

<213> ORGANISM: Homo sapiens

<400> SEQUENCE: 41

| | | | | | | |
|---|---|---|---|---|---|---|
| gtctgccctc | tctgctcgcc | ctgcctagct | tgaggatctg | tcaccccagc | catgaggatt | 60 |
| atcgccctcc | tcgctgctat | tctcttggta | gccctccagg | tccgggcagg | cccactccag | 120 |
| gcaagaggtg | atgaggctcc | aggccaggag | cagcgtgggc | cagaagacca | ggacatatct | 180 |
| atttcctttg | catgggataa | aagctctgct | cttcaggttt | caggctcaac | aaggggcatg | 240 |
| gtctgctctt | gcagattagt | attctgccgg | cgaacagaac | ttcgtgttgg | gaactgcctc | 300 |
| attggtggtg | tgagtttcac | atactgctgc | acgcgtgtcg | attaacgttc | tgctgtccaa | 360 |
| gagaatgtca | tgctgggaac | gccatcatcg | gtggtgttag | cttcacatgc | ttctgcagct | 420 |
| gagcttgcag | aatagagaaa | aatgagctca | taatttgctt | tgagagctac | aggaaatggt | 480 |
| tgtttctcct | atactttgtc | cttaacatct | ttcttgatcc | taaatatata | tctcgtaaca | 540 |
| ag | | | | | | 542 |

<210> SEQ ID NO 42
<211> LENGTH: 449
<212> TYPE: DNA
<213> ORGANISM: Homo sapiens

<400> SEQUENCE: 42

| | | | | | | |
|---|---|---|---|---|---|---|
| atatccactc | ctgctctccc | tcctgcaggt | gaccccagcc | atgaggacca | tcgccatcct | 60 |
| tgctgccatt | ctcctggtgg | ccctgcaggc | ccaggctgag | tcactccagg | aaagagctga | 120 |
| tgaggctaca | acccagaagc | agtctgggga | agacaaccag | gaccttgcta | tctcctttgc | 180 |
| aggaaatgga | ctctctgctc | ttagaacctc | aggttctcag | gcaagagcca | cctgctattg | 240 |
| ccgaaccggc | cgttgtgcta | cccgtgagtc | cctctccggg | gtgtgtgaaa | tcagtggccg | 300 |
| cctctacaga | ctctgctgtc | gctgagcttc | ctagatagaa | accaaagcag | tgcaagattc | 360 |
| agttcaaggt | cctgaaaaaa | gaaaaacatt | ttactctgtg | taccttgtgt | ctttctaaat | 420 |
| ttctctctcc | aaaataaagt | tcaagcatt | | | | 449 |

<210> SEQ ID NO 43
<211> LENGTH: 475
<212> TYPE: DNA
<213> ORGANISM: Homo sapiens

<400> SEQUENCE: 43

| | | | | | | |
|---|---|---|---|---|---|---|
| acacatctgc | tcctgctctc | tctcctccag | cgaccctagc | catgagaacc | ctcaccatcc | 60 |
| tcactgctgt | tctcctcgtg | gccctccagg | ccaaggctga | gccactccaa | gctgaggatg | 120 |
| atccactgca | ggcaaaagct | tatgaggctg | atgcccagga | gcagcgtggg | gcaaatgacc | 180 |
| aggactttgc | cgtctccttt | gcagaggatg | caagctcaag | tcttagagct | ttgggctcaa | 240 |
| caagggcttt | cacttgccat | tgcagaaggt | cctgttattc | aacagaatat | cctatgggaa | 300 |
| cctgcactgt | catgggtatt | aaccacagat | tctgctgcct | ctgagggatg | agaacagaga | 360 |
| gaaatatatt | cataatttac | tttatgacct | agaaggaaac | tgtcgtgtgt | cccatacatt | 420 |
| gccatcaact | ttgtttcctc | atctcaaata | aagtcctttc | agcaaaaaaa | aaaaa | 475 |

<210> SEQ ID NO 44
<211> LENGTH: 484
<212> TYPE: DNA
<213> ORGANISM: Homo sapiens

<400> SEQUENCE: 44

```
tcccttcagt tccgtcgacg aggttgtgca atccaccagt cttataaata cagtgacgct      60
ccagcctctg gaagcctctg tcagctcagc ctccaaagga gccagcgtct ccccagttcc     120
tgaaatcctg ggtgttgcct gccagtcgcc atgagaactt cctaccttct gctgtttact     180
ctctgcttac ttttgtctga gatggcctca ggtggtaact ttctcacagg ccttggccac     240
agatctgatc attacaattg cgtcagcagt ggagggcaat gtctctattc tgcctgcccg     300
atctttacca aaattcaagg cacctgttac agagggaagg ccaagtgctg caagtgagct     360
gggagtgacc agaagaaatg acgcagaagt gaaatgaact ttttataagc attcttttaa     420 taaggaaaa ttgcttttga agtataccctc ctttgggcca aaaaaaaaaa aaaaaaaaaa    480
aaaa                                                                  484

<210> SEQ ID NO 45
<211> LENGTH: 337
<212> TYPE: DNA
<213> ORGANISM: Homo sapiens

<400> SEQUENCE: 45
tgagtctcag cgtggggtga agcctagcag ctatgaggat ccattatctt ctgtttgctt      60
tgctcttcct gttttggtg cctgtcccag gtcatggagg aatcataaac acattacaga     120
aatattattg cagagtcaga ggcggccggt gtgctgtgct cagctgcctt ccaaaggagg     180
aacagatcgg caagtgctcg acgcgtggcc gaaaatgctg ccgaagaaag aataaaaac      240 cctgaaacat gacgagagtg ttgtaaagtg tggaaatgcc ttcttaaagt ttataaaagt     300
aaaatcaaat tacattttt tttcaaaaaa aaaaaaa                              337

<210> SEQ ID NO 46
<211> LENGTH: 336
<212> TYPE: DNA
<213> ORGANISM: Homo sapiens

<400> SEQUENCE: 46
agactcagct cctggtgaag ctcccagcca tcagccatga gggtcttgta tctcctcttc      60
tcgttcctct tcatattcct gatgcctctt ccaggtgttt ttggtggtat aggcgatcct     120
gttacctgcc ttaagagtgg agccatatgt catccagtct tttgccctag aaggtataaa     180
caaattggca cctgtggtct ccctggaaca aaatgctgca aaaagccatg aggaggccaa     240
gaagctgctg tggctgatgc ggattcagaa agggctccct catcagagac gtgcgacatg     300
taaaccaaat taaactatgg tgtccaaaga tacgca                              336

<210> SEQ ID NO 47
<211> LENGTH: 691
<212> TYPE: DNA
<213> ORGANISM: Homo sapiens

<400> SEQUENCE: 47
atggagaccc agagagccag cctgtgcctg gggcgctggt cactgtggct tctgctgctg      60
gcactcgtgg tgccctcggc cagcgcccag gccctcagct acaggaggc cgtgcttcgt     120 gctgtggatc gcctcaacga gcagtcctcg gaagctaatc tctaccgcct cctggagctg     180
gaccagccgc ccaaggccga cgaggacccg gcaccccga acctgtgag cttcacggtg     240 aaggagactg tgtgtcccag gccgaccccgg cagccccgg agctgtgtga cttcaaggag     300
aacgggcggg tgaaacagtg tgtggggaca gtcaccctgg atcagatcaa ggaccgctc      360
```

```
gacatcacct gcaatgaggt tcaaggtgtc aggggaggtc gcctgtgcta ttgtaggcgt    420
aggttctgcg tctgtgtcgg acaggatga cggttgcgac ggcaggcttt ccctccccca     480
attttcccgg ggccaggttt ccgtccccca attttttccgc ctccacctttt ccggcccgca  540 ccattcggtc caccaaggtt ccctggtaga cggtgaagga tttgcaggca actcacccag    600
aaggcctttc ggtacattaa atcccagca aggagaccta agcatctgct ttgcccaggc     660
ccgcatctgt caaataaatt cttgtgaaac c                                    691
```

<210> SEQ ID NO 48
<211> LENGTH: 691
<212> TYPE: DNA
<213> ORGANISM: Homo sapiens

<400> SEQUENCE: 48

```
atggagaccc agagagccag cctgtgcctg gggcgctggt cactgtggct tctgctgctg    60
gcactcgtgg tgccctcggc cagcgcccag gccctcagct acagggaggc cgtgcttcgt   120
gctgtggatc gcctcaacga gcagtcctcg gaagctaatc tctaccgcct cctggagctg   180
gaccagccgc ccaaggccga cgaggacccg ggcaccccga aacctgtgag cttcacggtg   240
aaggagactg tgtgtcccag gccgaccggg cagccccgg agctgtgtga cttcaaggag   300
aacgggcggg tgaaacagtg tgtggggaca gtcaccctgg atcagatcaa ggacccgctc   360
gacatcacct gcaatgaggt tcaaggtgtc aggggaggtg gcctgtgcta ttgtaggcgt   420
aggttctgcg tctgtgtcgg acaggatga cggttgcgac ggcaggcttt ccctccccca    480
attttcccgg ggccaggttt ccgtccccca attttttccgc ctccacctttt ccggcccgca  540 ccattcggtc caccaaggtt ccctggtaga cggtgaagga tttgcaggca actcacccag   600
aaggcctttc ggtacattaa atcccagca aggagaccta agcatctgct ttgcccaggc    660
ccgcatctgt caaataaatt cttgtgaaac c                                    691
```

<210> SEQ ID NO 49
<211> LENGTH: 691
<212> TYPE: DNA
<213> ORGANISM: Homo sapiens

<400> SEQUENCE: 49

```
atggagaccc agagagccag cctgtgcctg gggcgctggt cactgtggct tctgctgctg    60
gcactcgtgg tgccctcggc cagcgcccag gccctcagct acagggaggc cgtgcttcgt   120
gctgtggatc gcctcaacga gcagtcctcg gaagctaatc tctaccgcct cctggagctg   180
gaccagccgc ccaaggccga cgaggacccg ggcaccccga aacctgtgag cttcacggtg   240
aaggagactg tgtgtcccag gccgaccggg cagccccgg agctgtgtga cttcaaggag   300
aacgggcggg tgaaacagtg tgtggggaca gtcaccctgg atcagatcaa ggacccgctc   360
gacatcacct gcaatgaggt tcaaggtgtc aggggaggtc gcctgtgcta ttgtaggggt   420
tggatctgct tctgtgtcgg acaggatga cggttgcgac ggcaggcttt ccctccccca    480
attttcccgg ggccaggttt ccgtccccca attttttccgc ctccacctttt ccggcccgca  540 ccattcggtc caccaaggtt ccctggtaga cggtgaagga tttgcaggca actcacccag   600
aaggcctttc ggcacattaa atcccagca aggagaccta agcatctgct ttgcccaggc    660
ccgcatctgt caaataaatt cttgtgaaac c                                    691
```

<210> SEQ ID NO 50
<211> LENGTH: 55

```
<212> TYPE: DNA
<213> ORGANISM: Artificial Sequence
<220> FEATURE:
<223> OTHER INFORMATION: Construct containing an HPV target sequence,
      a hairpin sequence and BamH1 and SalI restriction sites.

<400> SEQUENCE: 50
gatcctaggt atttgaattt gcatttcaag agaatgcaaa ttcaaatacc ttttg         55

<210> SEQ ID NO 51
<211> LENGTH: 55
<212> TYPE: DNA
<213> ORGANISM: Artificial Sequence
<220> FEATURE:
<223> OTHER INFORMATION: Construct containing an HPV target sequence,
      a hairpin sequence and BamH1 and SalI restriction sites. Sequence
      given in 3' to 5' orientation.

<400> SEQUENCE: 51
gatccataaa cttaaacgta aagttctctt acgtttaagt ttatggaaaa cagct         55

<210> SEQ ID NO 52
<211> LENGTH: 21
<212> TYPE: DNA
<213> ORGANISM: Homo sapiens

<400> SEQUENCE: 52
agccaatggc ttggaatgag a                                              21

<210> SEQ ID NO 53
<211> LENGTH: 21
<212> TYPE: DNA
<213> ORGANISM: Homo sapiens

<400> SEQUENCE: 53
atcagctggc ctggtttgat a                                              21

<210> SEQ ID NO 54
<211> LENGTH: 21
<212> TYPE: DNA
<213> ORGANISM: Homo sapiens

<400> SEQUENCE: 54
ctgtgaactt gctcaggaca a                                              21

<210> SEQ ID NO 55
<211> LENGTH: 21
<212> TYPE: DNA
<213> ORGANISM: Homo sapiens

<400> SEQUENCE: 55
agcaatcagc tggcctggtt t                                              21

<210> SEQ ID NO 56
<211> LENGTH: 21
<212> TYPE: DNA
<213> ORGANISM: Homo sapiens

<400> SEQUENCE: 56
cctctgtgaa cttgctcagg a                                              21

<210> SEQ ID NO 57
<211> LENGTH: 21
<212> TYPE: DNA
<213> ORGANISM: Homo sapiens
```

```
<400> SEQUENCE: 57
ttccgaatgt ctgaggacaa g                                              21

<210> SEQ ID NO 58
<211> LENGTH: 21
<212> TYPE: DNA
<213> ORGANISM: Homo sapiens

<400> SEQUENCE: 58
ccaatggctt ggaatgagac t                                              21

<210> SEQ ID NO 59
<211> LENGTH: 21
<212> TYPE: DNA
<213> ORGANISM: Homo sapiens

<400> SEQUENCE: 59
ggtgctgact atccagttga t                                              21

<210> SEQ ID NO 60
<211> LENGTH: 21
<212> TYPE: DNA
<213> ORGANISM: Homo sapiens

<400> SEQUENCE: 60
caatcagctg gcctggtttg a                                              21

<210> SEQ ID NO 61
<211> LENGTH: 21
<212> TYPE: DNA
<213> ORGANISM: Homo sapiens

<400> SEQUENCE: 61
caccctggtg ctgactatcc a                                              21

<210> SEQ ID NO 62
<211> LENGTH: 21
<212> TYPE: DNA
<213> ORGANISM: Homo sapiens

<400> SEQUENCE: 62
caccaccctg gtgctgacta t                                              21

<210> SEQ ID NO 63
<211> LENGTH: 21
<212> TYPE: DNA
<213> ORGANISM: Homo sapiens

<400> SEQUENCE: 63
tgctttattc tcccattgaa a                                              21

<210> SEQ ID NO 64
<211> LENGTH: 21
<212> TYPE: DNA
<213> ORGANISM: Homo sapiens

<400> SEQUENCE: 64
ctggtgctga ctatccagtt g                                              21

<210> SEQ ID NO 65
<211> LENGTH: 21
<212> TYPE: DNA
```

```
<213> ORGANISM: Homo sapiens

<400> SEQUENCE: 65
tctgtgctct tcgtcatctg a                                              21

<210> SEQ ID NO 66
<211> LENGTH: 21
<212> TYPE: DNA
<213> ORGANISM: Homo sapiens

<400> SEQUENCE: 66
tgccatctgt gctcttcgtc a                                              21

<210> SEQ ID NO 67
<211> LENGTH: 21
<212> TYPE: DNA
<213> ORGANISM: Homo sapiens

<400> SEQUENCE: 67
tggtgctgac tatccagttg a                                              21

<210> SEQ ID NO 68
<211> LENGTH: 21
<212> TYPE: DNA
<213> ORGANISM: Homo sapiens

<400> SEQUENCE: 68
cctggtgctg actatccagt t                                              21

<210> SEQ ID NO 69
<211> LENGTH: 21
<212> TYPE: DNA
<213> ORGANISM: Homo sapiens

<400> SEQUENCE: 69
accctggtgc tgactatcca g                                              21

<210> SEQ ID NO 70
<211> LENGTH: 21
<212> TYPE: DNA
<213> ORGANISM: Homo sapiens

<400> SEQUENCE: 70
gagcctgcca tctgtgctct t                                              21

<210> SEQ ID NO 71
<211> LENGTH: 21
<212> TYPE: DNA
<213> ORGANISM: Homo sapiens

<400> SEQUENCE: 71
ctggtttgat actgacctgt a                                              21

<210> SEQ ID NO 72
<211> LENGTH: 21
<212> TYPE: DNA
<213> ORGANISM: Homo sapiens

<400> SEQUENCE: 72
tggtttgata ctgacctgta a                                              21

<210> SEQ ID NO 73
<211> LENGTH: 21
```

```
<212> TYPE: DNA
<213> ORGANISM: Homo sapiens

<400> SEQUENCE: 73
tcgaggagta acaatacaaa t                                              21

<210> SEQ ID NO 74
<211> LENGTH: 21
<212> TYPE: DNA
<213> ORGANISM: Homo sapiens

<400> SEQUENCE: 74
accatgcaga atacaaatga t                                              21

<210> SEQ ID NO 75
<211> LENGTH: 21
<212> TYPE: DNA
<213> ORGANISM: Homo sapiens

<400> SEQUENCE: 75
aggagtaaca atacaaatgg a                                              21

<210> SEQ ID NO 76
<211> LENGTH: 21
<212> TYPE: DNA
<213> ORGANISM: Homo sapiens

<400> SEQUENCE: 76
gtcgaggagt aacaatacaa a                                              21

<210> SEQ ID NO 77
<211> LENGTH: 21
<212> TYPE: DNA
<213> ORGANISM: Homo sapiens

<400> SEQUENCE: 77
ttgttgtaac ctgctgtgat a                                              21

<210> SEQ ID NO 78
<211> LENGTH: 21
<212> TYPE: DNA
<213> ORGANISM: Homo sapiens

<400> SEQUENCE: 78
gagtaatggt gtagaacact a                                              21

<210> SEQ ID NO 79
<211> LENGTH: 21
<212> TYPE: DNA
<213> ORGANISM: Homo sapiens

<400> SEQUENCE: 79
agtaatggtg tagaacacta a                                              21

<210> SEQ ID NO 80
<211> LENGTH: 21
<212> TYPE: DNA
<213> ORGANISM: Homo sapiens

<400> SEQUENCE: 80
cacactaacc aagctgagtt t                                              21

<210> SEQ ID NO 81
```

```
<211> LENGTH: 21
<212> TYPE: DNA
<213> ORGANISM: Homo sapiens

<400> SEQUENCE: 81
tttggtcgag gagtaacaat a                                              21

<210> SEQ ID NO 82
<211> LENGTH: 21
<212> TYPE: DNA
<213> ORGANISM: Homo sapiens

<400> SEQUENCE: 82
taccattcca ttgtttgtgc a                                              21

<210> SEQ ID NO 83
<211> LENGTH: 21
<212> TYPE: DNA
<213> ORGANISM: Homo sapiens

<400> SEQUENCE: 83
tagggtaaat cagtaagagg t                                              21

<210> SEQ ID NO 84
<211> LENGTH: 21
<212> TYPE: DNA
<213> ORGANISM: Homo sapiens

<400> SEQUENCE: 84
ctaaccaagc tgagtttcct a                                              21

<210> SEQ ID NO 85
<211> LENGTH: 21
<212> TYPE: DNA
<213> ORGANISM: Homo sapiens

<400> SEQUENCE: 85
tggtcgagga gtaacaatac a                                              21

<210> SEQ ID NO 86
<211> LENGTH: 21
<212> TYPE: DNA
<213> ORGANISM: Homo sapiens

<400> SEQUENCE: 86
ctggcctggt ttgatactga c                                              21

<210> SEQ ID NO 87
<211> LENGTH: 21
<212> TYPE: DNA
<213> ORGANISM: Homo sapiens

<400> SEQUENCE: 87
taacctcact tgcaataatt a                                              21

<210> SEQ ID NO 88
<211> LENGTH: 21
<212> TYPE: DNA
<213> ORGANISM: Homo sapiens

<400> SEQUENCE: 88
atcccactgg cctctgataa a                                              21
```

```
<210> SEQ ID NO 89
<211> LENGTH: 21
<212> TYPE: DNA
<213> ORGANISM: Homo sapiens

<400> SEQUENCE: 89
gaccacaagc agagtgctga a                                              21

<210> SEQ ID NO 90
<211> LENGTH: 21
<212> TYPE: DNA
<213> ORGANISM: Homo sapiens

<400> SEQUENCE: 90
cacaagcaga gtgctgaagg t                                              21

<210> SEQ ID NO 91
<211> LENGTH: 21
<212> TYPE: DNA
<213> ORGANISM: Homo sapiens

<400> SEQUENCE: 91
ctaacctcac ttgcaataat t                                              21

<210> SEQ ID NO 92
<211> LENGTH: 19
<212> TYPE: DNA
<213> ORGANISM: Homo sapiens

<400> SEQUENCE: 92
agctgatatt gatggacag                                                 19

<210> SEQ ID NO 93
<211> LENGTH: 23
<212> TYPE: DNA
<213> ORGANISM: Human papillomavirus

<400> SEQUENCE: 93
cggtgccaga aaccgttgaa tcc                                            23

<210> SEQ ID NO 94
<211> LENGTH: 23
<212> TYPE: DNA
<213> ORGANISM: Human papillomavirus

<400> SEQUENCE: 94
cactgcaaga catagaaata acc                                            23

<210> SEQ ID NO 95
<211> LENGTH: 23
<212> TYPE: DNA
<213> ORGANISM: Human papillomavirus

<400> SEQUENCE: 95
aggtgcctgc ggtgccagaa acc                                            23

<210> SEQ ID NO 96
<211> LENGTH: 23
<212> TYPE: DNA
<213> ORGANISM: Human papillomavirus

<400> SEQUENCE: 96
gcggtgccag aaaccgttga atc                                            23
```

```
<210> SEQ ID NO 97
<211> LENGTH: 23
<212> TYPE: DNA
<213> ORGANISM: Human papillomavirus

<400> SEQUENCE: 97
tcactgcaag acatagaaat aac                                              23

<210> SEQ ID NO 98
<211> LENGTH: 23
<212> TYPE: DNA
<213> ORGANISM: Human papillomavirus

<400> SEQUENCE: 98
cccatgctgc atgccataaa tgt                                              23

<210> SEQ ID NO 99
<211> LENGTH: 23
<212> TYPE: DNA
<213> ORGANISM: Human papillomavirus

<400> SEQUENCE: 99
atgctgcatg ccataaatgt ata                                              23

<210> SEQ ID NO 100
<211> LENGTH: 23
<212> TYPE: DNA
<213> ORGANISM: Human papillomavirus

<400> SEQUENCE: 100
gtggtgtata gagacagtat acc                                              23

<210> SEQ ID NO 101
<211> LENGTH: 23
<212> TYPE: DNA
<213> ORGANISM: Human papillomavirus

<400> SEQUENCE: 101
gcgcgctttg aggatccaac acg                                              23

<210> SEQ ID NO 102
<211> LENGTH: 23
<212> TYPE: DNA
<213> ORGANISM: Human papillomavirus

<400> SEQUENCE: 102
ctgcggtgcc agaaaccgtt gaa                                              23

<210> SEQ ID NO 103
<211> LENGTH: 23
<212> TYPE: DNA
<213> ORGANISM: Human papillomavirus

<400> SEQUENCE: 103
ccccatgctg catgccataa atg                                              23

<210> SEQ ID NO 104
<211> LENGTH: 23
<212> TYPE: DNA
<213> ORGANISM: Human papillomavirus

<400> SEQUENCE: 104
accccatgct gcatgccata aat                                              23
```

```
<210> SEQ ID NO 105
<211> LENGTH: 23
<212> TYPE: DNA
<213> ORGANISM: Human papillomavirus

<400> SEQUENCE: 105
aacactgggt tatacaatttt att                                    23

<210> SEQ ID NO 106
<211> LENGTH: 23
<212> TYPE: DNA
<213> ORGANISM: Human papillomavirus

<400> SEQUENCE: 106
acgacgcaga gaaacacaag tat                                     23

<210> SEQ ID NO 107
<211> LENGTH: 23
<212> TYPE: DNA
<213> ORGANISM: Human papillomavirus

<400> SEQUENCE: 107
aaggtgcctg cggtgccaga aac                                     23

<210> SEQ ID NO 108
<211> LENGTH: 23
<212> TYPE: DNA
<213> ORGANISM: Human papillomavirus

<400> SEQUENCE: 108
ggtgcctgcg gtgccagaaa ccg                                     23

<210> SEQ ID NO 109
<211> LENGTH: 23
<212> TYPE: DNA
<213> ORGANISM: Human papillomavirus

<400> SEQUENCE: 109
catgctgcat gccataaatg tat                                     23

<210> SEQ ID NO 110
<211> LENGTH: 23
<212> TYPE: DNA
<213> ORGANISM: Homo sapiens

<400> SEQUENCE: 110
gacgcagaga aacacaagta taa                                     23

<210> SEQ ID NO 111
<211> LENGTH: 23
<212> TYPE: DNA
<213> ORGANISM: Human papillomavirus

<400> SEQUENCE: 111
ttcactgcaa gacatagaaa taa                                     23

<210> SEQ ID NO 112
<211> LENGTH: 23
<212> TYPE: DNA
<213> ORGANISM: Human papillomavirus

<400> SEQUENCE: 112
```

```
ggtgccagaa accgttgaat cca                                          23

<210> SEQ ID NO 113
<211> LENGTH: 23
<212> TYPE: DNA
<213> ORGANISM: Human papillomavirus

<400> SEQUENCE: 113
tggcgcgctt tgaggatcca aca                                          23

<210> SEQ ID NO 114
<211> LENGTH: 23
<212> TYPE: DNA
<213> ORGANISM: Human papillomavirus

<400> SEQUENCE: 114
tgtggtgtat agagacagta tac                                          23

<210> SEQ ID NO 115
<211> LENGTH: 23
<212> TYPE: DNA
<213> ORGANISM: Human papillomavirus

<400> SEQUENCE: 115
gtgcctgcgg tgccagaaac cgt                                          23

<210> SEQ ID NO 116
<211> LENGTH: 23
<212> TYPE: DNA
<213> ORGANISM: Human papillomavirus

<400> SEQUENCE: 116
ctgcatgcca taaatgtata gat                                          23

<210> SEQ ID NO 117
<211> LENGTH: 23
<212> TYPE: DNA
<213> ORGANISM: Human papillomavirus

<400> SEQUENCE: 117
gactccaacg acgcagagaa aca                                          23

<210> SEQ ID NO 118
<211> LENGTH: 23
<212> TYPE: DNA
<213> ORGANISM: Human papillomavirus

<400> SEQUENCE: 118
ctgggcacta tagaggccag tgc                                          23

<210> SEQ ID NO 119
<211> LENGTH: 23
<212> TYPE: DNA
<213> ORGANISM: Human papillomavirus

<400> SEQUENCE: 119
tgctgcatgc cataaatgta tag                                          23

<210> SEQ ID NO 120
<211> LENGTH: 23
<212> TYPE: DNA
<213> ORGANISM: Human papillomavirus

<400> SEQUENCE: 120
```

-continued gtgccagaaa ccgttgaatc cag                                               23

<210> SEQ ID NO 121
<211> LENGTH: 23
<212> TYPE: DNA
<213> ORGANISM: Human papillomavirus

<400> SEQUENCE: 121
ttacagaggt atttgaattt gca                                               23

<210> SEQ ID NO 122
<211> LENGTH: 23
<212> TYPE: DNA
<213> ORGANISM: Human papillomavirus

<400> SEQUENCE: 122
gaggccagtg ccattcgtgc tgc                                               23

<210> SEQ ID NO 123
<211> LENGTH: 23
<212> TYPE: DNA
<213> ORGANISM: Human papillomavirus

<400> SEQUENCE: 123
attccggttg accttctatg tca                                               23

<210> SEQ ID NO 124
<211> LENGTH: 23
<212> TYPE: DNA
<213> ORGANISM: Human papillomavirus

<400> SEQUENCE: 124
gatggagtta atcatcaaca ttt                                               23

<210> SEQ ID NO 125
<211> LENGTH: 23
<212> TYPE: DNA
<213> ORGANISM: Human papillomavirus

<400> SEQUENCE: 125
aagccagaat tgagctagta gta                                               23

<210> SEQ ID NO 126
<211> LENGTH: 23
<212> TYPE: DNA
<213> ORGANISM: Human papillomavirus

<400> SEQUENCE: 126
catggaccta aggcaacatt gca                                               23

<210> SEQ ID NO 127
<211> LENGTH: 23
<212> TYPE: DNA
<213> ORGANISM: Human papillomavirus

<400> SEQUENCE: 127
aaccacaacg tcacacaatg ttg                                               23

<210> SEQ ID NO 128
<211> LENGTH: 23
<212> TYPE: DNA
<213> ORGANISM: Human papillomavirus

```
<400> SEQUENCE: 128
atggacctaa ggcaacattg caa                                              23

<210> SEQ ID NO 129
<211> LENGTH: 23
<212> TYPE: DNA
<213> ORGANISM: Human papillomavirus

<400> SEQUENCE: 129
taagcgactc agaggaagaa aac                                              23

<210> SEQ ID NO 130
<211> LENGTH: 23
<212> TYPE: DNA
<213> ORGANISM: Human papillomavirus

<400> SEQUENCE: 130
gaagccagaa ttgagctagt agt                                              23

<210> SEQ ID NO 131
<211> LENGTH: 23
<212> TYPE: DNA
<213> ORGANISM: Human papillomavirus

<400> SEQUENCE: 131
gagccgaacc acaacgtcac aca                                              23

<210> SEQ ID NO 132
<211> LENGTH: 23
<212> TYPE: DNA
<213> ORGANISM: Human papillomavirus

<400> SEQUENCE: 132
acgtcacaca atgttgtgta tgt                                              23

<210> SEQ ID NO 133
<211> LENGTH: 23
<212> TYPE: DNA
<213> ORGANISM: Human papillomavirus

<400> SEQUENCE: 133
gaaccacaac gtcacacaat gtt                                              23

<210> SEQ ID NO 134
<211> LENGTH: 23
<212> TYPE: DNA
<213> ORGANISM: Human papillomavirus

<400> SEQUENCE: 134
aggcaacatt gcaagacatt gta                                              23

<210> SEQ ID NO 135
<211> LENGTH: 23
<212> TYPE: DNA
<213> ORGANISM: Human papillomavirus

<400> SEQUENCE: 135
aagacattgt attgcattta gag                                              23

<210> SEQ ID NO 136
<211> LENGTH: 23
<212> TYPE: DNA
<213> ORGANISM: Human papillomavirus
```

```
<400> SEQUENCE: 136
taaggcaaca ttgcaagaca ttg                                          23

<210> SEQ ID NO 137
<211> LENGTH: 23
<212> TYPE: DNA
<213> ORGANISM: Human papillomavirus

<400> SEQUENCE: 137
ccagcccgac gagccgaacc aca                                          23

<210> SEQ ID NO 138
<211> LENGTH: 23
<212> TYPE: DNA
<213> ORGANISM: Human papillomavirus

<400> SEQUENCE: 138
aagctcagca gacgaccttc gag                                          23

<210> SEQ ID NO 139
<211> LENGTH: 23
<212> TYPE: DNA
<213> ORGANISM: Human papillomavirus

<400> SEQUENCE: 139
gcccgacgag ccgaaccaca acg                                          23

<210> SEQ ID NO 140
<211> LENGTH: 23
<212> TYPE: DNA
<213> ORGANISM: Human papillomavirus

<400> SEQUENCE: 140
ttccggttga ccttctatgt cac                                          23

<210> SEQ ID NO 141
<211> LENGTH: 23
<212> TYPE: DNA
<213> ORGANISM: Human papillomavirus

<400> SEQUENCE: 141
tgcatggacc taaggcaaca ttg                                          23

<210> SEQ ID NO 142
<211> LENGTH: 23
<212> TYPE: DNA
<213> ORGANISM: Human papillomavirus

<400> SEQUENCE: 142
ttccagcagc tgtttctgaa cac                                          23

<210> SEQ ID NO 143
<211> LENGTH: 23
<212> TYPE: DNA
<213> ORGANISM: Human papillomavirus

<400> SEQUENCE: 143
aacaccctgt cctttgtgtg tcc                                          23

<210> SEQ ID NO 144
<211> LENGTH: 23
<212> TYPE: DNA
```

<213> ORGANISM: Human papillomavirus

<400> SEQUENCE: 144
cttctatgtc acgagcaatt aag    23

<210> SEQ ID NO 145
<211> LENGTH: 23
<212> TYPE: DNA
<213> ORGANISM: Human papillomavirus

<400> SEQUENCE: 145
acgagccgaa ccacaacgtc aca    23

<210> SEQ ID NO 146
<211> LENGTH: 23
<212> TYPE: DNA
<213> ORGANISM: Human papillomavirus

<400> SEQUENCE: 146
ttgagctagt agtagaaagc tca    23

<210> SEQ ID NO 147
<211> LENGTH: 23
<212> TYPE: DNA
<213> ORGANISM: Human papillomavirus

<400> SEQUENCE: 147
cagcagacga ccttcgagca ttc    23

<210> SEQ ID NO 148
<211> LENGTH: 23
<212> TYPE: DNA
<213> ORGANISM: Human papillomavirus

<400> SEQUENCE: 148
agccagaatt gagctagtag tag    23

<210> SEQ ID NO 149
<211> LENGTH: 23
<212> TYPE: DNA
<213> ORGANISM: Human papillomavirus

<400> SEQUENCE: 149
gtcacacaat gttgtgtatg tgt    23

<210> SEQ ID NO 150
<211> LENGTH: 23
<212> TYPE: DNA
<213> ORGANISM: Human papillomavirus

<400> SEQUENCE: 150
ccgacgagcc gaaccacaac gtc    23

<210> SEQ ID NO 151
<211> LENGTH: 23
<212> TYPE: DNA
<213> ORGANISM: Human papillomavirus

<400> SEQUENCE: 151
aattccggtt gaccttctat gtc    23

<210> SEQ ID NO 152
<211> LENGTH: 23

```
<212> TYPE: DNA
<213> ORGANISM: Human papillomavirus

<400> SEQUENCE: 152
attccagcag ctgtttctga aca                                           23

<210> SEQ ID NO 153
<211> LENGTH: 19
<212> TYPE: DNA
<213> ORGANISM: Human papillomavirus

<400> SEQUENCE: 153
taggtatttg aatttgcat                                                19

<210> SEQ ID NO 154
<211> LENGTH: 19
<212> TYPE: DNA
<213> ORGANISM: Human papillomavirus

<400> SEQUENCE: 154
gaggtatttg aatttgcat                                                19

<210> SEQ ID NO 155
<211> LENGTH: 20
<212> TYPE: DNA
<213> ORGANISM: Homo sapiens

<400> SEQUENCE: 155
atgttgtctg gacaagcact                                               20

<210> SEQ ID NO 156
<211> LENGTH: 19
<212> TYPE: DNA
<213> ORGANISM: Homo sapiens

<400> SEQUENCE: 156
gttggagctg ttggcgtag                                                19

<210> SEQ ID NO 157
<211> LENGTH: 21
<212> TYPE: DNA
<213> ORGANISM: Homo sapiens

<400> SEQUENCE: 157
ctcctggaac tcatctttct a                                             21

<210> SEQ ID NO 158
<211> LENGTH: 21
<212> TYPE: DNA
<213> ORGANISM: Homo sapiens

<400> SEQUENCE: 158
gctctcctgc ttccggaaga g                                             21

<210> SEQ ID NO 159
<211> LENGTH: 21
<212> TYPE: DNA
<213> ORGANISM: Homo sapiens

<400> SEQUENCE: 159
ctccacgact ctggaaacta t                                             21

<210> SEQ ID NO 160
```

```
<211> LENGTH: 21
<212> TYPE: DNA
<213> ORGANISM: Homo sapiens

<400> SEQUENCE: 160
cagaagttct cctgccagtt a                                              21

<210> SEQ ID NO 161
<211> LENGTH: 21
<212> TYPE: DNA
<213> ORGANISM: Homo sapiens

<400> SEQUENCE: 161
ccggaagaca atgccactgt t                                              21

<210> SEQ ID NO 162
<211> LENGTH: 21
<212> TYPE: DNA
<213> ORGANISM: Homo sapiens

<400> SEQUENCE: 162
ctgaacggtc aaagacattc a                                              21

<210> SEQ ID NO 163
<211> LENGTH: 21
<212> TYPE: DNA
<213> ORGANISM: Homo sapiens

<400> SEQUENCE: 163
cacaacatgg atggtcaagg a                                              21

<210> SEQ ID NO 164
<211> LENGTH: 21
<212> TYPE: DNA
<213> ORGANISM: Homo sapiens

<400> SEQUENCE: 164
atgcaggcac ttactactaa t                                              21

<210> SEQ ID NO 165
<211> LENGTH: 21
<212> TYPE: DNA
<213> ORGANISM: Homo sapiens

<400> SEQUENCE: 165
atcgggctga acggtcaaag a                                              21

<210> SEQ ID NO 166
<211> LENGTH: 21
<212> TYPE: DNA
<213> ORGANISM: Homo sapiens

<400> SEQUENCE: 166
agctctcctg cttccggaag a                                              21

<210> SEQ ID NO 167
<211> LENGTH: 21
<212> TYPE: DNA
<213> ORGANISM: Homo sapiens

<400> SEQUENCE: 167
cagctctcct gcttccggaa g                                              21
```

```
<210> SEQ ID NO 168
<211> LENGTH: 21
<212> TYPE: DNA
<213> ORGANISM: Homo sapiens

<400> SEQUENCE: 168
caggcactta ctactaataa a                                              21

<210> SEQ ID NO 169
<211> LENGTH: 21
<212> TYPE: DNA
<213> ORGANISM: Homo sapiens

<400> SEQUENCE: 169
cacttgctgg tggatgttcc c                                              21

<210> SEQ ID NO 170
<211> LENGTH: 21
<212> TYPE: DNA
<213> ORGANISM: Homo sapiens

<400> SEQUENCE: 170
aacggtcaaa gacattcaca a                                              21

<210> SEQ ID NO 171
<211> LENGTH: 21
<212> TYPE: DNA
<213> ORGANISM: Homo sapiens

<400> SEQUENCE: 171
tgcacaagct gcaccctcag g                                              21

<210> SEQ ID NO 172
<211> LENGTH: 21
<212> TYPE: DNA
<213> ORGANISM: Mouse

<400> SEQUENCE: 172
atcctggagg gtgacaaagt a                                              21

<210> SEQ ID NO 173
<211> LENGTH: 21
<212> TYPE: DNA
<213> ORGANISM: Mouse

<400> SEQUENCE: 173
tgggtctgac aataccgtaa a                                              21

<210> SEQ ID NO 174
<211> LENGTH: 21
<212> TYPE: DNA
<213> ORGANISM: Mouse

<400> SEQUENCE: 174
aacgaagcgt ttcacagctt a                                              21

<210> SEQ ID NO 175
<211> LENGTH: 21
<212> TYPE: DNA
<213> ORGANISM: Mouse

<400> SEQUENCE: 175
ccgctgtttc ctataacaga a                                              21
```

```
<210> SEQ ID NO 176
<211> LENGTH: 21
<212> TYPE: DNA
<213> ORGANISM: Mouse

<400> SEQUENCE: 176
acgaagcgtt tcacagctta a                                              21

<210> SEQ ID NO 177
<211> LENGTH: 21
<212> TYPE: DNA
<213> ORGANISM: Mouse

<400> SEQUENCE: 177
ctgctgtgaa agggaaattt a                                              21

<210> SEQ ID NO 178
<211> LENGTH: 21
<212> TYPE: DNA
<213> ORGANISM: Mouse

<400> SEQUENCE: 178
aaccttgtgg tatcagccat a                                              21

<210> SEQ ID NO 179
<211> LENGTH: 21
<212> TYPE: DNA
<213> ORGANISM: Mouse

<400> SEQUENCE: 179
cacagtgtgg tgcttagatt a                                              21

<210> SEQ ID NO 180
<211> LENGTH: 21
<212> TYPE: DNA
<213> ORGANISM: Mouse

<400> SEQUENCE: 180
cagcttcgat accgacctgt a                                              21

<210> SEQ ID NO 181
<211> LENGTH: 21
<212> TYPE: DNA
<213> ORGANISM: Mouse

<400> SEQUENCE: 181
cagtgtggtg cttagattaa a                                              21

<210> SEQ ID NO 182
<211> LENGTH: 21
<212> TYPE: DNA
<213> ORGANISM: Mouse

<400> SEQUENCE: 182
cccggcagga atcctctgga a                                              21

<210> SEQ ID NO 183
<211> LENGTH: 21
<212> TYPE: DNA
<213> ORGANISM: Mouse

<400> SEQUENCE: 183
cccgctgttt cctataacag a                                              21
```

<210> SEQ ID NO 184
<211> LENGTH: 21
<212> TYPE: DNA
<213> ORGANISM: Mouse

<400> SEQUENCE: 184
aaccacgagg atcagtacga a                                        21

<210> SEQ ID NO 185
<211> LENGTH: 21
<212> TYPE: DNA
<213> ORGANISM: Mouse

<400> SEQUENCE: 185
acctgccgtc ttactgaact a                                        21

<210> SEQ ID NO 186
<211> LENGTH: 21
<212> TYPE: DNA
<213> ORGANISM: Mouse

<400> SEQUENCE: 186
accacgagga tcagtacgaa a                                        21

<210> SEQ ID NO 187
<211> LENGTH: 21
<212> TYPE: DNA
<213> ORGANISM: Mouse

<400> SEQUENCE: 187
acagcttgtg atgactgaat a                                        21

<210> SEQ ID NO 188
<211> LENGTH: 21
<212> TYPE: DNA
<213> ORGANISM: Mouse

<400> SEQUENCE: 188
aggatcagta cgaaagttct a                                        21

<210> SEQ ID NO 189
<211> LENGTH: 21
<212> TYPE: DNA
<213> ORGANISM: Mouse

<400> SEQUENCE: 189
aacccgctgt ttcctataac a                                        21

<210> SEQ ID NO 190
<211> LENGTH: 21
<212> TYPE: DNA
<213> ORGANISM: Mouse

<400> SEQUENCE: 190
cagtacgaaa gttctacaga a                                        21

<210> SEQ ID NO 191
<211> LENGTH: 21
<212> TYPE: DNA
<213> ORGANISM: Mouse

<400> SEQUENCE: 191
tacgcgagtg acaatttctc a                                         21

<210> SEQ ID NO 192
<211> LENGTH: 21
<212> TYPE: DNA
<213> ORGANISM: Mouse

<400> SEQUENCE: 192
acgaaagttc tacagaagca a                                         21

<210> SEQ ID NO 193
<211> LENGTH: 21
<212> TYPE: DNA
<213> ORGANISM: Mouse

<400> SEQUENCE: 193
caggcactta ctactaataa a                                         21

<210> SEQ ID NO 194
<211> LENGTH: 21
<212> TYPE: DNA
<213> ORGANISM: Mouse

<400> SEQUENCE: 194
cacttgctgg tggatgttcc c                                         21

<210> SEQ ID NO 195
<211> LENGTH: 21
<212> TYPE: DNA
<213> ORGANISM: Mouse

<400> SEQUENCE: 195
aacggtcaaa gacattcaca a                                         21

<210> SEQ ID NO 196
<211> LENGTH: 21
<212> TYPE: DNA
<213> ORGANISM: Mouse

<400> SEQUENCE: 196
tgcacaagct gcaccctcag g                                         21

<210> SEQ ID NO 197
<211> LENGTH: 21
<212> TYPE: DNA
<213> ORGANISM: Homo sapiens

<400> SEQUENCE: 197
taagagagtc ataaacctta a                                         21

<210> SEQ ID NO 198
<211> LENGTH: 21
<212> TYPE: DNA
<213> ORGANISM: Homo sapiens

<400> SEQUENCE: 198
aacaaggtcc aagataccta a                                         21

<210> SEQ ID NO 199
<211> LENGTH: 21
<212> TYPE: DNA
<213> ORGANISM: Homo sapiens

<400> SEQUENCE: 199

```
aagattgaac ctgcagacca a                                              21

<210> SEQ ID NO 200
<211> LENGTH: 21
<212> TYPE: DNA
<213> ORGANISM: Homo sapiens

<400> SEQUENCE: 200
aagagatttc aagagattta a                                              21

<210> SEQ ID NO 201
<211> LENGTH: 21
<212> TYPE: DNA
<213> ORGANISM: Homo sapiens

<400> SEQUENCE: 201
aagcgcaaag tagaaactga a                                              21

<210> SEQ ID NO 202
<211> LENGTH: 21
<212> TYPE: DNA
<213> ORGANISM: Homo sapiens

<400> SEQUENCE: 202
tagcatcatc tgattgtgat a                                              21

<210> SEQ ID NO 203
<211> LENGTH: 21
<212> TYPE: DNA
<213> ORGANISM: Homo sapiens

<400> SEQUENCE: 203
taagataata atatatgttt a                                              21

<210> SEQ ID NO 204
<211> LENGTH: 21
<212> TYPE: DNA
<213> ORGANISM: Homo sapiens

<400> SEQUENCE: 204
atggtcagca tcgatcaatt a                                              21

<210> SEQ ID NO 205
<211> LENGTH: 21
<212> TYPE: DNA
<213> ORGANISM: Homo sapiens

<400> SEQUENCE: 205
ttgcctgaat aatgaattta a                                              21

<210> SEQ ID NO 206
<211> LENGTH: 21
<212> TYPE: DNA
<213> ORGANISM: Homo sapiens

<400> SEQUENCE: 206
atctgtgatg ctaataagga a                                              21

<210> SEQ ID NO 207
<211> LENGTH: 21
<212> TYPE: DNA
<213> ORGANISM: Homo sapiens
```

<400> SEQUENCE: 207
aacaaactat tcttatata t                                            21

<210> SEQ ID NO 208
<211> LENGTH: 21
<212> TYPE: DNA
<213> ORGANISM: Homo sapiens

<400> SEQUENCE: 208
aacatttatc aatcagtata a                                           21

<210> SEQ ID NO 209
<211> LENGTH: 21
<212> TYPE: DNA
<213> ORGANISM: Homo sapiens

<400> SEQUENCE: 209
atcaatcagt ataattctgt a                                           21

<210> SEQ ID NO 210
<211> LENGTH: 21
<212> TYPE: DNA
<213> ORGANISM: Homo sapiens

<400> SEQUENCE: 210
aaggtatcag ttgcaataat a                                           21

<210> SEQ ID NO 211
<211> LENGTH: 21
<212> TYPE: DNA
<213> ORGANISM: Mouse

<400> SEQUENCE: 211
cggatcctac ggaagttatg g                                           21

<210> SEQ ID NO 212
<211> LENGTH: 21
<212> TYPE: DNA
<213> ORGANISM: Mouse

<400> SEQUENCE: 212
gaccatgttc catgtttctt t                                           21

<210> SEQ ID NO 213
<211> LENGTH: 21
<212> TYPE: DNA
<213> ORGANISM: Mouse

<400> SEQUENCE: 213
aacctaaatg acctttatta a                                           21

<210> SEQ ID NO 214
<211> LENGTH: 21
<212> TYPE: DNA
<213> ORGANISM: Mouse

<400> SEQUENCE: 214
caggagacta ggaccctata a                                           21

<210> SEQ ID NO 215
<211> LENGTH: 21
<212> TYPE: DNA
<213> ORGANISM: Mouse

```
<400> SEQUENCE: 215
tagggtctta ttcgtatcta a                                              21

<210> SEQ ID NO 216
<211> LENGTH: 21
<212> TYPE: DNA
<213> ORGANISM: Mouse

<400> SEQUENCE: 216
atgagccaat atgcttaatt a                                              21

<210> SEQ ID NO 217
<211> LENGTH: 21
<212> TYPE: DNA
<213> ORGANISM: Mouse

<400> SEQUENCE: 217
gccaatatgc ttaattagaa a                                              21

<210> SEQ ID NO 218
<211> LENGTH: 21
<212> TYPE: DNA
<213> ORGANISM: Mouse

<400> SEQUENCE: 218
cagcatcgat gaattggaca a                                              21

<210> SEQ ID NO 219
<211> LENGTH: 21
<212> TYPE: DNA
<213> ORGANISM: Mouse

<400> SEQUENCE: 219
ttgcctgaat aatgaattta a                                              21

<210> SEQ ID NO 220
<211> LENGTH: 21
<212> TYPE: DNA
<213> ORGANISM: Mouse

<400> SEQUENCE: 220
ctgatagtaa ttgcccgaat a                                              21

<210> SEQ ID NO 221
<211> LENGTH: 21
<212> TYPE: DNA
<213> ORGANISM: Mouse

<400> SEQUENCE: 221
aagggtttgc ttgtactgaa t                                              21

<210> SEQ ID NO 222
<211> LENGTH: 21
<212> TYPE: DNA
<213> ORGANISM: Mouse

<400> SEQUENCE: 222
aacatgtatg tgatgataca a                                              21

<210> SEQ ID NO 223
<211> LENGTH: 21
<212> TYPE: DNA
```

```
<213> ORGANISM: Mouse

<400> SEQUENCE: 223
ttgcaacatg taataattta a                                              21

<210> SEQ ID NO 224
<211> LENGTH: 21
<212> TYPE: DNA
<213> ORGANISM: Mouse

<400> SEQUENCE: 224
aagagactac tgagagaaat a                                              21

<210> SEQ ID NO 225
<211> LENGTH: 21
<212> TYPE: DNA
<213> ORGANISM: Mouse

<400> SEQUENCE: 225
aagaatctac tggttcatat a                                              21

<210> SEQ ID NO 226
<211> LENGTH: 21
<212> TYPE: DNA
<213> ORGANISM: Mouse

<400> SEQUENCE: 226
tgccgtcagc atatacatat a                                              21

<210> SEQ ID NO 227
<211> LENGTH: 21
<212> TYPE: DNA
<213> ORGANISM: Mouse

<400> SEQUENCE: 227
agggctcacg gtgatggata a                                              21

<210> SEQ ID NO 228
<211> LENGTH: 21
<212> TYPE: DNA
<213> ORGANISM: Homo sapiens

<400> SEQUENCE: 228
cgcctcccgc agaccatgtt c                                              21

<210> SEQ ID NO 229
<211> LENGTH: 21
<212> TYPE: DNA
<213> ORGANISM: Homo sapiens

<400> SEQUENCE: 229
tccgtgctgc tcgcaagttg a                                              21

<210> SEQ ID NO 230
<211> LENGTH: 21
<212> TYPE: DNA
<213> ORGANISM: Homo sapiens

<400> SEQUENCE: 230
gcctcccgca gaccatgttc c                                              21

<210> SEQ ID NO 231
<211> LENGTH: 21
```

```
<212> TYPE: DNA
<213> ORGANISM: Homo sapiens

<400> SEQUENCE: 231
cctcccgcag accatgttcc a                                              21

<210> SEQ ID NO 232
<211> LENGTH: 21
<212> TYPE: DNA
<213> ORGANISM: Homo sapiens

<400> SEQUENCE: 232
ctcccgcaga ccatgttcca t                                              21

<210> SEQ ID NO 233
<211> LENGTH: 21
<212> TYPE: DNA
<213> ORGANISM: Homo sapiens

<400> SEQUENCE: 233
tcccgcagac catgttccat g                                              21

<210> SEQ ID NO 234
<211> LENGTH: 21
<212> TYPE: DNA
<213> ORGANISM: Homo sapiens

<400> SEQUENCE: 234
cccgcagacc atgttccatg t                                              21

<210> SEQ ID NO 235
<211> LENGTH: 21
<212> TYPE: DNA
<213> ORGANISM: Homo sapiens

<400> SEQUENCE: 235
ccgcagacca tgttccatgt t                                              21

<210> SEQ ID NO 236
<211> LENGTH: 21
<212> TYPE: DNA
<213> ORGANISM: Homo sapiens

<400> SEQUENCE: 236
cgcagaccat gttccatgtt t                                              21

<210> SEQ ID NO 237
<211> LENGTH: 21
<212> TYPE: DNA
<213> ORGANISM: Homo sapiens

<400> SEQUENCE: 237
gcagaccatg ttccatgttt c                                              21

<210> SEQ ID NO 238
<211> LENGTH: 21
<212> TYPE: DNA
<213> ORGANISM: Homo sapiens

<400> SEQUENCE: 238
cagaccatgt tccatgtttc t                                              21

<210> SEQ ID NO 239
```

```
<211> LENGTH: 21
<212> TYPE: DNA
<213> ORGANISM: Homo sapiens

<400> SEQUENCE: 239
agaccatgtt ccatgtttct t                                              21

<210> SEQ ID NO 240
<211> LENGTH: 21
<212> TYPE: DNA
<213> ORGANISM: Homo sapiens

<400> SEQUENCE: 240
aacctgatcc tccacatatt a                                              21

<210> SEQ ID NO 241
<211> LENGTH: 21
<212> TYPE: DNA
<213> ORGANISM: Homo sapiens

<400> SEQUENCE: 241
cctgatcctc cacatattaa a                                              21

<210> SEQ ID NO 242
<211> LENGTH: 21
<212> TYPE: DNA
<213> ORGANISM: Homo sapiens

<400> SEQUENCE: 242
agaaatgttt ggagaccaga a                                              21

<210> SEQ ID NO 243
<211> LENGTH: 21
<212> TYPE: DNA
<213> ORGANISM: Homo sapiens

<400> SEQUENCE: 243
caaataatgg tcaaggataa t                                              21

<210> SEQ ID NO 244
<211> LENGTH: 21
<212> TYPE: DNA
<213> ORGANISM: Homo sapiens

<400> SEQUENCE: 244
ttcctgatcc tggcaagatt t                                              21

<210> SEQ ID NO 245
<211> LENGTH: 21
<212> TYPE: DNA
<213> ORGANISM: Homo sapiens

<400> SEQUENCE: 245
taaagaaatg tttggagacc a                                              21

<210> SEQ ID NO 246
<211> LENGTH: 21
<212> TYPE: DNA
<213> ORGANISM: Homo sapiens

<400> SEQUENCE: 246
atgtttggag accagaatga t                                              21
```

```
<210> SEQ ID NO 247
<211> LENGTH: 21
<212> TYPE: DNA
<213> ORGANISM: Homo sapiens

<400> SEQUENCE: 247
ctccaattcc tgatcctggc a                                              21

<210> SEQ ID NO 248
<211> LENGTH: 21
<212> TYPE: DNA
<213> ORGANISM: Mouse

<400> SEQUENCE: 248
caagaagact ctaatgatgt a                                              21

<210> SEQ ID NO 249
<211> LENGTH: 21
<212> TYPE: DNA
<213> ORGANISM: Mouse

<400> SEQUENCE: 249
cacagtcaga gtaagagtca a                                              21

<210> SEQ ID NO 250
<211> LENGTH: 21
<212> TYPE: DNA
<213> ORGANISM: Mouse

<400> SEQUENCE: 250
acccagggta tcatagttct a                                              21

<210> SEQ ID NO 251
<211> LENGTH: 21
<212> TYPE: DNA
<213> ORGANISM: Mouse

<400> SEQUENCE: 251
ctgctttgaa atttccagaa a                                              21

<210> SEQ ID NO 252
<211> LENGTH: 21
<212> TYPE: DNA
<213> ORGANISM: Mouse

<400> SEQUENCE: 252
atcatagttc taagaatgaa a                                              21

<210> SEQ ID NO 253
<211> LENGTH: 21
<212> TYPE: DNA
<213> ORGANISM: Mouse

<400> SEQUENCE: 253
aaggcttaag atcattatat t                                              21

<210> SEQ ID NO 254
<211> LENGTH: 21
<212> TYPE: DNA
<213> ORGANISM: Mouse

<400> SEQUENCE: 254
aactacttat aagaaagtaa a                                              21
```

```
<210> SEQ ID NO 255
<211> LENGTH: 21
<212> TYPE: DNA
<213> ORGANISM: Mouse

<400> SEQUENCE: 255
cacagaacat ctagcaaaca a                                              21

<210> SEQ ID NO 256
<211> LENGTH: 21
<212> TYPE: DNA
<213> ORGANISM: Mouse

<400> SEQUENCE: 256
ctcgttcttg ttcaatccta a                                              21

<210> SEQ ID NO 257
<211> LENGTH: 21
<212> TYPE: DNA
<213> ORGANISM: Mouse

<400> SEQUENCE: 257
aacttgtagg ttcacatatt a                                              21

<210> SEQ ID NO 258
<211> LENGTH: 21
<212> TYPE: DNA
<213> ORGANISM: Mouse

<400> SEQUENCE: 258
aaccatttct gcaaatttaa a                                              21

<210> SEQ ID NO 259
<211> LENGTH: 21
<212> TYPE: DNA
<213> ORGANISM: Mouse

<400> SEQUENCE: 259
ctcagtgtag tgccaatgaa a                                              21

<210> SEQ ID NO 260
<211> LENGTH: 21
<212> TYPE: DNA
<213> ORGANISM: Mouse

<400> SEQUENCE: 260
caggccttag ggactcataa a                                              21

<210> SEQ ID NO 261
<211> LENGTH: 21
<212> TYPE: DNA
<213> ORGANISM: Mouse

<400> SEQUENCE: 261
aagtatgaca tctatgagaa a                                              21

<210> SEQ ID NO 262
<211> LENGTH: 21
<212> TYPE: DNA
<213> ORGANISM: Mouse

<400> SEQUENCE: 262
gtggaggtca ataatactca a                                              21
```

```
<210> SEQ ID NO 263
<211> LENGTH: 21
<212> TYPE: DNA
<213> ORGANISM: Mouse

<400> SEQUENCE: 263
cagagtatag gtaaggagca a                                              21

<210> SEQ ID NO 264
<211> LENGTH: 21
<212> TYPE: DNA
<213> ORGANISM: Homo sapiens

<400> SEQUENCE: 264
ttgaatgacc aagttctctt c                                              21

<210> SEQ ID NO 265
<211> LENGTH: 21
<212> TYPE: DNA
<213> ORGANISM: Mouse

<400> SEQUENCE: 265
ctctctgtga aggatagtaa a                                              21

<210> SEQ ID NO 266
<211> LENGTH: 21
<212> TYPE: DNA
<213> ORGANISM: Mouse

<400> SEQUENCE: 266
ccgcagtaat acggaatata a                                              21

<210> SEQ ID NO 267
<211> LENGTH: 21
<212> TYPE: DNA
<213> ORGANISM: Mouse

<400> SEQUENCE: 267
caaggaaatg atgtttattg a                                              21

<210> SEQ ID NO 268
<211> LENGTH: 21
<212> TYPE: DNA
<213> ORGANISM: Mouse

<400> SEQUENCE: 268
cagactgata atatacatgt a                                              21

<210> SEQ ID NO 269
<211> LENGTH: 21
<212> TYPE: DNA
<213> ORGANISM: Mouse

<400> SEQUENCE: 269
ttggccgact tcactgtaca a                                              21

<210> SEQ ID NO 270
<211> LENGTH: 21
<212> TYPE: DNA
<213> ORGANISM: Mouse

<400> SEQUENCE: 270
```
ccagaccaga ctgataatat a        21

<210> SEQ ID NO 271
<211> LENGTH: 21
<212> TYPE: DNA
<213> ORGANISM: Mouse

<400> SEQUENCE: 271
aagatggagt ttgaatcttc a        21

<210> SEQ ID NO 272
<211> LENGTH: 21
<212> TYPE: DNA
<213> ORGANISM: Mouse

<400> SEQUENCE: 272
acgctttact ttatacctga a        21

<210> SEQ ID NO 273
<211> LENGTH: 21
<212> TYPE: DNA
<213> ORGANISM: Mouse

<400> SEQUENCE: 273
tacaaccgca gtaatacgga a        21

<210> SEQ ID NO 274
<211> LENGTH: 21
<212> TYPE: DNA
<213> ORGANISM: Mouse

<400> SEQUENCE: 274
ctgcatgatt tatagagtaa a        21

<210> SEQ ID NO 275
<211> LENGTH: 21
<212> TYPE: DNA
<213> ORGANISM: Mouse

<400> SEQUENCE: 275
cccgaggctg catgatttat a        21

<210> SEQ ID NO 276
<211> LENGTH: 21
<212> TYPE: DNA
<213> ORGANISM: Mouse

<400> SEQUENCE: 276
cacgctttac tttatacctg a        21

<210> SEQ ID NO 277
<211> LENGTH: 21
<212> TYPE: DNA
<213> ORGANISM: Mouse

<400> SEQUENCE: 277
cgcctgtatt tccataacag a        21

<210> SEQ ID NO 278
<211> LENGTH: 21
<212> TYPE: DNA
<213> ORGANISM: Mouse

<400> SEQUENCE: 278

```
cgcagtaata cggaatataa a                                              21

<210> SEQ ID NO 279
<211> LENGTH: 21
<212> TYPE: DNA
<213> ORGANISM: Mouse

<400> SEQUENCE: 279
tacatgtaca aagacagtga a                                              21

<210> SEQ ID NO 280
<211> LENGTH: 21
<212> TYPE: DNA
<213> ORGANISM: Mouse

<400> SEQUENCE: 280
caggcctgac atcttctgca a                                              21

<210> SEQ ID NO 281
<211> LENGTH: 21
<212> TYPE: DNA
<213> ORGANISM: Mouse

<400> SEQUENCE: 281
ttcgaggata tgactgatat t                                              21

<210> SEQ ID NO 282
<211> LENGTH: 21
<212> TYPE: DNA
<213> ORGANISM: Mouse

<400> SEQUENCE: 282
ctgtatttcc ataacagaat a                                              21

<210> SEQ ID NO 283
<211> LENGTH: 21
<212> TYPE: DNA
<213> ORGANISM: Mouse

<400> SEQUENCE: 283
gaggatatga ctgatattga t                                              21

<210> SEQ ID NO 284
<211> LENGTH: 21
<212> TYPE: DNA
<213> ORGANISM: Mouse

<400> SEQUENCE: 284
caagttctct tcgttgacaa a                                              21

<210> SEQ ID NO 285
<211> LENGTH: 21
<212> TYPE: DNA
<213> ORGANISM: Mouse

<400> SEQUENCE: 285
cactaactta catcaaagtt a                                              21

<210> SEQ ID NO 286
<211> LENGTH: 21
<212> TYPE: DNA
<213> ORGANISM: Mouse
```

```
<400> SEQUENCE: 286
accgcagtaa tacggaatat a                                              21

<210> SEQ ID NO 287
<211> LENGTH: 21
<212> TYPE: DNA
<213> ORGANISM: Mouse

<400> SEQUENCE: 287
ctctcactaa cttacatcaa a                                              21

<210> SEQ ID NO 288
<211> LENGTH: 21
<212> TYPE: DNA
<213> ORGANISM: Homo sapiens

<400> SEQUENCE: 288
atcatctttc acacaaagaa a                                              21

<210> SEQ ID NO 289
<211> LENGTH: 21
<212> TYPE: DNA
<213> ORGANISM: Homo sapiens

<400> SEQUENCE: 289
aacagacttg ggtgaaatat a                                              21

<210> SEQ ID NO 290
<211> LENGTH: 21
<212> TYPE: DNA
<213> ORGANISM: Homo sapiens

<400> SEQUENCE: 290
atggaattgg acatagccca a                                              21

<210> SEQ ID NO 291
<211> LENGTH: 21
<212> TYPE: DNA
<213> ORGANISM: Homo sapiens

<400> SEQUENCE: 291
gagggtttag tgcttatcta a                                              21

<210> SEQ ID NO 292
<211> LENGTH: 21
<212> TYPE: DNA
<213> ORGANISM: Homo sapiens

<400> SEQUENCE: 292
ctcactggac ttgtccaatt a                                              21

<210> SEQ ID NO 293
<211> LENGTH: 21
<212> TYPE: DNA
<213> ORGANISM: Homo sapiens

<400> SEQUENCE: 293
atcatagttt gctttgttta a                                              21

<210> SEQ ID NO 294
<211> LENGTH: 21
<212> TYPE: DNA
<213> ORGANISM: Homo sapiens
```

```
<400> SEQUENCE: 294
ttgtttaagc atcacattaa a                                          21

<210> SEQ ID NO 295
<211> LENGTH: 21
<212> TYPE: DNA
<213> ORGANISM: Homo sapiens

<400> SEQUENCE: 295
aagcatcaca ttaaagttaa a                                          21

<210> SEQ ID NO 296
<211> LENGTH: 21
<212> TYPE: DNA
<213> ORGANISM: Homo sapiens

<400> SEQUENCE: 296
cccaaagaac tgggtactca a                                          21

<210> SEQ ID NO 297
<211> LENGTH: 21
<212> TYPE: DNA
<213> ORGANISM: Homo sapiens

<400> SEQUENCE: 297
cacattaaag ttaaactgta t                                          21

<210> SEQ ID NO 298
<211> LENGTH: 21
<212> TYPE: DNA
<213> ORGANISM: Homo sapiens

<400> SEQUENCE: 298
cagatctgtt ctttgagcta a                                          21

<210> SEQ ID NO 299
<211> LENGTH: 21
<212> TYPE: DNA
<213> ORGANISM: Homo sapiens

<400> SEQUENCE: 299
ttggtttagt gcaaagtata a                                          21

<210> SEQ ID NO 300
<211> LENGTH: 21
<212> TYPE: DNA
<213> ORGANISM: Homo sapiens

<400> SEQUENCE: 300
cagaccgtat tcttcatcct a                                          21

<210> SEQ ID NO 301
<211> LENGTH: 21
<212> TYPE: DNA
<213> ORGANISM: Homo sapiens

<400> SEQUENCE: 301
aacattaata agacaaatat t                                          21

<210> SEQ ID NO 302
<211> LENGTH: 21
<212> TYPE: DNA
```

<213> ORGANISM: Homo sapiens

<400> SEQUENCE: 302
gaccgtattc ttcatcctaa a                                              21

<210> SEQ ID NO 303
<211> LENGTH: 21
<212> TYPE: DNA
<213> ORGANISM: Mouse

<400> SEQUENCE: 303
aagcttgtga cattaatgct a                                              21

<210> SEQ ID NO 304
<211> LENGTH: 21
<212> TYPE: DNA
<213> ORGANISM: Mouse

<400> SEQUENCE: 304
caataagcta ttgtaaagat a                                              21

<210> SEQ ID NO 305
<211> LENGTH: 21
<212> TYPE: DNA
<213> ORGANISM: Mouse

<400> SEQUENCE: 305
atcatctttc acacgaagaa a                                              21

<210> SEQ ID NO 306
<211> LENGTH: 21
<212> TYPE: DNA
<213> ORGANISM: Mouse

<400> SEQUENCE: 306
agctattgta aagatattta a                                              21

<210> SEQ ID NO 307
<211> LENGTH: 21
<212> TYPE: DNA
<213> ORGANISM: Mouse

<400> SEQUENCE: 307
cagcctaaga gtcaagaaga t                                              21

<210> SEQ ID NO 308
<211> LENGTH: 21
<212> TYPE: DNA
<213> ORGANISM: Mouse

<400> SEQUENCE: 308
cccagtggac ttgtcaatgg a                                              21

<210> SEQ ID NO 309
<211> LENGTH: 21
<212> TYPE: DNA
<213> ORGANISM: Mouse

<400> SEQUENCE: 309
atgaagttga ttcatattgc a                                              21

<210> SEQ ID NO 310
<211> LENGTH: 21

```
<212> TYPE: DNA
<213> ORGANISM: Mouse

<400> SEQUENCE: 310
aagttgattc atattgcatc a                                              21

<210> SEQ ID NO 311
<211> LENGTH: 21
<212> TYPE: DNA
<213> ORGANISM: Mouse

<400> SEQUENCE: 311
tcacattaga gttaagttgt a                                              21

<210> SEQ ID NO 312
<211> LENGTH: 21
<212> TYPE: DNA
<213> ORGANISM: Mouse

<400> SEQUENCE: 312
cacattagag ttaagttgta t                                              21

<210> SEQ ID NO 313
<211> LENGTH: 21
<212> TYPE: DNA
<213> ORGANISM: Mouse

<400> SEQUENCE: 313
tatgttattt atagatctga a                                              21

<210> SEQ ID NO 314
<211> LENGTH: 21
<212> TYPE: DNA
<213> ORGANISM: Mouse

<400> SEQUENCE: 314
atgtttagct atttaatgtt a                                              21

<210> SEQ ID NO 315
<211> LENGTH: 21
<212> TYPE: DNA
<213> ORGANISM: Mouse

<400> SEQUENCE: 315
ttagtggaag gattaatatt a                                              21

<210> SEQ ID NO 316
<211> LENGTH: 21
<212> TYPE: DNA
<213> ORGANISM: Mouse

<400> SEQUENCE: 316
acccagcact gagtacatca a                                              21

<210> SEQ ID NO 317
<211> LENGTH: 21
<212> TYPE: DNA
<213> ORGANISM: Mouse

<400> SEQUENCE: 317
tatgtttaag ggaatagttt a                                              21

<210> SEQ ID NO 318
```

```
<211> LENGTH: 21
<212> TYPE: DNA
<213> ORGANISM: Homo sapiens

<400> SEQUENCE: 318
atgaagttga ttcatattgc a                                              21

<210> SEQ ID NO 319
<211> LENGTH: 21
<212> TYPE: DNA
<213> ORGANISM: Homo sapiens

<400> SEQUENCE: 319
tgaagttgat tcatattgca t                                              21

<210> SEQ ID NO 320
<211> LENGTH: 21
<212> TYPE: DNA
<213> ORGANISM: Homo sapiens

<400> SEQUENCE: 320
gaagttgatt catattgcat c                                              21

<210> SEQ ID NO 321
<211> LENGTH: 21
<212> TYPE: DNA
<213> ORGANISM: Homo sapiens

<400> SEQUENCE: 321
aagttgattc atattgcatc a                                              21

<210> SEQ ID NO 322
<211> LENGTH: 21
<212> TYPE: DNA
<213> ORGANISM: Homo sapiens

<400> SEQUENCE: 322
agttgattca tattgcatca t                                              21

<210> SEQ ID NO 323
<211> LENGTH: 21
<212> TYPE: DNA
<213> ORGANISM: Homo sapiens

<400> SEQUENCE: 323
gttgattcat attgcatcat a                                              21

<210> SEQ ID NO 324
<211> LENGTH: 21
<212> TYPE: DNA
<213> ORGANISM: Homo sapiens

<400> SEQUENCE: 324
ttgattcata ttgcatcata g                                              21

<210> SEQ ID NO 325
<211> LENGTH: 21
<212> TYPE: DNA
<213> ORGANISM: Homo sapiens

<400> SEQUENCE: 325
tgattcatat tgcatcatag t                                              21
```

```
<210> SEQ ID NO 326
<211> LENGTH: 21
<212> TYPE: DNA
<213> ORGANISM: Homo sapiens

<400> SEQUENCE: 326
tcaatgctat catctttcac a                                              21

<210> SEQ ID NO 327
<211> LENGTH: 21
<212> TYPE: DNA
<213> ORGANISM: Homo sapiens

<400> SEQUENCE: 327
caatgctatc atctttcaca c                                              21

<210> SEQ ID NO 328
<211> LENGTH: 21
<212> TYPE: DNA
<213> ORGANISM: Homo sapiens

<400> SEQUENCE: 328
taatgaagtt gattcatatt g                                              21

<210> SEQ ID NO 329
<211> LENGTH: 21
<212> TYPE: DNA
<213> ORGANISM: Homo sapiens

<400> SEQUENCE: 329
aatgaagttg attcatattg c                                              21

<210> SEQ ID NO 330
<211> LENGTH: 21
<212> TYPE: DNA
<213> ORGANISM: Homo sapiens

<400> SEQUENCE: 330
agcatgaaat ttgagattgg a                                              21

<210> SEQ ID NO 331
<211> LENGTH: 21
<212> TYPE: DNA
<213> ORGANISM: Homo sapiens

<400> SEQUENCE: 331
tacagagcct ctgaaagacc a                                              21

<210> SEQ ID NO 332
<211> LENGTH: 21
<212> TYPE: DNA
<213> ORGANISM: Homo sapiens

<400> SEQUENCE: 332
cactacagag cctctgaaag a                                              21

<210> SEQ ID NO 333
<211> LENGTH: 21
<212> TYPE: DNA
<213> ORGANISM: Homo sapiens

<400> SEQUENCE: 333
ctgacagcat gaaatttgag a                                              21
```

<210> SEQ ID NO 334
<211> LENGTH: 21
<212> TYPE: DNA
<213> ORGANISM: Homo sapiens

<400> SEQUENCE: 334
atctctgtgg tgggcatgag a				21

<210> SEQ ID NO 335
<211> LENGTH: 21
<212> TYPE: DNA
<213> ORGANISM: Homo sapiens

<400> SEQUENCE: 335
catgaaattt gagattggag a				21

<210> SEQ ID NO 336
<211> LENGTH: 21
<212> TYPE: DNA
<213> ORGANISM: Homo sapiens

<400> SEQUENCE: 336
tctggctgag gttggctctt a				21

<210> SEQ ID NO 337
<211> LENGTH: 21
<212> TYPE: DNA
<213> ORGANISM: Homo sapiens

<400> SEQUENCE: 337
gtgggctaca tcctaggcct t				21

<210> SEQ ID NO 338
<211> LENGTH: 21
<212> TYPE: DNA
<213> ORGANISM: Mouse

<400> SEQUENCE: 338
cagcttcctg ctaaaccaca a				21

<210> SEQ ID NO 339
<211> LENGTH: 21
<212> TYPE: DNA
<213> ORGANISM: Mouse

<400> SEQUENCE: 339
caagagtgag ttcaactcat a				21

<210> SEQ ID NO 340
<211> LENGTH: 21
<212> TYPE: DNA
<213> ORGANISM: Mouse

<400> SEQUENCE: 340
ctggttcctg acagcatgaa a				21

<210> SEQ ID NO 341
<211> LENGTH: 21
<212> TYPE: DNA
<213> ORGANISM: Mouse

<400> SEQUENCE: 341
tggctgggac tatatatata a				21

<210> SEQ ID NO 342
<211> LENGTH: 21
<212> TYPE: DNA
<213> ORGANISM: Mouse

<400> SEQUENCE: 342
gagggcaatt gctatatctt a                                              21

<210> SEQ ID NO 343
<211> LENGTH: 21
<212> TYPE: DNA
<213> ORGANISM: Mouse

<400> SEQUENCE: 343
cagcagccaa acgacaagca a                                              21

<210> SEQ ID NO 344
<211> LENGTH: 21
<212> TYPE: DNA
<213> ORGANISM: Mouse

<400> SEQUENCE: 344
caagggtttc cttaaggaca a                                              21

<210> SEQ ID NO 345
<211> LENGTH: 21
<212> TYPE: DNA
<213> ORGANISM: Mouse

<400> SEQUENCE: 345
cagatacttg taaggaggaa a                                              21

<210> SEQ ID NO 346
<211> LENGTH: 21
<212> TYPE: DNA
<213> ORGANISM: Mouse

<400> SEQUENCE: 346
aagaaatgga ttagtcagta a                                              21

<210> SEQ ID NO 347
<211> LENGTH: 21
<212> TYPE: DNA
<213> ORGANISM: Mouse

<400> SEQUENCE: 347
aaggaaagca caagaagcca a                                              21

<210> SEQ ID NO 348
<211> LENGTH: 21
<212> TYPE: DNA
<213> ORGANISM: Mouse

<400> SEQUENCE: 348
ctggctgagg ttggctctta a                                              21

<210> SEQ ID NO 349
<211> LENGTH: 21
<212> TYPE: DNA
<213> ORGANISM: Mouse

<400> SEQUENCE: 349

```
aacctgggat ctaaagaaac a                                              21

<210> SEQ ID NO 350
<211> LENGTH: 21
<212> TYPE: DNA
<213> ORGANISM: Mouse

<400> SEQUENCE: 350
aagggcttgg gtatcaaaga a                                              21

<210> SEQ ID NO 351
<211> LENGTH: 21
<212> TYPE: DNA
<213> ORGANISM: Mouse

<400> SEQUENCE: 351
caggctccga agatacttct a                                              21

<210> SEQ ID NO 352
<211> LENGTH: 21
<212> TYPE: DNA
<213> ORGANISM: Mouse

<400> SEQUENCE: 352
cccaatatat aaattgccta a                                              21

<210> SEQ ID NO 353
<211> LENGTH: 21
<212> TYPE: DNA
<213> ORGANISM: Mouse

<400> SEQUENCE: 353
ctgacccagc ttcctgctaa a                                              21

<210> SEQ ID NO 354
<211> LENGTH: 21
<212> TYPE: DNA
<213> ORGANISM: Homo sapiens

<400> SEQUENCE: 354
acccacatca tctacagctt t                                              21

<210> SEQ ID NO 355
<211> LENGTH: 21
<212> TYPE: DNA
<213> ORGANISM: Homo sapiens

<400> SEQUENCE: 355
catcatctac agctttgcca a                                              21

<210> SEQ ID NO 356
<211> LENGTH: 21
<212> TYPE: DNA
<213> ORGANISM: Homo sapiens

<400> SEQUENCE: 356
cagctggtcc cagtaccggg a                                              21

<210> SEQ ID NO 357
<211> LENGTH: 21
<212> TYPE: DNA
<213> ORGANISM: Homo sapiens

<400> SEQUENCE: 357
```

-continued

| | |
|---|---|
| caccaaggag gcagggaccc t | 21 |

<210> SEQ ID NO 358
<211> LENGTH: 21
<212> TYPE: DNA
<213> ORGANISM: Homo sapiens

<400> SEQUENCE: 358

| | |
|---|---|
| ccggttcacc aaggaggcag g | 21 |

<210> SEQ ID NO 359
<211> LENGTH: 21
<212> TYPE: DNA
<213> ORGANISM: Homo sapiens

<400> SEQUENCE: 359

| | |
|---|---|
| agctggtccc agtaccggga a | 21 |

<210> SEQ ID NO 360
<211> LENGTH: 21
<212> TYPE: DNA
<213> ORGANISM: Homo sapiens

<400> SEQUENCE: 360

| | |
|---|---|
| caggccggtt caccaaggag g | 21 |

<210> SEQ ID NO 361
<211> LENGTH: 21
<212> TYPE: DNA
<213> ORGANISM: Homo sapiens

<400> SEQUENCE: 361

| | |
|---|---|
| ggccggttca ccaaggaggc a | 21 |

<210> SEQ ID NO 362
<211> LENGTH: 21
<212> TYPE: DNA
<213> ORGANISM: Mouse

<400> SEQUENCE: 362

| | |
|---|---|
| taggtttgac agatacagca a | 21 |

<210> SEQ ID NO 363
<211> LENGTH: 21
<212> TYPE: DNA
<213> ORGANISM: Mouse

<400> SEQUENCE: 363

| | |
|---|---|
| aaccctgtta aggaatgcaa a | 21 |

<210> SEQ ID NO 364
<211> LENGTH: 21
<212> TYPE: DNA
<213> ORGANISM: Mouse

<400> SEQUENCE: 364

| | |
|---|---|
| atcaagtagg caaatatctt a | 21 |

<210> SEQ ID NO 365
<211> LENGTH: 21
<212> TYPE: DNA
<213> ORGANISM: Mouse

```
<400> SEQUENCE: 365
cgcagctttg tcagcaggaa a                                              21

<210> SEQ ID NO 366
<211> LENGTH: 21
<212> TYPE: DNA
<213> ORGANISM: Mouse

<400> SEQUENCE: 366
ttggatcaag taggcaaata t                                              21

<210> SEQ ID NO 367
<211> LENGTH: 21
<212> TYPE: DNA
<213> ORGANISM: Mouse

<400> SEQUENCE: 367
ttgagggacc atactaatta t                                              21

<210> SEQ ID NO 368
<211> LENGTH: 21
<212> TYPE: DNA
<213> ORGANISM: Mouse

<400> SEQUENCE: 368
gaggacaagg agagtgtcaa a                                              21

<210> SEQ ID NO 369
<211> LENGTH: 21
<212> TYPE: DNA
<213> ORGANISM: Mouse

<400> SEQUENCE: 369
tgcgtacaag ctggtctgct a                                              21

<210> SEQ ID NO 370
<211> LENGTH: 21
<212> TYPE: DNA
<213> ORGANISM: Mouse

<400> SEQUENCE: 370
caggagttta atctcttgca a                                              21

<210> SEQ ID NO 371
<211> LENGTH: 21
<212> TYPE: DNA
<213> ORGANISM: Mouse

<400> SEQUENCE: 371
atcaaggaac tgaatgcgga a                                              21

<210> SEQ ID NO 372
<211> LENGTH: 21
<212> TYPE: DNA
<213> ORGANISM: Mouse

<400> SEQUENCE: 372
caccctgatc aaggaactga a                                              21

<210> SEQ ID NO 373
<211> LENGTH: 21
<212> TYPE: DNA
<213> ORGANISM: Mouse
```

```
<400> SEQUENCE: 373
cacttggatc aagtaggcaa a                                              21

<210> SEQ ID NO 374
<211> LENGTH: 21
<212> TYPE: DNA
<213> ORGANISM: Mouse

<400> SEQUENCE: 374
caggattgag ggaccatact a                                              21

<210> SEQ ID NO 375
<211> LENGTH: 21
<212> TYPE: DNA
<213> ORGANISM: Mouse

<400> SEQUENCE: 375
aactatgaca agctgaataa a                                              21

<210> SEQ ID NO 376
<211> LENGTH: 21
<212> TYPE: DNA
<213> ORGANISM: Mouse

<400> SEQUENCE: 376
atgcaaattc tcagactcta a                                              21

<210> SEQ ID NO 377
<211> LENGTH: 21
<212> TYPE: DNA
<213> ORGANISM: Mouse

<400> SEQUENCE: 377
atccttccct taggaactta a                                              21

<210> SEQ ID NO 378
<211> LENGTH: 79
<212> TYPE: DNA
<213> ORGANISM: Escherichia coli

<400> SEQUENCE: 378
gacttcatat acccaagctt ggaaaatttt ttttaaaaaa gtcttgacac tttatgcttc    60
cggctcgtat aatggatcc                                                 79

<210> SEQ ID NO 379
<211> LENGTH: 23
<212> TYPE: DNA
<213> ORGANISM: Escherichia coli

<400> SEQUENCE: 379
ggaaaatttt ttttaaaaaa gtc                                            23

<210> SEQ ID NO 380
<211> LENGTH: 65
<212> TYPE: DNA
<213> ORGANISM: Artificial Sequence
<220> FEATURE:
<223> OTHER INFORMATION: Hairpin sequence which contains BamHI and SalI
      restriction sites.

<400> SEQUENCE: 380
ggatccagga gtaacaatac aaatggattc aagagatcca tttgtattgt tactcctttg    60
```

-continued

```
tcgac                                                              65

<210> SEQ ID NO 381
<211> LENGTH: 21
<212> TYPE: DNA
<213> ORGANISM: Human papillomavirus

<400> SEQUENCE: 381
ctgatctgtg cacggaactg a                                            21

<210> SEQ ID NO 382
<211> LENGTH: 25
<212> TYPE: DNA
<213> ORGANISM: Human papillomavirus

<400> SEQUENCE: 382
tgtctaagtt tttctgctgg attca                                        25

<210> SEQ ID NO 383
<211> LENGTH: 25
<212> TYPE: DNA
<213> ORGANISM: Human papillomavirus

<400> SEQUENCE: 383
ttggaactta cagaggtgcc tgcgc                                        25

<210> SEQ ID NO 384
<211> LENGTH: 61
<212> TYPE: DNA
<213> ORGANISM: Artificial Sequence
<220> FEATURE:
<223> OTHER INFORMATION: HPV shRNA

<400> SEQUENCE: 384
ggatcctagg tatttgaatt tgcatttcaa gagaatgcaa attcaaatac cttttgtcga  60
c                                                                  61

<210> SEQ ID NO 385
<211> LENGTH: 61
<212> TYPE: DNA
<213> ORGANISM: Artificial Sequence
<220> FEATURE:
<223> OTHER INFORMATION: HPV shRNA

<400> SEQUENCE: 385
gtcgacaaaa ggtatttgaa tttgcattct cttgaaatgc aaattcaaat acctaggatc  60
c                                                                  61

<210> SEQ ID NO 386
<211> LENGTH: 61
<212> TYPE: DNA
<213> ORGANISM: Artificial Sequence
<220> FEATURE:
<223> OTHER INFORMATION: HPV shRNA

<400> SEQUENCE: 386
ggatcctcag aaaaacttag acaccttcaa gagaggtgtc taagttttc tgtttgtcga   60 c                                                                  61

<210> SEQ ID NO 387
<211> LENGTH: 61
<212> TYPE: DNA
```

```
<213> ORGANISM: Artificial Sequence
<220> FEATURE:
<223> OTHER INFORMATION: HPV shRNA

<400> SEQUENCE: 387
gtcgacaaac agaaaaactt agacacctct cttgaaggtg tctaagtttt tctgaggatc    60
c                                                                    61

<210> SEQ ID NO 388
<211> LENGTH: 9
<212> TYPE: DNA
<213> ORGANISM: Artificial Sequence
<220> FEATURE:
<223> OTHER INFORMATION: Loop Sequence

<400> SEQUENCE: 388 ttcaagaga                                                             9

<210> SEQ ID NO 389
<211> LENGTH: 55
<212> TYPE: DNA
<213> ORGANISM: Artificial Sequence
<220> FEATURE:
<223> OTHER INFORMATION: HPV shRNA

<400> SEQUENCE: 389
gatcctaggt atttgaattt gcatttcaag agaatgcaaa ttcaaatacc ttttg         55

<210> SEQ ID NO 390
<211> LENGTH: 55
<212> TYPE: DNA
<213> ORGANISM: Artificial Sequence
<220> FEATURE:
<223> OTHER INFORMATION: HPV shRNA, sequence written in 3' to 5'
      orientation

<400> SEQUENCE: 390
gatccataaa cttaaacgta agttctctct acgtttaagt ttatggaaaa cagct         55

<210> SEQ ID NO 391
<211> LENGTH: 21
<212> TYPE: DNA
<213> ORGANISM: Artificial Sequence
<220> FEATURE:
<223> OTHER INFORMATION: siRNA sense strand

<400> SEQUENCE: 391
gcuugugaca uuaaugcuat t                                              21

<210> SEQ ID NO 392
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 392
uagcauuaau gucacaagct t                                              21

<210> SEQ ID NO 393
<211> LENGTH: 21
<212> TYPE: DNA
<213> ORGANISM: Artificial Sequence
<220> FEATURE:
<223> OTHER INFORMATION: siRNA sense strand
```

```
<400> SEQUENCE: 393
auaagcuauu guaaagauat t                                              21

<210> SEQ ID NO 394
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 394
uaucuuuaca auagcuuaut g                                              21

<210> SEQ ID NO 395
<211> LENGTH: 21
<212> TYPE: DNA
<213> ORGANISM: Artificial Sequence
<220> FEATURE:
<223> OTHER INFORMATION: siRNA sense strand

<400> SEQUENCE: 395
caucuuucac acgaagaaat t                                              21

<210> SEQ ID NO 396
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 396
uuucuucgug ugaaagauga t                                              21

<210> SEQ ID NO 397
<211> LENGTH: 21
<212> TYPE: DNA
<213> ORGANISM: Artificial Sequence
<220> FEATURE:
<223> OTHER INFORMATION: siRNA sense strand

<400> SEQUENCE: 397
cuauuguaaa gauauuuaat t                                              21

<210> SEQ ID NO 398
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 398
uuaaauaucu uuacaauagc t                                              21

<210> SEQ ID NO 399
<211> LENGTH: 21
<212> TYPE: DNA
<213> ORGANISM: Artificial Sequence
<220> FEATURE:
<223> OTHER INFORMATION: siRNA sense strand

<400> SEQUENCE: 399
gccuaagagu caagaagaut t                                              21

<210> SEQ ID NO 400
<211> LENGTH: 21
```

```
<212> TYPE: DNA
<213> ORGANISM: Artificial Sequence
<220> FEATURE:
<223> OTHER INFORMATION: siRNA antisense strand

<400> SEQUENCE: 400
aucuucuuga cucuuaggct g                                              21

<210> SEQ ID NO 401
<211> LENGTH: 21
<212> TYPE: DNA
<213> ORGANISM: Artificial Sequence
<220> FEATURE:
<223> OTHER INFORMATION: siRNA sense strand

<400> SEQUENCE: 401
caguggacuu gucaauggat t                                              21

<210> SEQ ID NO 402
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 402
uccauugaca aguccacugg g                                              21

<210> SEQ ID NO 403
<211> LENGTH: 21
<212> TYPE: DNA
<213> ORGANISM: Artificial Sequence
<220> FEATURE:
<223> OTHER INFORMATION: siRNA sense strand

<400> SEQUENCE: 403
gaaguugauu cauauugcat t                                              21

<210> SEQ ID NO 404
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 404
ugcaauauga aucaacuuca t                                              21

<210> SEQ ID NO 405
<211> LENGTH: 21
<212> TYPE: DNA
<213> ORGANISM: Artificial Sequence
<220> FEATURE:
<223> OTHER INFORMATION: siRNA sense strand

<400> SEQUENCE: 405
guugauucau auugcaucat t                                              21

<210> SEQ ID NO 406
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 406
```
ugaugcaaua ugaaucaact t    21

<210> SEQ ID NO 407
<211> LENGTH: 21
<212> TYPE: DNA
<213> ORGANISM: Artificial Sequence
<220> FEATURE:
<223> OTHER INFORMATION: siRNA sense strand

<400> SEQUENCE: 407
acauuagagu uaaguuguau t    21

<210> SEQ ID NO 408
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 408
uacaacuuaa cucuaaugug a    21

<210> SEQ ID NO 409
<211> LENGTH: 21
<212> TYPE: DNA
<213> ORGANISM: Artificial Sequence
<220> FEATURE:
<223> OTHER INFORMATION: siRNA sense strand

<400> SEQUENCE: 409
cauuagaguu aaguuguaut t    21

<210> SEQ ID NO 410
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 410
auacaacuua acucuaaugt g    21

<210> SEQ ID NO 411
<211> LENGTH: 21
<212> TYPE: DNA
<213> ORGANISM: Artificial Sequence
<220> FEATURE:
<223> OTHER INFORMATION: siRNA sense strand

<400> SEQUENCE: 411
uguuauuuau agaucugaat t    21

<210> SEQ ID NO 412
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 412
uucagaucua uaaauaacat a    21

<210> SEQ ID NO 413
<211> LENGTH: 21
<212> TYPE: DNA
<213> ORGANISM: Artificial Sequence

```
<220> FEATURE:
<223> OTHER INFORMATION: siRNA sense strand

<400> SEQUENCE: 413
guuuagcuau uuaauguuat t                                              21

<210> SEQ ID NO 414
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 414
uaacauuaaa uagcuaaaca t                                              21

<210> SEQ ID NO 415
<211> LENGTH: 21
<212> TYPE: DNA
<213> ORGANISM: Artificial Sequence
<220> FEATURE:
<223> OTHER INFORMATION: siRNA sense strand

<400> SEQUENCE: 415
aguggaagga uuaauauuat t                                              21

<210> SEQ ID NO 416
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 416
uaauauuaau ccuuccacua a                                              21

<210> SEQ ID NO 417
<211> LENGTH: 21
<212> TYPE: DNA
<213> ORGANISM: Artificial Sequence
<220> FEATURE:
<223> OTHER INFORMATION: siRNA sense strand

<400> SEQUENCE: 417
ccagcacuga guacaucaat t                                              21

<210> SEQ ID NO 418
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 418
uugauguacu cagugcuggg t                                              21

<210> SEQ ID NO 419
<211> LENGTH: 21
<212> TYPE: DNA
<213> ORGANISM: Artificial Sequence
<220> FEATURE:
<223> OTHER INFORMATION: siRNA sense strand

<400> SEQUENCE: 419
uguuuaaggg aauaguuuat t                                              21
```

```
<210> SEQ ID NO 420
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 420
uaaacuauuc ccuuaaacat a                                              21

<210> SEQ ID NO 421
<211> LENGTH: 21
<212> TYPE: DNA
<213> ORGANISM: Artificial Sequence
<220> FEATURE:
<223> OTHER INFORMATION: siRNA sense strand

<400> SEQUENCE: 421
gcugggacua uauauauaat t                                              21

<210> SEQ ID NO 422
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 422
uuauauauau agucccagcc a                                              21

<210> SEQ ID NO 423
<211> LENGTH: 21
<212> TYPE: DNA
<213> ORGANISM: Artificial Sequence
<220> FEATURE:
<223> OTHER INFORMATION: siRNA sense strand

<400> SEQUENCE: 423
gggcaauugc uauaucuuat t                                              21

<210> SEQ ID NO 424
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 424
uaagauauag caauugcccu c                                              21

<210> SEQ ID NO 425
<211> LENGTH: 21
<212> TYPE: DNA
<213> ORGANISM: Artificial Sequence
<220> FEATURE:
<223> OTHER INFORMATION: siRNA sense strand

<400> SEQUENCE: 425
gcagccaaac gacaagcaat t                                              21

<210> SEQ ID NO 426
<211> LENGTH: 21
<212> TYPE: DNA
<213> ORGANISM: Artificial Sequence
<220> FEATURE:
<223> OTHER INFORMATION: siRNA antisense strand
```

-continued

<210> SEQ ID NO 427
<211> LENGTH: 21
<212> TYPE: DNA
<213> ORGANISM: Artificial Sequence
<220> FEATURE:
<223> OTHER INFORMATION: siRNA sense strand

<400> SEQUENCE: 426
uugcuugucg uuuggcugct g                                              21

<210> SEQ ID NO 427
<211> LENGTH: 21
<212> TYPE: DNA
<213> ORGANISM: Artificial Sequence
<220> FEATURE:
<223> OTHER INFORMATION: siRNA sense strand

<400> SEQUENCE: 427 agg guuuccu uaaggacaat t                                             21

<210> SEQ ID NO 428
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 428
uuguccuuaa ggaaacccut g                                              21

<210> SEQ ID NO 429
<211> LENGTH: 21
<212> TYPE: DNA
<213> ORGANISM: Artificial Sequence
<220> FEATURE:
<223> OTHER INFORMATION: siRNA sense strand

<400> SEQUENCE: 429
gaaauggauu agucaguaat t                                              21

<210> SEQ ID NO 430
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 430
uuacugacua auccauuuct t                                              21

<210> SEQ ID NO 431
<211> LENGTH: 21
<212> TYPE: DNA
<213> ORGANISM: Artificial Sequence
<220> FEATURE:
<223> OTHER INFORMATION: siRNA sense strand

<400> SEQUENCE: 431
ggcuccgaag auacuucuat t                                              21

<210> SEQ ID NO 432
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 432
uagaaguauc uucggagcct g                                              21

<210> SEQ ID NO 433

```
<211> LENGTH: 21
<212> TYPE: DNA
<213> ORGANISM: Artificial Sequence
<220> FEATURE:
<223> OTHER INFORMATION: siRNA sense strand

<400> SEQUENCE: 433
ccuggagggu gacaaaguat t                                            21

<210> SEQ ID NO 434
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 434
uacuuuguca cccuccagga t                                            21

<210> SEQ ID NO 435
<211> LENGTH: 21
<212> TYPE: DNA
<213> ORGANISM: Artificial Sequence
<220> FEATURE:
<223> OTHER INFORMATION: siRNA sense strand

<400> SEQUENCE: 435
ggucugacaa uaccguaaat t                                            21

<210> SEQ ID NO 436
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 436
uuuacgguau ugucagaccc a                                            21

<210> SEQ ID NO 437
<211> LENGTH: 21
<212> TYPE: DNA
<213> ORGANISM: Artificial Sequence
<220> FEATURE:
<223> OTHER INFORMATION: siRNA sense strand

<400> SEQUENCE: 437
gcuguuuccu auaacagaat t                                            21

<210> SEQ ID NO 438
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 438
uucuguuaua ggaaacagcg g                                            21

<210> SEQ ID NO 439
<211> LENGTH: 21
<212> TYPE: DNA
<213> ORGANISM: Artificial Sequence
<220> FEATURE:
<223> OTHER INFORMATION: siRNA sense strand

<400> SEQUENCE: 439
```
gcugugaaag ggaaauuuat t                                    21

<210> SEQ ID NO 440
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 440
uaaauuuccc uuucacagca g                                    21

<210> SEQ ID NO 441
<211> LENGTH: 21
<212> TYPE: DNA
<213> ORGANISM: Artificial Sequence
<220> FEATURE:
<223> OTHER INFORMATION: siRNA sense strand

<400> SEQUENCE: 441
ccuuguggua ucagccauat t                                    21

<210> SEQ ID NO 442
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 442
uauggcugau accacaaggt t                                    21

<210> SEQ ID NO 443
<211> LENGTH: 21
<212> TYPE: DNA
<213> ORGANISM: Artificial Sequence
<220> FEATURE:
<223> OTHER INFORMATION: siRNA sense strand

<400> SEQUENCE: 443
gcuucgauac cgaccuguat t                                    21

<210> SEQ ID NO 444
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 444
uacaggucgg uaucgaagct g                                    21

<210> SEQ ID NO 445
<211> LENGTH: 21
<212> TYPE: DNA
<213> ORGANISM: Artificial Sequence
<220> FEATURE:
<223> OTHER INFORMATION: siRNA sense strand

<400> SEQUENCE: 445
cggcaggaau ccucuggaat t                                    21

<210> SEQ ID NO 446
<211> LENGTH: 21
<212> TYPE: DNA

```
<213> ORGANISM: Artificial Sequence
<220> FEATURE:
<223> OTHER INFORMATION: siRNA antisense strand

<400> SEQUENCE: 446
uuccagagga uuccugccgg g                                              21

<210> SEQ ID NO 447
<211> LENGTH: 21
<212> TYPE: DNA
<213> ORGANISM: Artificial Sequence
<220> FEATURE:
<223> OTHER INFORMATION: siRNA sense strand

<400> SEQUENCE: 447
ccacgaggau caguacgaat t                                              21

<210> SEQ ID NO 448
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 448
uucguacuga uccucguggt t                                              21

<210> SEQ ID NO 449
<211> LENGTH: 21
<212> TYPE: DNA
<213> ORGANISM: Artificial Sequence
<220> FEATURE:
<223> OTHER INFORMATION: siRNA sense strand

<400> SEQUENCE: 449
cacgaggauc aguacgaaat t                                              21

<210> SEQ ID NO 450
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 450
uuucguacug auccucgugg t                                              21

<210> SEQ ID NO 451
<211> LENGTH: 21
<212> TYPE: DNA
<213> ORGANISM: Artificial Sequence
<220> FEATURE:
<223> OTHER INFORMATION: siRNA sense strand

<400> SEQUENCE: 451
gaucaguacg aaaguucuat t                                              21

<210> SEQ ID NO 452
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 452
uagaacuuuc guacugaucc t                                              21
```

<210> SEQ ID NO 453
<211> LENGTH: 21
<212> TYPE: DNA
<213> ORGANISM: Artificial Sequence
<220> FEATURE:
<223> OTHER INFORMATION: siRNA sense strand

<400> SEQUENCE: 453
guacgaaagu ucuacagaat t                                         21

<210> SEQ ID NO 454
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 454
uucuguagaa cuuucguact g                                         21

<210> SEQ ID NO 455
<211> LENGTH: 21
<212> TYPE: DNA
<213> ORGANISM: Artificial Sequence
<220> FEATURE:
<223> OTHER INFORMATION: siRNA sense strand

<400> SEQUENCE: 455
gaaaguucua cagaagcaat t                                         21

<210> SEQ ID NO 456
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 456
uugcuucugu agaacuuucg t                                         21

<210> SEQ ID NO 457
<211> LENGTH: 21
<212> TYPE: DNA
<213> ORGANISM: Artificial Sequence
<220> FEATURE:
<223> OTHER INFORMATION: siRNA sense strand

<400> SEQUENCE: 457
gggucugaca auaccguaat t                                         21

<210> SEQ ID NO 458
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 458
uuacgguauu gucagaccca g                                         21

<210> SEQ ID NO 459
<211> LENGTH: 21
<212> TYPE: DNA
<213> ORGANISM: Artificial Sequence
<220> FEATURE:

<223> OTHER INFORMATION: siRNA sense strand

<400> SEQUENCE: 459
agaagacucu aaugauguat t                          21

<210> SEQ ID NO 460
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 460
uacaucauua gagucuucut g                          21

<210> SEQ ID NO 461
<211> LENGTH: 21
<212> TYPE: DNA
<213> ORGANISM: Artificial Sequence
<220> FEATURE:
<223> OTHER INFORMATION: siRNA sense strand

<400> SEQUENCE: 461
cagucagagu aagagucaat t                          21

<210> SEQ ID NO 462
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 462
uugacucuua cucugacugt g                          21

<210> SEQ ID NO 463
<211> LENGTH: 21
<212> TYPE: DNA
<213> ORGANISM: Artificial Sequence
<220> FEATURE:
<223> OTHER INFORMATION: siRNA sense strand

<400> SEQUENCE: 463
cagaacaucu agcaaacaat t                          21

<210> SEQ ID NO 464
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 464
uuguuugcua gauguucugt g                          21

<210> SEQ ID NO 465
<211> LENGTH: 21
<212> TYPE: DNA
<213> ORGANISM: Artificial Sequence
<220> FEATURE:
<223> OTHER INFORMATION: siRNA sense strand

<400> SEQUENCE: 465
cuuguagguu cacauauuat t                          21

```
<210> SEQ ID NO 466
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 466
uaauauguga accuacaagt t                                             21

<210> SEQ ID NO 467
<211> LENGTH: 21
<212> TYPE: DNA
<213> ORGANISM: Artificial Sequence
<220> FEATURE:
<223> OTHER INFORMATION: siRNA sense strand

<400> SEQUENCE: 467
caguguagug ccaaugaaat t                                             21

<210> SEQ ID NO 468
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 468
uuucauuggc acuacacuga g                                             21

<210> SEQ ID NO 469
<211> LENGTH: 21
<212> TYPE: DNA
<213> ORGANISM: Artificial Sequence
<220> FEATURE:
<223> OTHER INFORMATION: siRNA sense strand

<400> SEQUENCE: 469
guaugacauc uaugagaaat t                                             21

<210> SEQ ID NO 470
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 470
uuucucauag augucauact t                                             21

<210> SEQ ID NO 471
<211> LENGTH: 21
<212> TYPE: DNA
<213> ORGANISM: Artificial Sequence
<220> FEATURE:
<223> OTHER INFORMATION: siRNA sense strand

<400> SEQUENCE: 471
aggaaaugau guuuauugat t                                             21

<210> SEQ ID NO 472
<211> LENGTH: 21
<212> TYPE: DNA
<213> ORGANISM: Artificial Sequence
<220> FEATURE:
<223> OTHER INFORMATION: siRNA antisense strand
```

```
<400> SEQUENCE: 472
ucaauaaaca ucauuccut g                                               21

<210> SEQ ID NO 473
<211> LENGTH: 21
<212> TYPE: DNA
<213> ORGANISM: Artificial Sequence
<220> FEATURE:
<223> OTHER INFORMATION: siRNA sense strand

<400> SEQUENCE: 473
ggccgacuuc acuguacaat t                                              21

<210> SEQ ID NO 474
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 474
uuguacagug aagucggcca a                                              21

<210> SEQ ID NO 475
<211> LENGTH: 21
<212> TYPE: DNA
<213> ORGANISM: Artificial Sequence
<220> FEATURE:
<223> OTHER INFORMATION: siRNA sense strand

<400> SEQUENCE: 475
gauggaguuu gaaucuucat t                                              21

<210> SEQ ID NO 476
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 476
ugaagauuca aacuccauct t                                              21

<210> SEQ ID NO 477
<211> LENGTH: 21
<212> TYPE: DNA
<213> ORGANISM: Artificial Sequence
<220> FEATURE:
<223> OTHER INFORMATION: siRNA sense strand

<400> SEQUENCE: 477
caaccgcagu aauacggaat t                                              21

<210> SEQ ID NO 478
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 478
uuccguauua cugcgguugt a                                              21

<210> SEQ ID NO 479
<211> LENGTH: 21
```

```
<212> TYPE: DNA
<213> ORGANISM: Artificial Sequence
<220> FEATURE:
<223> OTHER INFORMATION: siRNA sense strand

<400> SEQUENCE: 479
cgaggcugca ugauuuauat t                                               21

<210> SEQ ID NO 480
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 480
uauaaaucau gcagccucgg g                                               21

<210> SEQ ID NO 481
<211> LENGTH: 21
<212> TYPE: DNA
<213> ORGANISM: Artificial Sequence
<220> FEATURE:
<223> OTHER INFORMATION: siRNA sense strand

<400> SEQUENCE: 481
ccuguauuuc cauaacagat t                                               21

<210> SEQ ID NO 482
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 482
ucuguuaugg aaauacaggc g                                               21

<210> SEQ ID NO 483
<211> LENGTH: 21
<212> TYPE: DNA
<213> ORGANISM: Artificial Sequence
<220> FEATURE:
<223> OTHER INFORMATION: siRNA sense strand

<400> SEQUENCE: 483
cauguacaaa gacagugaat t                                               21

<210> SEQ ID NO 484
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 484
uucacugucu uuguacaugt a                                               21

<210> SEQ ID NO 485
<211> LENGTH: 21
<212> TYPE: DNA
<213> ORGANISM: Artificial Sequence
<220> FEATURE:
<223> OTHER INFORMATION: siRNA sense strand

<400> SEQUENCE: 485
```
cgaggauaug acugauauut t                                              21

<210> SEQ ID NO 486
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 486
aauaucaguc auauccucga a                                              21

<210> SEQ ID NO 487
<211> LENGTH: 21
<212> TYPE: DNA
<213> ORGANISM: Artificial Sequence
<220> FEATURE:
<223> OTHER INFORMATION: siRNA sense strand

<400> SEQUENCE: 487
ggauaugacu gauauugaut t                                              21

<210> SEQ ID NO 488
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 488
aucaauauca gucauaucct c                                              21

<210> SEQ ID NO 489
<211> LENGTH: 21
<212> TYPE: DNA
<213> ORGANISM: Artificial Sequence
<220> FEATURE:
<223> OTHER INFORMATION: siRNA sense strand

<400> SEQUENCE: 489
cuaacuuaca ucaaguuat t                                               21

<210> SEQ ID NO 490
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 490
uaacuuugau guaaguuagt g                                              21

<210> SEQ ID NO 491
<211> LENGTH: 21
<212> TYPE: DNA
<213> ORGANISM: Artificial Sequence
<220> FEATURE:
<223> OTHER INFORMATION: siRNA sense strand

<400> SEQUENCE: 491
cucacuaacu uacaucaaat t                                              21

<210> SEQ ID NO 492
<211> LENGTH: 21
<212> TYPE: DNA
<213> ORGANISM: Artificial Sequence

```
<220> FEATURE:
<223> OTHER INFORMATION: siRNA antisense strand

<400> SEQUENCE: 492
uuugauguaa guuagugaga g                                              21

<210> SEQ ID NO 493
<211> LENGTH: 21
<212> TYPE: DNA
<213> ORGANISM: Artificial Sequence
<220> FEATURE:
<223> OTHER INFORMATION: siRNA sense strand

<400> SEQUENCE: 493
gauccuacgg aaguuauggt t                                              21

<210> SEQ ID NO 494
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 494
ccauaacuuc cguaggaucc g                                              21

<210> SEQ ID NO 495
<211> LENGTH: 21
<212> TYPE: DNA
<213> ORGANISM: Artificial Sequence
<220> FEATURE:
<223> OTHER INFORMATION: siRNA sense strand

<400> SEQUENCE: 495
ccauguucca uguuucuuut t                                              21

<210> SEQ ID NO 496
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 496
aaagaaacau ggaacauggt c                                              21

<210> SEQ ID NO 497
<211> LENGTH: 21
<212> TYPE: DNA
<213> ORGANISM: Artificial Sequence
<220> FEATURE:
<223> OTHER INFORMATION: siRNA sense strand

<400> SEQUENCE: 497
ccucccgcag accauguuct t                                              21

<210> SEQ ID NO 498
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 498
gaacaugguc ugcgggaggc g                                              21
```

```
<210> SEQ ID NO 499
<211> LENGTH: 21
<212> TYPE: DNA
<213> ORGANISM: Artificial Sequence
<220> FEATURE:
<223> OTHER INFORMATION: siRNA sense strand

<400> SEQUENCE: 499
cucccgcaga ccauguucct t                                                  21

<210> SEQ ID NO 500
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 500
ggaacauggu cugcgggagg c                                                  21

<210> SEQ ID NO 501
<211> LENGTH: 21
<212> TYPE: DNA
<213> ORGANISM: Artificial Sequence
<220> FEATURE:
<223> OTHER INFORMATION: siRNA sense strand

<400> SEQUENCE: 501
ucccgcagac cauguuccat t                                                  21

<210> SEQ ID NO 502
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 502
uggaacaugg ucugcgggag g                                                  21

<210> SEQ ID NO 503
<211> LENGTH: 21
<212> TYPE: DNA
<213> ORGANISM: Artificial Sequence
<220> FEATURE:
<223> OTHER INFORMATION: siRNA sense strand

<400> SEQUENCE: 503
cccgcagacc auguuccaut t                                                  21

<210> SEQ ID NO 504
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 504
auggaacaug gucugcggga g                                                  21

<210> SEQ ID NO 505
<211> LENGTH: 21
<212> TYPE: DNA
<213> ORGANISM: Artificial Sequence
<220> FEATURE:
<223> OTHER INFORMATION: siRNA sense strand
```

```
<400> SEQUENCE: 505
ccgcagacca uguuccaugt t                                              21

<210> SEQ ID NO 506
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 506
cauggaacau ggucugcggg a                                              21

<210> SEQ ID NO 507
<211> LENGTH: 21
<212> TYPE: DNA
<213> ORGANISM: Artificial Sequence
<220> FEATURE:
<223> OTHER INFORMATION: siRNA sense strand

<400> SEQUENCE: 507
cgcagaccau guuccaugut t                                              21

<210> SEQ ID NO 508
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 508
acauggaaca uggucugcgg g                                              21

<210> SEQ ID NO 509
<211> LENGTH: 21
<212> TYPE: DNA
<213> ORGANISM: Artificial Sequence
<220> FEATURE:
<223> OTHER INFORMATION: siRNA sense strand

<400> SEQUENCE: 509
agaccauguu ccauguuuct t                                              21

<210> SEQ ID NO 510
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 510
gaaacaugga acauggucug c                                              21

<210> SEQ ID NO 511
<211> LENGTH: 21
<212> TYPE: DNA
<213> ORGANISM: Artificial Sequence
<220> FEATURE:
<223> OTHER INFORMATION: siRNA sense strand

<400> SEQUENCE: 511
accauguucc auguuucuut t                                              21

<210> SEQ ID NO 512
```

```
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 512
aagaaacaug gaacaugguc t                                              21

<210> SEQ ID NO 513
<211> LENGTH: 21
<212> TYPE: DNA
<213> ORGANISM: Artificial Sequence
<220> FEATURE:
<223> OTHER INFORMATION: siRNA sense strand

<400> SEQUENCE: 513
ccacaucauc uacagcuuut t                                              21

<210> SEQ ID NO 514
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 514
aaagcuguag augauguggg t                                              21

<210> SEQ ID NO 515
<211> LENGTH: 21
<212> TYPE: DNA
<213> ORGANISM: Artificial Sequence
<220> FEATURE:
<223> OTHER INFORMATION: siRNA sense strand

<400> SEQUENCE: 515
gguuugacag auacagcaat t                                              21

<210> SEQ ID NO 516
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 516
uugcuguauc ugucaaacct a                                              21

<210> SEQ ID NO 517
<211> LENGTH: 21
<212> TYPE: DNA
<213> ORGANISM: Artificial Sequence
<220> FEATURE:
<223> OTHER INFORMATION: siRNA sense strand

<400> SEQUENCE: 517
ucaucuacag cuuugccaat t                                              21

<210> SEQ ID NO 518
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 518
```

```
uuggcaaagc uguagaugat g                                              21

<210> SEQ ID NO 519
<211> LENGTH: 21
<212> TYPE: DNA
<213> ORGANISM: Artificial Sequence
<220> FEATURE:
<223> OTHER INFORMATION: siRNA sense strand

<400> SEQUENCE: 519
cccuguuaag gaaugcaaat t                                              21

<210> SEQ ID NO 520
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 520
uuugcauucc uuaacagggt t                                              21

<210> SEQ ID NO 521
<211> LENGTH: 21
<212> TYPE: DNA
<213> ORGANISM: Artificial Sequence
<220> FEATURE:
<223> OTHER INFORMATION: siRNA sense strand

<400> SEQUENCE: 521
caaguaggca aauaucuuat t                                              21

<210> SEQ ID NO 522
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 522
uaagauauuu gccuacuuga t                                              21

<210> SEQ ID NO 523
<211> LENGTH: 21
<212> TYPE: DNA
<213> ORGANISM: Artificial Sequence
<220> FEATURE:
<223> OTHER INFORMATION: siRNA sense strand

<400> SEQUENCE: 523
cagcuuuguc agcaggaaat t                                              21

<210> SEQ ID NO 524
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 524
uuuccugcug acaaagcugc g                                              21

<210> SEQ ID NO 525
<211> LENGTH: 21
<212> TYPE: DNA
```

```
<213> ORGANISM: Artificial Sequence
<220> FEATURE:
<223> OTHER INFORMATION: siRNA sense strand

<400> SEQUENCE: 525
gguucaccaa ggaggcaggt t                                              21

<210> SEQ ID NO 526
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 526
ccugccuccu uggugaaccg g                                              21

<210> SEQ ID NO 527
<211> LENGTH: 21
<212> TYPE: DNA
<213> ORGANISM: Artificial Sequence
<220> FEATURE:
<223> OTHER INFORMATION: siRNA sense strand

<400> SEQUENCE: 527
ggaucaagua ggcaaauaut t                                              21

<210> SEQ ID NO 528
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 528
auauuugccu acuugaucca a                                              21

<210> SEQ ID NO 529
<211> LENGTH: 21
<212> TYPE: DNA
<213> ORGANISM: Artificial Sequence
<220> FEATURE:
<223> OTHER INFORMATION: siRNA sense strand

<400> SEQUENCE: 529
gagggaccau acuaauuaut t                                              21

<210> SEQ ID NO 530
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 530
auaauuagua ugguccuca a                                               21

<210> SEQ ID NO 531
<211> LENGTH: 21
<212> TYPE: DNA
<213> ORGANISM: Artificial Sequence
<220> FEATURE:
<223> OTHER INFORMATION: siRNA sense strand

<400> SEQUENCE: 531
ggccgguuca ccaaggaggt t                                              21
```

<210> SEQ ID NO 532
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 532
ccuccuuggu gaaccggcct g                                              21

<210> SEQ ID NO 533
<211> LENGTH: 21
<212> TYPE: DNA
<213> ORGANISM: Artificial Sequence
<220> FEATURE:
<223> OTHER INFORMATION: siRNA sense strand

<400> SEQUENCE: 533
ggacaaggag agugucaaat t                                              21

<210> SEQ ID NO 534
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 534
uuugacacuc uccuugucct c                                              21

<210> SEQ ID NO 535
<211> LENGTH: 21
<212> TYPE: DNA
<213> ORGANISM: Artificial Sequence
<220> FEATURE:
<223> OTHER INFORMATION: siRNA sense strand

<400> SEQUENCE: 535
ccgguucacc aaggaggcat t                                              21

<210> SEQ ID NO 536
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 536
ugccuccuug gugaaccggc c                                              21

<210> SEQ ID NO 537
<211> LENGTH: 21
<212> TYPE: DNA
<213> ORGANISM: Artificial Sequence
<220> FEATURE:
<223> OTHER INFORMATION: siRNA sense strand

<400> SEQUENCE: 537
cguacaagcu ggucugcuat t                                              21

<210> SEQ ID NO 538
<211> LENGTH: 21
<212> TYPE: DNA
<213> ORGANISM: Artificial Sequence
<220> FEATURE:

<223> OTHER INFORMATION: siRNA antisense strand

<400> SEQUENCE: 538
uagcagacca gcuuguacgc a            21

<210> SEQ ID NO 539
<211> LENGTH: 21
<212> TYPE: DNA
<213> ORGANISM: Artificial Sequence
<220> FEATURE:
<223> OTHER INFORMATION: siRNA sense strand

<400> SEQUENCE: 539
ggaguuuaau cucuugcaat t            21

<210> SEQ ID NO 540
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 540
uugcaagaga uuaaacucct g            21

<210> SEQ ID NO 541
<211> LENGTH: 21
<212> TYPE: DNA
<213> ORGANISM: Artificial Sequence
<220> FEATURE:
<223> OTHER INFORMATION: siRNA sense strand

<400> SEQUENCE: 541
caaggaacug aaugcggaat t            21

<210> SEQ ID NO 542
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 542
uuccgcauuc aguccuuga t            21

<210> SEQ ID NO 543
<211> LENGTH: 21
<212> TYPE: DNA
<213> ORGANISM: Artificial Sequence
<220> FEATURE:
<223> OTHER INFORMATION: siRNA sense strand

<400> SEQUENCE: 543
cccugaucaa ggaacugaat t            21

<210> SEQ ID NO 544
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 544
uucaguuccu ugaucagggt g            21

```
<210> SEQ ID NO 545
<211> LENGTH: 21
<212> TYPE: DNA
<213> ORGANISM: Artificial Sequence
<220> FEATURE:
<223> OTHER INFORMATION: siRNA sense strand

<400> SEQUENCE: 545
cuuggaucaa guaggcaaat t                                              21

<210> SEQ ID NO 546
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 546
uuugccuacu ugauccaagt g                                              21

<210> SEQ ID NO 547
<211> LENGTH: 21
<212> TYPE: DNA
<213> ORGANISM: Artificial Sequence
<220> FEATURE:
<223> OTHER INFORMATION: siRNA sense strand

<400> SEQUENCE: 547
ggauugaggg accauacuat t                                              21

<210> SEQ ID NO 548
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 548
uaguaugguc ccucaaucct g                                              21

<210> SEQ ID NO 549
<211> LENGTH: 21
<212> TYPE: DNA
<213> ORGANISM: Artificial Sequence
<220> FEATURE:
<223> OTHER INFORMATION: siRNA sense strand

<400> SEQUENCE: 549
gcaaauucuc agacucuaat t                                              21

<210> SEQ ID NO 550
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 550
uuagagucug agaauuugca t                                              21

<210> SEQ ID NO 551
<211> LENGTH: 21
<212> TYPE: DNA
<213> ORGANISM: Artificial Sequence
<220> FEATURE:
<223> OTHER INFORMATION: siRNA sense strand
```

```
<400> SEQUENCE: 551
ccuucccuua ggaacuuaat t                                              21

<210> SEQ ID NO 552
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 552
uuaaguuccu aagggaagga t                                              21

<210> SEQ ID NO 553
<211> LENGTH: 100
<212> TYPE: DNA
<213> ORGANISM: Artificial Sequence
<220> FEATURE:
<223> OTHER INFORMATION: OHBOT Oligonucleotide

<400> SEQUENCE: 553
gacttcatat acccaagctt ggaaaatttt ttttaaaaaa gtcttgacac tttatgcttc     60
cggctcgtat aatggatcca ggagtaacaa tacaaatgga                         100

<210> SEQ ID NO 554
<211> LENGTH: 100
<212> TYPE: DNA
<213> ORGANISM: Artificial Sequence
<220> FEATURE:
<223> OTHER INFORMATION: OHBOT Oligonucleotide

<400> SEQUENCE: 554
ttcaagagat ccatttgtat tgttactcct tttttttttt gtcgacgatc cttagcgaaa     60
gctaaggatt ttttttttac tcgagcggat tactacatac                         100

<210> SEQ ID NO 555
<211> LENGTH: 70
<212> TYPE: DNA
<213> ORGANISM: Artificial Sequence
<220> FEATURE:
<223> OTHER INFORMATION: OHBOT Oligonucleotide

<400> SEQUENCE: 555
gtatgtagta atccgctcga gtaaaaaaaa aatccttagc tttcgctaag gatcgtcgac     60
aaaaaaaaaa                                                           70

<210> SEQ ID NO 556
<211> LENGTH: 60
<212> TYPE: DNA
<213> ORGANISM: Artificial Sequence
<220> FEATURE:
<223> OTHER INFORMATION: OHBOT Oligonucleotide

<400> SEQUENCE: 556
aggagtaaca atacaaatgg atctcttgaa tccatttgta ttgttactcc tggatccatt     60

<210> SEQ ID NO 557
<211> LENGTH: 70
<212> TYPE: DNA
<213> ORGANISM: Artificial Sequence
<220> FEATURE:
<223> OTHER INFORMATION: OHBOT Oligonucleotide

<400> SEQUENCE: 557
```

```
atacgagccg gaagcataaa gtgtcaagac ttttttaaaa aaaattttcc aagcttgggt    60
atatgaagtc                                                           70

<210> SEQ ID NO 558
<211> LENGTH: 8884
<212> TYPE: DNA
<213> ORGANISM: Artificial Sequence
<220> FEATURE:
<223> OTHER INFORMATION: pKSII-inv-hly

<400> SEQUENCE: 558
ctaaattgta agcgttaata ttttgttaaa attcgcgtta aattttttgtt aaatcagctc    60 atttttttaac caataggccg aaatcggcaa atcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc ctaaagggag    300 cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta gggcgaat ggagctcca    660 ccgcggtggc ggccgctcta gaactagtgg atccccccggg ctgcagctgg gccgtaagat   720
cggcatttaa tcgcgacaat ccttttaaaa aaacagcgcc gctcaattaa cctgagcggc   780
gttgttcttc tggacgtttg ctacttatgg ggcgagtcta ggattgccgg actcccattc   840
gcgccccaaa taatcagctc attaaactgt tcttattgct atctgttatc tggttatatt   900
gacagcgcac agagcgggaa cgccaagtat gcaggccctg gttgcagtgc gcctgtgtcc   960
atattcatgg tttcaaaatc cgtgctggtc ttttttgaccc aatattcacc agattgccaa  1020
tcagaactat acgcggtcaa gctcccccac tcgccccaca atgtcccgtc aggcgcacgc  1080
gttccgttgg ttgcacgtga ggattcaaga accgcagaca tatctgaacc ttggcattgt  1140
ctgctggcct cgagactgga taccagcgat ctgccgccat cgtatatcca ccgatttggg  1200
tagaaccgat aactcaccga ataacttggg aatttttttac ttttcgccgt cacagccact  1260
tcgctatagg tttggtaggt aatcgtcacc tgaccctgat cgttaaccga tacattgggt  1320
gtgaatgacg acgaccactc atactgagta ttattagcaa catcgttatc catctgtaac  1380
tggaatgtgg cgtttttaaa gatcgttttc gggaacccctt tatccgtagc gaaatttttgc  1440 ccgttaacca gaataccggt cagcgtaggt accgggaata gggatatttt tttctgcaat  1500
gtactcagta tcagggtatc aacctgcggc gtgattgtga catcaccgac actattccca  1560
accaccgtcg cggtatagct atctggctgc tcggtaatgg gctaatact caccggcaca  1620 ccgttttgag taaaactcaa gccctgcatc ccactgataa aatggccatt cttatcgaca  1680
gggacaaagg ataatgtgga actcatcgtg ccatcagcca agatatccgg tgtggagacg  1740
gtgaaactgg agcggccagc atctggaata ggatctgccg tgaaattaac cgtcacactc  1800
ggcacactga acgcagcccc atccacttttc accgttactg ttgctacccc caacgtggta  1860
ctggtcaatg gtgcgctata agtgccgtca ttgtgatccg tgataacgcc catattgcct  1920
```

| | |
|---|---|
| aaggttgtgt caaaagccac attcgcgcca gcctgcgggt ccccataggt atccttcaac | 1980 |
| tccaacgtga tggttgaagc cattagacca tcagcgatga tagatgtcgg taccgcagcc | 2040 |
| agagtggatt tatccgccgc gatagtaccc ttaacaaagt gggtatcaac actttgccgt | 2100 |
| tgcccctcca cttctgctgt gactaccgtc acgccatctg tcgtattggt taatgcaatg | 2160 |
| cgcgcgacgc catttgcatc tgtcttttcc gtgattttat tcggtagcgc accattattg | 2220 |
| gtggttatca ccacctcctg cccggctaag ggtttcccct caaaatcagc aacggtgaac | 2280 |
| tcaacggtga ttgcagtttt cccattagcc ggtgcgccat caccaatgac ggccgccgtt | 2340 |
| aatgtcaact gaggctgctg aacggtgacg ctcaatgtga atgagttaga tcggtttcct | 2400 |
| tggtgatcaa ccgcgagcgc actaagcgaa taaaagttgg ctgtcaggtc gtccgttacc | 2460 |
| cgactcactt gtgctgtgcg tttataaggc ggtaaaacca agttgaattg tgtggtactc | 2520 |
| agtggtgtta atgtgccgcc agcggcaatc agttcggcat cactccagac aatttcccctt | 2580 |
| acagcagatg cccccttgtac ttgtgcgttc acctgataaa cctgacccgg caggccggag | 2640 |
| atagttgctg gcgataatgt cagtttaacc acctgctgtt tctgatactc caacacgata | 2700 |
| ttattgttac gatcgacaag gttatagcgg ctctccgcca gtagacgtgt tcctgccacc | 2760 |
| gctgaagggc taagttgcga ctgaaaactc tcgcccaggc gatagttcat ttggaggttc | 2820 |
| cactgtgttt catgcttact gcttttcccc atacgctgat ctaccccgac agtgagtaga | 2880 |
| ggcacggggg tgtaattgat cccggcagtc acggcataag ggttgcgttg cagattatct | 2940 |
| ttaccaaata aagcaacacg ctcaccggtg tattgctcat acatcaactt ccccccccagt | 3000 |
| tgtgggagtg caggtaaata agcattgcg cgcaaatccc ccccagtggc tgggcgctct | 3060 |
| ttatagtcgg agaaatcacg cgacgagtgc catccattga ggcgaaaata cccattggca | 3120 |
| gccaactgta ataatcggt ccaggcctcg gcaccaagac cgatacggtg gttgtggccg | 3180 |
| gtcaaatcat tatcataaaa agtattaagt ccgtacagcc aaccgttctc caatgtacgt | 3240 |
| atcccgacgc caaggttaag tgtgttgcgg ctgtctttat tgcgaatacc taactgacta | 3300 |
| aaaagagga atgaagcaga gtcataccaa ggagccagcc aatcaagaga gctttctttt | 3360 |
| agcgaaaaat ttttgtcaaa attcagatta acttgagccg taccgaatcg atttaaccac | 3420 |
| tgtttgattt cttgattaac cgcatcgccc accattgagt gagcaacatc agatgccctg | 3480 |
| cctgatgcag ctaacctggc cccgtgctt atcatcttat tcaccgcttc agtctcctgc | 3540 |
| tccttattgg cgcgatctat tattgcagca tttctttctg tatccgatgc ggaaaaggga | 3600 |
| ttgattgaac tctccatttc attattagga tggagatttt caaatgcaga tgaagagaca | 3660 |
| gaataaggct ggacctgttg cggtgcgtta gcatcatatt tttctgaagc cccagccatg | 3720 |
| aacattccac atatcaaaaa gatacaaata actattcgtg aaataatatt aaatgaaatt | 3780 |
| attttattaa aatacataga cattcccgca ttccttatca agagaaactc actgattggc | 3840 |
| tggaaaacca tcataattta aatgaaataa agcatacctg tcatacgtca aactgcatgt | 3900 |
| gcgttggctg tgctcaacaa cttgagttat ttgaggtata actggccaca aacgagcatt | 3960 |
| tgaaatcacc ttgaccatta attaaagatg caatagttga aagtgaaact tgtttctaa | 4020 |
| tttagtaaag acattaagag gatagcactt ttttaaaaaa ccagactggg cagattaaaa | 4080 |
| atattcaaaa tatataataa aacagtctat accatacagc gatagaattg atttattgta | 4140 |
| actaagcagg tgagaatatc aaaaaaaaca aaaatacaaa atgaactatt atcatataaa | 4200 |
| taatatcaat tagaataagc ccccttcatt tgatgttgtc agttgtctgc tgcggttttt | 4260 |
| atttctactt tcagtctgaa gtgttactcc gcaatatccg cattaatcct gatggttgcc | 4320 |

```
ttgatgactg caggaattcg atccctcctt tgattagtat attcctatct taaagtgact    4380
tttatgttga ggcattaaca tttgttaacg acgataaagg gacagcagga ctagaataaa    4440
gctataaagc aagcatataa tattgcgttt catctttaga agcgaatttc gccaatatta    4500
taattatcaa aagagagggg tggcaaacgg tatttggcat tattaggtta aaaaatgtag    4560
aaggagagtg aaacccatga aaaaaataat gctagttttt attacactta tattagttag    4620
tctaccaatt gcgcaacaaa ctgaagcaaa ggatgcatct gcattcaata aagaaaattc    4680
aatttcatcc atggcaccac cagcatctcc gcctgcaagt cctaagacgc caatcgaaaa    4740
gaaacacgcg gatgaaatcg ataagtatat acaaggattg gattacaata aaacaatgt    4800
attagtatac cacggagatg cagtgacaaa tgtgccgcca agaaaaggtt acaaagatgg    4860
aaatgaatat attgttgtgg agaaaaagaa gaaatccatc aatcaaaata atgcagacat    4920
tcaagttgtg aatgcaattt cgagcctaac ctatccaggt gctctcgtaa agcgaattc    4980
ggaattagta gaaaatcaac cagatgttct ccctgtaaaa cgtgattcat taacactcag    5040
cattgatttg ccaggtatga ctaatcaaga caataaaatc gttgtaaaaa atgccactaa    5100
atcaaacgtt aacaacgcag taaatacatt agtggaaaga tggaatgaaa atatgctca    5160
agcttatcca aatgtaagtg caaaaattga ttatgatgac gaaatggctt acagtgaatc    5220
acaattaatt gcgaaatttg gtacagcatt taaagctgta aataatagct tgaatgtaaa    5280
cttcggcgca atcagtgaag ggaaaatgca agaagaagtc attagttta aacaaattta    5340
ctataacgtg aatgttaatg aacctacaag accttccaga ttttcggca agctgttac    5400
taaagagcag ttgcaagcgc ttggagtgaa tgcagaaaat cctcctgcat atatctcaag    5460
tgtggcgtat ggccgtcaag tttatttgaa attatcaact aattcccata gtactaaagt    5520
aaaagctgct tttgatgctg ccgtaagcgg aaaatctgtc tcaggtgatg tagaactaac    5580
aaatatcatc aaaaattctt ccttcaaagc cgtaattac ggaggttccg caaaagatga    5640
agttcaaatc atcgacggca acctcggaga cttacgcgat attttgaaaa aaggcgctac    5700
ttttaatcga gaaacaccag gagttcccat tgcttataca acaaacttcc taaagacaa    5760
tgaattagct gttattaaaa acaactcaga atatattgaa acaacttcaa aagcttatac    5820
agatggaaaa attaacatcg atcactctgg aggatacgtt gctcaattca acatttcttg    5880
ggatgaagta aattatgatc ctgaaggtaa cgaaattgtt caacataaaa actggagcga    5940
aaacaataaa agcaagctag ctcatttcac atcgtccatc tatttgccag gtaacgcgag    6000
aaatatttaat gtttacgcta aagaatgcac tggtttagct tgggaatggt ggagaacggt    6060
aattgatgac cggaacttac cacttgtgaa aaatagaaat atctccatct ggggcaccac    6120
gctttatccg aaatatagta ataaagtaga taatccaatc gaataattgt aaaagtaata    6180
aaaaattaag aataaaaccg cttaacacac acgaaaaaat aagcttgtt tgcactcttc    6240
gtaaattatt ttgtgaagaa tgtagaaaca ggcttatttt ttaatttttt tagaagaatt    6300
aacaaatgta aagaatatc tgactgttta tccatataat ataagcatat cccaaagttt    6360
aagccaccta gtttctac tgcaaaacgt ataatttagt tcccacatat actaaaaaac    6420
gtgtccttaa ctctctctgt cagattagtt gtaggtggct taaacttagt tttacgaatt    6480
aaaaaggagc ggtgaaatga aaagtaaact tatttgtatc atcatggtaa tagctttta    6540
ggctcatttc actatgacgg taaaagcaga ttctgtcggg gaagaaaaac ttcaaaataa    6600
tacacaagcc aaaaagaccc ctgctgattt aaaagcttat caagcttatc gataccgtcg    6660
```

```
acctcgaggg ggggcccggt acccagcttt tgttcccttt agtgagggtt aattgcgcgc    6720
ttggcgtaat catggtcata gctgtttcct gtgtgaaatt gttatccgct cacaattcca    6780
cacaacatac gagccggaag cataaagtgt aaagcctggg gtgcctaatg agtgagctaa    6840
ctcacattaa ttgcgttgcg ctcactgccc gctttccagt cgggaaacct gtcgtgccag    6900
ctgcattaat gaatcggcca acgcgcgggg agaggcggtt tgcgtattgg gcgctcttcc    6960
gcttcctcgc tcactgactc gctgcgctcg gtcgttcggc tgcggcgagc ggtatcagct    7020
cactcaaagg cggtaatacg gttatccaca gaatcagggg ataacgcagg aaagaacatg    7080
tgagcaaaag gccagcaaaa ggccaggaac cgtaaaaagg ccgcgttgct ggcgtttttc    7140
cataggctcc gcccccctga cgagcatcac aaaaatcgac gctcaagtca gaggtggcga    7200
aacccgacag gactataaag ataccaggcg tttccccctg gaagctccct cgtgcgctct    7260
cctgttccga ccctgccgct taccggatac ctgtccgcct ttctcccttc gggaagcgtg    7320
gcgctttctc atagctcacg ctgtaggtat ctcagttcgg tgtaggtcgt tcgctccaag    7380
ctgggctgtg tgcacgaacc ccccgttcag cccgaccgct gcgccttatc cggtaactat    7440
cgtcttgagt ccaacccggt aagacacgac ttatcgccac tggcagcagc cactggtaac    7500
aggattagca gagcgaggta tgtaggcggt gctacagagt tcttgaagtg gtggcctaac    7560
tacggctaca ctagaaggac agtatttggt atctgcgctc tgctgaagcc agttaccttc    7620
ggaaaaagag ttggtagctc ttgatccggc aaacaaacca ccgctggtag cggtggtttt    7680
tttgtttgca agcagcagat tacgcgcaga aaaaaggat ctcaagaaga tcctttgatc    7740
ttttctacgg ggtctgacgc tcagtggaac gaaaactcac gttaagggat tttggtcatg    7800
agattatcaa aaaggatctt cacctagatc cttttaaatt aaaaatgaag ttttaaatca    7860
atctaaagta tatatgagta aacttggtct gacagttacc aatgcttaat cagtgaggca    7920
cctatctcag cgatctgtct atttcgttca tccatagttg cctgactccc cgtcgtgtag    7980
ataactacga tacgggaggg cttaccatct ggccccagtg ctgcaatgat accgcgagac    8040
ccacgctcac cggctccaga tttatcagca ataaaccagc cagccggaag ggccgagcgc    8100
agaagtggtc ctgcaacttt atccgcctcc atccagtcta ttaattgttg ccgggaagct    8160
agagtaagta gttcgccagt taatagtttg cgcaacgttg ttgccattgc tacaggcatc    8220
gtggtgtcac gctcgtcgtt tggtatggct tcattcagct ccggttccca acgatcaagg    8280
cgagttacat gatccccat gttgtgcaaa aaagcggtta gctccttcgg tcctccgatc    8340
gttgtcagaa gtaagttggc cgcagtgtta tcactcatgg ttatggcagc actgcataat    8400
tctcttactg tcatgccatc cgtaagatgc ttttctgtga ctggtgagta ctcaaccaag    8460
tcattctgag aatagtgtat gcggcgaccg agttgctctt gcccggcgtc aatacgggat    8520
aataccgcgc cacatagcag aactttaaaa gtgctcatca ttggaaaacg ttcttcgggg    8580
cgaaaactct caaggatctt accgctgttg agatccagtt cgatgtaacc cactcgtgca    8640
cccaactgat cttcagcatc ttttactttc accagcgttt ctgggtgagc aaaaacagga    8700
aggcaaaatg ccgcaaaaaa gggaataagg gcgacacgga aatgttgaat actcatactc    8760
ttcctttttc aatattattg aagcatttat cagggttatt gtctcatgag cggatacata    8820
tttgaatgta tttagaaaaa taaacaaata ggggttccgc gcacatttcc ccgaaaagtg    8880
ccac                                                                 8884
```

<210> SEQ ID NO 559
<211> LENGTH: 8538

<212> TYPE: DNA
<213> ORGANISM: Artificial Sequence
<220> FEATURE:
<223> OTHER INFORMATION: pMBV40

<400> SEQUENCE: 559

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatcga cggtatcgat aagcttgata agcttttaaa tcagcagggg tcttttggc      240
ttgtgtatta ttttgaagtt tttcttcccc gacagaatct gcttttaccg tcatagtgaa     300
atgagcctga aaagctatta ccatgatgat acaaataagt ttacttttca tttcaccgct     360
ccttttaat tcgtaaaact aagtttaagc cacctacaac taatctgaca gagagagtta     420
aggacacgtt ttttagtata tgtgggaact aaattatacg ttttgcagta gaaactatag     480
gtggcttaaa cttgggata tgcttatatt atatggataa acagtcagat attcttttac      540
atttgttaat tcttctaaaa aaattaaaaa ataagcctgt ttctacattc ttcacaaaat     600
aatttacgaa gagtgcaaaa caagcttatt ttttcgtgtg tgttaagcgg ttttattctt     660
aattttttat tactttttaca attattcgat tggattatct actttattac tatatttcgg   720
ataaagcgtg gtgccccaga tggagatatt tctattttc acaagtggta agttccggtc     780
atcaattacc gttctccacc attcccaagc taaaccagtg cattctttag cgtaaacatt     840
aatatttctc gcgttacctg gcaaatagat ggacgatgtg aaatgagcta gcttgctttt    900
attgttttcg ctccagtttt tatgttgaac aatttcgtta ccttcaggat cataatttac    960
ttcatcccaa gaaatgttga attgagcaac gtatcctcca gagtgatcga tgttaatttt   1020
tccatctgta taagcttttg aagttgtttc aatatattct gagttgtttt taataacagc   1080
taattcattg tctttttagga agtttgttgt ataagcaatg ggaactcctg gtgtttctcg   1140
attaaaagta gcgccttttt tcaaaatatc gcgtaagtct ccgaggttgc cgtcgatgat   1200
ttgaacttca tcttttgcgg aacctccgta aattacggct ttgaaggaag aattttgat    1260
gatatttgtt agttctacat cacctgagac agattttccg cttacggcag catcaaaagc   1320
agcttttact ttagtactat gggaattagt tgataatttc aaataaactt gacggccata   1380
cgccacactt gagatatatg caggaggatt ttctgcattc actccaagcg cttgcaactg   1440
ctctttagta acagctttgc cgaaaaatct ggaaggtctt gtaggttcat aacattcac    1500
gttatagtaa atttgtttaa aactaatgac ttcttcttgc atttccctt cactgattgc    1560
gccgaagttt acattcaagc tattatttac agctttaaat gctgtaccaa atttcgcaat   1620
taattgtgat tcactgtaag ccatttcgtc atcataatca attttgcac ttacatttgg    1680
ataagcttga gcatattttt cattccatct ttccactaat gtatttactg cgttgttaac   1740
gtttgattta gtggcatttt ttacaacgat tttattgtct tgattagtca tacctggcaa   1800
atcaatgctg agtgttaatg aatcacgttt tacagggaga acatctggtt gattttctac   1860
taattccgaa ttcgctttta cgagagcacc tggataggtt aggctcgaaa ttgcattcac   1920
aacttgaatg tctgcattat tttgattgat ggatttcttc ttttttctcca caacaatata   1980
ttcatttcca tctttgtaac cttttcttgg cggcacattt gtcactgcat ctccgtggta   2040
tactaataca ttgttttttat tgtaatccaa tccttgtata tacttatcga tttcatccgc   2100
gtgtttcttt tcgattggcg tcttaggact tgcaggcgga gatgctggtg gtgccatgga   2160
```

```
tgaaattgaa ttttctttat tgaatgcaga tgcatccttt gcttcagttt gttgcgcaat     2220
tggtagacta actaatataa gtgtaataaa aactagcatt attttttca tgggtttcac      2280 tctccttcta cattttttaa cctaataatg ccaaataccg tttgccaccc ctctcttttg     2340
ataattataa tattggcgaa attcgcttct aaagatgaaa cgcaatatta tatgcttgct    2400
ttatagcttt attctagtcc tgctgtccct ttatcgtcgt taacaaatgt taatgcctca    2460
acataaaagt cactttaaga taggaatata ctaatcaaag gagggatcga attcctgcag    2520
tcatcaaggc aaccatcagg attaatgcgg atattgcgga gtaacacttc agactgaaag    2580
tagaaataaa aaccgcagca gacaactgac aacatcaaat gaaggggct tattctaatt     2640 gatattattt atatgataat agttcatttt gtattttgt ttttttgat attctcacct       2700 gcttagttac aataaatcaa ttctatcgct gtatggtata gactgtttta ttatatattt    2760
tgaatatttt taatctgccc agtctggttt tttaaaaaag tgctatcctc ttaatgtctt    2820
tactaaatta gaaacaagt ttcactttca actattgcat ctttaattaa tggtcaaggt     2880
gatttcaaat gctcgtttgt ggccagttat acctcaaata actcaagttg ttgagcacag   2940
ccaacgcaca tgcagtttga cgtatgacag gtatgcttta tttcatttaa attatgatgg   3000
ttttccagcc aatcagtgag tttctcttga taaggaatgc gggaatgtct atgtatttta   3060 ataaataat ttcatttaat attatttcac gaatagttat ttgtatcttt ttgatatgtg    3120
gaatgttcat ggctggggct tcagaaaaat atgatgctaa cgcaccgcaa caggtccagc   3180
cttattctgt ctcttcatct gcatttgaaa atctccatcc taataatgaa atggagagtt   3240
caatcaatcc cttttccgca tcggatacag aaagaaatgc tgcaataata gatcgcgcca   3300
ataaggagca ggagactgaa gcggtgaata agatgataag caccggggcc aggttagctg   3360
catcaggcag ggcatctgat gttgctcact caatggtggg cgatgcggtt aatcaagaaa   3420
tcaaacagtg gttaaatcga ttcggtacgg ctcaagttaa tctgaatttt gacaaaaatt   3480
tttcgctaaa agaaagctct cttgattggc tggctccttg gtatgactct gcttcattcc   3540
tcttttttag tcagttaggt attcgcaata agacagccg caacacactt aaccttggcg     3600
tcgggatacg tacattggag aacggttggc tgtacggact taatactttt tatgataatg   3660
atttgaccgg ccacaaccac cgtatcggtc ttggtgccga ggcctggacc gattatttac   3720
agttggctgc caatgggtat tttcgcctca atggatggca ctcgtcgcgt gatttctccg   3780
actataaaga gcgcccagcc actgggggg atttgcgcgc gaatgcttat ttacctgcac    3840
tcccacaact gggggggaag ttgatgtatg agcaatacac cggtgagcgt gttgctttat   3900
ttggtaaaga taatctgcaa cgcaacccct tatgccgtgac tgccgggatc aattacaccc   3960
ccgtgcctct actcactgtc ggggtagatc agcgtatggg gaaaagcagt aagcatgaaa   4020
cacagtggaa cctccaaatg aactatcgcc tgggcgagag ttttcagtcg caacttagcc   4080
cttcagcggt ggcaggaaca cgtctactgg cggagagccg ctataacctt gtcgatcgta   4140
acaataatat cgtgttggag tatcagaaac agcaggtggt taaactgaca ttatcgccag   4200
caactatctc cggcctgccg ggtcaggttt atcaggtgaa cgcacaagta caaggggcat   4260
ctgctgtaag ggaaattgtc tggagtgatg ccgaactgat tgccgctggc ggcacattaa   4320
caccactgag taccacacaa ttcaacttgg ttttaccgcc ttataaacgc acagcacaag   4380
tgagtcgggt aacggacgac ctgacagcca actttttattc gcttagtgcg ctcgcggttg   4440
atcaccaagg aaaccgatct aactcattca cattgagcgt caccgttcag cagcctcagt   4500
tgacattaac ggcggccgtc attggtgatg gcgcaccggc taatgggaaa actgcaatca   4560
```

```
ccgttgagtt caccgttgct gattttgagg ggaaacccct tagccgggcag gaggtggtga   4620
taaccaccaa taatggtgcg ctaccgaata aaatcacgga aaagacagat gcaaatggcg   4680
tcgcgcgcat tgcattaacc aatacgacag atggcgtgac ggtagtcaca gcagaagtgg   4740
aggggcaacg gcaaagtgtt gatacccact ttgttaaggg tactatcgcg gcggataaat   4800
ccactctggc tgcggtaccg acatctatca tcgctgatgg tctaatggct tcaaccatca   4860
cgttggagtt gaaggatacc tatggggacc cgcaggctgg cgcgaatgtg gcttttgaca   4920
caaccttagg caatatgggc gttatcacgg atcacaatga cggcacttat agcgcaccat   4980
tgaccagtac cacgttgggg gtagcaacag taacggtgaa agtggatggg gctgcgttca   5040
gtgtgccgag tgtgacggtt aatttcacgg cagatcctat tccagatgct ggccgctcca   5100
gtttcaccgt ctccacaccg gatatcttgg ctgatggcac gatgagttcc acattatcct   5160
ttgtccctgt cgataagaat ggccatttta tcagtgggat gcagggcttg agttttactc   5220
aaaacggtgt gccggtgagt attagcccca ttaccgagca gccagatagc tataccgcga   5280
cggtggttgg gaatagtgtc ggtgatgtca caatcacgcc gcaggttgat accctgatac   5340
tgagtacatt gcagaaaaaa atatccctat tcccggtacc tacgctgacc ggtattctgg   5400
ttaacgggca aaatttcgct acggataaag ggttcccgaa aacgatcttt aaaaacgcca   5460
cattccagtt acagatggat aacgatgttg ctaataatac tcagtatgag tggtcgtcgt   5520
cattcacacc caatgtatcg gttaacgatc agggtcaggt gacgattacc taccaaacct   5580
atagcgaagt ggctgtgacg gcgaaaagta aaaaattccc aagttattcg gtgagttatc   5640
ggttctaccc aaatcggtgg atatacgatg gcggcagatc gctggtatcc agtctcgagg   5700
ccagcagaca atgccaaggt tcagatatgt ctgcggttct tgaatcctca cgtgcaacca   5760
acggaacgcg tgccgcctgac gggacattgt ggggcgagtg ggggagcttg accgcgtata   5820
gttctgattg gcaatctggt gaatattggg tcaaaaagac cagcacggat tttgaaacca   5880
tgaatatgga cacaggcgca ctgcaaccag gcctgcata cttggcgttc ccgctctgtg   5940
cgctgtcaat ataaccagat aacagatagc aataagaaca gtttaatgag ctgattattt   6000
ggggcgcgaa tgggagtccg gcaatcctag actcgcccca taagtagcaa acgtccagaa   6060
gaacaacgcc gctcaggtta attgagcggc gctgtttttt taaaaggatt gtcgcgatta   6120
aatgccgatc ttacggccca gctgcagccc gggggatcta tgcggtgtga aataccgcac   6180
agatgcgtaa ggagaaaata ccgcatcagg cgccattcgc cattcaggct gcgcaactgt   6240
tgggaagggc gatcggtgcg ggcctcttcg ctattacgcc aggacttcat atacccaagc   6300
ttggaaaatt tttttaaaa aagtcttgac actttatgct tccggctcgt ataatggatc   6360
caggagtaac aatacaaatg gattcaagag atccatttgt attgttactc ctttttttt   6420
ttgtcgacga tccttagcga aagctaagga tttttttttt actcgagcgg attactacat   6480
acctgcatta atgaatcggc caacgcgcgg ggagaggcgg tttgcgtatt gggcgctctt   6540
ccgcttcctc gctcactgac tcgctgcgct cggtcgttcg gctgcggcga gcggtatcag   6600
ctcactcaaa ggcggtaata cggttatcca cagaatcagg ggataacgca ggaaagaaca   6660
tgtgagcaaa aggccagcaa aaggccagga accgtaaaaa ggccgcgttg ctggcgtttt   6720
tccataggct ccgcccccct gacgagcatc acaaaaatcg acgctcaagt cagaggtggc   6780
gaaacccgac aggactataa agataccagg cgtttccccc tggaagctcc ctcgtgcgct   6840
ctcctgttcc gaccctgccg cttaccggat acctgtccgc ctttctccct tcgggaagcg   6900
```

```
tggcgctttc tcatagctca cgctgtaggt atctcagttc ggtgtaggtc gttcgctcca   6960
agctgggctg tgtgcacgaa ccccccgttc agcccgaccg ctgcgcctta tccggtaact   7020
atcgtcttga gtccaacccg gtaagacacg acttatcgcc actggcagca gccactggta   7080
acaggattag cagagcgagg tatgtaggcg gtgctacaga gttcttgaag tggtggccta   7140
actacggcta cactagaagg acagtatttg gtatctgcgc tctgctgaag ccagttacct   7200
tcggaaaaag agttggtagc tcttgatccg gcaaacaaac caccgctggt agcggtggtt   7260
tttttgtttg caagcagcag attacgcgca gaaaaaaagg atctcaagaa gatcctttga   7320
tcttttctac ggggtctgac gctcagtgga acgaaaactc acgttaaggg attttggtca   7380
tgagattatc aaaaaggatc ttcacctaga tccttttaaa ttaaaaatga agttttaaat   7440
caatctaaag tatatatgag taaacttggt ctgacagtta ccaatgctta atcagtgagg   7500
cacctatctc agcgatctgt ctatttcgtt catccatagt tgcctgactc cccgtcgtgt   7560
agataactac gatacgggag ggcttaccat ctggccccag tgctgcaatg ataccgcgag   7620
acccacgctc accggctcca gatttatcag caataaacca gccagccgga agggccgagc   7680
gcagaagtgg tcctgcaact ttatccgcct ccatccagtc tattaattgt tgccgggaag   7740
ctagagtaag tagttcgcca gttaatagtt tgcgcaacgt tgttgccatt gctacaggca   7800
tcgtggtgtc acgctcgtcg tttggtatgg cttcattcag ctccggttcc caacgatcaa   7860
ggcgagttac atgatccccc atgttgtgca aaaaagcggt tagctccttc ggtcctccga   7920
tcgttgtcag aagtaagttg gccgcagtgt tatcactcat ggttatggca gcactgcata   7980
attctcttac tgtcatgcca tccgtaagat gcttttctgt gactggtgag tactcaacca   8040
agtcattctg agaatagtgt atgcggcgac cgagttgctc ttgcccggcg tcaatacggg   8100
ataataccgc gccacatagc agaactttaa aagtgctcat cattggaaaa cgttcttcgg   8160
ggcgaaaact ctcaaggatc ttaccgctgt tgagatccag ttcgatgtaa cccactcgtg   8220
cacccaactg atcttcagca tcttttactt tcaccagcgt ttctgggtga gcaaaaacag   8280
gaaggcaaaa tgccgcaaaa aagggaataa gggcgacacg gaaatgttga atactcatac   8340
tcttcctttt tcaatattat tgaagcattt atcagggtta ttgtctcatg agcggataca   8400
tatttgaatg tatttagaaa aataaacaaa taggggttcc gcgcacattt ccccgaaaag   8460
tgccacctga cgtctaagaa accattatta tcatgacatt aacctataaa aataggcgta   8520
tcacgaggcc ctttcgtc                                                 8538

<210> SEQ ID NO 560
<211> LENGTH: 8427
<212> TYPE: DNA
<213> ORGANISM: Artificial Sequence
<220> FEATURE:
<223> OTHER INFORMATION: pMBV43

<400> SEQUENCE: 560
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatcga cggtatcgat aagcttgata agcttttaaa tcagcagggg tcttttttggc   240
ttgtgtatta ttttgaagtt tttcttcccc gacagaatct gctttaccg tcatagtgaa    300
atgagcctga aaagctatta ccatgatgat acaaataagt ttacttttca tttcaccgct   360
ccttttaat tcgtaaaact aagtttaagc cacctacaac taatctgaca gagagagtta    420
```

```
aggacacgtt ttttagtata tgtgggaact aaattatacg ttttgcagta gaaactatag    480
gtggcttaaa ctttgggata tgcttatatt atatggataa acagtcagat attcttttac    540
atttgttaat tcttctaaaa aaattaaaaa ataagcctgt ttctacattc ttcacaaaat    600
aatttacgaa gagtgcaaaa caagcttatt ttttcgtgtg tgttaagcgg ttttattctt    660 aatttttat tacttttaca attattcgat tggattatct actttattac tatatttcgg     720
ataaagcgtg gtgccccaga tggagatatt tctattttc acaagtggta agttccggtc     780
atcaattacc gttctccacc attcccaagc taaaccagtg cattctttag cgtaaacatt    840
aatatttctc gcgttacctg gcaaatagat ggacgatgtg aaatgagcta gcttgctttt    900
attgttttcg ctccagtttt tatgttgaac aatttcgtta ccttcaggat cataatttac    960
ttcatcccaa gaaatgttga attgagcaac gtatcctcca gagtgatcga tgttaatttt   1020
tccatctgta taagcttttg aagttgtttc aatatattct gagttgtttt taataacagc   1080
taattcattg tcttttagga agtttgttgt ataagcaatg ggaactcctg gtgtttctcg    1140
attaaaagta gcgccttttt tcaaaatatc gcgtaagtct ccgaggttgc cgtcgatgat    1200
ttgaacttca tcttttgcgg aacctccgta aattacggct ttgaaggaag aattttttgat  1260 gatatttgtt agttctacat cacctgagac agattttccg cttacggcag catcaaaagc   1320
agcttttact ttagtactat gggaattagt tgataaattc aaataaactt gacggccata   1380
cgccacactt gagatatatg caggaggatt ttctgcattc actccaagcg cttgcaactg   1440
ctctttagta acagctttgc cgaaaaatct ggaaggtctt gtaggttcat taacattcac    1500
gttatagtaa atttgtttaa aactaatgac ttcttcttgc attttccctt cactgattgc    1560
gccgaagttt acattcaagc tattatttac agctttaaat gctgtaccaa atttcgcaat   1620
taattgtgat tcactgtaag ccatttcgtc atcataatca attttttgcac ttacatttgg  1680 ataagcttga gcatattttt cattccatct ttccactaat gtatttactg cgttgttaac   1740
gtttgattta gtggcatttt ttacaacgat tttattgtct tgattagtca tacctggcaa   1800
atcaatgctg agtgttaatg aatcacgttt tacagggaga acatctggtt gatttttctac 1860 taattccgaa ttcgctttta cgagagcacc tggataggtt aggctcgaaa ttgcattcac   1920
aacttgaatg tctgcattat tttgattgat ggatttcttc ttttttctcca caacaatata  1980 ttcatttcca tctttgtaac cttttcttgg cggcacattt gtcactgcat ctccgtggta   2040
tactaataca ttgtttttat tgtaatccaa tccttgtata tacttatcga tttcatccgc   2100
gtgtttcttt tcgattggcg tcttaggact tgcaggcgga gatgctggtg gtgccatgga   2160
tgaaattgaa ttttcttat tgaatgcaga tgcatccttt gcttcagttt gttgcgcaat    2220
tggtagacta actaatataa gtgtaataaa aactagcatt attttttca tgggtttcac    2280 tctccttcta cattttttaa cctaataatg ccaaataccg tttgccaccc ctctcttttg   2340
ataattataa tattggcgaa attcgcttct aaagatgaaa cgcaatatta tatgcttgct   2400
ttatagcttt attctagtcc tgctgtccct ttatcgtcgt taacaaatgt taatgcctca   2460
acataaaagt cactttaaga taggaatata ctaatcaaag gagggatcga attcctgcag  2520
tcatcaaggc aaccatcagg attaatgcgg atattgcgga gtaacacttc agactgaaag   2580
tagaaataaa aaccgcagca gacaactgac aacatcaaat gaaggggct tattctaatt    2640 gatattattt atatgataat agttcatttt gtattttgt ttttttgat attctcacct     2700 gcttagttac aataaatcaa ttctatcgct gtatggtata gactgtttta ttatatattt   2760
```

```
tgaatatttt taatctgccc agtctggttt tttaaaaaag tgctatcctc ttaatgtctt    2820
tactaaatta gaaaacaagt ttcactttca actattgcat ctttaattaa tggtcaaggt    2880
gatttcaaat gctcgtttgt ggccagttat acctcaaata actcaagttg ttgagcacag    2940
ccaacgcaca tgcagtttga cgtatgacag gtatgcttta tttcatttaa attatgatgg    3000
ttttccagcc aatcagtgag tttctcttga taaggaatgc gggaatgtct atgtatttta    3060
ataaaataat ttcatttaat attatttcac gaatagttat ttgtatcttt ttgatatgtg    3120
gaatgttcat ggctggggct tcagaaaaat atgatgctaa cgcaccgcaa caggtccagc    3180
cttattctgt ctcttcatct gcatttgaaa atctccatcc taataatgaa atggagagtt    3240
caatcaatcc cttttccgca tcggatacag aaagaaatgc tgcaataata gatcgcgcca    3300
ataaggagca ggagactgaa gcggtgaata agatgataag caccggggcc aggttagctg    3360
catcaggcag ggcatctgat gttgctcact caatggtggg cgatgcggtt aatcaagaaa    3420
tcaaacagtg gttaaatcga ttcggtacgg ctcaagttaa tctgaatttt gacaaaaatt    3480
tttcgctaaa agaaagctct cttgattggc tggctccttg gtatgactct gcttcattcc    3540 tctttttttag tcagttaggt attcgcaata aagacagccg caacacactt aaccttggcg    3600
tcgggatacg tacattggag aacggttggc tgtacggact taatacttttt tatgataatg    3660 atttgaccgg ccacaaccac cgtatcggtc ttggtgccga ggcctggacc gattatttac    3720
agttggctgc caatgggtat tttcgcctca atggatggca ctcgtcgcgt gatttctccg    3780
actataaaga gcgcccagcc actgggggggg atttgcgcgc gaatgcttat ttacctgcac    3840
tcccacaact gggggggaag ttgatgtatg agcaatacac cggtgagcgt gttgctttat    3900
ttggtaaaga taatctgcaa cgcaacccctt atgccgtgac tgccgggatc aattacaccc    3960
ccgtgcctct actcactgtc ggggtagatc agcgtatggg gaaaagcagt aagcatgaaa    4020
cacagtggaa cctccaaatg aactatcgcc tgggcgagag ttttcagtcg caacttagcc    4080
cttcagcggt ggcaggaaca cgtctactgg cggagagccg ctataacctt gtcgatcgta    4140
acaataatat cgtgttggag tatcagaaac agcaggtggt taaactgaca ttatcgccag    4200
caactatctc cggcctgccg ggtcaggttt atcaggtgaa cgcacaagta caaggggcat    4260
ctgctgtaag ggaaattgtc tggagtgatg ccgaactgat tgccgctggc ggcacattaa    4320
caccactgag taccacacaa ttcaacttgg ttttaccgcc ttataaacgc acagcacaag    4380
tgagtcgggt aacggacgac ctgacagcca acttttattc gcttagtgcg ctcgcggttg    4440
atcaccaagg aaaccgatct aactcattca cattgagcgt caccgttcag cagcctcagt    4500
tgacattaac ggcggccgtc attggtgatg gcgcaccggc taatgggaaa actgcaatca    4560
ccgttgagtt caccgttgct gattttgagg ggaaaccctt agccgggcag gaggtggtga    4620
taaccaccaa taatggtgcg ctaccgaata aaatcacgga aaagacagat gcaaatggcg    4680
tcgcgcgcat tgcattaacc aatacgacag atggcgtgac ggtagtcaca gcagaagtgg    4740
aggggcaacg gcaaagtgtt gatacccact ttgttaaggg tactatcgcg gcggataaat    4800
ccactctggc tgcggtaccg acatctatca tcgctgatgg tctaatggct tcaaccatca    4860
cgttggagtt gaaggatacc tatgggggacc cgcaggctgg cgcgaatgtg gcttttgaca    4920
caaccttagg caatatgggc gttatcacgg atcacaatga cggcacttat agcgcaccat    4980
tgaccagtac cacgttgggg gtagcaacag taacggtgaa agtggatggg gctgcgttca    5040
gtgtgccgag tgtgacggtt aatttcacgg cagatcctat tccagatgct ggccgctcca    5100
gtttcaccgt ctccacaccg gatatcttgg ctgatggcac gatgagttcc acattatcct    5160
```

| | |
|---|---|
| ttgtccctgt cgataagaat ggccatttta tcagtgggat gcagggcttg agttttactc | 5220 |
| aaaacggtgt gccggtgagt attagcccca ttaccgagca gccagatagc tataccgcga | 5280 |
| cggtggttgg gaatagtgtc ggtgatgtca caatcacgcc gcaggttgat accctgatac | 5340 |
| tgagtacatt gcagaaaaaa atatccctat tcccggtacc tacgctgacc ggtattctgg | 5400 |
| ttaacgggca aaatttcgct acggataaag ggttcccgaa aacgatcttt aaaaacgcca | 5460 |
| cattccagtt acagatggat aacgatgttg ctaataatac tcagtatgag tggtcgtcgt | 5520 |
| cattcacacc caatgtatcg gttaacgatc agggtcaggt gacgattacc taccaaacct | 5580 |
| atagcgaagt ggctgtgacg gcgaaaagta aaaaattccc aagttattcg gtgagttatc | 5640 |
| ggttctaccc aaatcggtgg atatacgatg gcggcagatc gctggtatcc agtctcgagg | 5700 |
| ccagcagaca atgccaaggt tcagatatgt ctgcggttct tgaatcctca cgtgcaacca | 5760 |
| acggaacgcg tgcgcctgac gggacattgt ggggcgagtg ggggagcttg accgcgtata | 5820 |
| gttctgattg gcaatctggt gaatattggg tcaaaaagac cagcacggat tttgaaacca | 5880 |
| tgaatatgga cacaggcgca ctgcaaccag gcctgcata cttggcgttc ccgctctgtg | 5940 |
| cgctgtcaat ataaccagat aacagatagc aataagaaca gtttaatgag ctgattattt | 6000 |
| ggggcgcgaa tgggagtccg gcaatcctag actcgcccca taagtagcaa acgtccagaa | 6060 |
| gaacaacgcc gctcaggtta attgagcggc gctgtttttt taaaaggatt gtcgcgatta | 6120 |
| aatgccgatc ttacggccca gctgcagccc ggggatcta tgcggtgtga ataccgcac | 6180 |
| agatgcgtaa ggagaaaata ccgcatcagg cgccattcgc cattcaggct gcgcaactgt | 6240 |
| tgggaagggc gatcggtgcg ggcctcttcg ctattacgcc aggacttcat atacccaagc | 6300 |
| ttggaaaatt ttttttaaaa aagtcttgac actttatgct tccggctcgt ataatggatc | 6360 |
| caggagtaac aatacaaatg gattcaagag atccatttgt attgttactc cttttttttt | 6420 |
| ttgtcgacga tccttagcga aagctaagga ttttttttt actcgagcgg attactacat | 6480 |
| acctgcatta atgaatcggc caacgcgcgg ggagaggcgg tttgcgtatt gggcgctctt | 6540 |
| ccgcttcctc gctcactgac tcgctgcgct cggtcgttcg gctgcggcga gcggtatcag | 6600 |
| ctcactcaaa ggcggtaata cggttatcca cagaatcagg ggataacgca ggaaagaaca | 6660 |
| tgtgagcaaa aggccagcaa aaggccagga accgtaaaaa ggccgcgttg ctggcgtttt | 6720 |
| tccataggct ccgcccccct gacgagcatc acaaaaatcg acgctcaagt cagaggtggc | 6780 |
| gaaacccgac aggactataa agataccagg cgtttccccc tggaagctcc ctcgtgcgct | 6840 |
| ctcctgttcc gaccctgccg cttaccggat acctgtccgc ctttctccct cgggaagcg | 6900 |
| tggcgctttc tcatagctca cgctgtaggt atctcagttc ggtgtaggtc gttcgctcca | 6960 |
| agctgggctg tgtgcacgaa ccccccgttc agcccgaccg ctgcgcctta tccggtaact | 7020 |
| atcgtcttga gtccaacccg gtaagacacg acttatcgcc actggcagca gccactggta | 7080 |
| acaggattag cagagcgagg tatgtaggcg gtgctacaga gttcttgaag tggtggccta | 7140 |
| actacggcta cactagaagg acagtatttg gtatctgcgc tctgctgaag ccagttacct | 7200 |
| tcggaaaaag agttggtagc tcttgatccg gcaaacaaac caccgctggt agcggtggtt | 7260 |
| tttttgtttg caagcagcag attacgcgca gaaaaaaagg atctcaagaa gatcctttga | 7320 |
| tcttttctac ggggtctgac gctcagtgga acgaaaactc acgttaaggg attttggtca | 7380 |
| tgatctggta aggttgggaa gccctgcaaa gtaaactgga tggctttctt gccgccaagg | 7440 |
| atctgatggc gcaggggatc aagatctgat caagagacag gatgaggatc gtttcgcatg | 7500 |

```
attgaacaag atggattgca cgcaggttct ccggccgctt gggtggagag gctattcggc    7560
tatgactggg cacaacagac aatcggctgc tctgatgccg ccgtgttccg gctgtcagcg    7620
caggggcgcc cggttctttt tgtcaagacc gacctgtccg gtgccctgaa tgaactgcag    7680
gacgaggcag cgcggctatc gtggctggcc acgacgggcg ttccttgcgc agctgtgctc    7740
gacgttgtca ctgaagcggg aagggactgg ctgctattgg gcgaagtgcc ggggcaggat    7800
ctcctgtcat ctcaccttgc tcctgccgag aaagtatcca tcatggctga tgcaatgcgg    7860
cggctgcata cgcttgatcc ggctacctgc ccattcgacc accaagcgaa acatcgcatc    7920
gagcgagcac gtactcggat ggaagccggt cttgtcgatc aggatgatct ggacgaagag    7980
catcaggggc tcgcgccagc cgaactgttc gccaggctca aggcgcgcat gcccgacggc    8040
gaggatctcg tcgtgaccca tggcgatgcc tgcttgccga atatcatggt ggaaaatggc    8100
cgcttttctg gattcatcga ctgtggccgg ctgggtgtgg cggaccgcta tcaggacata    8160
gcgttggcta cccgtgatat tgctgaagag cttggcggcg aatgggctga ccgcttcctc    8220
gtgctttacg gtatcgccgc tcccgattcg cagcgcatcg ccttctatcg ccttcttgac    8280
gagttcttct gagcgggact ctggggttcg aaatgaccga ccaagcgacg cccaacctgc    8340
catcacgaga tttcgattcc accgccgcct tctatgaaat catgacatta acctataaaa    8400
ataggcgtat cacgaggccc tttcgtc                                         8427

<210> SEQ ID NO 561
<211> LENGTH: 8427
<212> TYPE: DNA
<213> ORGANISM: Artificial Sequence
<220> FEATURE:
<223> OTHER INFORMATION: pMBV44

<400> SEQUENCE: 561
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga cggtatcgat aagcttgata agcttttaaa tcagcagggg tcttttggc     240 ttgtgtatta ttttgaagtt tttcttcccc gacagaatct gcttttaccg tcatagtgaa     300
atgagcctga aaagctatta ccatgatgat acaaataagt ttactttca tttcaccgct     360 cctttttaat tcgtaaaact aagtttaagc cacctacaac taatctgaca gagagagtta     420
aggacacgtt tttagtata tgtgggaact aaattatacg ttttgcagta gaaactatag     480
gtggcttaaa ctttgggata tgcttatatt atatggataa acagtcagat attctttac     540 atttgttaat tcttctaaaa aaattaaaaa ataagcctgt ttctacattc ttcacaaaat     600
aatttacgaa gagtgcaaaa caagcttatt ttttcgtgtg tgttaagcgg ttttattctt     660 aatttttat tacttttaca attattcgat tggattatct actttattac tatatttcgg     720
ataaagcgtg gtgccccaga tggagatatt tctatttttc acaagtggta agttccggtc     780
atcaattacc gttctccacc attcccaagc taaaccagtg cattctttag cgtaaacatt     840
aatatttctc gcgttacctg gcaaatagat ggacgatgtg aaatgagcta gcttgctttt     900
attgttttcg ctccagtttt tatgttgaac aatttcgtta ccttcaggat cataatttac     960
ttcatcccaa gaaatgttga attgagcaac gtatcctcca gagtgatcga tgttaatttt    1020
tccatctgta taagctttg aagttgtttc aatatattct gagttgtttt taataacagc    1080
taattcattg tcttttagga agtttgttgt ataagcaatg ggaactcctg gtgtttctcg    1140
```

-continued

```
attaaaagta gcgccttttt tcaaaatatc gcgtaagtct ccgaggttgc cgtcgatgat    1200
ttgaacttca tcttttgcgg aacctccgta aattacggct ttgaaggaag aatttttgat    1260
gatatttgtt agttctacat cacctgagac agattttccg cttacggcag catcaaaagc    1320
agcttttact ttagtactat gggaattagt tgataatttc aaataaactt gacggccata    1380
cgccacactt gagatatatg caggaggatt ttctgcattc actccaagcg cttgcaactg    1440
ctctttagta acagctttgc cgaaaaatct ggaaggtctt gtaggttcat taacattcac    1500
gttatagtaa atttgtttaa aactaatgac ttcttcttgc attttccctt cactgattgc    1560
gccgaagttt acattcaagc tattatttac agctttaaat gctgtaccaa atttcgcaat    1620
taattgtgat tcactgtaag ccatttcgtc atcataatca attttttgcac ttacatttgg    1680 ataagcttga gcatattttt cattccatct ttccactaat gtatttactg cgttgttaac    1740
gtttgattta gtggcatttt ttacaacgat tttattgtct tgattagtca tacctggcaa    1800
atcaatgctg agtgttaatg aatcacgttt tacagggaga acatctggtt gattttctac    1860
taattccgaa ttcgctttta cgagagcacc tggataggtt aggctcgaaa ttgcattcac    1920
aacttgaatg tctgcattat tttgattgat ggatttcttc ttttttctcca caacaatata    1980 ttcatttcca tctttgtaac cttttcttgg cggcacattt gtcactgcat ctccgtggta    2040
tactaataca ttgtttttat tgtaatccaa tccttgtata tacttatcga tttcatccgc    2100
gtgtttcttt tcgattggcg tcttaggact tgcaggcgga gatgctggtg gtgccatgga    2160
tgaaattgaa ttttcttttat tgaatgcaga tgcatccttt gcttcagttt gttgcgcaat    2220
tggtagacta actaatataa gtgtaataaa aactagcatt attttttca tgggtttcac    2280 tctccttcta catttttaa cctaataatg ccaaataccg tttgccaccc ctctcttttg    2340
ataattataa tattggcgaa attcgcttct aaagatgaaa cgcaatatta tatgcttgct    2400
ttatagcttt attctagtcc tgctgtccct ttatcgtcgt taacaaatgt taatgcctca    2460
acataaaagt cactttaaga taggaatata ctaatcaaag gagggatcga attcctgcag    2520
tcatcaaggc aaccatcagg attaatgcgg atattgcgga gtaacacttc agactgaaag    2580
tagaaataaa aaccgcagca gacaactgac aacatcaaat gaaggggggct tattctaatt    2640 gatattattt atatgataat agttcatttt gtatttttgt ttttttttgat attctcacct    2700 gcttagttac aataaatcaa ttctatcgct gtatggtata gactgtttta ttatatattt    2760
tgaatatttt taatctgccc agtctggttt tttaaaaaag tgctatcctc ttaatgtctt    2820
tactaaatta gaaaacaagt ttcactttca actattgcat cttttaattaa tggtcaaggt    2880 gatttcaaat gctcgtttgt ggccagttat acctcaaata actcaagttg ttgagcacag    2940
ccaacgcaca tgcagtttga cgtatgacag gtatgcttta tttcatttaa attatgatgg    3000
ttttccagcc aatcagtgag tttctcttga taaggaatgc gggaatgtct atgtatttta    3060 ataaataat ttcatttaat attatttcac gaatagttat ttgtatcttt ttgatatgtg    3120
gaatgttcat ggctggggct tcagaaaaat atgatgctaa cgcaccgcaa caggtccagc    3180
cttattctgt ctcttcatct gcatttgaaa atctccatcc taataatgaa atggagagtt    3240
caatcaatcc cttttccgca tcggatacag aaagaaatgc tgcaataata gatcgcgcca    3300
ataaggagca ggagactgaa gcggtgaata agatgataag caccggggcc aggttagctg    3360
catcaggcag ggcatctgat gttgctcact caatggtggg cgatgcggtt aatcaagaaa    3420
tcaaacagtg gttaaatcga ttcggtacgg ctcaagttaa tctgaatttt gacaaaaatt    3480
```

-continued

```
tttcgctaaa agaaagctct cttgattggc tggctccttg gtatgactct gcttcattcc   3540
tcttttttag tcagttaggt attcgcaata aagacagccg caacacactt aaccttggcg   3600
tcgggatacg tacattggag aacggttggc tgtacggact taatactttt tatgataatg   3660
atttgaccgg ccacaaccac cgtatcggtc ttggtgccga ggcctggacc gattatttac   3720
agttggctgc caatgggtat tttcgcctca atggatggca ctcgtcgcgt gatttctccg   3780
actataaaga gcgcccagcc actgggggg atttgcgcgc gaatgctttat ttacctgcac   3840
tcccacaact gggggggaag ttgatgtatg agcaatacac cggtgagcgt gttgctttat   3900
ttggtaaaga taatctgcaa cgcaacccctt atgccgtgac tgccgggatc aattacaccc   3960
ccgtgcctct actcactgtc ggggtagatc agcgtatggg gaaaagcagt aagcatgaaa   4020
cacagtggaa cctccaaatg aactatcgcc tgggcgagag ttttcagtcg caacttagcc   4080
cttcagcggt ggcaggaaca cgtctactgg cggagagccg ctataacctt gtcgatcgta   4140
acaataatat cgtgttggag tatcagaaac agcaggtggt taaactgaca ttatcgccag   4200
caactatctc cggcctgccg ggtcaggttt atcaggtgaa cgcacaagta caaggggcat   4260
ctgctgtaag ggaaattgtc tggagtgatg ccgaactgat tgccgctggc ggcacattaa   4320
caccactgag taccacacaa ttcaacttgg ttttaccgcc ttataaacgc acagcacaag   4380
tgagtcgggt aacggacgac ctgacagcca acttttattc gcttagtgcg ctcgcggttg   4440
atcaccaagg aaaccgatct aactcattca cattgagcgt caccgttcag cagcctcagt   4500
tgacattaac ggcggccgtc attggtgatg gcgcaccggc taatgggaaa actgcaatca   4560
ccgttgagtt caccgttgct gattttgagg ggaaaccctt agccgggcag gaggtggtga   4620
taaccaccaa taatggtgcg ctaccgaata aaatcacgga aaagacagat gcaaatggcg   4680
tcgcgcgcat tgcattaacc aatacgacag atggcgtgac ggtagtcaca gcagaagtgg   4740
aggggcaacg gcaaagtgtt gatacccact ttgttaaggg tactatcgcg gcggataaat   4800
ccactctggc tgcggtaccg acatctatca tcgctgatgg tctaatggct caaccatca   4860
cgttggagtt gaaggatacc tatggggacc cgcaggctgg cgcgaatgtg gcttttgaca   4920
caaccttagg caatatgggc gttatcacgg atcacaatga cggcacttat agcgcaccat   4980
tgaccagtac cacgttgggg gtagcaacag taacggtgaa agtggatggg gctgcgttca   5040
gtgtgccgag tgtgacggtt aatttcacgg cagatcctat tccagatgct ggccgctcca   5100
gtttcaccgt ctccacaccg gatatcttgg ctgatggcac gatgagttcc acattatcct   5160
ttgtccctgt cgataagaat ggccatttta tcagtgggat gcagggcttg agttttactc   5220
aaaacggtgt gccggtgagt attagcccca ttaccgagca gccagatagc tataccgcga   5280
cggtggttgg gaatagtgtc ggtgatgtca caatcacgcc gcaggttgat accctgatac   5340
tgagtacatt gcagaaaaaa atatccctat tcccggtacc tacgctgacc ggtattctgg   5400
ttaacgggca aaatttcgct acggataaag ggttcccgaa aacgatcttt aaaaacgcca   5460
cattccagtt acagatggat aacgatgttg ctaataatac tcagtatgag tggtcgtcgt   5520
cattcacacc caatgtatcg gttaacgatc agggtcaggt gacgattacc taccaaacct   5580
atagcgaagt ggctgtgacg gcgaaaagta aaaaattccc aagttattcg gtgagttatc   5640
ggttctaccc aaatcggtgg atatacgatg gcggcagatc gctggtatcc agtctcgagg   5700
ccagcagaca atgccaaggt tcagatatgt ctgcggttct tgaatcctca cgtgcaacca   5760
acggaacgcg tgcgcctgac gggacattgt ggggcgagtg ggggagcttg accgcgtata   5820
gttctgattg gcaatctggt gaatattggg tcaaaaagac cagcacggat tttgaaacca   5880
```

```
tgaatatgga cacaggcgca ctgcaaccag ggcctgcata cttggcgttc ccgctctgtg    5940
cgctgtcaat ataaccagat aacagatagc aataagaaca gtttaatgag ctgattattt    6000
ggggcgcgaa tgggagtccg gcaatcctag actcgcccca taagtagcaa acgtccagaa    6060
gaacaacgcc gctcaggtta attgagcggc gctgtttttt taaaaggatt gtcgcgatta    6120
aatgccgatc ttacggccca gctgcagccc ggggatcta tgcggtgtga aataccgcac    6180
agatgcgtaa ggagaaaata ccgcatcagg cgccattcgc cattcaggct gcgcaactgt    6240
tgggaagggc gatcggtgcg ggcctcttcg ctattacgcc aggacttcat atacccaagc    6300
ttggaaaatt ttttttaaaa aagtcttgac actttatgct tccggctcgt ataatggatc    6360
caggagtaac aatacaaatg gattcaagag atccatttgt attgttactc ctttttttt    6420 ttgtcgacga tccttagcga aagctaagga ttttttttt actcgagcgg attactacat    6480
acctgcatta atgaatcggc caacgcgcgg ggagaggcgg tttgcgtatt gggcgctctt    6540
ccgcttcctc gctcactgac tcgctgcgct cggtcgttcg gctgcggcga gcggtatcag    6600
ctcactcaaa ggcggtaata cggttatcca cagaatcagg gataacgca ggaaagaaca    6660 tgtgagcaaa aggccagcaa aaggccagga accgtaaaaa ggccgcgttg ctggcgtttt    6720
tccataggct ccgccccct gacgagcatc acaaaaatcg acgctcaagt cagaggtggc    6780
gaaacccgac aggactataa agataccagg cgtttccccc tggaagctcc ctcgtgcgct    6840
ctcctgttcc gaccctgccg cttaccggat acctgtccgc ctttctccct cgggaagcg    6900 tggcgctttc tcatagctca cgctgtaggt atctcagttc ggtgtaggtc gttcgctcca    6960
agctgggctg tgtgcacgaa ccccccgttc agcccgaccg ctgcgcctta ccggtaact    7020 atcgtcttga gtccaacccg gtaagacacg acttatcgcc actggcagca gccactggta    7080
acaggattag cagagcgagg tatgtaggcg gtgctacaga gttcttgaag tggtggccta    7140
actacggcta cactagaagg acagtatttg gtatctgcgc tctgctgaag ccagttacct    7200
tcggaaaaag agttggtagc tcttgatccg gcaaacaaac caccgctggt agcggtggtt    7260
tttttgtttg caagcagcag attacgcgca gaaaaaaagg atctcaagaa gatcctttga    7320
tcttttctac ggggtctgac gctcagtgga acgaaaactc acgttaaggg attttggtca    7380
tgatttcata aaggcggcg gtggaatcga atctcgtga tggcaggttg ggcgtcgctt    7440
ggtcggtcat ttcgaacccc agagtcccgc tcagaagaac tcgtcaagaa ggcgatagaa    7500
ggcgatgcgc tgcgaatcgg gagcggcgat accgtaaagc acgaggaagc ggtcagccca    7560
ttcgccgcca agctcttcag caatatcacg ggtagccaac gctatgtcct gatagcggtc    7620
cgccacaccc agccggccac agtcgatgaa tccagaaaag cggcccatttt ccaccatgat    7680 attcggcaag caggcatcgc catgggtcac gacgagatcc tcgccgtcgg catgcgcgc    7740 cttgagcctg gcgaacagtt cggctggcgc gagcccctga tgctcttcgt ccagatcatc    7800
ctgatcgaca gaccggctt ccatccgagt acgtgctcgc tcgatgcgat gtttcgcttg    7860
gtggtcgaat gggcaggtag ccggatcaag cgtatgcagc cgccgcattg catcagccat    7920
gatggatact ttctcggcag gagcaaggtg agatgacagg agatcctgcc ccggcacttc    7980
gcccaatagc agccagtccc ttcccgcttc agtgacaacg tcgagcacag ctgcgcaagg    8040
aacgcccgtc gtggccagcc acgatagccg cgctgcctcg tcctgcagtt cattcagggc    8100
accggacagg tcggtcttga caaaaagaac cgggcgcccc tgcgctgaca gccgaacac    8160 ggcggcatca gagcagccga ttgtctgttg tgcccagtca tagccgaata gcctctccac    8220
```

| | |
|---|---:|
| ccaagcggcc ggagaacctg cgtgcaatcc atcttgttca atcatgcgaa acgatcctca | 8280 |
| tcctgtctct tgatcagatc ttgatcccct gcgccatcag atccttggcg gcaagaaagc | 8340 |
| catccagttt actttgcagg gcttcccaac cttaccagat catgacatta acctataaaa | 8400 |
| ataggcgtat cacgaggccc tttcgtc | 8427 |

<210> SEQ ID NO 562
<211> LENGTH: 18936
<212> TYPE: DNA
<213> ORGANISM: Artificial Sequence
<220> FEATURE:
<223> OTHER INFORMATION: pNJSZc

<400> SEQUENCE: 562

| | |
|---|---:|
| ggccgctcga gcatgcatct agagggccca attcgcccta tagtgagtcg tattacaatt | 60 |
| cactggccgt cgttttacaa cgtcgtgact gggaaaaccc tggcgttacc caacttaatc | 120 |
| gccttgcagc acatccccct ttcgccagct ggcgtaatag cgaagaggcc cgcaccgatc | 180 |
| gcccttccca acagttgcgc agcctgaaaa accgcgccat ggtgtgtagg ctggagctgc | 240 |
| ttcgaagttc ctatactttc tagagaatag gaacttcgga ataggaactt caagatcccc | 300 |
| cacgctgccg caagcactca gggcgcaagg gctgctaaag gaaacggaac acgtagaaag | 360 |
| ccagtccgca gaaacggtgc tgaccccgga tgaatgtcag ctactgggct atctggacaa | 420 |
| gggaaaacgc aagcgcaaag agaaagcagg tagcttgcag tgggcttaca tggcgatagc | 480 |
| tagactgggc ggttttatgg acagcaagcg aaccggaatt gccagctggg gcgccctctg | 540 |
| gtaaggttgg gaagccctgc aaagtaaact ggatggcttt cttgccgcca aggatctgat | 600 |
| ggcgcagggg atcaagatct gatcaagaga caggatgagg atcgtttcgc atgattgaac | 660 |
| aagatggatt gcacgcaggt tctccggccg cttgggtgga gaggctattc ggctatgact | 720 |
| gggcacaaca gacaatcggc tgctctgatg ccgccgtgtt ccggctgtca gcgcagggggc | 780 |
| gcccggttct ttttgtcaag accgacctgt ccggtgccct gaatgaactg caggacgagg | 840 |
| cagcgcggct atcgtggctg gccacgacgg gcgttccttg cgcagctgtg ctcgacgttg | 900 |
| tcactgaagc gggaagggac tggctgctat tgggcgaagt gccggggcag gatctcctgt | 960 |
| catctcacct tgctcctgcc gagaaagtat ccatcatggc tgatgcaatg cggcggctgc | 1020 |
| atacgcttga tccggctacc tgcccattcg accaccaagc gaaacatcgc atcgagcgag | 1080 |
| cacgtactcg gatggaagcc ggtcttgtcg atcaggatga tctggacgaa gagcatcagg | 1140 |
| ggctcgcgcc agccgaactg ttcgccaggc tcaaggcgcg catgcccgac ggcgaggatc | 1200 |
| tcgtcgtgac ccatggcgat gcctgcttgc cgaatatcat ggtggaaaat ggccgctttt | 1260 |
| ctggattcat cgactgtggc cggctgggtg tggcggaccg ctatcaggac atagcgttgg | 1320 |
| ctacccgtga tattgctgaa gagcttggcg gcgagtgggc tgaccgcttc ctcgtgcttt | 1380 |
| acggtatcgc cgctcccgat tcgcagcgca tcgccttcta tcgccttctt gacgagttct | 1440 |
| tctgagcggg actctggggt tcgaaatgac cgaccaagcg acgcccaacc tgccatcacg | 1500 |
| agatttcgat tccaccgccg ccttctatga aggttgggc ttcggaatcg ttttccggga | 1560 |
| cgccggctgg atgatcctcc agcgcgggga tctcatgctg gagttcttcg cccacccccag | 1620 |
| cttcaaaagc gctctgaagt tcctatactt tctagagaat aggaacttcg gaataggaac | 1680 |
| taaggaggat attcatatgg accatggcgc ggcatgcaag ctcggtatca ttgcagcact | 1740 |
| ggggccagat ggtaagccct cccgtatcgt agttatctac acgacgggga gtcaggcaac | 1800 |
| tatggatgaa cgaaatagac agatcgctga gataggtgcc tcactgatta gcattggta | 1860 |

```
actgtcagac caagtttact catatatact ttagattgat ttaaaacttc atttttaatt   1920
taaaaggatc taggtgaaga tccttttga taatctcatg accaaaatcc cttaacgtga    1980
gttttcgttc cactgagcgt cagaccccgt agaaaagatc aaaggatctt cttgagatcc   2040 ttttttctg cgcgtaatct gctgcttgca acaaaaaaa ccaccgctac cagcggtggt     2100
ttgtttgccg gatcaagagc taccaactct ttttccgaag gtaactggct tcagcagagc   2160
gcagatacca aatactgttc ttctagtgta gccgtagtta ggccaccact tcaagaactc   2220
tgtagcaccg cctacatacc tcgctctgct aatcctgtta ccagtggctg ctgccagtgg   2280
cgataagtcg tgtcttaccg ggttggactc aagacgatag ttaccggata aggcgcagcg   2340
gtcgggctga acggggggtt cgtgcacaca gcccagcttg gagcgaacga cctacaccga   2400
actgagatac ctacagcgtg agctatgaga aagcgccacg cttcccgaag ggagaaaggc   2460
ggacaggtat ccggtaagcg gcagggtcgg aacaggagag cgcacgaggg agcttccagg   2520
gggaaacgcc tggtatcttt atagtcctgt cgggtttcgc cacctctgac ttgagcgtcg   2580
atttttgtga tgctcgtcag ggggcggag cctatggaaa aacgccagca acgcggcctt    2640
tttacggttc ctggccttt gctggccttt tgctcacatg ttctttcctg cgttatcccc    2700
tgattctgtg gataaccgta ttaccgcctt tgagtgagct gataccgctc gccgcagccg   2760
aacgaccgag cgcagcgagt cagtgagcga ggaagcggaa gagcgcccaa tacgcaaacc   2820
gcctctcccc gcgcgttggc cgattcatta atgcagctgg cacgacagta tcgataagct   2880
tgataagctt ttaaatcagc agggg tcttt ttggcttgtg tattattttg aagttttcct  2940
tccccgacag aatctgcttt taccgtcata gtgaaatgag cctgaaaagc tattaccatg   3000
atgatacaaa taagtttact tttcatttca ccgctccttt ttaattcgta aaactaagtt   3060
taagccacct acaactaatc tgacagagag agttaaggac acgttttta gtatatgtgg    3120 gaactaaatt atacgttttg cagtagaaac tataggtggc ttaaactttg ggatatgctt   3180
atattatatg gataaacagt cagatattct tttacatttg ttaattcttc taaaaaaatt   3240
aaaaaataag cctgtttcta cattcttcac aaaataattt acgaagagtg caaaacaagc   3300
ttattttttc gtgtgtgtta agcggttta ttcttaattt tttattactt ttacaattat    3360
tcgattggat tatctacttt attactatat ttcggataaa gcgtggtgcc ccagatggag   3420
atatttctat ttttcacaag tggtaagttc cggtcatcaa ttaccgttct ccaccattcc   3480
caagctaaac cagtgcattc tttagcgtaa acattaatat ttctcgcgtt acctggcaaa   3540
tagatggacg atgtgaaatg agctagcttg cttttattgt tttcgctcca gttttatgt    3600 tgaacaattt cgttaccttc aggatcataa tttacttcat cccaagaaat gttgaattga   3660
gcaacgtatc ctccagagtg atcgatgtta attttccat ctgtataagc ttttgaagtt    3720
gtttcaatat attctgagtt gttttaata acagctaatt cattgtcttt taggaagttt    3780
gttgtataag caatgggaac tcctggtgtt ctcgattaa aagtagcgcc ttttttcaaa    3840
atatcgcgta agtctccgag gttgccgtcg atgatttgaa cttcatcttt tgcggaacct   3900
ccgtaaatta cggctttgaa ggaagaattt ttgatgtat ttgttagttc tacatcacct    3960
gagacagatt ttccgcttac ggcagcatca aaagcagctt ttactttagt actatgggaa   4020
ttagttgata atttcaaata aacttgacgg ccatacgcca cacttgagat atatgcagga   4080
ggattttctg cattcactcc aagcgcttgc aactgctctt tagtaacagc tttgccgaaa   4140
aatctggaag gtcttgtagg ttcattaaca ttcacgttat agtaaatttg tttaaaacta   4200
```

```
atgacttctt cttgcatttt cccttcactg attgcgccga agtttacatt caagctatta    4260
tttacagctt taaatgctgt accaaatttc gcaattaatt gtgattcact gtaagccatt    4320
tcgtcatcat aatcaatttt tgcacttaca tttggataag cttgagcata ttttttcattc   4380
catctttcca ctaatgtatt tactgcgttg ttaacgtttg atttagtggc attttttaca    4440
acgattttat tgtcttgatt agtcatacct ggcaaatcaa tgctgagtgt taatgaatca   4500
cgttttacag ggagaacatc tggttgattt tctactaatt ccgaattcgc ttttacgaga    4560
gcacctggat aggttaggct cgaaattgca ttcacaactt gaatgtctgc attattttga    4620
ttgatggatt tcttcttttt ctccacaaca atatattcat ttccatcttt gtaaccttt     4680
cttggcggca catttgtcac tgcatctccg tggtatacta atacattgtt tttattgtaa    4740
tccaatcctt gtatatactt atcgatttca tccgcgtgtt tcttttcgat tggcgtctta    4800
ggacttgcag gcggagatgc tggtggtgcc atggatgaaa ttgaattttc tttattgaat    4860
gcagatgcat cctttgcttc agtttgttgc gcaattggta gactaactaa tataagtgta    4920
ataaaaacta gcattatttt tttcatgggt ttcactctcc ttctacattt tttaacctaa    4980
taatgccaaa taccgtttgc caccctctc ttttgataat tataatattg gcgaaattcg     5040
cttctaaaga tgaaacgcaa tattatatgc ttgctttata gctttattct agtcctgctg    5100
tcccttatc gtcgttaaca aatgttaatg cctcaacata aaagtcactt taagatagga     5160
atatactaat caaggagggg atcgaattcc tgcagtcatc aaggcaacca tcaggattaa    5220
tgcggatatt gcggagtaac acttcagact gaaagtagaa ataaaaccg cagcagacaa     5280
ctgacaacat caaatgaagg gggcttattc taattgatat tatttatatg ataatagttc    5340
attttgtatt ttgttttttt gatattctca cctgcttagt tacaataaat caattctatc    5400
gctgtatggt atagactgtt ttattatata ttttgaatat ttttaatctg cccagtctgg    5460
ttttttaaaa aagtgctatc ctcttaatgt ctttactaaa ttagaaaaca gtttcacttt   5520
tcaactattg catctttaat taatggtcaa ggtgatttca aatgctcgtt tgtgccagt     5580
tatacctcaa ataactcaag ttgttgagca cagccaacgc acatgcagtt tgacgtatga    5640
caggtatgct ttatttcatt taaattatga tggttttcca gccaatcagt gagtttctct    5700
tgataaggaa tgcgggaatg tctatgtatt ttaataaaat aatttcattt aatattattt    5760
cacgaatagt tatttgtatc ttttttgatat gtggaatgtt catggctggg gcttcagaaa   5820
aatatgatgc taacgcaccg caacaggtcc agccttattc tgtctcttca tctgcatttg    5880
aaaatctcca tcctaataat gaaatggaga gttcaatcaa tcccttttcc gcatcggata    5940
cagaaagaaa tgctgcaata atagatcgcg ccaataagga gcaggagact gaagcggtga    6000
ataagatgat aagcaccggg gccaggttag ctgcatcagg cagggcatct gatgttgctc    6060
actcaatggt gggcgatgcg gttaatcaag aaatcaaaca gtggttaaat cgattcggta    6120
cggctcaagt taatctgaat tttgacaaaa atttttcgct aaaagaaagc tctcttgatt    6180
ggctggctcc ttggtatgac tctgcttcat tcctcttttt tagtcagtta ggtattcgca    6240
ataaagacag ccgcaacaca cttaaccttg gcgtcgggat acgtacattg gagaacggtt    6300
ggctgtacgg acttaatact ttttatgata atgatttgac cggccacaac caccgtatcg    6360
gtcttggtgc cgaggcctgg accgattatt tacagttggc tgccaatggg tatttttcgcc   6420
tcaatggatg gcactcgtcg cgtgattct ccgactataa agagcgccca gccactgggg    6480
gggatttgcg cgcgaatgct tatttacctg cactcccaca actggggggg aagttgatgt    6540
atgagcaata caccggtgag cgtgttgctt tatttggtaa agataatctg caacgcaacc    6600
```

```
cttatgccgt gactgccggg atcaattaca cccccgtgcc tctactcact gtcggggtag    6660
atcagcgtat ggggaaaagc agtaagcatg aaacacagtg gaacctccaa atgaactatc    6720
gcctgggcga gagttttcag tcgcaactta gcccttcagc ggtggcagga acacgtctac    6780
tggcggagag ccgctataac cttgtcgatc gtaacaataa tatcgtgttg gagtatcaga    6840
aacagcaggt ggttaaactg acattatcgc cagcaactat ctccggcctg ccgggtcagg    6900
tttatcaggt gaacgcacaa gtacaagggg catctgctgt aagggaaatt gtctggagtg    6960
atgccgaact gattgccgct ggcggcacat aacaccact gagtaccaca caattcaact     7020
tggttttacc gccttataaa cgcacagcac aagtgagtcg ggtaacggac gacctgacag    7080 ccaacttta ttcgcttagt gcgctcgcgg ttgatcacca aggaaaccga tctaactcat      7140
tcacattgag cgtcaccgtt cagcagcctc agttgacatt aacggcggcc gtcattggtg    7200
atggcgcacc ggctaatggg aaaactgcaa tcaccgttga gttcaccgtt gctgattttg    7260
agggaaaacc cttagccggg caggaggtgg tgataaccac caataatggt gcgctaccga    7320
ataaaatcac ggaaaagaca gatgcaaatg gcgtcgcgcg cattgcatta accaatacga    7380
cagatggcgt gacggtagtc acagcagaag tggaggggca acggcaaagt gttgataccc    7440
actttgttaa gggtactatc gcggcggata aatccactct ggctgcggta ccgacatcta    7500
tcatcgctga tggtctaatg gcttcaacca tcacgttgga gttgaaggat acctatgggg    7560
acccgcaggc tggcgcgaat gtggcttttg acacaacctt aggcaatatg ggcgttatca    7620
cggatcacaa tgacggcact tatagcgcac cattgaccag taccacgttg ggggtagcaa    7680
cagtaacggt gaaagtggat ggggctgcgt tcagtgtgcc gagtgtgacg gttaatttca    7740
cggcagatcc tattccagat gctggccgct ccagtttcac cgtctccaca ccggatatct    7800
tggctgatgg cacgatgagt tccacattat cctttgtccc tgtcgataag aatggccatt    7860
ttatcagtgg gatgcaggc ttgagttta ctcaaaacgg tgtgccggtg agtattagcc        7920
ccattaccga gcagccagat agctataccg cgacggtggt tgggaatagt gtcggtgatg    7980
tcacaatcac gccgcaggtt gataccctga tactgagtac attgcagaaa aaatatcccc    8040
tattcccggt acctacgctg accggtattc tggttaacgg gcaaaatttc gctacggata    8100
aagggttccc gaaaacgatc tttaaaaacg ccacattcca gttacagatg gataacgatg    8160
ttgctaataa tactcagtat gagtggtcgt cgtcattcac acccaatgta tcggttaacg    8220
atcagggtca ggtgacgatt acctaccaaa cctatagcga agtggctgtg acggcgaaaa    8280
gtaaaaaatt cccaagttat tcggtgagtt atcggttcta cccaaatcgg tggatatacg    8340
atggcggcag atcgctggta tccagtctcg aggccagcag acaatgccaa ggttcagata    8400
tgtctgcggt tcttgaatcc tcacgtgcaa ccaacggaac gcgtgcgcct gacgggacat    8460
tgtggggcga gtggggagc ttgaccgcgt atagttctga ttggcaatct ggtgaatatt     8520
gggtcaaaaa gaccagcacg gattttgaaa ccatgaatat ggacacaggc gcactgcaac    8580
cagggcctgc atacttggcg ttcccgctct gtgcgctgtc aatataacca gataacagat    8640
agcaataaga acagtttaat gagctgatta tttgggggcgc gaatgggagt ccggcaatcc    8700
tagactcgcc ccataagtag caaacgtcca gagaacaacg ccgctcaggt taattgagcg    8760
gcgttgtttt tttaaaagga tttgtcgcga taagcgtgag ctggcgttaa atgccgatct    8820 tacgcccag ctgcagcccg gctagtaacg gccgccagtg tgctgaatt cgcccttaat      8880 cggcatcatt caccaagctt gccaggcgac tgtcttcaat attacagccg caactactga    8940
```

| | |
|---|---|
| catggcgggt gatggtgttc actattccag ggcgatcggc acccaacgca gtgatcacca | 9000 |
| gataatgttg cgatgacagt gtcaaactgg ttattccttc aagggtgag ttgttcttaa | 9060 |
| gcatgccggt ttgctgtaaa gtttagggag atttgatggc ttactctgtt caaaagtcgc | 9120 |
| gcctggcaaa ggttgcggt gtttcgcttg ttttattact cgctgcctgt agttctgact | 9180 |
| cacgctataa gcgtcaggtc agtggtgatg aagcctacct ggaagcgcca tggcatgcaa | 9240 |
| gggcgaattc tgcagatatc catcacactg gcggccctag accaggcttt acactttatg | 9300 |
| cttccggctc gtataatgtg tggaaggatc caggagtaac aatacaaatg gattcaagag | 9360 |
| atccatttgt attgttactc ctttgtcgac tggacagttc aagagactgt ccatcaatat | 9420 |
| cagctttgtc acaaccccg ccaccggcgg gttttttttc tgctctaggg ccgctcgagc | 9480 |
| atgcatctag agggcccaat tcgccctata gtgagtcgta ttacaattca ctggccgtcg | 9540 |
| ttttacaacg tcgtgactgg gaaaaccctg gcgttaccca acttaatcgc cttgcagcac | 9600 |
| atccccctt cgccagctgg cgtaatagcg aagaggcccg caccgatcgc ccttcccaac | 9660 |
| agttgcgcag cctgaaaaac gcgccatgg tgtgtaggct ggagctgctt cgaagttcct | 9720 |
| atactttcta gagaatagga acttcggaat aggaacttca agatccccca cgctgccgca | 9780 |
| agcactcagg gcgcaagggc tgctaaagga acggaacac gtagaaagcc agtccgcaga | 9840 |
| aacggtgctg accccggatg aatgtcagct actgggctat ctggacaagg gaaaacgcaa | 9900 |
| gcgcaaagag aaagcaggta gcttgcagtg ggcttacatg gcgatagcta gactgggcgg | 9960 |
| ttttatggac agcaagcgaa ccggaattgc cagctggggc gccctctggt aaggttggga | 10020 |
| agccctgcaa agtaaactgg atggctttct gccgccaag gatctgatgg cgcaggggat | 10080 |
| caagatctga tcaagagaca ggatgaggat cgtttcgcat gattgaacaa gatggattgc | 10140 |
| acgcaggttc tccggccgct tgggtggaga ggctattcgg ctatgactgg gcacaacaga | 10200 |
| caatcggctg ctctgatgcc gccgtgttcc ggctgtcagc gcagggcgc ccggttcttt | 10260 |
| ttgtcaagac cgacctgtcc ggtgccctga atgaactgca ggacgaggca gcgcggctat | 10320 |
| cgtggctggc cacgacgggc gttccttgcg cagctgtgct cgacgttgtc actgaagcgg | 10380 |
| gaagggactg gctgctattg ggcgaagtgc cggggcagga tctcctgtca tctcaccttg | 10440 |
| ctcctgccga gaaagtatcc atcatggctg atgcaatgcg gcggctgcat acgcttgatc | 10500 |
| cggctacctg cccattcgac caccaagcga aacatcgcat cgagcgagca cgtactcgga | 10560 |
| tggaagccgg tcttgtcgat caggatgatc tggacgaaga gcatcagggg ctcgcgccag | 10620 |
| ccgaactgtt cgccaggctc aaggcgcgca tgcccgacgg cgaggatctc gtcgtgaccc | 10680 |
| atggcgatgc ctgcttgccg aatatcatgg tggaaaatgg ccgcttttct ggattcatcg | 10740 |
| actgtggccg gctgggtgtg gcggaccgct atcaggacat agcgttggct acccgtgata | 10800 |
| ttgctgaaga gcttggcggc gagtgggctg accgcttcct cgtgctttac ggtatcgccg | 10860 |
| ctcccgattc gcagcgcatc gccttctatc gccttcttga cgagttcttc tgagcgggac | 10920 |
| tctggggttc gaaatgaccg accaagcgac gcccaacctg ccatcacgag atttcgattc | 10980 |
| caccgccgcc ttctatgaaa ggttgggctt cggaatcgtt ttccgggacg ccggctggat | 11040 |
| gatcctccag cgcggggatc tcatgctgga gttcttcgcc cacccagct tcaaaagcgc | 11100 |
| tctgaagttc ctatactttc tagagaatag gaacttcgga ataggaacta aggaggatat | 11160 |
| tcatatggac catggcgcgg catgcaagct cggtatcatt gcagcactgg ggccagatgg | 11220 |
| taagccctcc cgtatcgtag ttatctacac gacggggagt caggcaacta tggatgaacg | 11280 |
| aaatagacag atcgctgaga taggtgcctc actgattaag cattggtaac tgtcagacca | 11340 |

```
agtttactca tatatacttt agattgattt aaaacttcat ttttaattta aaaggatcta   11400
ggtgaagatc cttttgata atctcatgac caaaatccct taacgtgagt tttcgttcca   11460
ctgagcgtca gaccccgtag aaaagatcaa aggatcttct tgagatcctt tttttctgcg   11520
cgtaatctgc tgcttgcaaa caaaaaaacc accgctacca gcggtggttt gtttgccgga   11580
tcaagagcta ccaactcttt ttccgaaggt aactggcttc agcagagcgc agataccaaa   11640
tactgttctt ctagtgtagc cgtagttagg ccaccacttc aagaactctg tagcaccgcc   11700 tacataccte getctgctaa teetgttace agtggctgct gecagtggeg ataagtegtg   11760 tcttaccggg ttggactcaa gacgatagtt accggataag gcgcagcggt cgggctgaac   11820 gggggggttcg tgcacacagc ccagcttgga gcgaacgacc tacaccgaac tgagatacct   11880
acagcgtgag ctatgagaaa gcgccacgct tcccgaaggg agaaaggcgg acaggtatcc   11940
ggtaagcggc agggtcggaa caggagagcg cacgagggag cttccagggg gaaacgcctg   12000
gtatctttat agtcctgtcg ggtttcgcca cctctgactt gagcgtcgat ttttgtgatg   12060
ctcgtcaggg gggcggagcc tatggaaaaa cgccagcaac gcggcctttt tacggttcct   12120
ggccttttgc tggccttttg ctcacatgtt ctttcctgcg ttatcccctg attctgtgga   12180
taaccgtatt accgcctttg agtgagctga taccgctcgc cgcagccgaa cgaccgagcg   12240
cagcgagtca gtgagcgagg aagcggaaga gcgcccaata cgcaaaccgc ctctccccgc   12300
gcgttggccg attcattaat gcagctggca cgacagtatc gataagcttg ataagctttt   12360
aaatcagcag gggtcttttt ggcttgtgta ttattttgaa gtttttcttc cccgacagaa   12420
tctgctttta ccgtcatagt gaaatgagcc tgaaaagcta ttaccatgat gatacaaata   12480
agtttacttt tcatttcacc gctccttttt aattcgtaaa actaagttta agccacctac   12540
aactaatctg acagagagag ttaaggacac gttttttagt atatgtggga actaaattat   12600
acgttttgca gtagaaacta taggtggctt aaacttgggg atatgcttat attatatgga   12660
taaacagtca gatattcttt tacatttgtt aattcttcta aaaaaattaa aaaataagcc   12720
tgtttctaca ttcttcacaa aataatttac gaagagtgca aaacaagctt attttttcgt   12780
gtgtgttaag cggttttatt cttaattttt tattactttt acaattattc gattggatta   12840
tctactttat tactatattt cggataaagc gtggtgcccc agatggagat atttctattt   12900
ttcacaagtg gtaagttccg gtcatcaatt accgttctcc accattccca agctaaacca   12960
gtgcattctt tagcgtaaac attaatattt ctcgcgttac ctggcaaata gatggacgat   13020
gtgaaatgag ctagcttgct tttattgttt tcgctccagt ttttatgttg aacaatttcg   13080
ttaccttcag gatcataatt tacttcatcc caagaaatgt tgaattgagc aacgtatcct   13140
ccagagtgat cgatgttaat ttttccatct gtataagctt ttgaagttgt ttcaatatat   13200
tctgagttgt ttttaataac agctaattca ttgtctttta ggaagtttgt tgtataagca   13260
atgggaactc ctggtgtttc tcgattaaaa gtagcgcctt ttttcaaaat atcgcgtaag   13320
tctccgaggt tgccgtcgat gatttgaact tcatcttttg cggaacctcc gtaaattacg   13380
gctttgaagg aagaattttt gatgatattt gttagttcta catcacctga gacagatttt   13440
ccgcttacgg cagcatcaaa agcagctttt actttagtac tatgggaatt agttgataat   13500
ttcaaataaa cttgacggcc atacgccaca cttgagatat atgcaggagg atttctgca   13560 ttcactccaa gcgcttgcaa ctgctcttta gtaacagctt tgccgaaaaa tctggaaggt   13620
cttgtaggtt cattaacatt cacgttatag taaatttgtt taaaactaat gacttcttct   13680
```

```
tgcattttcc cttcactgat tgcgccgaag tttacattca agctattatt tacagcttta    13740
aatgctgtac caaatttcgc aattaattgt gattcactgt aagccatttc gtcatcataa    13800 tcaattttg  cacttacatt tggataagct tgagcatatt tttcattcca tctttccact    13860
aatgtattta ctgcgttgtt aacgtttgat ttagtggcat tttttacaac gattttattg    13920
tcttgattag tcatacctgg caaatcaatg ctgagtgtta atgaatcacg ttttacaggg    13980
agaacatctg gttgattttc tactaattcc gaattcgctt ttacgagagc acctggatag    14040
gttaggctcg aaattgcatt cacaacttga atgtctgcat tattttgatt gatggatttc    14100 ttcttttttct ccacaacaat atattcattt ccatctttgt aaccttttct tggcggcaca    14160
tttgtcactg catctccgtg gtatactaat acattgtttt tattgtaatc caatccttgt    14220
atatacttat cgatttcatc cgcgtgtttc ttttcgattg gcgtcttagg acttgcaggc    14280
ggagatgctg gtggtgccat ggatgaaatt gaattttctt tattgaatgc agatgcatcc    14340
tttgcttcag tttgttgcgc aattggtaga ctaactaata taagtgtaat aaaaactagc    14400 attattttt  tcatgggttt cactctcctt ctacatttt  taacctaata atgccaaata    14460
ccgtttgcca cccctctctt ttgataatta taatattggc gaaattcgct tctaaagatg    14520
aaacgcaata ttatatgctt gctttatagc tttattctag tcctgctgtc cctttatcgt    14580
cgttaacaaa tgttaatgcc tcaacataaa agtcacttta agataggaat atactaatca    14640
aaggagggat cgaattcctg cagtcatcaa ggcaaccatc aggattaatg cggatattgc    14700
ggagtaacac ttcagactga aagtagaaat aaaaaccgca gcagacaact gacaacatca    14760
aatgaagggg gcttattcta attgatatta tttatatgat aatagttcat tttgtatttt    14820
gtttttttga tattctcacc tgcttagtta caataaatca attctatcgc tgtatggtat    14880
agactgtttt attatatatt ttgaatattt ttaatctgcc cagtctggtt ttttaaaaaa    14940
gtgctatcct cttaatgtct ttactaaatt agaaaacaag tttcactttc aactattgca    15000
tctttaatta atggtcaagg tgatttcaaa tgctcgtttg tggccagtta tacctcaaat    15060
aactcaagtt gttgagcaca gccaacgcac atgcagtttg acgtatgaca ggtatgcttt    15120
atttcattta aattatgatg gttttccagc caatcagtga gtttctcttg ataaggaatg    15180
cgggaatgtc tatgtatttt aataaaataa tttcatttaa tattatttca cgaatagtta    15240
tttgtatctt tttgatatgt ggaatgttca tggctggggc ttcagaaaaa tatgatgcta    15300
acgcaccgca acaggtccag ccttattctg tctcttcatc tgcatttgaa aatctccatc    15360
ctaataatga aatggagagt tcaatcaatc ccttttccgc atcggataca gaaagaaatg    15420
ctgcaataat agatcgcgcc aataaggagc aggagactga agcggtgaat aagatgataa    15480
gcaccggggc caggttagct gcatcaggca gggcatctga tgttgctcac tcaatggtgg    15540
gcgatgcggt taatcaagaa atcaaacagt ggttaaatcg attcggtacg gctcaagtta    15600 atctgaatttt tgacaaaaat ttttcgctaa aagaaagctc tcttgattgg ctggctcctt    15660
ggtatgactc tgcttcattc ctcttttta  gtcagttagg tattcgcaat aaagacagcc    15720
gcaacacact taaccttggc gtcgggatac gtacattgga gaacggttgg ctgtacggac    15780
ttaatacttt ttatgataat gatttgaccg gccacaacca ccgtatcggt cttggtgccg    15840
aggcctggac cgattattta cagttggctg ccaatgggta ttttcgcctc aatggatggc    15900
actcgtcgcg tgatttctcc gactataaag agcgcccagc cactgggggg gatttgcgcg    15960
cgaatgctta tttacctgca ctcccacaac tgggggggaa gttgatgtat gagcaataca    16020
ccggtgagcg tgttgcttta tttggtaaag ataatctgca acgcaaccct tatgccgtga    16080
```

```
ctgccgggat caattacacc cccgtgcctc tactcactgt cggggtagat cagcgtatgg    16140
ggaaaagcag taagcatgaa acacagtgga acctccaaat gaactatcgc ctgggcgaga    16200
gttttcagtc gcaacttagc ccttcagcgg tggcaggaac acgtctactg gcggagagcc    16260
gctataacct tgtcgatcgt aacaataata tcgtgttgga gtatcagaaa cagcaggtgg    16320
ttaaactgac attatcgcca gcaactatct ccggcctgcc gggtcaggtt tatcaggtga    16380
acgcacaagt acaaggggca tctgctgtaa gggaaattgt ctggagtgat gccgaactga    16440
ttgccgctgg cggcacatta acaccactga gtaccacaca attcaacttg gttttaccgc    16500
cttataaacg cacagcacaa gtgagtcggg taacggacga cctgacagcc aactttttatt   16560 cgcttagtgc gctcgcggtt gatcaccaag gaaaccgatc taactcattc acattgagcg    16620
tcaccgttca gcagcctcag ttgacattaa cggcggccgt cattggtgat ggcgcaccgg    16680
ctaatgggaa aactgcaatc accgttgagt tcaccgttgc tgattttgag gggaaaccct    16740
tagccgggca ggaggtggtg ataaccacca ataatggtgc gctaccgaat aaaatcacgg    16800
aaaagacaga tgcaaatggc gtcgcgcgca ttgcattaac caatacgaca gatggcgtga    16860
cggtagtcac agcagaagtg gaggggcaac ggcaaagtgt tgatacccac tttgttaagg    16920
gtactatcgc ggcggataaa tccactctgg ctgcggtacc gacatctatc atcgctgatg    16980
gtctaatggc ttcaaccatc acgttggagt tgaaggatac ctatgggac ccgcaggctg     17040 gcgcgaatgt ggcttttgac acaaccttag gcaatatggg cgttatcacg gatcacaatg    17100
acggcactta tagcgcacca ttgaccagta ccacgttggg ggtagcaaca gtaacggtga    17160
aagtggatgg ggctgcgttc agtgtgccga gtgtgacggt taatttcacg gcagatccta    17220
ttccagatgc tggccgctcc agtttcaccg tctccacacc ggatatcttg gctgatggca    17280
cgatgagttc cacattatcc tttgtccctg tcgataagaa tggccatttt atcagtggga    17340
tgcagggctt gagttttact caaaacggtg tgccggtgag tattagcccc attaccgagc    17400
agccagatag ctataccgcg acggtggttg ggaatagtgt cggtgatgtc acaatcacgc    17460
cgcaggttga taccctgata ctgagtacat tgcagaaaaa aatatcccta ttcccggtac    17520
ctacgctgac cggtattctg gttaacgggc aaaatttcgc tacggataaa gggttcccga    17580
aaacgatctt taaaaacgcc acattccagt tacagatgga taacgatgtt gctaataata    17640
ctcagtatga gtggtcgtcg tcattcacac ccaatgtatc ggttaacgat cagggtcagg    17700
tgacgattac ctaccaaacc tatagcgaag tggctgtgac ggcgaaaagt aaaaaattcc    17760
caagttattc ggtgagttat cggttctacc caaatcggtg gatatacgat ggcggcagat    17820
cgctggtatc cagtctcgag gccagcagac aatgccaagg ttcagatatg tctgcggttc    17880
ttgaatcctc acgtgcaacc aacggaacgc gtgcgcctga cggacattg tggggcgagt    17940 gggggagctt gaccgcgtat agttctgatt ggcaatctgg tgaatattgg gtcaaaaaga    18000
ccagcacgga ttttgaaacc atgaatatgg acacaggcgc actgcaacca gggcctgcat    18060
acttggcgtt cccgctctgt gcgctgtcaa tataaccaga taacagatag caataagaac    18120 agttaatga gctgattatt tggggcgcga atgggagtcc ggcaatccta gactcgcccc     18180
ataagtagca aacgtccaga gaacaacgcc gctcaggtta ttgagcggc gttgtttttt     18240 taaaaggatt tgtcgcgata agcgtgagct ggcgttaaat gccgatctta cggcccagct    18300
gcagcccggc tagtaacggc cgccagtgtg ctggaattcg cccttaatcg gcatcattca    18360
ccaagcttgc caggcgactg tcttcaatat tacagccgca actactgaca tggcgggtga    18420
```

```
tggtgttcac tattccaggg cgatcggcac ccaacgcagt gatcaccaga taatgttgcg    18480
atgacagtgt caaactggtt attccttcaa ggggtgagtt gttcttaagc atgccggttt    18540
gctgtaaagt ttagggagat ttgatggctt actctgttca aaagtcgcgc ctggcaaagg    18600
ttgcgggtgt ttcgcttgtt ttattactcg ctgcctgtag ttctgactca cgctataagc    18660
gtcaggtcag tggtgatgaa gcctacctgg aagcgccatg gcatgcaagg gcgaattctg    18720
cagatatcca tcacactggc ggccctagac caggctttac actttatgct tccggctcgt    18780
ataatgtgtg gaaggatcca ggagtaacaa tacaaatgga ttcaagagat ccatttgtat    18840
tgttactcct ttgtcgactg gacagttcaa gagactgtcc atcaatatca gctttgtcac    18900 aaacccgcc accggcgggg ttttttctg ctctag                                18936

<210> SEQ ID NO 563
<211> LENGTH: 8
<212> TYPE: DNA
<213> ORGANISM: Artificial Sequence
<220> FEATURE:
<223> OTHER INFORMATION: Loop Sequence

<400> SEQUENCE: 563 gagacagg                                                                 8
```

BACTERIA MEDIATED GENE SILENCING

RELATED APPLICATIONS

This application is a continuation of U.S. application Ser. No. 12/157,969, filed Jun. 13, 2008, now abandoned which claims priority to, and the benefit of, U.S. Provisional Patent Application No. 60/934,751, filed Jun. 15, 2007 and U.S. Provisional Patent Application No. 61/010,028, filed Jan. 4, 2008. The contents of each of these applications are herein incorporated by reference in their entireties.

BACKGROUND

Gene silencing through RNAi (RNA-interference) by use of short interfering RNA (siRNA) has emerged as a powerful tool for molecular biology and holds the potential to be used for therapeutic gene silencing. Short hairpin RNA (shRNA) transcribed from small DNA plasmids within the target cell has also been shown to mediate stable gene silencing and achieve gene knockdown at levels comparable to those obtained by transfection with chemically synthesized siRNA (T. R. Brummelkamp, R. Bernards, R. Agami, Science 296, 550 (2002), P. J. Paddison, A. A. Caudiy, G. J. Hannon, PNAS 99, 1443 (2002)).

Possible applications of RNAi for therapeutic purposes are extensive and include silencing and knockdown of disease genes such as oncogenes or viral genes. One major obstacle for the therapeutic use of RNAi is the delivery of siRNA to the target cell (Zamore P D, Aronin N. Nature Medicine 9, (3): 266-8 (2003)). In fact, delivery has been described as the major hurdle now for RNAi (Phillip Sharp, cited by Nature news feature, Vol 425, 2003, 10-12).

Therefore, new methods are needed for the safe and predictable administration of interfering RNAs to mammals.

SUMMARY OF THE INVENTION

The present invention provides at least one invasive bacterium, or at least one bacterial therapeutic particle (BTP), including one or more siRNAs or one or more DNA molecules encoding one or more siRNAs. The present invention also provides at least one prokaryotic vector including at least one DNA molecule encoding one or more siRNAs and at least one RNA-polymerase III compatible promoter or at least one prokaryotic promoter, wherein the expressed siRNAs interfere with at least one mRNA of a gene of interest.

The present invention also provides methods of using the various bacterium, BTP and vectors provided in the invention. For example, the present invention provides methods of delivering one or more siRNAs to mammalian cells. The methods include introducing at least one invasive bacterium, or at least one bacterial therapeutic particle (BTP), containing one or more siRNAs or one or more DNA molecules encoding one or more siRNAs to the mammalian cells.

The present invention also provides methods of regulating gene expression in mammalian cells. The method includes introducing at least one invasive bacterium, or at least one bacterial therapeutic particle (BTP), containing one or more siRNAs or one or more DNA molecules encoding one or more siRNAs to the mammalian cells, where the expressed siRNAs interfere with at least one mRNA of a gene of interest thereby regulating gene expression.

The present invention also provides methods of treating or preventing a viral disease or disorder in a mammal. The methods include regulating the expression of at least one gene in a cell known to cause a viral disease or disorder (e.g., known to increase proliferation, growth or dysplasia) by introducing to the cells of the mammal at least one invasive bacterium, or at least one bacterial therapeutic particle (BTP), containing one or more siRNAs or one or more DNA molecules encoding one or more siRNAs, where the expressed siRNAs interfere with the mRNA of the gene known to cause a viral disease or disorder.

Preferably, the viral disease or disorder can be, but is not limited to, infection, epithelial dysplasia and cancer caused by HPV infection The present invention also provides a composition containing at least one invasive bacterium or BTP and a pharmaceutically acceptable carrier. The present invention also provides a eukaryotic host cell containing at least one invasive bacterium or BTP and a pharmaceutically acceptable carrier.

The invasive bacterium or BTPs of the present invention can be non-pathogenic, non-virulent bacterium or therapeutic bacterium The mammalian cells can be ex vivo, in vivo or in vitro. The mammalian cells can be, but are not limited to, human, bovine, ovine, porcine, feline, buffalo, canine, goat, equine, donkey, deer, avian, bird, chicken, and primate cells. Preferably, the mammalian cells are human cells. In some preferred embodiments, the mammalian cells can be, but are not limited to, gastrointestinal epithelial cells, macrophages, cervical epithelial cells, rectal epithelial cells and a pharyngeal epithelial cells.

The mammalian cells can be infected with about $10^3$ to $10^{11}$ viable invasive bacterium or BTPs (or any integer within said ranges). Preferably, the mammalian cells can be infected with about $10^5$ to $10^9$ viable invasive bacterium or BTPs (or any integer within said ranges). The mammalian cells can be infected at a multiplicity of infection ranging from about 0.1 to $10^6$ (or any integer within said ranges). Preferably, the mammalian cells can be infected at a multiplicity of infection ranging from about $10^2$ to $10^4$ (or any integer within said ranges).

The mammal can be, but is not limited to, human, bovine, ovine, porcine, feline, buffalo, canine, goat, equine, donkey, deer, avian, bird, chicken, and primate. Preferably, the mammal is a human.

The one or more DNA molecules encoding the one or more siRNAs can be transcribed within the animal cell or transcribed within the bacterium. Preferably, the one or more siRNAs are transcribed within the animal cell as shRNAs.

The one or more DNA molecules encoding the one or more siRNAs can include one or more promoter sequences, enhancer sequences, terminator sequences, invasion factor sequences or lysis regulation sequences. The promoter can be a prokaryotic promoter. Preferably, the prokaryotic promoter is a T7 promoter, a $P_{gapA}$ promoter, a $P_{araBAD}$ promoter, a $P_{tac}$ promoter, a $P_{lacUV5}$ promoter, or a recA promoter.

The expressed siRNAs can direct the multienzyme complex RNA-induced silencing complex of the cell to interact with the mRNA of one or more genes of interest. Preferably, the siRNAs interact with the mRNA of one or more HPV oncogenes. Preferably, the complex can degrade the mRNA. Preferably, the expression of one or more genes of interest is decreased or inhibited. The expression is decreased or inhibited as compared to the expression of the gene prior to administration or treatment with an invasive bacterium or BTP containing one or more siRNA or a DNA encoding for one or more siRNAs. Preferably, the expression of one or more HPV oncogenes is decreased or inhibited.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
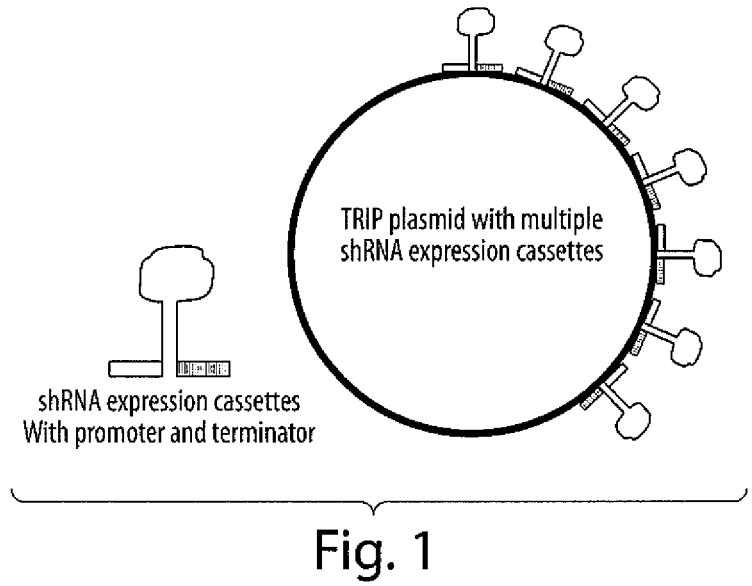
FIG. 1 is a schematic showing the Transkingdom RNA Interference Plasmid (TRIP) with multiple hairpin express cassettes.

The invention pertains to compositions and methods of delivering small interfering RNAs (siRNAs) to eukaryotic cells using non-pathogenic or therapeutic strains of bacteria or bacterial therapeutic particles (BTPs). The bacteria or BTPs deliver DNA encoding siRNA, or siRNA itself, to effect RNA interference (RNAi)) by invading into the eukaryotic host cells. Generally, to trigger RNA interference in a target cell, it is required to introduce siRNA into the cell. The siRNA is either introduced into the target cell directly or by transfection or can be transcribed within the target cell as hairpin-structured dsRNA (shRNA) from specific plasmids with RNA-polymerase III compatible promoters (e.g., U6, H1) (P. J. Paddison, A. A. Caudiy, G. J. Hannon, *PNAS* 99, 1443 (2002), T. R. Brummelkamp, R. Bernards, R. Agami, *Science* 296, 550 (2002)).

The interfering RNA of the invention regulates gene expression in eukaryotic cells. It silences or knocks down genes of interest inside target cells (e.g., decreases gene activity). The interfering RNA directs the cell-owned multienzyme-complex RISC(RNA-induced silencing complex) to the mRNA of the gene to be silenced. Interaction of RISC and mRNA results in degradation or sequestration of the mRNA. This leads to effective post-transcriptional silencing of the gene of interest. This method is referred to as Bacteria Mediated Gene Silencing (BMGS).

In the case of BMGS through delivery of siRNA expressing DNA plasmids, shRNA or siRNA are produced within the target cell after liberation of the eukaryotic transcription plasmid and trigger the highly specific process of mRNA degradation, which results in silencing of the targeted gene. Additionally, one or more cell-specific eukaryotic promoters may be used that limit the expression of siRNA or shRNA to specific target cells or tissues that are in particular metabolic states. In one embodiment of this method, the cell-specific promoter is albumin and the target cell or tissue is the liver. In another embodiment of this method, the cell-specific promoter is keratin and the specific target cell or tissue is the skin.

The non-virulent bacteria and BTPs of the invention have invasive properties (or are modified to have invasive properties) and may enter a mammalian host cell through various mechanisms. In contrast to uptake of bacteria or BTPs by professional phagocytes, which normally results in the destruction of the bacterium or BTP within a specialized lysosome, invasive bacteria or BTP strains have the ability to invade non-phagocytic host cells. Naturally occurring examples of such bacteria or BTPs are intracellular pathogens such as *Yersinia, Rickettsia, Legionella, Brucella, Mycobacterium, Helicobacter, Coxiella, Chlamydia, Neisseria, Burkolderia, Bordetella, Borrelia, Listeria, Shigella, Salmonella, Staphylococcus, Streptococcus, Porphyromonas, Treponema*, and *Vibrio*, but this property can also be transferred to other bacteria or BTPs such as *E. coli, Lactobacillus* or *Bifidobacteriae*, including probiotics through transfer of invasion-related genes (P. Courvalin, S. Goussard, C. Grillot-Courvalin, *C.R. Acad. Sci. Paris* 318, 1207 (1995)). In other embodiments of the invention, bacteria or BTPs used to deliver interfering RNAs to host cells include *Shigella flexneri* (D. R. Sizemore, A. A. Branstrom, J. C. Sadoff, *Science* 270, 299 (1995)), invasive *E. coli* (P. Courvalin, S. Goussard, C. Grillot-Courvalin, *C.R. Acad. Sci. Paris* 318, 1207 (1995), C. Grillot-Courvalin, S. Goussard, F. Huetz, D. M. Ojcius, P. Courvalin, *Nat Biotechnol* 16, 862 (1998)), *Yersinia enterocolitica* (A. Al-Mariri A, A. Tibor, P. Lestrate, P. Mertens, X. De Bolle, J. J. Letesson *Infect Immun* 70, 1915 (2002)) and *Listeria monocytogenes* (M. Hense, E. Domann, S. Krusch, P. Wachholz, K. E. Dittmar, M. Rohde, J. Wehland, T. Chakraborty, S. Weiss, *Cell Microbiol* 3, 599 (2001), S. Pilgrim, J. Stritzker, C. Schoen, A. Kolb-Mäurer, G. Geginat, M. J. Loessner, I. Gentschev, W. Goebel, *Gene Therapy* 10, 2036 (2003)). Any invasive bacterium or BTP is useful for DNA transfer into eukaryotic cells (S. Weiss, T. Chakraborty, *Curr Opinion Biotechnol* 12, 467 (2001)).

BMGS is performed using the naturally invasive pathogen *Salmonella typhimurium*. In one aspect of this embodiment, the strains of *Salmonella typhimurium* include SL 7207 and VNP20009 (S. K. Hoiseth, B. A. D. Stocker, *Nature* 291, 238 (1981); Pawelek J M, Low K B, Bermudes D. *Cancer Res.* 57(20): 4537-44 (Oct. 15, 1997)). In another embodiment of the invention, BMGS is performed using attenuated *E. coli*. In another aspect of this embodiment, the CEQ201 strain is engineered to possess cell-invading properties through an invasion plasmid. In one aspect of the invention, this plasmid is a TRIP (Transkingdom RNA interference plasmid) plasmid or pNJSZ.

A double "trojan horse" technique is also used with an invasive and auxotrophic bacterium or BTP carrying a eukaryotic transcription plasmid. This plasmid is, in turn, transcribed by the target cell to form one or more hairpin RNA structures that triggers the intracellular process of RNAi. This method of the invention induces significant gene silencing of a variety of genes. In certain aspects of this embodiment, the genes include a transgene (GFP), a mutated oncogene (k-Ras) and a cancer related gene (β-catenin) in vitro.

Another aspect of BMGS according to this invention is termed Transkingdom RNAi (tkRNAi). In this aspect of the invention, siRNA is directly produced by the invasive bacteria, or accumulated in the BTPs after production in the bacteria, as opposed to the target cell. A transcription plasmid controlled by a prokaryotic promoter (e.g., T7) is inserted into the carrier bacteria through standard transformation protocols. siRNA is produced within the bacteria and is liberated within the mammalian target cell after bacterial lysis triggered either by auxotrophy or by timed addition of antibiotics.

The RNAi methods of the invention, including BMGS and tkRNAi are used to create transient "knockdown" genetic animal models as opposed to genetically engineered knockout models to discover gene functions. The methods are also used as in vitro transfection tool for research and drug development These methods use bacteria with desirable properties (invasiveness, attenuation, steerability) to perform BMGS and tkRNAi. Invasiveness as well as eukaryotic or prokaryotic transcription of one or several shRNA is conferred to a bacterium or BTP using plasmids (e.g., TRIP) and vectors as described in greater detail herein.

1. Bacterium and/or Bacterial Therapeutic Particles (BTPs)

The present invention provides at least one invasive bacterium, or at least one bacterial therapeutic particle (BTP), including one or more siRNAs or one or more DNA molecules encoding one or more siRNAs.

According to the invention, any microorganism that is capable of delivering a molecule, e.g., an RNA molecule or an RNA-encoding DNA molecule, into the cytoplasm of a target cell, such as by traversing the membrane and entering the cytoplasm of a cell, can be used to deliver RNA to such cells. In a preferred embodiment, the microorganism is a prokaryote. In an even more preferred embodiment, the prokaryote is a bacterium or BTP. Also within the scope of the invention are microorganisms other than bacteria that can be used for delivering RNA to a cell. For example, the microorganism can be a fungus, e.g., *Cryptococcus neoformans*, protozoan, e.g., *Trypanosoma cruzi, Toxoplasma gondii, Leishmania donovani*, and *plasmodia*.

In a preferred embodiment, the microorganism is a bacterium or BTP. A preferred invasive bacterium or BTP is capable of delivering at least one molecule, e.g., an RNA or RNA-encoding DNA molecule, to a target cells, such as by entering the cytoplasm of a eukaryotic cell. Preferably, the RNA is siRNA or shRNA and the RNA-encoding DNA molecule encodes for siRNA or shRNA.

BTPs are fragments of bacteria used for therapeutic or preventive purposes. BTPs may include particles known in the art as minicells. Minicells are small cells produced by cell division that is faulty near the pole. They are devoid of nucleoid and, therefore, unable to grow and form colonies (Alder et al., (1967) Proc. Nat. Acad. Sci. U.S.A. 57, 321-326; for reviews see Sullivan and Maddock, (2000) Curr. Biol. 10:R249-R252; Margolin, (2001) Curr. Biol. 11, R395-R398; Howard and Kruse, (2005) J. Cell Biol. 168, 533-536). Minicell formation results due to mutations causing a defect in selection of the site for the septum formation for cell division. Such mutations include null alleles of minC, minD (Davie et al, (1984) J. Bacteriol. 158, 1202-1203; de Boer et al., 1988) J. Bacteriol. 170, 2106-2112) and certain alleles of ftsZ (Bi and Lutkenhaus, (1992) J. Bacteriol. 174, 5414-5423). Overexpression of FtsZ or MinC-MinD proteins has also been reported to cause the formation of minicells (Ward and Lutkenhaus, 1985; de Boer et al., 1988). Although minicells are devoid of nucleoid, they are capable of transcription and translation (Roozen et al., (1971) J. Bacteriol. 107, 21-33; Shepherd et al., (2001) J. Bacteriol. 183, 2527-34).

BTPs are distinct from bacteria in that they lack the bacterial genome and, therefore, provide a decreased risk of bacterial proliferation in patients. This is of particular value for immune-compromised patients. Furthermore, the inability of BTPs to proliferate allows for their use in sensitive tissues, e.g., the brain, and other areas of the body traditionally considered inaccessible to traditional siRNA. For example, the intraperitoneal delivery of bacteria can include the risk of adhesions and peritonitis, which is eliminated by utilizing BTPs. However, like the bacteria of this invention, BTPs contain the bacterial cell wall, some bacterial plasma contents and subcellular particles, one or more therapeutic components, e.g., one or more siRNAs, one or more invasion factors, one or more phagosome degradation factors, and one or more factors for targeting specific tissues. The BTPs are produced from bacteria that have produced and accumulated siRNAs inside the bacteria, and then segregate the bacterial fragment (BTP) during cell division. In one embodiment of this invention, BTPs are obtained by fermenting the bacteria, during which the BTPs form abundantly, followed by isolation of the BTPs from live bacteria using differential size filtration, which will retain the bacteria but allow passage and collection of BTPs. In another embodiment of this invention, BTPs are separated from bacteria by centrifugation. In another embodiment of this invention, live bacterial cells are lysed through activation of a death signal. Once isolated, the BTPs can be lyophilized and formulated for use.

As used herein, the term "invasive" when referring to a microorganism, e.g., a bacterium or BTP, refers to a microorganism that is capable of delivering at least one molecule, e.g., an RNA or RNA-encoding DNA molecule, to a target cell. An invasive microorganism can be a microorganism that is capable of traversing a cell membrane, thereby entering the cytoplasm of said cell, and delivering at least some of its content, e.g., RNA or RNA-encoding DNA, into the target cell. The process of delivery of the at least one molecule into the target cell preferably does not significantly modify the invasion apparatus.

Invasive microorganisms include microorganisms that are naturally capable of delivering at least one molecule to a target cell, such as by traversing the cell membrane, e.g., a eukaryotic cell membrane, and entering the cytoplasm, as well as microorganisms which are not naturally invasive and which have been modified, e.g., genetically modified, to be invasive. In another preferred embodiment, a microorganism that is not naturally invasive can be modified to become invasive by linking the bacterium or BTP to an "invasion factor", also termed "entry factor" or "cytoplasm-targeting factor". As used herein, an "invasion factor" is a factor, e.g., a protein or a group of proteins which, when expressed by a non-invasive bacterium or BTP, render the bacterium or BTP invasive. As used herein, an "invasion factor" is encoded by a "cytoplasm-targeting gene".

In one embodiment of this invention, the microorganism is a naturally invasive bacterium or BTP selected from the group that includes, but is not limited to, *Yersinia, Rickettsia, Legionella, Brucella, Mycobacterium, Helicobacter, Coxiella, Chlamydia, Neisseria, Burkolderia, Bordetella, Borrelia, Listeria, Shigella, Salmonella, Staphylococcus, Streptococcus, Porphyromonas, Treponema, Vibrio, E. coli,* and *Bifidobacteriae*. Optionally, the naturally invasive bacterium or BTP is *Yersinia* expressing an invasion factor selected from the group including, but not limited to, invasin and YadA (*Yersinia enterocolitica* plasmid adhesion factor). Optionally, the naturally invasive bacterium or BTP is *Rickettsia* expressing the invasion factor RickA (actin polymerization protein). Optionally, the naturally invasive bacterium or BTP is *Legionella* expressing the invasion factor RalF (guanine exchange factor). Optionally, the naturally invasive bacterium or BTP is *Neisseria* expressing an invasion factor selected from the group including, but not limited to, NadA (*Neisseria* adhesion/invasion factor), OpA and OpC (opacity-associated adhesions). Optionally, the naturally invasive bacterium or BTP is *Listeria* expressing an invasion factor selected from the group including, but not limited to, In1A (internalin factor), In1B (internalin factor), Hpt (hexose phosphate transporter), and ActA (actin polymerization protein). Optionally, the naturally invasive bacterium or BTP is *Shigella* expressing an invasion factor selected from the group including, but not limited to, the *Shigella* secreting factors IpaA (invasion plasmid antigen), IpaB, IpaC, IpgD, IpaB-IpaC complex, VirA, and IcsA. Optionally, the naturally invasive bacterium or BTP is *Salmonella* expressing an invasion factor selected from the group including, but not limited to, *Salmonella* secreting/exchange factors SipA, SipC, SpiC, SigD, SopB, SopE, SopE2, and SptP. Optionally, the naturally invasive bacterium or BTP is *Staphylococcus* expressing an invasion factor selected from the group including, but not limited to, the fibronectin binding proteins FnBPA and FnBPB. Optionally, the naturally invasive bacterium or BTP is *Streptococcus* expressing an invasion factor selected from the group including, but not limited to, the fibronectin binding proteins ACP, Fba, F2, Sfb1, Sfb2, SOF, and PFBP. Optionally, the naturally invasive bacterium or BTP is *Porphyromonas gingivalis* expressing the invasion factor FimB (integrin binding protein fibriae).

In another embodiment of this invention, the microorganism is a bacterium or BTP that is not naturally invasive but has been modified, e.g., genetically modified, to be invasive. Optionally, the bacterium or BTP that is not naturally invasive has been genetically modified to be invasive by expressing an invasion factor selected from the group including, but not limited to, invasin, YadA, RickA, RalF, NadA, OpA, OpC, In1A, In1B, Hpt, ActA, IpaA, IpaB, IpaC, IpgD, IpaB-IpaC complex, VirA, IcsA, SipA, SipC, SpiC, SigD, SopB, SopE, SopE2, SptP, FnBPA, FnBPB, ACP, Fba, F2, Sfb1, Sfb2, SOF, PFBP, and FimB.

In another embodiment of this invention, the microorganism is a bacterium or BTP that may be naturally invasive but has been modified, e.g., genetically modified, to express one or more additional invasion factors. Optionally, the invasion factor is selected from the group that includes, but is not limited to, invasin, YadA, RickA, RalF, NadA, OpA, OpC, In1A, In1B, Hpt, ActA, IpaA, IpaB, IpaC, IpgD, IpaB-IpaC complex, VirA, IcsA, SipA, SipC, SpiC, SigD, SopB, SopE, SopE2, SptP, FnBPA, FnBPB, ACP, Fba, F2, Sfb1, Sfb2, SOF, PFBP, and FimB.

Naturally invasive microorganisms, e.g., bacteria or BTPs, may have a certain tropism, i.e., preferred target cells. Alternatively, microorganisms, e.g., bacteria or BTPs can be modified, e.g., genetically, to mimic the tropism of a second microorganism. Optionally, the bacterium or BTP is *Streptococcus* and the preferred target cells are selected from the group including, but not limited to, pharyngeal epithelial cells, buccal epithelial cells of the tongue, and mucosal epithelial cells. Optionally, the bacterium or BTP is *Porphyromonas* and the preferred target cells are selected from the group including, but not limited to, oral epithelial cells. Optionally, the bacterium or BTP is *Staphylococcus* and the preferred target cells are mucosal epithelial cells. Optionally, the bacterium or BTP is *Neisseria* and the preferred target cells are selected from the group including, but not limited to, urethral epithelial cells and cervical epithelial cells. Optionally, the bacterium or BTP is *E. coli* and the preferred target cells are selected from the group, including but not limited to, intestinal epithelial cells, urethral epithelial cells, and the cells of the upper urinary tract. Optionally, the bacterium or BTP is *Bordetella* and the preferred target cells are respiratory epithelial cells. Optionally, the bacterium or BTP is *Vibrio* and the preferred target cells are intestinal epithelial cells. Optionally, the bacterium or BTP is *Treponema* and the preferred target cells are mucosal epithelial cells. Optionally, the bacterium or BTP is *Mycoplasma* and the preferred target cells are respiratory epithelial cells. Optionally, the bacterium or BTP is *Helicobacter* and the preferred target cells are the endothelial cells of the stomach. Optionally, the bacterium or BTP is *Chlamydia* and the preferred target cells are selected from the group including, but not limited to, conjunctival cells and urethral epithelial cells.

In another embodiment of this invention, the microorganism is a bacterium or BTP that has been modified, e.g., genetically modified, to have a certain tropism. Optionally, the preferred target cells are selected from the group including, but not limited to, pharyngeal epithelial cells, buccal epithelial cells of the tongue, mucosal epithelial cells, oral epithelial cells, epithelial cells of the urethra, cervical epithelial cells, intestinal epithelial cells, respiratory epithelial cells, cells of the upper urinary tract, epithelial cells of the stomach, and conjunctival cells. Optionally, the preferred target cells are dysplastic or cancerous epithelial cells. Optionally, the preferred target cells are activated or resting immune cells.

Delivery of at least one molecule into a target cell can be determined according to methods known in the art. For example, the presence of the molecule, by the decrease in expression of an RNA or protein silenced thereby, can be detected by hybridization or PCR methods, or by immunological methods that may include the use of an antibody.

Determining whether a microorganism is sufficiently invasive for use in the invention may include determining whether sufficient siRNA was delivered to host cells, relative to the number of microorganisms contacted with the host cells. If the amount of siRNA is low relative to the number of microorganisms used, it may be desirable to further modify the microorganism to increase its invasive potential.

Bacterial or BTP entry into cells can be measured by various methods. Intracellular bacteria or BTPs survive treatment by aminoglycoside antibiotics, whereas extracellular bacteria are rapidly killed. A quantitative estimate of bacterial or BTP uptake can be achieved by treating cell monolayers with the antibiotic gentamicin to inactivate extracellular bacteria or BTPs, then by removing said antibiotic before liberating the surviving intracellular organisms with gentle detergent and determining viable counts on standard bacteriological medium. Furthermore, bacterial or BTP entry into cells can be directly observed, e.g., by thin-section-transmission electron microscopy of cell layers or by immunofluorescent techniques (Falkow et al. (1992) Annual Rev. Cell Biol. 8:333). Thus, various techniques can be used to determine whether a specific bacterium or BTP is capable of invading a specific type of cell or to confirm bacterial invasion following modification of the bacteria or BTP, such modification of the tropism of the bacteria to mimic that of a second bacterium.

Bacteria or BTPs that can be used for delivering RNA according to the method of the invention are preferably non-pathogenic. However, pathogenic bacteria or BTPs can also be used, so long as their pathogenicity has been attenuated, to thereby render the bacteria non-harmful to a subject to which it is administered. As used herein, the term "attenuated bacterium or BTP" refers to a bacterium or BTP that has been modified to significantly reduce or eliminate its harmfulness to a subject. A pathogenic bacterium or BTP can be attenuated by various methods, set forth below.

Without wanting to be limited to a specific mechanism of action, the bacterium or BTP delivering the RNA into the eukaryotic cell can enter various compartments of the cell, depending on the type of bacterium or BTP. For example, the bacterium or BTP can be in a vesicle, e.g., a phagocytic vesicle. Once inside the cell, the bacterium or BTP can be destroyed or lysed and its contents delivered to the eukaryotic cell. A bacterium or BTP can also be engineered to express a phagosome degrading protein to allow leakage of RNA from the phagosome. In one embodiment of this invention, the bacterium or BTP expresses, either naturally or through modification, e.g., genetic modification, a protein that contributes to pore-formation, breakage or degradation of the phagosome. Optionally, the protein is a cholesterol-dependent cytolysin. Optionally, the protein is selected from the group consisting of listeriolysin, ivanolysin, streptolysin, sphingomyelinase, perfiringolysin, botulinolysin, leukocidin, anthrax toxin, phospholipase, IpaB (invasion plasmid antigen), IpaH, IcsB (intercellular spread), DOT/Icm (defect in organelle trafficking/intracellular multiplication defective), DOTU (stabilization factor for the DOT/Icm complex), IcmF, and PmrA (multidrug resistance efflux pump).

In some embodiments, the bacterium can stay alive for various times in the eukaryotic cell and may continue to produce RNA. The RNA or RNA-encoding DNA can then be released from the bacterium into the cell by, e.g., leakage. In certain embodiments of the invention, the bacterium can also replicate in the eukaryotic cell. In a preferred embodiment, bacterial replication does not kill the host cell. The invention is not limited to delivery of RNA or RNA-encoding DNA by a specific mechanism and is intended to encompass methods and compositions permitting delivery of RNA or RNA-encoding DNA by a bacterium independently of the mechanism of delivery.

In one embodiment, the bacterium or BTP for use in the present invention is non-pathogenic or non-virulent. In another aspect of this embodiment, the bacterium or BTP is therapeutic. In another aspect of this embodiment, the bacterium or BTP is an attenuated strain or derivative thereof selected from, but not limited to, *Yersinia, Rickettsia, Legionella, Brucella, Mycobacterium, Helicobacter, Haemophilus, Coxiella, Chlamydia, Neisseria, Burkolderia, Bordetella, Borrelia, Listeria, Shigella, Salmonella, Staphylococcus, Streptococcus, Porphyromonas, Treponema, Vibrio, E. coli*, and *Bifidobacteriae*. Optionally, the *Yersinia* strain is an attenuated strain of the *Yersinia pseudotuberculosis* species. Optionally, the *Yersinia* strain is an attenuated strain of the *Yersinia enterocolitica* species. Optionally, the *Rickettsia* strain is an attenuated strain of the *Rickettsia coronii* species. Optionally, the *Legionella* strain is an attenuated strain of the *Legionella pneumophilia* species. Optionally, the *Mycobacterium* strain is an attenuated strain of the *Mycobacterium tuberculosis* species. Optionally, the *Mycobacterium* strain is an attenuated strain of the *Mycobacterium bovis* BCG species. Optionally, the *Helicobacter* strain is an attenuated strain of the *Helicobacter pylori* species. Optionally, the *Coxiella* strain is an attenuated strain of *Coxiella burnetti*. Optionally, the *Haemophilus* strain is an attenuated strain of the *Haemophilus influenza* species. Optionally, the *Chlamydia* strain is an attenuated strain of the *Chlamydia trachomatis* species. Optionally, the *Chlamydia* strain is an attenuated strain of the *Chlamydia pneumoniae* species. Optionally, the *Neisseria* strain is an attenuated strain of the *Neisseria gonorrheae* species. Optionally, the *Neisseria* strain is an attenuated strain of the *Neisseria meningitides* species. Optionally, the *Burkolderia* strain is an attenuated strain of the *Burkolderia cepacia* species. Optionally, the *Bordetella* strain is an attenuated strain of the *Bordetella pertussis* species. Optionally, the *Borrelia* strain is an attenuated strain of the *Borrelia hermisii* species. Optionally, the *Listeria* strain is an attenuated strain of the *Listeria monocytogenes* species. Optionally, the *Listeria* strain is an attenuated strain of the *Listeria*

*ivanovii* species. Optionally, the *Salmonella* strain is an attenuated strain of the *Salmonella enterica* species. Optionally, the *Salmonella* strain is an attenuated strain of the *Salmonella typhimurium* species. Optionally, the *Salmonella typhimurium* strain is SL 7207 or VNP20009. Optionally, the *Staphylococcus* strain is an attenuated strain of the *Staphylococcus aureus* species. Optionally, the *Streptococcus* strain is an attenuated strain of the *Streptococcus pyogenes* species. Optionally, the *Streptococcus* strain is an attenuated strain of the *Streptococcus mutans* species. Optionally, the *Streptococcus* strain is an attenuated strain of the *Streptococcus salivarius* species. Optionally, the *Streptococcus* strain is an attenuated strain of the *Streptococcus pneumonia* species. Optionally, the *Porphyromonas* strain is an attenuated strain of the *Porphyromonas gingivalis* species. Optionally, the *Pseudomonas* strain is an attenuated strain of the *Pseudomonas aeruginosa* species. Optionally, the *Treponema* strain is an attenuated strain of the *Treponema pallidum* species. Optionally, the *Vibrio* strain is an attenuated strain of the *Vibrio cholerae* species. Optionally, the *E. coli* strain is MM294.

Set forth below are examples of bacteria that have been described in the literature as being naturally invasive (section 1.1), as well as bacteria which have been described in the literature as being naturally non-invasive bacteria (section 1.2), as well as bacteria which are naturally non-pathogenic or which are attenuated. Although some bacteria have been described as being non-invasive (section 1.2), these may still be sufficiently invasive for use according to the invention. Whether traditionally described as naturally invasive or non-invasive, any bacterial strain can be modified to modulate, in particular to increase, its invasive characteristics (e.g., as described in section 1.3).

1.1 Naturally Invasive Bacteria

The particular naturally invasive bacteria employed in the present invention are not critical thereto. Examples of such naturally occurring invasive bacteria include, but are not limited to, *Shigella* spp., *Salmonella* spp., *Listeria* spp., *Rickettsia* spp., and enteroinvasive *Escherichia coli*.

The particular *Shigella* strain employed is not critical to the present invention. Examples of *Shigella* strains that can be employed in the present invention include *Shigella flexneri* 2a (ATCC No. 29903), *Shigella sonnei* (ATCC No. 29930), and *Shigella disenteriae* (ATCC No. 13313). An attenuated *Shigella* strain, such as *Shigella flexneri* 2a 2457T aroA virG mutant CVD 1203 (Noriega et al. supra), *Shigella flexneri* M90T icsA mutant (Goldberg et al. Infect. Immun., 62:5664-5668 (1994)), *Shigella flexneri* Y SFL114 aroD mutant (Karnell et al. Vacc., 10:167-174 (1992)), and *Shigella flexneri* aroA aroD mutant (Verma et al. Vacc., 9:6-9 (1991)) are preferably employed in the present invention. Alternatively, new attenuated *Shigella* spp. strains can be constructed by introducing an attenuating mutation either singularly or in conjunction with one or more additional attenuating mutations.

At least one advantage to *Shigella* bacteria as delivery vectors is their tropism for lymphoid tissue in the colonic mucosal surface. In addition, the primary site of *Shigella* replication is believed to be within dendritic cells and macrophages, which are commonly found at the basal lateral surface of M cells in mucosal lymphoid tissues (reviewed by McGhee, J. R. et al. (1994) Reproduction, Fertility, & Development 6:369; Pascual, D. W. et al. (1994) Immunomethods 5:56). As such, *Shigella* vectors may provide a means to target RNA interference or deliver therapeutic molecules to these professional antigen-presenting cells. Another advantage of *Shigella* vectors is that attenuated *Shigella* strains deliver nucleic acid reporter genes in vitro and in vivo (Sizemore, D. R. et al. (1995) Science 270:299; Courvalin, P. et al. (1995) Comptes Rendus de 1 Academie des Sciences Serie III-Sciences de la Vie-Life Sciences 318:1207; Powell, R. J. et al. (1996) In: Molecular approaches to the control of infectious diseases. F. Brown, E. Norrby, D. Burton and J. Mekalanos, eds. Cold Spring Harbor Laboratory Press, New York. 183; Anderson, R. J. et al. (1997) Abstracts for the 97th General Meeting of the American Society for Microbiology:E.). On the practical side, the tightly restricted host specificity of *Shigella* stands to prevent the spread of *Shigella* vectors into the food chain via intermediate hosts. Furthermore, attenuated strains that are highly attenuated in rodents, primates and volunteers have been developed (Anderson et al. (1997) supra; Li, A. et al. (1992) Vaccine 10:395; Li, A. et al. (1993) Vaccine 11:180; Karnell, A. et al. (1995) Vaccine 13:88; Sansonetti, P. J. and J. Arondel (1989) Vaccine 7:443; Fontaine, A. et al. (1990) Research in Microbiology 141:907; Sansonetti, P. J. et al. (1991) Vaccine 9:416; Noriega, F. R. et al. (1994) Infection & Immunity 62:5168; Noriega, F. R. et al. (1996) Infection & Immunity 64:3055; Noriega, F. R. et al. (1996) Infection & Immunity 64:23; Noriega, F. R. et al. (1996) Infection & Immunity 64:3055; Kotloff, K. L. et al. (1996) Infection & Immunity 64:4542). This latter knowledge will allow the development of well-tolerated *Shigella* vectors for use in humans.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i) auxotrophic mutations, such as aro (Hoiseth et al. Nature, 291:238-239 (1981)), gua (McFarland et al. Microbiol. Path., 3:129-141 (1987)), nad (Park et al. J. Bact., 170: 3725-3730 (1988), thy (Nnalue et al. Infect. Immun., 55:955-962 (1987)), and asd (Curtiss, supra) mutations;

(ii) mutations that inactivate global regulatory functions, such as cya (Curtiss et al. Infect. Immun., 55:3035-3043 (1987)), crp (Curtiss et al (1987), supra), phoP/phoQ (Groisman et al. Proc. Natl. Acad. Sci., USA, 86:7077-7081 (1989); and Miller et al. Proc. Natl. Acad. Sci., USA, 86:5054-5058 (1989)), phop$^c$ (Miller et al. J. Bact., 172:2485-2490 (1990)) or ompR (Dorman et al. Infect. Immun., 57:2136-2140 (1989)) mutations;

(iii) mutations that modify the stress response, such as recA (Buchmeier et al. Mol. Micro., 7:933-936 (1993)), htrA (Johnson et al. Mol. Micro., 5:401-407 (1991)), htpR (Neidhardt et al. Biochem. Biophys. Res. Com., 100:894-900 (1981)), hsp (Neidhardt et al. Ann. Rev. Genet., 18:295-329 (1984)) and groEL (Buchmeier et al. Sci., 248:730-732 (1990)) mutations;

(iv) mutations in specific virulence factors, such as IsyA (Libby et al. Proc. Natl. Acad. Sci., USA, 91:489-493 (1994)), pag or prg (Miller et al (1990), supra; and Miller et al (1989), supra), iscA or virG (d'Hauteville et al. Mol. Micro., 6:833-841 (1992)), plcA (Mengaud et al. Mol. Microbiol., 5:367-72 (1991); Camilli et al. J. Exp. Med, 173:751-754 (1991)), and act (Brundage et al. Proc. Natl. Acad. Sci., USA, 90:11890-11894 (1993)) mutations;

(v) mutations that affect DNA topology, such as topA (Galan et al. Infect. Immun., 58:1879-1885 (1990));

(vi) mutations that disrupt or modify the cell cycle, such as min (de Boer et al. Cell, 56:641-649 (1989)).

(vii) introduction of a gene encoding a suicide system, such as sacB (Recorbet et al. App. Environ. Micro., 59:1361-1366 (1993); Quandt et al. Gene, 127:15-21 (1993)), nuc (Ahrenholtz et al. App. Environ. Micro., 60:3746-3751 (1994)), hok, gef, kil, or phlA (Molin et al. Ann. Rev. Microbiol., 47:139-166 (1993));

(viii) mutations that alter the biogenesis of lipopolysaccharide and/or lipid A, such as rFb (Raetz in *Esherishia coli* and *Salmonella typhimurium*, Neidhardt et al., Ed., ASM Press, Washington D.C. pp 1035-1063 (1996)), galE (Hone et al. J. Infect. Dis., 156:164-167 (1987)) and htrB (Raetz, supra), msbB (Reatz, supra)

(ix) introduction of a bacteriophage lysis system, such as lysogens encoded by P22 (Rennell et al. Virol, 143:280-289 (1985)), λ murein transglycosylase (Bienkowska-Szewczyk et al. Mol. Gen. Genet., 184:111-114 (1981)) or S-gene (Reader et al. Virol, 43:623-628 (1971)); and The attenuating mutations can be either constitutively expressed or under the control of inducible promoters, such as the temperature sensitive heat shock family of promoters (Neidhardt et al. supra), or the anaerobically induced nirB promoter (Harborne et al. Mol. Micro., 6:2805-2813 (1992)) or repressible promoters, such as uapA (Gorfinkiel et al. J. Biol. Chem., 268:23376-23381 (1993)) or gcv (Stauffer et al. J. Bact., 176:6159-6164 (1994)).

The particular *Listeria* strain employed is not critical to the present invention. Examples of *Listeria* strains that can be employed in the present invention include *Listeria monocytogenes* (ATCC No. 15313). Attenuated *Listeria* strains, such as *L. monocytogenes* actA mutant (Brundage et al. supra) or *L. monocytogenes* plcA (Camilli et al. J. Exp. Med., 173:751-754 (1991)) are preferably used in the present invention. Alternatively, new attenuated *Listeria* strains can be constructed by introducing one or more attenuating mutations in groups (i) to (vii) as described for *Shigella* spp. above.

The particular *Salmonella* strain employed is not critical to the present invention. Examples of *Salmonella* strains that can be employed in the present invention include *Salmonella typhi* (ATCC No. 7251) and *S. typhimurium* (ATCC No. 13311). Attenuated *Salmonella* strains are preferably used in the present invention and include *S. typhi*-aroC-aroD (Hone et al. Vacc. 9:810 (1991) and *S. typhimurium*-aroA mutant (Mastroeni et al. Micro. Pathol. 13:477 (1992)). Alternatively, new attenuated *Salmonella* strains can be constructed by introducing one or more attenuating mutations as described for *Shigella* spp. above.

The particular *Rickettsia* strain employed is not critical to the present invention. Examples of *Rickettsia* strains which can be employed in the present invention include *Rickettsia Rickettsiae* (ATCC Nos. VR149 and VR891), *Ricketsia prowaseckii* (ATCC No. VR233), *Rickettsia tsutsugamuchi* (ATCC Nos. VR312, VR150 and VR609), *Rickettsia mooseri* (ATCC No. VR144), *Rickettsia sibirica* (ATCC No. VR151), and *Rochalimaea quitana* (ATCC No. VR358). Attenuated *Rickettsia* strains are preferably used in the present invention and can be constructed by introducing one or more attenuating mutations in groups (i) to (vii) as described for *Shigella* spp. above.

The particular enteroinvasive *Escherichia* strain employed is not critical to the present invention. Examples of enteroinvasive *Escherichia* strains which can be employed in the present invention include *Escherichia coli* strains 4608-58, 1184-68, 53638-C-17, 13-80, and 6-81 (Sansonetti et al. Ann. Microbiol. (Inst. Pasteur), 132A:351-355 (1982). Attenuated enteroinvasive *Escherichia* strains are preferably used in the present invention and can be constructed by introducing one or more attenuating mutations in groups (i) to (vii) as described for *Shigella* spp. above.

Furthermore, since certain microorganisms other than bacteria can also interact with integrin molecules (which are receptors for certain invasion factors) for cellular uptake, such microorganisms can also be used for introducing RNA into target cells. For example, viruses, e.g., foot-and-mouth disease virus, echovirus, and adenovirus, and eukaryotic pathogens, e.g., *Histoplasma capsulatum* and *Leishmania major* interact with integrin molecules.

1.2 Less Invasive Bacteria

Examples of bacteria which can be used in the invention and which have been described in the literature as being non-invasive or at least less invasive than the bacteria listed in the previous section (1.1) include, but are not limited to, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. It may be necessary to modify these bacteria to increase their invasive potential.

The particular *Yersinia* strain employed is not critical to the present invention. Examples of *Yersinia* strains that can be employed in the present invention include *Y. enterocolitica* (ATCC No. 9610) or *Y. pestis* (ATCC No. 19428). Attenuated *Yersinia* strains, such as *Y. enterocolitica* Ye03-R2 (al-Hendy et al. Infect. Immun., 60:870-875 (1992)) or *Y. enterocolitica* aroA (O'Gaora et al. Micro. Path., 9:105-116 (1990)) are preferably used in the present invention. Alternatively, new attenuated *Yersinia* strains can be constructed by introducing one or more attenuating mutations in groups (i) to (vii) as described for *Shigella* spp. above.

The particular *Escherichia* strain employed is not critical to the present invention. Examples of *Escherichia* strains that can be employed in the present invention include *E. coli* Nissle 1917, MM294, H10407 (Elinghorst et al. Infect. Immun., 60:2409-2417 (1992)), and *E. coli* EFC4, CFT325 and CPZ005 (Donnenberg et al. J. Infect. Dis., 169:831-838 (1994)). Attenuated *Escherichia* strains, such as the attenuated turkey pathogen *E. coli* 02 carAB mutant (Kwaga et al. Infect. Immun., 62:3766-3772 (1994)) or CEQ201 are preferably used in the present invention. Alternatively, new attenuated *Escherichia* strains can be constructed by introducing one or more attenuating mutations in groups (i) to (vii) as described for *Shigella* spp. above.

The particular *Klebsiella* strain employed is not critical to the present invention. Examples of *Klebsiella* strains that can be employed in the present invention include *K. pneumoniae* (ATCC No. 13884). Attenuated *Klebsiella* strains are preferably used in the present invention, and can be constructed by introducing one or more attenuating mutations in groups (i) to (vii) as described for *Shigella* spp. above.

The particular *Bordetella* strain employed is not critical to the present invention. Examples of *Bordetella* strains that can be employed in the present invention include *B. bronchiseptica* (ATCC No. 19395). Attenuated *Bordetella* strains are preferably used in the present invention, and can be constructed by introducing one or more attenuating mutations in groups (i) to (vii) as described for *Shigella* spp. above.

The particular *Neisseria* strain employed is not critical to the present invention. Examples of *Neisseria* strains that can be employed in the present invention include *N. meningitidis* (ATCC No. 13077) and *N. gonorrhoeae* (ATCC No. 19424). Attenuated *Neisseria* strains, such as *N. gonorrhoeae* MS11 aro mutant (Chamberlain et al. Micro. Path., 15:51-63 (1993)) are preferably used in the present invention. Alternatively, new attenuated *Neisseria* strains can be constructed by introducing one or more attenuating mutations in groups (i) to (vii) as described for *Shigella* spp. above.

The particular *Aeromonas* strain employed is not critical to the present invention. Examples of *Aeromonas* strains that can be employed in the present invention include *A. eucrenophila* (ATCC No. 23309). Alternatively, new attenuated *Aeromonas* strains can be constructed by introducing one or more attenuating mutations in groups (i) to (vii) as described for *Shigella* spp. above.

The particular *Franciesella* strain employed is not critical to the present invention. Examples of *Franciesella* strains that can be employed in the present invention include *F. tularensis* (ATCC No. 15482). Attenuated *Franciesella* strains are preferably used in the present invention, and can be constructed by introducing one or more attenuating mutations in groups (i) to (vii) as described for *Shigella* spp. above.

The particular *Corynebacterium* strain employed is not critical to the present invention. Examples of *Corynebacterium* strains that can be employed in the present invention include *C. pseudotuberculosis* (ATCC No. 19410). Attenuated *Corynebacterium* strains are preferably used in the present invention, and can be constructed by introducing one or more attenuating mutations in groups (i) to (vii) as described for *Shigella* spp. above.

The particular *Citrobacter* strain employed is not critical to the present invention. Examples of *Citrobacter* strains that can be employed in the present invention include *C. freundii* (ATCC No. 8090). Attenuated *Citrobacter* strains are preferably used in the present invention, and can be constructed by introducing one or more attenuating mutations in groups (i) to (vii) as described for *Shigella* spp. above.

The particular *Chlamydia* strain employed is not critical to the present invention. Examples of *Chlamydia* strains that can be employed in the present invention include *C. pneumoniae* (ATCC No. VR1310). Attenuated *Chlamydia* strains are preferably used in the present invention, and can be constructed by introducing one or more attenuating mutations in groups (i) to (vii) as described for *Shigella* spp. above.

The particular *Hemophilus* strain employed is not critical to the present invention. Examples of *Hemophilus* strains that can be employed in the present invention include *H. sornnus* (ATCC No. 43625). Attenuated *Hemophilus* strains are preferably used in the present invention, and can be constructed by introducing one or more attenuating mutations in groups (i) to (vii) as described for *Shigella* spp. above.

The particular *Brucella* strain employed is not critical to the present invention. Examples of *Brucella* strains that can be employed in the present invention include *B. abortus* (ATCC No. 23448). Attenuated *Brucella* strains are preferably used in the present invention, and can be constructed by introducing one or more attenuating mutations in groups (i) to (vii) as described for *Shigella* spp. above.

The particular *Mycobacterium* strain employed is not critical to the present invention. Examples of *Mycobacterium* strains that can be employed in the present invention include *M. intracellulare* (ATCC No. 13950) and *M. tuberculosis* (ATCC No. 27294). Attenuated *Mycobacterium* strains are preferably used in the present invention, and can be constructed by introducing one or more attenuating mutations in groups (i) to (vii) as described for *Shigella* spp. above.

The particular *Legionella* strain employed is not critical to the present invention. Examples of *Legionella* strains that can be employed in the present invention include *L. pneumophila* (ATCC No. 33156). Attenuated *Legionella* strains, such as a *L. pneumophila* mip mutant (Ott, FEMS Micro. Rev., 14:161-176 (1994)) are preferably used in the present invention. Alternatively, new attenuated *Legionella* strains can be constructed by introducing one or more attenuating mutations in groups (i) to (vii) as described for *Shigella* spp. above.

The particular *Rhodococcus* strain employed is not critical to the present invention. Examples of *Rhodococcus* strains that can be employed in the present invention include *R. equi* (ATCC No. 6939). Attenuated *Rhodococcus* strains are preferably used in the present invention, and can be constructed by introducing one or more attenuating mutations in groups (i) to (vii) as described for *Shigella* spp. above.

The particular *Pseudomonas* strain employed is not critical to the present invention. Examples of *Pseudomonas* strains that can be employed in the present invention include *P. aeruginosa* (ATCC No. 23267). Attenuated *Pseudomonas* strains are preferably used in the present invention, and can be constructed by introducing one or more attenuating mutations in groups (i) to (vii) as described for *Shigella* spp. above.

The particular *Helicobacter* strain employed is not critical to the present invention. Examples of *Helicobacter* strains that can be employed in the present invention include *H. mustelae* (ATCC No. 43772). Attenuated *Helicobacter* strains are preferably used in the present invention, and can be constructed by introducing one or more attenuating mutations in groups (i) to (vii) as described for *Shigella* spp. above.

The particular *Salmonella* strain employed is not critical to the present invention. Examples of *Salmonella* strains that can be employed in the present invention include *Salmonella typhi* (ATCC No. 7251) and *S. typhimurium* (ATCC No. 13311). Attenuated *Salmonella* strains are preferably used in the present invention and include *S. typhi* aroC aroD (Hone et al. Vacc., 9:810-816 (1991)) and *S. typhimurium* aroA mutant (Mastroeni et al. Micro. Pathol, 13:477-491 (1992))). Alternatively, new attenuated *Salmonella* strains can be constructed by introducing one or more attenuating mutations in groups (i) to (vii) as described for *Shigella* spp. above.

The particular *Vibrio* strain employed is not critical to the present invention. Examples of *Vibrio* strains that can be employed in the present invention include *Vibrio cholerae* (ATCC No. 14035) and *Vibrio cincinnatiensis* (ATCC No. 35912). Attenuated *Vibrio* strains are preferably used in the present invention and include *V. cholerae* RSI virulence mutant (Taylor et al. J. Infect. Dis., 170:1518-1523 (1994)) and *V. cholerae* ctxA, ace, zot, cep mutant (Waldor et al. J. Infect. Dis., 170:278-283 (1994)). Alternatively, new attenuated *Vibrio* strains can be constructed by introducing one or more attenuating mutations in groups (i) to (vii) as described for *Shigella* spp. above.

The particular *Bacillus* strain employed is not critical to the present invention. Examples of *Bacillus* strains that can be employed in the present invention include *Bacillus subtilis* (ATCC No. 6051). Attenuated *Bacillus* strains are preferably used in the present invention and include *B. anthracis* mutant pX01 (Welkos et al. Micro. Pathol, 14:381-388 (1993)) and attenuated BCG strains (Stover et al. Nat., 351:456-460 (1991)). Alternatively, new attenuated *Bacillus* strains can be constructed by introducing one or more attenuating mutations in groups (i) to (vii) as described for *Shigella* spp. above.

The particular *Erysipelothrix* strain employed is not critical to the present invention. Examples of *Erysipelothrix* strains that can be employed in the present invention include *Erysipelothrix rhusiopathiae* (ATCC No. 19414) and *Erysipelothrix tonsillarum* (ATCC No. 43339). Attenuated *Erysipelothrix* strains are preferably used in the present invention and include *E. rhusiopathiae* Kg-1a and Kg-2 (Watarai et al. J. Vet. Med. Sci., 55:595-600 (1993)) and *E. rhusiopathiae*

ORVAC mutant (Markowska-Daniel et al. Int. J. Med. Microb. Virol. Parisit. Infect. Dis., 277:547-553 (1992)). Alternatively, new attenuated *Erysipelothrix* strains can be constructed by introducing one or more attenuating mutations in groups (i) to (vii) as described for *Shigella* spp. above.

1.3. Methods for Increasing the Invasive Properties of a Bacterial Strain

Whether organisms have been traditionally described as invasive or non-invasive, these organisms can be engineered to increase their invasive properties, e.g., by mimicking the invasive properties of *Shigella* spp., *Listeria* spp., *Rickettsia* spp., or enteroinvasive *E. coli* spp. For example, one or more genes that enable the microorganism to access the cytoplasm of a cell, e.g., a cell in the natural host of said non-invasive bacteria, can be introduced into the microorganism.

Examples of such genes referred to herein as "cytoplasm-targeting genes" include genes encoding the proteins that enable invasion by *Shigella* or the analogous invasion genes of enteroinvasive *Escherichia*, or listeriolysin O of *Listeria*, as such techniques are known to result in rendering a wide array of invasive bacteria capable of invading and entering the cytoplasm of animal cells (Formal et al. Infect. Immun., 46:465 (1984); Bielecke et al. Nature, 345:175-176 (1990); Small et al. In: Microbiology-1986, pages 121-124, Levine et al. Eds., American Society for Microbiology, Washington, D.C. (1986); Zychlinsky et al. Molec. Micro., 11:619-627 (1994); Gentschev et al. (1995) Infection & Immunity 63:4202; Isberg, R. R. and S. Falkow (1985) Nature 317:262; and Isberg, R. R. et al. (1987) Cell 50:769). Methods for transferring the above cytoplasm-targeting genes into a bacterial strain are well known in the art. Another preferred gene that can be introduced into bacteria to increase their invasive character encodes the invasin protein from *Yersinia pseudotuberculosis*, (Leong et al. EMBO J., 9:1979 (1990)). Invasin can also be introduced in combination with listeriolysin, thereby further increasing the invasive character of the bacteria relative to the introduction of either of these genes. The above genes have been described for illustrative purposes; however, it will be obvious to those skilled in the art that any gene or combination of genes, from one or more sources, that participates in the delivery of a molecule, in particular an RNA or RNA-encoding DNA molecule, from a microorganism into the cytoplasm of a cell, e.g., an animal cell, will suffice. Thus, such genes are not limited to bacterial genes, and include viral genes, such as influenza virus hemagglutinin HA-2 that promotes endosmolysis (Plank et al. J. Biol. Chem., 269:12918-12924 (1994)).

The above cytoplasm-targeting genes can be obtained by, e.g., PCR amplification from DNA isolated from an invasive bacterium carrying the desired cytoplasm-targeting gene. Primers for PCR can be designed from the nucleotide sequences available in the art, e.g., in the above-listed references and/or in GenBank, which is publicly available on the interne (www.ncbi.nlm.nih.gov/). The PCR primers can be designed to amplify a cytoplasm-targeting gene, a cytoplasm-targeting operon, a cluster of cytoplasm-targeting genes, or a regulon of cytoplasm-targeting genes. The PCR strategy employed will depend on the genetic organization of the cytoplasm-targeting gene or genes in the target invasive bacteria. The PCR primers are designed to contain a sequence that is homologous to DNA sequences at the beginning and end of the target DNA sequence. The cytoplasm-targeting genes can then be introduced into the target bacterial strain, e.g., by using Hfr transfer or plasmid mobilization (Miller, A Short Course in Bacterial Genetics, Cold Spring Harbor Laboratory Press, Cold Spring Harbor, N.Y. (1992); Bothwell et al. supra; and Ausubel et al. supra), bacteriophage-mediated transduction (de Boer, supra; Miller, supra; and Ausubel et al. supra), chemical transformation (Bothwell et al. supra; Ausubel et al. supra), electroporation (Bothwell et al. supra; Ausubel et al. supra; and Sambrook, Molecular Cloning: A Laboratory Manual, Cold Spring Harbor Laboratory Press, Cold Spring Harbor, N.Y.) and physical transformation techniques (Johnston et al. supra; and Bothwell, supra). The cytoplasm-targeting genes can be incorporated into lysogenic bacteriophage (de Boer et al. Cell, 56:641-649 (1989)), plasmids vectors (Curtiss et al. supra) or spliced into the chromosome (Hone et al. supra) of the target strain.

In addition to genetically engineering bacteria and BTPs to increase their invasive properties, as set forth above, bacteria and can also be modified by linking an invasion factor to the bacteria. Accordingly, in one embodiment, a bacterium is rendered more invasive by coating the bacterium, either covalently or non-covalently, with an invasion factor, e.g., the protein invasin, invasin derivatives, or a fragment thereof sufficient for invasiveness. In fact, it has been shown that non-invasive bacterial cells coated with purified invasin from *Yersinia pseudotuberculosis* or the carboxyl-terminal 192 amino acids of invasin are able to enter mammalian cells (Leong et al. (1990) EMBO J. 9:1979). Furthermore, latex beads coated with the carboxyl terminal region of invasin are efficiently internalized by mammalian cells, as are strains of *Staphylococcus aureus* coated with antibody-immobilized invasin (reviewed in Isberg and Tran van Nhieu (1994) Ann. Rev. Genet. 27:395). Alternatively, a bacterium can also be coated with an antibody, variant thereof, or fragment thereof, which binds specifically to a surface molecule recognized by a bacterial entry factor. For example, it has been shown that bacteria are internalized if they are coated with a monoclonal antibody directed against an integrin molecule, e.g., $\alpha 5\beta 1$, known to be the surface molecule with which the bacterial invasin protein interacts (Isberg and Tran van Nhieu, supra). Such antibodies can be prepared according to methods known in the art. The antibodies can be tested for efficacy in mediating bacterial invasiveness by, e.g., coating bacteria with the antibody, contacting the bacteria with eukaryotic cells having a surface receptor recognized by the antibody, and monitoring the presence of intracellular bacteria, according to the methods described above. Methods for linking an invasion factor to the surface of a bacterium are known in the art and include cross-linking.

3. Plasmids and Vectors

The present invention also provides at least one vector or plasmid including at least one DNA molecule encoding one or more siRNAs and at least one promoter, wherein the expressed siRNAs interfere with at least one mRNA of a gene of interest. In one preferred embodiment, the present invention provides at least one prokaryotic vector including at least one DNA molecule encoding one or more siRNAs and at least one RNA-polymerase III compatible promoter or at least one prokaryotic promoter, wherein the expressed siRNAs interfere with at least one mRNA of a gene of interest.

The TRIP (transkingdom RNA interference plasmid) vectors and plasmids of the present invention include a multiple cloning site, a promoter sequence and a terminator sequence. The TRIP vectors and plasmids also include one or more sequences encoding for an invasion factor to permit the non-invasive bacterium or BTP to enter mammalian cells (e.g., the Inv locus that encodes invasion that permits the bacterium or BTP to enter β1-integrin-positive mammalian cells) (Young et al., *J. Cell Biol.* 116, 197-207 (1992)) and one or more sequences to permit the genetic material to escape from the entry vesicles (e.g., Hly A gene that encodes listeriolysin O) (Mathew et al., *Gene Ther.* 10, 1105-1115 (2003) and Grillot-Courvalin et al., *Nat. Biotechnol.* 16, 862-866 (1998)). TRIP is further described (including a vector/plasmid schematic) in PCT Publication No. WO 06/066048. In preferred embodiments, the TRIP vectors and plasmids will incorporate a hairpin RNA expression cassette encoding short hairpin RNA under the control of an appropriate promoter sequence and terminator sequence.

In the design of these constructs, an algorithm was utilized to take into account some known difficulties with the development of siRNA, namely: (1) Exclusion of disqualifying properties (SNPs, interferon motifs); (2) Exclusion of the sequence if there was homology in ref seq (19/21, >17 contiguous to any other genes) and (3) Exclusion of the sequence if there were significant miRNA seed type matches.

As described herein, the one or more DNA molecules encoding the one or more siRNAs are transcribed within the eukaryotic target cell or transcribed within the bacterium or BTP.

In embodiments where the DNA is transcribed within the eukaryotic cell, the one or more siRNAs are transcribed within the eukaryotic cells as shRNAs. The eukaryotic cell can be in vivo, in vitro or ex vivo. In one aspect of this embodiment, the one or more DNA molecules encoding the one or more siRNAs contain a eukaryotic promoter. Optionally, the eukaryotic promoter is a RNA-polymerase III promoter. Optionally, the RNA polymerase III promoter is a U6 promoter or an H1 promoter.

In embodiments where the DNA is transcribed within the bacterium or BTP, the one or more DNA molecules contain a prokaryotic promoter. Optionally, the prokaryotic promoter is an *E. coli* promoter. Preferably, the *E. coli* promoter can be a T7 promoter, lacUV5 promoter, RNA polymerase promoter, gapA promoter, pA1 promoter, lac regulated promoter, araC+$P_{araBAD}$ promoter, T5 promoter, $P_{tac}$ promoter (Estrem et al, 1998, Proc. Natl. Acad. Sci. USA 95, 9761-9766; Meng et al., 2001, Nucleic Acids Res. 29, 4166-417; De Boer et al., 1983, Proc. NatL Acad. Sci. USA 80, 21-25) or recA promoter.

Preferable, promoter sequences are recited in Table 1.

TABLE 1

| Promoter | Sequence | SEQ ID NO: |
| --- | --- | --- |
| T7 promoter | TAATACGACTCACTATAG | 1 |
| lacUV5 promoter | TAACCAGGCTTTACACTTTATG CTTCCGGCTCGTATAATGTGTG GAAGGATCC | 2 |
| RNA polymerase promoter | TAACCAGGCTTTACACTTTATG CTTCCGGCTCGTATAATGTGTG GAA | 3 |
| RNA polymerase promoter | TAAAATTCAAAAATTTATTTGC TTTCAGGAAAATTTTTCTGTAT AATAGATTC | 4 |
| RNA polymerase promoter | TAATTGATACTTTATGCTTTTT TCTGTATAAT | 5 |
| gapA promoter | AAGCTTTCAGTCGCGTAATGCT TAGGCACAGGATTGATTTGTCG CAATGATTGACACGATTCCGCT TGACACTGCGTAAGTTTTGTGT TATAATGGATCC | 6 |
| pA1 promoter | AAGCTTAAGGAGAGACAACTTA AAGAGACTTAAAAGATTAATTT AAAATTTATCAAAAAGAGTATT GACTTAAAGTCTAACCTATAGG ATACTTGGATCC | 7 |
| lac regulated promoter | AAGCTTTGTGTGGAATTGTGAG CGGATAACAATTCCACACATTG ACACTTTATGCTTCCGGCTCGT ATAATGGATCC | 8 |
| lac regulated promoter | AAGCTTGGAAAATTTTTTTTAA AAAAGTCATGTGTGGAATTGTG AGCGGATAACAATTCCACATAT AATGGATCC | 9 |
| araC+ $P_{araBAD}$ promoter | GACTTCATATACCCAAGCTTTA AAAAAAAATCCTTAGCTTTCG CTAAGGATCTCCGTCAAGCCGT CAATTGTCTGATTCGTTACCAA | 10 |

TABLE 1-continued

| Promoter | Sequence | SEQ ID NO: |
|---|---|---|
| | TTATGACAACTTGACGGCTACA | |
| | TCATTCACTTTTTCTTCACAAC | |
| | CGGCACGAAACTCGCTCGGGCT | |
| | GGCCCCGGTGCATTTTTTAAAT | |
| | ACTCGCGAGAAATAGAGTTGAT | |
| | CGTCAAAACCAACATTGCGACC | |
| | GACGGTGGCGATAGGCATCCGG | |
| | GTAGTGCTCAAAAGCAGCTTCG | |
| | CCTGACTAATGCGTTGGTCCTC | |
| | GCGCCAGCTTAAGACGCTAATC | |
| | CCTAACTGCTGGCGGAAAAGAT | |
| | GTGACAGACGCGACGGCGACAA | |
| | GCAAACATGCTGTGCGACGCTG | |
| | GCGATATCAAAATTGCTGTCTG | |
| | CCAGGTGATCGCTGATGTACTG | |
| | ACAAGCCTCGCGTACCCGATTA | |
| | TCCATCGGTGGATGGAGCGACT | |
| | CGTTAATCGCTTCCATGCGCCG | |
| | CAGTAACAATTGCTCAAGCAGA | |
| | TTTATCGCCAGCAGCTCCGAAT | |
| | AGCGCCCTTCCCCTTGCCCGGC | |
| | GTTAATGATTTGCCCAAACAGG | |
| | TCGCTGAAATGCGGCTGGTGCG | |
| | CTTCATCCGGGCGAAAGAAACC | |
| | CGTATTGGCAAATATTGACGGC | |
| | CAGTTAAGCCATTCATGCCAGT | |
| | AGGCGCGCGGACGAAAGTAAAC | |
| | CCACTGGTGATACCATTCGCGA | |
| | GCCTCCGGATGACGACCGTAGT | |
| | GATGAATCTCTCCTGGCGGGAA | |
| | CAGCAAAATATCACCCGGTCGG | |
| | CAGACAAATTCTCGTCCCTGAT | |
| | TTTTCACCACCCCTGACCGCG | |
| | AATGGTGAGATTGAGAATATAA | |
| | CCTTTCATTCCCAGCGGTCGGT | |
| | CGATAAAAAAATCGAGATAACC | |
| | GTTGGCCTCAATCGGCGTTAAA | |
| | CCCGCCACCAGATGGGCGTTAA | |
| | ACGAGTATCCCGGCAGCAGGGG | |
| | ATCATTTTGCGCTTCAGCCATA | |
| | CTTTTCATACTCCCACCATTCA | |
| | GAGAAGAAACCAATTGTCCATA | |
| | TTGCATCAGACATTGCCGTCAC | |
| | TGCGTCTTTTACTGGCTCTTCT | |
| | CGCTAACCCAACCGGTAACCCC | |
| | GCTTATTAAAAGCATTCTGTAA | |
| | CAAAGCGGGACCAAAGCCATGA | |
| | CAAAAACGCGTAACAAAAGTGT | |
| | CTATAATCACGGCAGAAAAGTC | |
| | CACATTGATTATTTGCACGGCG | |
| | TCACACTTTGCTATGCCATAGC | |
| | ATTTTTATCCATAAGATTAGCG | |
| | GATCCTACCTGACGCTTTTTAT | |
| | CGCAACTCTCTACTGTAGATCT | |
| | ATCTGCGAT | |
| T5 promoter | TAAAATTCAAAAATTTATTTGC TTTCAGGAAAATTTTTCTGTAT AATAGATTCGGATCC | 11 |
| recA promoter | TAATTGATACTTTATGCTTTTT TCTGTATAATGGATCC | 12 |
| P$_{tac}$ promoter | GACTTCATATACCCAAGCTTGG AAAATTTTTTTAAAAAAGTCT TGACACTTTATGCTTCCGGCTC GTATAATGGATCC | 378 |
| P$_{atac}$ promoter | GGAAAATTTTTTTAAAAAAGTC | 379 |

In embodiments where the DNA is transcribed within the bacterium or BTP, the E. coli promoter is associated with a terminator. Preferably, the E. coli terminator can be a T7 terminator, lacUV5 terminator, Rho-independent terminator, Rho-dependent terminator, or RNA polymerase terminator. Preferable, terminator sequences are recited in Table 2.

TABLE 2

| Terminator | Sequence | SEQ ID NO: |
|---|---|---|
| T7 terminator | TAGCATAACCCCTTGGGGCCTC TAAACGGGTCTTGAGGGGTTTT TTG | 13 |
| lacUV5 terminator | TTGTCACGTGAGCGGATAACAA TTTCACACAGGAAACAGAATTC TTAAT | 14 |
| Rho-independent terminator | TTGTCACAAACCCCGCCACCGG CGGGGTTTTTTCTGCTTAAT | 15 |
| Rho-dependent terminator | TTGTCACAATTCTATGGTGTAT GCATTTATTTGCATACATTCAA TCAATTGGATCCTGCATTAAT | 16 |
| RNA polymerase terminator | GTGAGCGGATAACAATTTCACA CAGGAAACAGAATTCTTAAT | 17 |
| RNA polymerase terminator | AAACCCCGCCACCGGCGGGGTT TTTTTCTGCTTAAT | 18 |
| RNA polymerase terminator | AATTCTATGGTGTATGCATTTA TTTGCATACATTCAATCAATTG GATCCTGCATTAAT | 19 |

In additional embodiments, the vectors and plasmids of the present invention further include one or more enhancer sequences, selection markers, or lysis regulation system sequences.

In one aspect of the invention, the one or more DNA molecules contain a prokaryotic enhancer. Optionally, the prokaryotic enhancer is a T7 enhancer. Optionally, the T7 enhancer has the sequence GAGACAGG (SEQ ID NO: 563). In another aspect of this embodiment, the one or more DNA molecules contain a prokaryotic terminator.

In another aspect of the, the one or more DNA molecules are associated with one or more selection markers. In one aspect of this embodiment, the selection marker is an amber suppressor containing one or more mutations or an diamino pimelic acid (DAP) containing one or more mutations. Optionally, the dap gene is selected from, but not limited to, dapA and dapE.

Preferable, selection marker sequences are recited in Table 3.

TABLE 3

| Selection Marker | Sequence | SEQ ID NO: |
|---|---|---|
| amber suppressor gene sequence | AATTCGGGGCTATAGCTCAGCT GGGAGAGCGCTTGCATCTAATG CAAGAGGTCAGCGGTTCGATCC CGCTTAGCTCCACCACTGCA | 20 |
| amber suppressor sequence | AATTCGCCCGGATAGCTCAGTC GGTAGAGCAGGGGATTCTAAAT CCCCGTGTCCTTGGTTCGATTC CGAGTCCGGGCACTGCA | 21 |
| Rho-lgt with double amber mutation (lgt am-am allele of lgt gene) sequence | ATGACCAGTAGCTATCTGCATT AGCCGGAGTAGGATCCGGTCAT TTTCTCAATAGGACCCGTGGCG CTTCACTGGTACGGCCTGATGT ATCTGGTGGGTTTCATTTTTGC AATGTGGCTGGCAACACGACGG GCGAATCGTCCGGGCAGCGGCT GGACCAAAAATGAAGTTGAAAA CTTACTCTATGCGGGCTTCCTC GGCGTCTTCCTCGGGGGACGTA TTGGTTATGTTCTGTTCTACAA TTTCCCGCAGTTTATGGCCGAT CCGCTGTATCTGTTCCGTGTCT GGGACGGCGGCATGTCTTTCCA CGGCGGCCTGATTGGCGTTATC GTGGTGATGATTATCTTCGCCC GCCGTACTAAACGTTCCTTCTT CCAGGTCTCTGATTTTATCGCA CCACTCATTCCGTTTGGTCTTG GTGCCGGGCGTCTGGGCAACTT TATTAACGGTGAATTGTGGGGC CGCGTTGACCCGAACTTCCCGT TGCCATGCTGTTCCCTGGCTC | 22 |

TABLE 3-continued

| Selection Marker | Sequence | SEQ ID NO: |
|---|---|---|
| | CCGTACAGAAGATATTTTGCTG CTGCAAACCAACCCGCAGTGGC AATCCATTTTCGACACTTACGG TGTCCTGCCGCGCCACCCATCA CAGCTTTACGAGCTGCTGCTGG AAGGTGTGGTGCTGTTTATTAT CCTCAACCTGTATATTCGTAAA CCACGCCCAATGGGAGCTGTCT CAGGTTTGTTCCTGATTGGTTA CGGCGCGTTTCGCATCATTGTT GAGTTTTTCCGCCAGCCCGACG CGCAGTTTACCGGTGCCTGGGT GCAGTACATCAGCATGGGGCAA ATTCTTTCCATCCCGATGATTG TCGCGGGTGTGATCATGATGGT CTGGGCATATCGTCGCAGCCCA CAGCAACACGTTTCCTGA | |
| murA with double amber mutation (murA am-am allele of murA gene) sequence | ATGGATAAATTTCGTGTTCAGG GGCCAACGAAGCTCCAGGGCGA AGTCACAATTTCCGGCGCTAAA AATTAGTAGCTGCCTATCCTTT TTGCCGCACTACTGGCGGAAGA ACCGGTAGAGATCCAGAACGTC CCGAAACTGAAAGACGTCGATA CATCAATGAAGCTGCTAAGCCA GCTGGGTGCGAAAGTAGAACGT AATGTTCTGTGCATATTGATG CCCGCGACGTTAATGTATTCTG CGCACCTTACGATCTGGTTAAA ACCATGCGTGCTTCTATCTGGG CGCTGGGGCCGCTGGTAGCGCG CTTTGGTCAGGGGCAAGTTTCA CTACCTGGCGGTTGTACGATCG GTGCGCGTCCGGTTGATCTACA CATTTCTGGCCTCGAACAATTA GGCGCGACCATCAAACTGGAAG AAGGTTACGTTAAAGCTTCCGT CGATGGTCGTTTGAAAGGTGCA CATATCGTGATGGATAAAGTCA GCGTTGGCGCAACGGTGACCAT CATGTGTGCTGCAACCCTGGCG GAAGGCACCACGATTATTGAAA ACGCAGCGCGTGAACCGGAAAT CGTCGATACCGCGAACTTCCTG ATTACGCTGGGTGCGAAAATTA GCGGTCAGGGCACCGATCGTAT CGTCATCGAAGGTGTGGAACGT TTAGGCGGCGGTGTCTATCGCG TTCTGCCGGATCGTATCGAAAC CGGTACTTTCCTGGTGGCGGCG GCGATTTCTCGCGGCAAAATTA TCTGCCGTAACGCGCAGCCAGA TACTCTCGACGCCGTGCTGGCG AAACTGCGTGACGCTGGAGCGG ACATCGAAGTCGGCGAAGACTG GATTAGCCTGGATATGCATGGC AAACGTCCGAAGGCTGTTAACG TACGTACCGCGCCGCATCCGGC ATTCCCGACCGATATGCAGGCC CAGTTCACGCTGTTGAACCTGG TGGCAGAAGGGACCGGGTTTAT CACCCGAAACGGTCTTTGAAAAC CGCTTTATGCATGTGCCAGAGC TGAGCCGTATGGGCGCGCACGC CGAAATCGAAAGCAATACCGTT ATTTGTCACGGTGTTGAAAAAC TTTCTGGCGCACAGGTTATGGC AACCGATCTGCGTGCATCAGCA AGCCTGGTGCTGGCTGGCTGTA TTGCGGAAGGGACGACGGTGGT TGATCGTATTTATCACATCGAT CGTGGCTACAACGCATTGAAG ACAAACTGCGCGCTTTAGGTGC AAATATTGAGCGTGTGAAAGGC GAATAA | 23 |

TABLE 3-continued

| Selection Marker | Sequence | SEQ ID NO: |
|---|---|---|
| dapA sequence | GCCAGGCGACTGTCTTCAATAT<br>TACAGCCGCAACTACTGACATG<br>ACGGGTGATGGTGTTCACAATT<br>CCAGGGCGATCGGCACCCAACG<br>CAGTGATCACCAGATAATGTTG<br>CGATGACAGTGTCAAACTGGTT<br>ATTCCTTTAAGGGGTGAGTTGT<br>TCTTAAGGAAAGCATAAAAAAA<br>ACATGCATACAACAATCAGAAC<br>GGTTCTGTCTGCTTGCTTTTAA<br>TGCCATACCAAACGTACCATTG<br>AGACACTTGTTTGCACAGAGGA<br>TGGCCCATGTTCACGGGAAGTA<br>TTGTCGCGATTGTTACTCCGAT<br>GGATGAAAAAGGTAATGTCTGT<br>CGGGCTAGCTTGAAAAAACTGA<br>TTGATTATCATGTCGCCAGCGG<br>TACTTCGGCGATCGTTTCTGTT<br>GGCACCACTGGCGAGTCCGCTA<br>CCTTAAATCATGACGAACATGC<br>TGATGTGGTGATGATGACGCTG<br>GATCTGGCTGATGGGCGCATTC<br>CGGTAATTGCCGGGACCGGCGC<br>TAACGCTACTGCGGAAGCCATT<br>AGCCTGACGCAGCGCTTCAATG<br>ACAGTGGTATCGTCGGCTGCCT<br>GACGGTAACCCCTTACTACAAT<br>CGTCCGTCGCAAGAAGGTTTGT<br>ATCAGCATTTCAAAGCCATCGC<br>TGAGCATACTGACCTGCCGCAA<br>ATTCTGTATAATGTGCCGTCCC<br>GTACTGGCTGCGATCTGCTCCC<br>GGAAACGGTGGGCCGTCTGGCG<br>AAAGTAAAAAATATTATCGGAA<br>TCAAAGAGGCAACAGGGAACTT<br>AACGCGTGTAAACCAGATCAAA<br>GAGCTGGTTTCAGATGATTTTG<br>TTCTGCTGAGCGGCGATGATGC<br>GAGCGCGCTGGACTTCATGCAA<br>TTGGGCGGTCATGGGGTTATTT<br>CCGTTACGGCTAACGTCGCAGC<br>GCGTGATATGGCCCAGATGTGC<br>AAACTGGCAGCAGAAGGGCATT<br>TTGCCGAGGCACGCGTTATTAA<br>TCAGCGTCTGATGCCATTACAC<br>AACAAACTATTTGTCGAACCCA<br>ATCCAATCCCGGTGAAATGGGC<br>ATGTAAGGAACTGGGTCTTGTG<br>GCGACCGATACGCTGCGCCTGC<br>CAATGACACCAATCACCGACAG<br>TGGTCGTGAGACGGTCAGAGCG<br>GCGCTTAAGCATGCCGGTTTGC<br>TGTAAAGTTTAGGGAGATTTGA<br>TGGCTTACTCTGTTCAAAAGTC<br>GCGCCTGGCAAAGGTTGCGGGT<br>GTTTCGCTTGTTTTATTACTCG<br>CTGCCTGTAGTTCTGACTCACG<br>CTATAAGCGTCAGGTCAGTGGT<br>GATGAAGCCTACCTGGAAGCG | 24 |

Optionally, the amber suppressor is associated with a promoter or a terminator. Optionally, the promoter is a lipoprotein promoter. Preferable, promoter sequences are recited in Table 4.

TABLE 4

| Amber Suppressor<br>Promoter Sequence | Sequence | SEQ<br>ID NO: |
|---|---|---|
| lipoprotein promoter | CATGGCGCCGCTTCTTTGAGCG<br>AACGATCAAAAATAAGTGGCGC<br>CCCATCAAAAAAAATATTCTCAA | 25 |

TABLE 4-continued

| Amber Suppressor<br>Promoter Sequence | Sequence | SEQ<br>ID NO: |
|---|---|---|
|  | CATAAAAAACTTTGTGTAATAC<br>TTGTAACGCTG |  |
| lipoprotein promoter | CATGGCGCCCCATCAAAAAAAT<br>ATTCTCAACATAAAAAACTTTG<br>TGTAATACTTGTAACGCTG | 26 |

Optionally, the terminator is an rrnC terminator. Preferable, terminator sequences are recited in Table 5.

TABLE 5

| Amber Suppressor Terminator Sequence | Sequence | SEQ ID NO: |
|---|---|---|
| rrnC terminator | GATCCTTAGCGAAAGCTAAGGATTTTTTTTAC | 27 |
| rrnC terminator | GATCCTTAGCGAAAGCTAAGGATTTTTTTTTT | 28 |

Bacterial and BTP delivery is more attractive than viral delivery because they are more accessible to genetic manipulation, which allows the production of vector strains specifically tailored to certain applications. In one embodiment of the invention, the methods of the invention are used to create bacteria and BTPs that cause RNAi in a tissue specific manner.

Liberation of the siRNA encoding plasmid or the one or more siRNAs from the intracellular bacteria or BTPs occurs through active mechanisms. One mechanism involves the type III export system in *S. typhimurium*, a specialized multiprotein complex spanning the bacterial or BTP cell membrane whose functions include secretion of virulence factors to the outside of the cell to allow signaling towards the target cell, but which can also be used to deliver antigens into target cells (Rüssmann H. *Int J Med Microbiol*, 293:107-12 (2003)), or through bacterial lysis and liberation of bacterial or BTP contents into the cytoplasm. The lysis of intracellular bacteria or BTPs is triggered through various mechanisms, including addition of an intracellularly active antibiotic (tetracycline), naturally through bacterial metabolic attenuation (auxotrophy), or through a lysis regulation system or bacterial suicide system comprising a bacterial regulator, promoter and sensor that is sensitive to the environment, e.g., the pH, magnesium concentration, phosphate concentration, ferric ion concentration, osmolarity, anaerobic conditions, nutritional deficiency and general stress of the target cell or the host phagosome. When the bacteria or BTP lysis regulation system senses one or more of the above environmental conditions, bacterial or BTP lysis is triggered by one or more mechanisms including but not limited to antimicrobial proteins, bacteriophage lysins and autolysins expressed by the bacteria or BTP, either naturally or through modification, or through pore-forming proteins expressed by the bacteria or BTPs, either naturally or through modification, e.g., genetic modification, which break the phagosomes containing the bacteria or BTPs and liberate the siRNA-encoding plasmid or the one or more siRNAs.

The regulator of the lysis regulation system may be selected from the group that includes but is not limited to OmpR, ArcA, PhoP, PhoB, Fur, RstA, EvgA and RpoS. Preferable, lysis regulator sequences are recited in Table 6.

TABLE 6

| Lysis Regulation System Regulator Sequence | Sequence | SEQ ID NO: |
|---|---|---|
| OmpR regulator | ATGCAAGAGAACTACAAGATTCTGGTGGTCGATGACGACATGCGCCTGCGTGCGCTGCTGGAACGTTATCTCACCGAACAAGGCTTCCAGGTTCGAAGCGTCGCTAATGCAGAACAGATGGATCGCCTGCTGACTCGTGAATCTTTCCATCTTATGGTACTGGATTTAATGTTACCTGGTGAAGATGGCTTGTCGATTTGCCGACGTCTTCGTAGTCAGAGCAACCCGATGCCGATCATTAT | 29 |

TABLE 6-continued

| Lysis Regulation System Regulator Sequence | Sequence | SEQ ID NO: |
|---|---|---|
| | GGTGACGGCGAAAGGGGAAGAAGTGGACCGTATCGTAGGCCTGGAGATTGGCGCTGACGACTACATTCCAAAACCGTTTAACCCGCGTGAACTGCTGGCCCGTATCCGTGCGGTGCTGCGTCGTCAGGCGAACGAACTGCCAGGCGCACCGTCACAGGAAGAGGCGGTAATTGCTTTCGGTAAGTTCAAACTTAACCTCGGTACGCGCGAAATGTTCCGCGAAGACGAGCCGATGCCGCTCACCAGCGGTGAGTTTGCGGTACTGAAGGCACTGGTCAGCCATCCGCGTGAGCCGCTCTCCCGCGATAAGCTGATGAACCTTGCCCGTGGTCGTGAATATTCCGCAATGGAACGCTCCATCGACGTGCAGATTTCGCGTCTGCGCCGCATGGTGGAAGAAGATCCAGCGCATCCGCGTTACATTCAGACCGTCTGGGGTCTGGGCTACGTCTTTGTACCGGACGGCTCTAAAGCATGA | |
| PhoP regulator | ATGCGCGTACTGGTTGTTGAAGACAATGCGTTGTTACGTCACCACCTTAAAGTTCAGATTCAGGATGCTGGTCATCAGGTCGATGACGCAGAAGATGCCAAAGAAGCCGATTATTATCTCAATGAACATATACCGGATATTGCGATTGTCGATCTCGGATTGCCAGACGAGGACGGTCTGTCACTGATTCGCCGCTGGCGTAGCAACGATGTTTCACTGCCGATTCTGGTATTAACCGCCCGTGAAAGCTGGCAGGACAAAGTCGAAGTATTAAGTGCCGGTGCTGATGATTATGTGACTAAACCGTTTCATATTGAAGAGGTGATGGCGCGAATGCAGGCATTAATGCGGCGTAATAGCGGTCTGGCTTCACAGGTCATTTCGCTCCCCCCGTTTCAGGTTGATCTCTCTCGCCGTGAATTATCTATTAATGACGAAGTGATCAAACTGACCGCGTTCGAATACACTATTATGGAAACGTTGATACGCAATAATGGCAAAGTGGTCAGCAAAGATTCGTTAATGCTCCAACTCTATCCGGATGCGGAGCTGCGGGAAAGCCATACCATTGATGTACTGATGGGACGTCTGCGCAAAAAAATTCAGGCACAATATCCCCAAGAAGTGATTACCACCGTTCGCGGCCAGGGCTATCTGTTCGAATTGCGCTGA | 30 |

The promoter of the lysis regulation system may be selected from the group that includes but is not limited to ompF, ompC, fadB, phoPQ, mgtA, mgrB, psiB, phnD, Ptrp, sodA, sodB, sltA, sltB, asr, csgD, emrKY, yhiUV, acrAB, mdfA and tolC. Preferable, lysis regulation system promoter sequences are recited in Table 7.

TABLE 7

| Lysis Regulation System Promoter Sequence | Sequence | SEQ ID NO: |
|---|---|---|
| ompF promoter | GATCATCCTGTTACGGAATATTACATTGCAACATTTACGCGCAAAAACTAATCCGCATTCTTATTGCGGATTAGTTTTTTCTTAGCTAATAGCACAATTTTCATACTATT | 31 |

TABLE 7-continued

| Lysis Regulation System Promoter Sequence | Sequence | SEQ ID NO: |
|---|---|---|
| | TTTTGGCATTCTGGATGTCTGA AAGAAGATTTTGTGCCAGGTCG ATAAAGTTTCCATCAGAAACAA AATTTCCGTTTAGTTAATTTAA ATATAAGGAAATCATATAAATA GATTAAAATTGCTGTAAATATC ATCACGTCTCTATGGAAATATG ACGGTGTTCACAAAGTTCCTTA AATTTTACTTTTGGTTACATAT TTTTTCTTTTTGAAACCAAATC TTTATCTTTGTAGCACTTTCAC GGTAGCGAAACGTTAGTTTGAA TGGAAAGATGCCTGCA | |
| ompC promoter | TTTAAAAAAGTTCCGTAAAATT CATATTTTGAAACATCTATGTA GATAACTGTAACATCTTAAAAG TTTTAGTATCATATTCGTGTTG GATTATTCTGTATTTTTGCGGA GAATGGACTTGCCGACTGGTTA ATGAGGGTTAACCAGTAAGCAG TGGCATAAAAAAGCAATAAAGG CATATAACAGAGGGTTAATAAC | 32 |
| fadB promoter | AGTGATTCCATTTTTTACCCTT CTGTTTTTTTGACCTTAAGTCT CCGCATCTTAGCACATCGTTCA TCCAGAGCGTGATTTCTGCCGA GCGTGATCAGATCGGCATTTCT TTAATCTTTTGTTTGCATATTT TTAACACAAAATACACACTTCG ACTCATCTGGTACGACCAGATC ACCTTGCGGATTCAGGAGACTG AC | 33 |
| phoPQ promoter | GAGCTATCACGATGGTTGATGA GCTGAAATAAACCTCGTATCAG TGCCGGATGGCGATGCTGTCCG GCCTGCTTATTAAGATTATCCG CTTTTTATTTTTCACTTTACC TCCCCTCCCCGCTGGTTTATTT AATGTTTACCCCCATAACCACA TAATCGCGTTACACTATTTTAA TAATTAAGACAGGGAGAAATAA AA | 34 |
| mgtA promoter | GCTTCAACACGCTCGCGGGTGA GCTGGCTCACGCCGCTTTCGTT ATTCAGCACCCGGGAAACTGTA GATTTCCCCACGCCGCTTAAGC GCGCGATATCTTTGATGGTCAG CCGATTTTGCATCCTGTTGTCC TGTAACGTGTTGTTTAATTATT TGAGCCTAACGTTACCCGTGCA TTCAGCAATGGGTAAAGTCTGG TTTATCGTTGGTTTAGTTGTCA GCAGGTATTATATCGCCA | 35 |
| Ptrp promoter | GAGCTGTTGACAATTAATCATC GAACTAGTTAACTAGTACGCAA GTTCACGTAAAAAGGGTATCTA GAATTCT | 36 |

The sensor of the lysis regulation system may be selected from the group that includes but is not limited to EnvZ, ArcB, PhoQ, PhoR, RstB and EvgS. Preferable, lysis regulation system sensor sequences are recited in Table 8.

TABLE 8

| Lysis Regulation System Sensor Sequence | Sequence | SEQ ID NO: |
|---|---|---|
| EnvZ sensor | ATGAGGCGATTGCGCTTCTCGC CACGAAGTTCATTTGCCCGTAC GTTATTGCTCATCGTCACCTTG CTGTTCGCCAGCCTGGTGACGA CTTATCTGGTGGTGCTGAACTT CGCGATTTTGCCGAGCCTCCAG CAGTTTAATAAAGTCCTCGCGT ACGAAGTGCGTATGTTGATGAC CGACAAACTGCAACTGGAGGAC GGCACGCAGTTGGTTGTGCCTC CCGCTTTCCGTCGGGAGATCTA CCGTGAGCTGGGGATCTCTCTC TACTCCAACGAGGCTGCCGAAG AGGCAGGTCTGCGTTGGGCGCA ACACTATGAATTCTTAAGCCAT CAGATGGCGCAGCAACTGGGCG GCCCGACGGAAGTGCGCGTTGA GGTCAACAAAGTTCGCCTGTC GTCTGGCTGAAAACCTGGCTGT CGCCCAATATCTGGGTACGCGT GCCGCTGACCGAAATTCATCAG GGCGATTTCTCTCCGCTGTTCC GCTATACGCTGGCGATTATGCT ATTGGCGATAGGCGGGCGTGG CTGTTTATTCGTATCCAGAACC GACCGTTGGTCGATCTCGAACA CGCAGCCTTGCAGGTTGGTAAA GGGATTATTCCGCCGCCGCTGC GTGAGTATGGCGCTTCGGAGGT GCGTTCCGTTACCCGTGCCTTT AACCATATGGCGGCTGGTGTTA AGCAACTGGCGGATGACCGCAC GCTGCTGATGGCGGGGGTAAGT CACGACTTGCGCACGCCGCTGA CGCGTATTCGCCTGGCGACTGA GATGATGAGCGAGCAGGATGGC TATCTGGCAGAATCGATCAATA AAGATATCGAAGAGTGCAACGC CATCATTGAGCAGTTTATCGAC TACCTGCGCACCGGGCAGGAGA TGCCGATGGAAATGGCGGATCT TAATGCAGTACTCGGTGAGGTG ATTGCTGCCGAAAGTGGCTATG AGCGGGAAATTGAAACCGCGCT TTACCCCGGCAGCATTGAAGTG AAAATGCACCCGCTGTCGATCA AACGCGCGGTGGCGAATATGGT GGTCAACGCCGCCCGTTATGGC AATGGCTGGATCAAAGTCAGCA GCGGAACGGAGCCGAATCGCGC CTGGTTCCAGGTGGAAGATGAC GGTCCGGGAATTGCGCCGGAAC AACGTAAGCACCTGTTCCAGCC GTTTGTCCGCGGCGACAGTGCG CGCACCATTAGCGGCACGGGAT TAGGGCTGGCAATTGTGCAGCG TATCGTGGATAACCATAACGGG ATGCTGGAGCTTGGCACCAGCG AGCGGGCGGGCTTTCATTCG CGCCTGGCTGCCAGTGCCGGTA ACGCGGGCGCAGGGCACGACAA AAGAAGGGTAA | 37 |
| PhoQ sensor | ATGAAAAAATTACTGCGTCTTT TTTTCCCGCTCTCGCTGCGGGT ACGTTTTCTGTTGGCAACGGCA GCGGTAGTACTGGTGCTTTCGC TTGCCTACGGAATGGTCGCGCT GATCGGTTATAGCGTCAGTTTC GATAAAACTACGTTTCGGCTGT TACGTGGCGAGAGCAATCTGTT CTATACCCTTGCGAAGTGGGAA AACAATAAGTTGCATGTCGAGT TACCCGAAAATATCGACAAGCA AAGCCCCACCATGACGCTAATT TATGATGAGAACGGGCAGCTTT | 38 |

TABLE 8-continued

| Lysis Regulation System Sensor Sequence | Sequence | SEQ ID NO: |
|---|---|---|
| | TATGGGCGCAACGTGACGTGCC CTGGCTGATGAAGATGATCCAG CCTGACTGGCTGAAATCGAATG GTTTTCATGAAATTGAAGCGGA TGTTAACGATACCAGCCTCTTG CTGAGTGGAGATCATTCGATAC AGCAACAGTTGCAGGAAGTGCG GGAAGATGATGACGACGCGGAG ATGACCCACTCGGTGGCAGTAA ACGTCTACCCGGCAACATCGCG GATGCCAAAATTAACCATTGTG GTGGTGGATACCATTCCGGTGG AGCTAAAAAGTTCCTATATGGT CTGGAGCTGGTTTATCTATGTG CTCTCAGCCAATCTGCTGTTAG TGATCCCGCTGCTGTGGGTCGC CGCCTGGTGGAGTTTACGCCCC ATCGAAGCCCTGGCAAAAGAAG TCCGCGAACTGGAAGAACATAA CCGCGAATTGCTCAATCCAGCC ACAACGCGAGAACTGACCAGTC TGGTACGAAACCTGAACCGATT GTTAAAAAGTGAACGCGAACGT TACGACAAATACCGTACGACGC TCACCGACCTGACCCATAGTCT GAAAACGCCACTGGCGGTGCTG CAAAGTACGCTGCGTTCTCTGC GTAGTGAAAAGATGAGCGTCAG TGATGCTGAGCCGGTAATGCTG GAGCAAATCAGCCGCATTTCAC AGCAAATTGGCTACTACCTGCA TCGTGCCAGTATGCGCGGCGGG ACATTGCTCAGCCGCGAGCTGC ATCCGGTCGCCCCACTGCTGGA CAATCTCACCTCAGCGCTGAAC AAAGTGTATCAACGCAAAGGGG TCAATATCTCTCTCGATATTTC GCCAGAGATCAGCTTTGTCGGT GAGCAGAACGATTTTGTCGAGG TGATGGGCAACGTGCTGGATAA TGCCTGTAAATATTGCCTCGAG TTTGTCGAAATTTCTGCAAGGC AAACCGACGAGCATCTCTATAT TGTGGTCGAGGATGATGGCCCC GGTATTCCATTAAGCAAGCGAG AGGTCATTTTCGACCGTGGTCA ACGGGTTGATACTTTACGCCCT GGGCAAGGTGTAGGGCTGGCGG TAGCCCGCGAAATCACCGAGCA ATATGAGGGTAAAATCGTCGCC GGAGAGAGCATGCTGGGCGGTG CGCGGATGGAGGTGATTTTTGG TCGCCAGCATTCTGCGCCGAAA GATGAATAA | |

The lysis regulation system may comprise any combination of one or more of the above regulators, promoters and sensors.

In one example of this embodiment, the lysis regulation system comprises OmpR as the regulator, ompF as the promoter and EnvZ as the sensor and the stimulus is reduced osmolarity. In another example of this embodiment, the lysis regulation system comprises OmpR as the regulator, ompC as the promoter and EnvZ as the sensor and the stimulus is reduced osmolarity.

In another example of this embodiment, the lysis regulation system comprises the ArcA as the regulator, fad as the promoter and Arc B as the sensor and the stimulus is anaerobic conditions.

In another example of this embodiment, the lysis regulation system comprises PhoP as the regulator, phoPQ as the promoter and PhoQ as the sensor and the stimulus is reduced magnesium concentration. In another example of this embodiment, the lysis regulation system comprises PhoP as the regulator, mgtA as the promoter and PhoQ as the sensor and the stimulus is reduced magnesium concentration. In another example of this embodiment, the lysis regulation system comprises PhoP as the regulator, mgrB as the promoter and PhoQ as the sensor and the stimulus is reduced magnesium concentration.

In another example of this embodiment, the lysis regulation system comprises PhoB as the regulator, psiB as the promoter and PhoR as the sensor and the stimulus is reduced phosphate concentration. In another example of this embodiment, the lysis regulation system comprises PhoB as the regulator, phnD as the promoter and PhoR as the sensor and the stimulus is reduced phosphate concentration. In another example of this embodiment, the lysis regulation system comprises RstA as the regulator, asr as the promoter and RstB as the sensor. In another example of this embodiment, the lysis regulation system comprises RstA as the regulator, csgD as the promoter and RstB as the sensor.

In another example of this embodiment, the lysis regulation system comprises EvgA as the regulator, emrKY as the promoter and EvgS as the sensor. In another example of this embodiment, the lysis regulation system comprises EvgA as the regulator, yhiUV as the promoter and EvgS as the sensor. In another example of this embodiment, the lysis regulation system comprises EvgA as the regulator, acrAB as the promoter and EvgS as the sensor. In another example of this embodiment, the lysis regulation system comprises EvgA as the regulator, mdfA as the promoter and EvgS as the sensor. In another example of this embodiment, the lysis regulation system comprises EvgA as the regulator, tolC as the promoter and EvgS as the sensor.

In another example of this embodiment, the lysis regulation system comprises Fur as the regulator in combination with a promoter selected from the group comprising sodA, sodB, sltA or sltB.

The antimicrobial protein may be selected from the group that includes but is not limited to α- and β-defensins, protegrins, cathelicidins (e.g., indolicidin and bactenecins), granulysin, lysozyme, lactoferrin, azurocidin, elastase, bactericidal permeability inducing peptide (BPI), adrenomedullin, brevinin, histatins and hepcidin. Additional antimicrobial proteins are disclosed in the following, each of which is incorporated herein by reference in its entirety: Devine, D. A. et al., *Current Pharmaceutical Design*, 8, 703-714 (2002); Jack R. W., et al., *Microbiological Reviews*, 59 (2), 171-200 (June 1995).

Optionally, the antimicrobial protein is an α-defensin, β-defensin, or protegrin. Preferable, antimicrobial protein sequences are recited in Table 9.

TABLE 9

| Antimicrobial Protein Sequence | Sequence | SEQ ID NO: |
|---|---|---|
| α-defensin-1 protein | CTATAGAAGACCTGGGACAGAG GACTGCTGTCTGCCCTCTCTGG TCACCCTGCCTAGCTAGAGGAT CTGTGACCCCAGCCATGAGGAC CCTCGCCATCCTTGCTGCCATT CTCCTGGTGGCCCTGCAGGCCC AGGCTGAGCCACTCCAGGCAAG AGCTGATGAGGTTGCTGCAGCC CCGGAGCAGATTGCAGCGGACA TCCCAGAAGTGGTTGTTTCCCT TGCATGGGACGAAAGCTTGGCT CCAAAGCATCCAGGCTCAAGGA AAAACATGGCCTGCTATTGCAG | 39 |

TABLE 9-continued

| Antimicrobial Protein Sequence | Sequence | SEQ ID NO: |
|---|---|---|
| | AATACCAGCGTGCATTGCAGGA GAACGTCGCTATGGAACCTGCA TCTACCAGGGAAGACTCTGGGC ATTCTGCTGCTGAGCTTGCAGA AAAAGAAAAATGAGCTCAAAAT TTGCTTTGAGAGCTACAGGGAA TTGCTATTACTCCTGTACCTTC TGCTCAATTTCCTTTCCTCATC CCAAATAAATGCCTTGGTACAA GAAAAG | |
| α-defensin-3 protein | CCTTGCTATAGAAGACCTGGGA CAGAGGACTGCTGTCTGCCCTC TCTGGTCACCCTGCCTAGCTAG AGGATCTGTGACCCCAGCCATG AGGACCCTCGCCATCCTTGCTG CCATTCTCCTGGTGGCCCTGCA GGCCCAGGCTGAGCCACTCCAG GCAAGAGCTGATGAGGTTGCTG CAGCCCCGGAGCAGATTGCAGC GGACATCCCAGAAGTGGTTGTT TCCCTTGCATGGGACGAAAGCT TGGCTCCAAAGCATCCAGGCTC AAGGAAAAACATGGACTGCTAT TGCAGAATACCAGCGTGCATTG CAGGAGAACGTCGCTATGGAAC CTGCATCTACCAGGGAAGACTC TGGGCATTCTGCTGCTGAGCTT GCAGAAAAAGAAAAATGAGCTC AAAATTTGCTTTGAGAGCTACA GGGAATTGCTATTACTCCTGTA CCTTCTGCTCAATTTCCTTTCC TCATCTCAAATAAATGCCTTGT TAC | 40 |
| α-defensin-4 protein | GTCTGCCCTCTCTGCTCGCCCT GCCTAGCTTGAGGATCTGTCAC CCCAGCCATGAGGATTATCGCC CTCCTCGCTGCTATTCTCTTGG TAGCCCTCCAGGTCCGGGCAGG CCCCACTCCAGGCAAGAGGTGAT GAGGCTCCAGGCCAGGAGCAGC GTGGGCCAGAAGACCAGGACAT ATCTATTTCCTTTGCATGGGAT AAAAGCTCTGCTCTTCAGGTTT CAGGCTCAACAAGGGGCATGGT CTGCTCTTGCAGATTAGTATTC TGCCGGCGAACAGAACTTCGTG TTGGGAACTGCCTCATTGGTGG TGTGAGTTTCACATACTGCTGC ACGCGTGTCGATTAACGTTCTG CTGTCCAAGAGAATGTCATGCT GGGAACGCCATCATCGGTGGTG TTAGCTTCACATGCTTCTGCAG CTGAGCTTGCAGAATAGAGAAA AATGAGCTCATAATTTGCTTTG AGAGCTACAGGGAAATGGTTGTT TCTCCTATACTTTGTCCTTAAC ATCTTTCTTGATCCTAAATATA TATCTCGTAACAAG | 41 |
| α-defensin-5 protein | ATATCCACTCCTGCTCTCCCTC CTGCAGGTGACCCCAGCCATGA GGACCATCGCCATCCTTGCTGC CATTCTCCTGGTGGCCCTGCAG GCCCAGGCTGAGTCACTCCAGG AAAGAGCTGATGAGGCTACAAC CCAGAAGCAGTCTGGGGAAGAC AACCAGGACCTTGCTATCTCCT TTGCAGGAAATGGACTCTCTGC TCTTAGAACCTCAGGTTCTCAG GCAAGACCACCTGCTATTGCC GAACCGGCCGTTGTGCTACCCG TGAGTCCCTCTCCGGGGTGTGT GAAATCAGTGGCCGCCTCTACA GACTCTGCTGTCGCTGAGCTTC CTAGATAGAAACCAAAGCAGTG | 42 |

TABLE 9-continued

| Antimicrobial Protein Sequence | Sequence | SEQ ID NO: |
|---|---|---|
| | CAAGATTCAGTTCAAGGTCCTG AAAAAAGAAAAACATTTTACTC TGTGTACCTTGTGTCTTTCTAA ATTTCTCTCTCCAAAATAAAGT TCAAGCATT | |
| α-defensin-6 protein | ACACATCTGCTCCTGCTCTCTC TCCTCCAGCGACCCTAGCCATG AGAACCCTCACCATCCTCACTG CTGTTCCTCCGTGGCCCTCCA GGCCAAGGCTGAGCCACTCCAA GCTGAGGATGATCCACTGCAGG CAAAAGCTTATGAGGCTGATGC CCAGGAGCAGCGTGGGGCAAAT GACCAGGACTTTGCCGTCTCCT TTGCAGAGGATGCAAGCTCAAG TCTTAGAGCTTTGGGCTCAACA AGGGCTTTCACTTGCCATTGCA GAAGGTCCTGTTATTCAACAGA ATATTCCTATGGGACCTGCACT GTCATGGGTATTAACCACAGAT TCTGCTGCCTCTGAGGGATGAG AACAGAGAGAAATATATTCATA ATTTACTTTATGACCTAGAAGG AAACTGTCGTGTGTCCCATACA TTGCCATCAACTTTGTTTCCTC ATCTCAAATAAAGTCCTTTCAG CAAAAAAAAAAA | 43 |
| β-defensin-1 protein | TCCCTTCAGTTCCGTCGACGAG GTTGTGCAATCCACCAGTCTTA TAAATACAGTGACGCTCCAGCC TCTGGAAGCCTCTGTCAGCTCA GCCTCCAAAGGAGCCAGCGTCT CCCCAGTTCCTGAAATCCTGGG TGTTGCCTGCCAGTCGCCATGA GAACTTCCTACCTTCTGCTGTT TACTCTCTGCTTACTTTTGTCT GAGATGGCCTCAGGTGGTAACT TTCTCACAGGCCTTGGCCACAG ATCTGATCATTACAATTGCGTC AGCAGTGGAGGGCAATGTCTCT ATTCTGCCTGCCCGATCTTTAC CAAAATTCAAGGCACCTGTTAC AGAGGGAAGGCCAAGTGCTGCA AGTGAGCTGGGAGTGACCAGAA GAAATGACGCAGAAGTGAAATG AACTTTTTATAAGCATTCTTTT AATAAAGGAAAATTGCTTTTGA AGTATACCTCCTTTGGGCCAAA AAAAAAAAAAAAAAAAAAAAAA | 44 |
| β-defensin-3 protein | TGAGTCTCAGCGTGGGGTGAAG CCTAGCAGCTATGAGGATCCAT TATCTTCTGTTTGCTTTGCTCT TCCTGTTTTTGGTGCCTGTCCC AGGTCATGGAGGAATCATAAAC ACATTACAGAAATATTATTGCA GAGTCAGAGGCGGCCGGTGTGC TGTGCTCAGCTGCCTTCCAAAG GAGGAACAGATCGGCAAGTGCT CGACGCGTGGCCGAAATGCTGC CCGAAGAAAGAAATAAAAACCC TGAAACATGACGAGAGTGTTGT AAAGTGTGGAAATGCCTTCTTA AAGTTTATAAAAGTAAAATCAA ATTACATTTTTTTTCAAAAAA AAAAAAA | 45 |
| β-defensin-4 protein | AGACTCAGCTCCTGGTGAAGCT CCCAGCCATCAGCCATGAGGGT CTTGTATCTCCTCTTCTCGTTC CTCTTCATATTCCTGATGCCTC TTCCAGGTGTTTTTGGTGGTAT AGGCGATCCTGTTACCTGCCTT AAGAGTGGAGCCATATGTCATC CAGTCTTTTGCCCTAGAAGGTA | 46 |

TABLE 9-continued

| Antimicrobial Protein Sequence | Sequence | SEQ ID NO: |
|---|---|---|
| | TAAACAAATTGGCACCTGTGGT<br>CTCCCTGGAACAAAATGCTGCA<br>AAAAGCCATGAGGAGGCCAAGA<br>AGCTGCTGTGGCTGATGCGGAT<br>TCAGAAAGGGCTCCCTCATCAG<br>AGACGTGCGACATGTAAACCAA<br>ATTAAACTATGGTGTCCAAAGA<br>TACGCA | 5 |
| protegrin-1 protein | ATGGAGACCCAGAGAGCCAGCC<br>TGTGCCTGGGGCGCTGGTCACT<br>GTGGCTTCTGCTGCTGGCACTC<br>GTGGTGCCCTCGGCCAGCGCCC<br>AGGCCCTCAGCTACAGGGAGGC<br>CGTGCTTCGTGCTGTGGATCGC<br>CTCAACGAGCAGTCCTCGGAAG<br>CTAATCTCTACCGCCTCCTGGA<br>GCTGGACCAGCCGCCCAAGGCC<br>GACGAGGACCCGGGCACCCCGA<br>AACCTGTGAGCTTCACGGTGAA<br>GGAGACTGTGTGTCCCAGGCCG<br>ACCCGGCAGCCCCCGGAGCTGT<br>GTGACTTCAAGGAGAACGGGCG<br>GGTGAAACAGTGTGTGGGGACA<br>GTCACCCTGGATCAGATCAAGG<br>ACCCGCTCGACATCACCTGCAA<br>TGAGGTTCAAGGTGTCAGGGGA<br>GGTCGCCTGTGCTATTGTAGGC<br>GTAGGTTCTGCGTCTGTGTCGG<br>ACGAGGATGACGGTTGCGACGG<br>CAGGCTTTCCCTCCCCCAATTT<br>TCCCGGGGCCAGGTTTCCGTCC<br>CCCAATTTTTCCGCCTCCACCT<br>TTCCGGCCCGCACCATTCGGTC<br>CACCAAGGTTCCCTGGTAGACG<br>GTGAAGGATTTGCAGGCAACTC<br>ACCCAGAAGGCCTTTCGGTACA<br>TTAAAATCCCAGCAAGGAGACC<br>TAAGCATCTGCTTTGCCCAGGC<br>CCGCATCTGTCAAATAAATTCT<br>TGTGAAACC | 47 |
| protegrin-3 protein | ATGGAGACCCAGAGAGCCAGCC<br>TGTGCCTGGGGCGCTGGTCACT<br>GTGGCTTCTGCTGCTGGCACTC<br>GTGGTGCCCTCGGCCAGCGCCC<br>AGGCCCTCAGCTACAGGGAGGC<br>CGTGCTTCGTGCTGTGGATCGC<br>CTCAACGAGCAGTCCTCGGAAG<br>CTAATCTCTACCGCCTCCTGGA<br>GCTGGACCAGCCGCCCAAGGCC<br>GACGAGGACCCGGGCACCCCGA<br>AACCTGTGAGCTTCACGGTGAA<br>GGAGACTGTGTGTCCCAGGCCG<br>ACCCGGCAGCCCCCGGAGCTGT<br>GTGACTTCAAGGAGAACGGGCG<br>GGTGAAACAGTGTGTGGGGACA<br>GTCACCCTGGATCAGATCAAGG<br>ACCCGCTCGACATCACCTGCAA<br>TGAGGTTCAAGGTGTCAGGGGA<br>GGTGGCCTGTGCTATTGTAGGC<br>GTAGGTTCTGCGTCTGTGTCGG<br>ACGAGGATGACGGTTGCGACGG<br>CAGGCTTTCCCTCCCCCAATTT<br>TCCCGGGGCCAGGTTTCCGTCC<br>CCCAATTTTTCCGCCTCCACCT<br>TTCCGGCCCGCACCATTCGGTC<br>CACCAAGGTTCCCTGGTAGACG<br>GTGAAGGATTTGCAGGCAACTC<br>ACCCAGAAGGCCTTTCGGTACA<br>TTAAAATCCCAGCAAGGAGACC<br>TAAGCATCTGCTTTGCCCAGGC<br>CCGCATCTGTCAAATAAATTCT<br>TGTGAAACC | 48 |
| protegrin-4 protein | ATGGAGACCCAGAGAGCCAGCC<br>TGTGCCTGGGGCGCTGGTCACT<br>GTGGCTTCTGCTGCTGGCACTC<br>GTGGTGCCCTCGGCCAGCGCCC<br>AGGCCCTCAGCTACAGGGAGGC<br>CGTGCTTCGTGCTGTGGATCGC<br>CTCAACGAGCAGTCCTCGGAAG<br>CTAATCTCTACCGCCTCCTGGA<br>GCTGGACCAGCCGCCCAAGGCC<br>GACGAGGACCCGGGCACCCCGA<br>AACCTGTGAGCTTCACGGTGAA<br>GGAGACTGTGTGTCCCAGGCCG<br>ACCCGGCAGCCCCCGGAGCTGT<br>GTGACTTCAAGGAGAACGGGCG<br>GGTGAAACAGTGTGTGGGGACA<br>GTCACCCTGGATCAGATCAAGG<br>ACCCGCTCGACATCACCTGCAA<br>TGAGGTTCAAGGTGTCAGGGGA<br>GGTCGCCTGTGCTATTGTAGGG<br>GTTGGATCTGCTTCTGTGTCGG<br>ACGAGGATGACGGTTGCGACGG<br>CAGGCTTTCCCTCCCCCAATTT<br>TCCCGGGGCCAGGTTTCCGTCC<br>CCCAATTTTTCCGCCTCCACCT<br>TTCCGGCCCGCACCATTCGGTC<br>CACCAAGGTTCCCTGGTAGACG<br>GTGAAGGATTTGCAGGCAACTC<br>ACCCAGAAGGCCTTTCGGCACA<br>TTAAAATCCCAGCAAGGAGACC<br>TAAGCATCTGCTTTGCCCAGGC<br>CCGCATCTGTCAAATAAATTCT<br>TGTGAAACC | 49 |

The bacteriophase lysin may be selected from the group that includes but is not limited to holins and endolysins or lysins (e.g., lysozyme, amidase and transglycoslate). Additional lysins are disclosed in the following, each of which is incorporated herein by reference in its entirety: Kloos D.-U., et al., *Journal of Bacteriology*, 176 (23), 7352-7361 (December 1994); Jain V., et al., *Infection and Immunity*, 68 (2), 986-989 (February 2000); Srividhya K. V., et al., *J. Biosci.*, 32, 979-990 (2007); Young R. V., *Microbiological Reviews*, 56 (3), 430-481 (September 1992).

The autolysin may be selected from the group that includes but is not limited to peptidoglycan hydrolases, amidases (e.g., N-acetylmuramyl-L-alanine amidases), transglycosylases, endopeptidases and glucosaminidases. Additional autolysins are disclosed in the following, each of which is incorporated herein by reference in its entirety: Heidrich C., et al., *Molecular Microbiology*, 41 (1), 167-178 (2001); Kitano K., et al., *Journal of Bacteriology*, 167 (3), 759-765 (September 1986); Lommatzsch J., et al., *Journal of Bacteriology*, 179 (17), 5465-5470 (September 1997); Oshida T., et al., *PNAS*, 92, 285-289 (January 1995); Lenz L. L., et al., *PNAS*, 100 (21), 12432-12437 (Oct. 14, 2003); Ramadurai L., et al., *Journal of Bacteriology*, 179 (11), 3625-3631 (June 1997); Kraft A. R., et al., *Journal of Bacteriology*, 180 (12), 3441-3447 (July 1998); Dijkstra A. J., et al., *FEBS Letters*, 366, 115-118 (1995); Huard C., et al., *Microbiology*, 149, 695-705 (2003).

In one aspect of the invention, the control exerted by the lysis regulation system may further be enhanced by bacterial or BTP strain-specific regulation. In one aspect of this embodiment, the strain-specific regulation is attenuation caused by deletion of a nutritional gene. The nutritional gene may be selected from the group that includes but is not limited to dapA, aroA and guaBA. In one example of this embodiment, dapA attenuation results in deficiency in the biosynthesis of lysine and peptidoglycan. In this particular embodiment, transcription of genes including but not limited to lysC may be activated by mechanisms such as transcriptional induction, antitermination and riboswitch. In another example of this embodiment, aroA attenuation results in deficiency in aromatic amino acids and derepression of one or more genes including but not limited to aroF, aroG and aroH by regulators such as TrpR and TyrR. In another example of this embodiment, guaBA attenuation results in derepression of one or more genes that are repressed by PurR.

In addition to the lysis regulation system and strain-specific regulation, the bacteria or BTP may further contain an inducible system that includes but is not limited to a Tet-on expression system to facilitate bacterial or BTP lysis at a time desired by the clinician. Upon administration of tetracycline, which activates the Tet-on promoter, the bacteria or BTP express a protein that triggers lysis of the bacteria or BTP. In one example of this embodiment, the protein expressed under the Tet-on expression system is selected from the group that includes but is not limited to defensins and protegrins.

Figure 30:
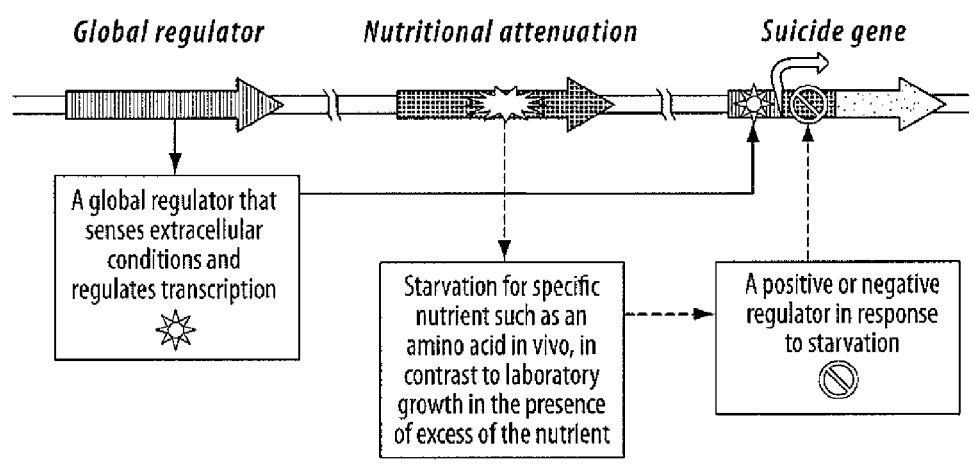
FIG. 30 is a schematic showing a lysis regulation system in combination with strain-specific nutritional attenuation.
Figure 31:
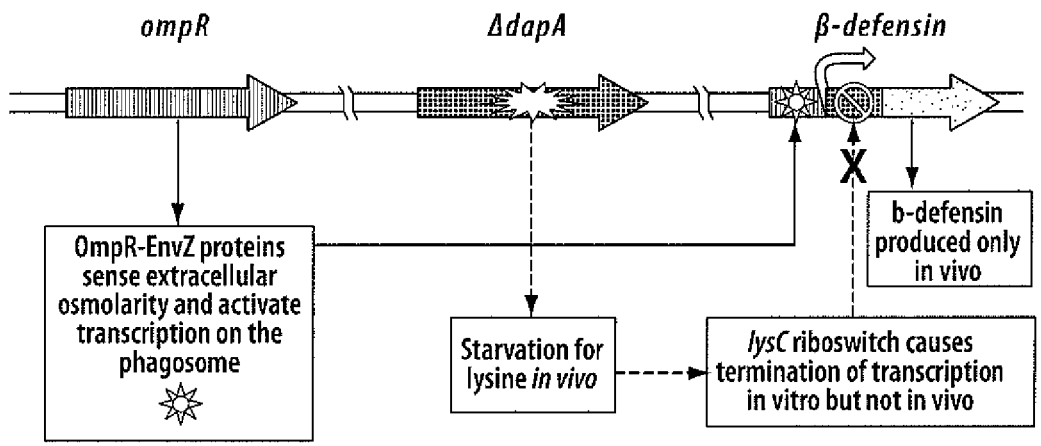
FIG. 31 is a schematic showing three cassettes in the combination lysis regulation system/nutritional attenuation system.

The present invention also provides a lysis regulation system in combination with strain-specific attenuation (e.g., nutritional attenuation). As shown in FIG. 30, a global regulator can sense an extracellular condition and regulate transcription, starvation for specific nutrient such as an amino acid in vivo, in contrast to laboratory growth in the presence of excess of the nutrient and a positive or negative regulator in response to starvation. In the schematic shown in FIG. 31 there can be three cassettes, any of which may be place on either the bacterial chromosome or on a plasmid.

Figure 32:
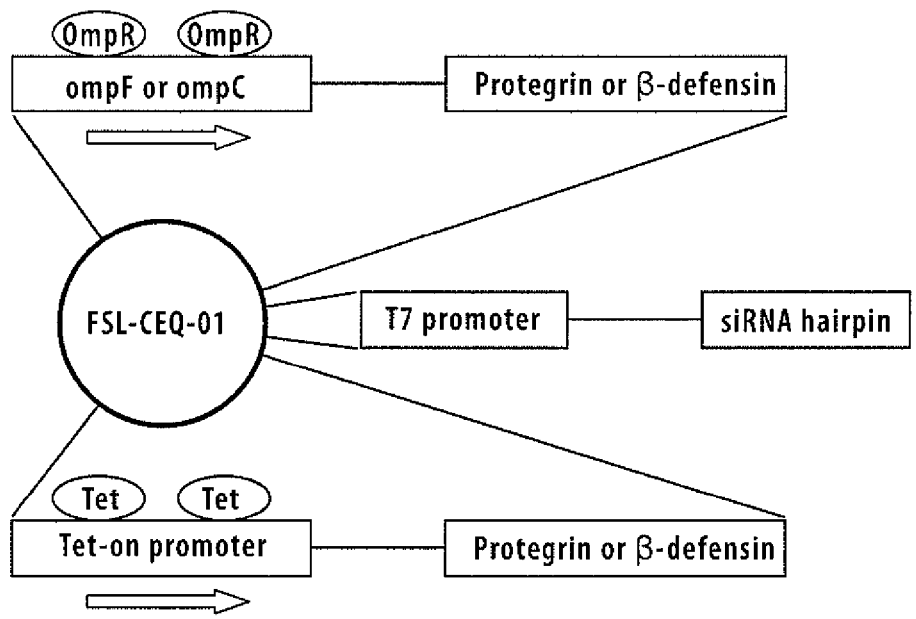
FIG. 32 is a schematic showing a lysis regulation system in combination with a Tet-on expression system.

As described, the present invention provides a plasmid containing a lysis regulation system comprising OmpR as the regulator, ompF or ompC as the promoter and protegrin or β-defensin as the antimicrobial protein, in combination with a Tet-on expression system, which provides two levels of control of bacterial lysis. This embodiment is illustrated in FIG. 32.

In another aspect of the invention, the DNA insert comprises one or more of the following constructs, each of which contains an HPV target sequence, a hairpin sequence and BamH1 and Sal1 restriction sites to facilitate incorporation into the hairpin RNA expression cassette of the TRIP plasmid as shown in Table 10.

The invention provides a method for delivering RNA to any type of target cell. As used herein, the term "target cell" refers to a cell that can be invaded by a bacterium, i.e., a cell that has the necessary surface receptor for recognition by the bacterium.

Preferred target cells are eukaryotic cells. Even more preferred target cells are animal cells. "Animal cells" are defined as nucleated, non-chloroplast containing cells derived from or present in multicellular organisms whose taxonomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, canine, goat, equine, and primate cells. The most preferred mammalian cells are human cells. The cells can be in vivo, in vitro or ex vivo.

In some embodiments of the invention, the cell is a cervical epithelial cell, a rectal epithelial cell or a pharyngeal epithelial cell, macrophage, gastrointestinal epithelial cell, skin cell, melanocyte, keratinocyte, hair follicle, colon cancer cell, an ovarian cancer cell, a bladder cancer cell, a pharyngeal cancer cell, a rectal cancer cell, a prostate cancer cell, a breast cancer cell, a lung cancer cell, a renal cancer cell, a pancreatic cancer cell, or a hematologic cancer cell such as a lymphoma or leukemia cell. In one aspect of this embodiment, the colon cancer cell is an SW 480 cell. In another aspect of this embodiment, the pancreatic cancer cell is a CAPAN-1 cell.

In a preferred embodiment, the target cell is in a mucosal surface. Certain enteric pathogens, e.g., *E. coli, Shigella, Listeria*, and *Salmonella*, are naturally adapted for this application, as these organisms possess the ability to attach to and invade host mucosal surfaces (Kreig et al. supra). Therefore, in the present invention, such bacteria can deliver RNA molecules or RNA-encoding DNA to cells in the host mucosal compartment.

TABLE 10

HPV Target Sequence Construct

| BamHI | sense (19bp) | loop | antisense (21bp) | SalI | |
|---|---|---|---|---|---|
| 5'-GATCC | TAGGTATTTGAATTTGCAT | TTCAAGAGA | ATGCAAATTCAAATACCTTTT | G-3' | (SEQ ID NO: 50) |
| 3'-G | ATCCATAAACTTAAACGTA | AAGTTCTCT | TACGTTTAAGTTTATGGAAAA | CAGCT- 5' | (SEQ ID NO: 51) |

4. Cell and Gene Targets

The present invention also provides methods of using the various bacterium, BTP and vectors provided in the invention. For example, the present invention provides methods of delivering one or more siRNAs to mammalian cells. The methods include introducing at least one invasive bacterium, or at least one bacterial therapeutic particle (BTP), containing one or more siRNAs or one or more DNA molecules encoding one or more siRNAs to the mammalian cells.

The present invention also provides methods of regulating gene expression in mammalian cells. The method includes introducing at least one invasive bacterium, or at least one bacterial therapeutic particle (BTP), containing one or more siRNAs or one or more DNA molecules encoding one or more siRNAs to the mammalian cells, where the expressed siRNAs interfere with at least one mRNA of a gene of interest thereby regulating gene expression.

Although certain types of bacteria may have a certain tropism, i.e., preferred target cells, delivery of RNA or RNA-encoding DNA to a certain type of cell can be achieved by choosing a bacterium which has a tropism for the desired cell type or which is modified such as to be able to invade the desired cell type. Thus, e.g., a bacterium could be genetically engineered to mimic mucosal tissue tropism and invasive properties, as discussed above, to thereby allow said bacteria to invade mucosal tissue, and deliver RNA or RNA-encoding DNA to cells in those sites.

Bacteria can also be targeted to other types of cells. For example, bacteria can be targeted to erythrocytes of humans and primates by modifying bacteria to express on their surface either, or both of, the *Plasmodium vivax* reticulocyte binding proteins-1 and -2, which bind specifically to erythrocytes in humans and primates (Galinski et al. Cell, 69:1213-

1226 (1992)). In another embodiment, bacteria are modified to have on their surface asialoorosomucoid, which is a ligand for the asilogycoprotein receptor on hepatocytes (Wu et al. J. Biol. Chem., 263:14621-14624 (1988)). In yet another embodiment, bacteria are coated with insulin-poly-L-lysine, which has been shown to target plasmid uptake to cells with an insulin receptor (Rosenkranz et al. Expt. Cell Res., 199: 323-329 (1992)). Also within the scope of the invention are bacteria modified to have on their surface p60 of *Listeria monocytogenes*, which allows for tropism for hepatocytes (Hess et al. Infect. Immun., 63:2047-2053 (1995)), or a 60 kD surface protein from *Trypanosoma cruzi* which causes specific binding to the mammalian extra-cellular matrix by binding to heparin, heparin sulfate and collagen (Ortega-Barria et al. Cell, 67:411-421 (1991)).

Yet in another embodiment, a cell can be modified to become a target cell of a bacterium for delivery of RNA. Accordingly, a cell can be modified to express a surface antigen that is recognized by a bacterium for its entry into the cell, i.e., a receptor of an invasion factor. The cell can be modified either by introducing into the cell a nucleic acid encoding a receptor of an invasion factor, such that the surface antigen is expressed in the desired conditions. Alternatively, the cell can be coated with a receptor of an invasion factor. Receptors of invasion factors include proteins belonging to the integrin receptor superfamily. A list of the type of integrin receptors recognized by various bacteria and other microorganisms can be found, e.g., in Isberg and Tran Van Nhieu (1994) Ann. Rev. Genet. 27:395. Nucleotide sequences for the integrin subunits can be found, e.g., in GenBank, publicly available on the internet.

As set forth above, yet other target cells include fish, avian, and reptilian cells. Examples of bacteria that are naturally invasive for fish, avian, and reptilian cells are set forth below.

Examples of bacteria that can naturally access the cytoplasm of fish cells include, but are not limited to, *Aeromonas salminocida* (ATCC No. 33658) and *Aeromonas schuberii* (ATCC No. 43700). Attenuated bacteria are preferably used in the invention, and include *A. salmonicidia* vapA (Gustafson et al. J. Mol. Biol., 237:452-463 (1994)) or *A. salmonicidia* aromatic-dependent mutant (Vaughan et al. Infect. Immun., 61:2172-2181 (1993)).

Examples of bacteria that can naturally access the cytoplasm of avian cells include, but are not restricted to, *Salmonella galinarum* (ATCC No. 9184), *Salmonella enteriditis* (ATCC No. 4931) and *Salmonella typhimurium* (ATCC No. 6994). Attenuated bacteria are preferred to the invention and include attenuated *Salmonella* strains such as *S. galinarum* cya crp mutant (Curtiss et al. (1987) supra) or *S. enteritidis* aroA aromatic-dependent mutant CVL30 (Cooper et al. Infect. Immun., 62:4739-4746 (1994)).

Examples of bacteria that can naturally access the cytoplasm of reptilian cells include, but are not restricted to, *Salmonella typhimurium* (ATCC No. 6994). Attenuated bacteria are preferable to the invention and include, attenuated strains such as *S. typhimurium* aromatic-dependent mutant (Hormaeche et al. supra).

The invention also provides for delivery of RNA to other eukaryotic cells, e.g., plant cells, so long as there are microorganisms that are capable of invading such cells, either naturally or after having been modified to become invasive. Examples of microorganisms which can invade plant cells include *Agrobacterium tumerfacium*, which uses a pilus-like structure which binds to the plant cell via specific receptors, and then through a process that resembles bacterial conjugation, delivers at least some of its content to the plant cell.

Set forth below are examples of cell lines to which RNA can be delivered according to the method of this invention.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390.

Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include CRL 6077, CRL 6113, CRL 6140, CRL 6164, CCL 94, CCL 150, CRL 6075 and CRL 6123.

Examples of buffalo cell lines include CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193-6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangutan cell line ATCC No. CRL 1850; and gorilla cell line ATCC No. CRL 1854.

The invention also provides methods of regulating the expression of one or more genes. Preferably, regulating the expression of one or more genes means decreasing or lessening the expression of the gene and/or decreasing or lessening the activity of the gene and its corresponding gene product.

In one embodiment, the expressed siRNAs direct the multienzyme complex RISC(RNA-induced silencing complex) of the cell to interact with the mRNAs to be regulated. This complex degrades or sequesters the mRNA. This causes the expression of the gene to be decreased or inhibited.

In some embodiments, the gene is an animal gene. Preferred animal genes are mammalian genes, such as humans, bovine, ovine, porcine, feline, canine, goat, equine, and primate genes. The most preferred mammalian genes are human cells.

The gene to be regulated can be a viral gene, anti-inflammatory gene, obesity gene or autoimmune disease or disorder gene. In some embodiments, more than one gene can be regulated from a single plasmid or vector.

In preferred embodiments, the gene can be, but is not limited to, ras, β-catenin, one or more HPV oncogenes, APC, HER-2, MDR-1, MRP-2, FATP4, SGLUT-1, GLUT-2, GLUT-5, apobec-1, MTP, IL-6, IL-6R, IL-7, IL-12, IL-13, IL-13 Ra-1, IL-18, p38/JNK MAP kinase, p65/NF-κB, CCL20 (MIP-3α), Claudin-2, Chitinase 3-like 1, apoA-IV, MHC class I and MHC class II. In one aspect of this embodiment, the ras is k-Ras. In another aspect of this embodiment, the HPV oncogene is E6 or E7.

Preferable β-catenin target gene sequences are recited in Table 11. The sequences in Table 11 are cross-species target sequences as they are capable of silencing the beta-catenin gene (CTNNB1) in human, mouse, rat, dog and monkey.

TABLE 11

| β-catenin target gene sequences | SEQ ID NO: |
|---|---|
| AGCCAATGGCTTGGAATGAGA | 52 |
| ATCAGCTGGCCTGGTTTGATA | 53 |
| CTGTGAACTTGCTCAGGACAA | 54 |
| AGCAATCAGCTGGCCTGGTTT | 55 |
| CCTCTGTGAACTTGCTCAGGA | 56 |
| TTCCGAATGTCTGAGGACAAG | 57 |
| CCAATGGCTTGGAATGAGACT | 58 |
| GGTGCTGACTATCCAGTTGAT | 59 |
| CAATCAGCTGGCCTGGTTTGA | 60 |
| CACCCTGGTGCTGACTATCCA | 61 |
| CACCACCCTGGTGCTGACTAT | 62 |
| TGCTTTATTCTCCCATTGAAA | 63 |
| CTGGTGCTGACTATCCAGTTG | 64 |
| TCTGTGCTCTTCGTCATCTGA | 65 |
| TGCCATCTGTGCTCTTCGTCA | 66 |
| TGGTGCTGACTATCCAGTTGA | 67 |
| CCTGGTGCTGACTATCCAGTT | 68 |
| ACCCTGGTGCTGACTATCCAG | 69 |
| GAGCCTGCCATCTGTGCTCTT | 70 |
| CTGGTTTGATACTGACCTGTA | 71 |
| TGGTTTGATACTGACCTGTAA | 72 |
| TCGAGGAGTAACAATACAAAT | 73 |
| ACCATGCAGAATACAAATGAT | 74 |
| AGGAGTAACAATACAAATGGA | 75 |
| GTCGAGGAGTAACAATACAAA | 76 |
| TTGTTGTAACCTGCTGTGATA | 77 |
| GAGTAATGGTGTAGAACACTA | 78 |
| AGTAATGGTGTAGAACACTAA | 79 |
| CACACTAACCAAGCTGAGTTT | 80 |
| TTTGGTCGAGGAGTAACAATA | 81 |
| TACCATTCCATTGTTTGTGCA | 82 |
| TAGGGTAAATCAGTAAGAGGT | 83 |
| CTAACCAAGCTGAGTTTCCTA | 84 |
| TGGTCGAGGAGTAACAATACA | 85 |
| CTGGCCTGGTTTGATACTGAC | 86 |
| TAACCTCACTTGCAATAATTA | 87 |
| ATCCCACTGGCCTCTGATAAA | 88 |
| GACCACAAGCAGAGTGCTGAA | 89 |
| CACAAGCAGAGTGCTGAAGGT | 90 |

TABLE 11-continued

| β-catenin target gene sequences | SEQ ID NO: |
|---|---|
| CTAACCTCACTTGCAATAATT | 91 |
| AGCTGATATTGATGGACAG | 92 |

Preferable HPV target gene sequences are recited in Table 12. The sequences in Table 12 are target sequences as they are capable of silencing the HPV E6 oncogene.

TABLE 12

| HPV target gene sequences | SEQ ID NO: |
|---|---|
| CGGTGCCAGAAACCGTTGAATCC | 93 |
| CACTGCAAGACATAGAAATAACC | 94 |
| AGGTGCCTGCGGTGCCAGAAACC | 95 |
| GCGGTGCCAGAAACCGTTGAATC | 96 |
| TCACTGCAAGACATAGAAATAAC | 97 |
| CCCATGCTGCATGCCATAAATGT | 98 |
| ATGCTGCATGCCATAAATGTATA | 99 |
| GTGGTGTATAGAGACAGTATACC | 100 |
| GCGCGCTTTGAGGATCCAACACG | 101 |
| CTGCGGTGCCAGAAACCGTTGAA | 102 |
| CCCCATGCTGCATGCCATAAATG | 103 |
| ACCCCATGCTGCATGCCATAAAT | 104 |
| AACACTGGGTTATACAATTTATT | 105 |
| ACGACGCAGAGAAACACAAGTAT | 106 |
| AAGGTGCCTGCGGTGCCAGAAAC | 107 |
| GGTGCCTGCGGTGCCAGAAACCG | 108 |
| CATGCTGCATGCCATAAATGTAT | 109 |
| GACGCAGAGAAACACAAGTATAA | 110 |
| TTCACTGCAAGACATAGAAATAA | 111 |
| GGTGCCAGAAACCGTTGAATCCA | 112 |
| TGGCGCGCTTTGAGGATCCAACA | 113 |
| TGTGGTGTATAGAGACAGTATAC | 114 |
| GTGCCTGCGGTGCCAGAAACCGT | 115 |
| CTGCATGCCATAAATGTATAGAT | 116 |
| GACTCCAACGACGCAGAGAAACA | 117 |
| CTGGGCACTATAGAGGCCAGTGC | 118 |
| TGCTGCATGCCATAAATGTATAG | 119 |
| GTGCCAGAAACCGTTGAATCCAG | 120 |
| TTACAGAGGTATTTGAATTTGCA | 121 |
| GAGGCCAGTGCCATTCGTGCTGC | 122 |

Additional preferable HPV target gene sequences are recited in Table 13. The sequences in Table 13 are target sequences as they are capable of silencing the HPV E7 oncogene.

TABLE 13

| HPV target gene sequences | SEQ ID NO: |
|---|---|
| ATTCCGGTTGACCTTCTATGTCA | 123 |
| GATGGAGTTAATCATCAACATTT | 124 |
| AAGCCAGAATTGAGCTAGTAGTA | 125 |
| CATGGACCTAAGGCAACATTGCA | 126 |
| AACCACAACGTCACACAATGTTG | 127 |
| ATGGACCTAAGGCAACATTGCAA | 128 |
| TAAGCGACTCAGAGGAAGAAAAC | 129 |
| GAAGCCAGAATTGAGCTAGTAGT | 130 |
| GAGCCGAACCACAACGTCACACA | 131 |
| ACGTCACACAATGTTGTGTATGT | 132 |
| GAACCACAACGTCACACAATGTT | 133 |
| AGGCAACATTGCAAGACATTGTA | 134 |
| AAGACATTGTATTGCATTTAGAG | 135 |
| TAAGGCAACATTGCAAGACATTG | 136 |
| CCAGCCCGACGAGCCGAACCACA | 137 |
| AAGCTCAGCAGACGACCTTCGAG | 138 |
| GCCCGACGAGCCGAACCACAACG | 139 |
| TTCCGGTTGACCTTCTATGTCAC | 140 |
| TGCATGGACCTAAGGCAACATTG | 141 |
| TTCCAGCAGCTGTTTCTGAACAC | 142 |
| AACACCCTGTCCTTTGTGTGTCC | 143 |
| CTTCTATGTCACGAGCAATTAAG | 144 |
| ACGAGCCGAACCACAACGTCACA | 145 |
| TTGAGCTAGTAGTAGAAAGCTCA | 146 |
| CAGCAGACGACCTTCGAGCATTC | 147 |
| AGCCAGAATTGAGCTAGTAGTAG | 148 |
| GTCACACAATGTTGTGTATGTGT | 149 |
| CCGACGAGCCGAACCACAACGTC | 150 |
| AATTCCGGTTGACCTTCTATGTC | 151 |
| ATTCCAGCAGCTGTTTCTGAACA | 152 |

Additional preferable HPV target gene sequences are recited in Table 14. The sequences in Table 14 are target sequences shared by both HPV E6 and E7.

TABLE 14

| HPV target gene sequences | SEQ ID NO: |
|---|---|
| TAGGTATTTGAATTTGCAT | 153 |
| GAGGTATTTGAATTTGCAT | 154 |

A preferable MDR-1 target gene sequence is recited in Table 15. The sequence in Table 15 is capable of silencing the MDR-1 gene in human.

TABLE 15

| MDR-1 target gene sequences | SEQ ID NO: |
|---|---|
| ATGTTGTCTGGACAAGCACT | 155 |

A preferable k-Ras target gene sequence is recited in Table 16. The sequence in Table 16 is capable of silencing the k-Ras gene in human.

TABLE 16

| k-Ras target gene sequences | SEQ ID NO: |
|---|---|
| GTTGGAGCTGTTGGCGTAG | 156 |

Preferable IL-6R target gene sequence are recited in Table 17. The sequences in Table 17 are capable of silencing IL-6R in human.

TABLE 17

| IL-6R target gene sequences | SEQ ID NO: |
|---|---|
| CTCCTGGAACTCATCTTTCTA | 157 |
| GCTCTCCTGCTTCCGGAAGAG | 158 |
| CTCCACGACTCTGGAAACTAT | 159 |
| CAGAAGTTCTCCTGCCAGTTA | 160 |
| CCGGAAGACAATGCCACTGTT | 161 |
| CTGAACGGTCAAAGACATTCA | 162 |
| CACAACATGGATGGTCAAGGA | 163 |
| ATGCAGGCACTTACTACTAAT | 164 |
| ATCGGGCTGAACGGTCAAAGA | 165 |
| AGCTCTCCTGCTTCCGGAAGA | 166 |
| CAGCTCTCCTGCTTCCGGAAG | 167 |
| CAGGCACTTACTACTAATAAA | 168 |
| CACTTGCTGGTGGATGTTCCC | 169 |
| AACGGTCAAAGACATTCACAA | 170 |
| TGCACAAGCTGCACCCTCAGG | 171 |

Additional referable IL-6R target gene sequences are recited in Table 18. The sequences in Table 18 are capable of silencing the IL-6R gene in mouse.

TABLE 18

| IL-6R target gene sequences | SEQ ID NO: |
|---|---|
| ATCCTGGAGGGTGACAAAGTA | 172 |
| TGGGTCTGACAATACCGTAAA | 173 |
| AACGAAGCGTTTCACAGCTTA | 174 |
| CCGCTGTTTCCTATAACAGAA | 175 |
| ACGAAGCGTTTCACAGCTTAA | 176 |
| CTGCTGTGAAAGGGAAATTTA | 177 |
| AACCTTGTGGTATCAGCCATA | 178 |

TABLE 18-continued

| IL-6R target gene sequences | SEQ ID NO: |
|---|---|
| CACAGTGTGGTGCTTAGATTA | 179 |
| CAGCTTCGATACCGACCTGTA | 180 |
| CAGTGTGGTGCTTAGATTAAA | 181 |
| CCCGGCAGGAATCCTCTGGAA | 182 |
| CCCGCTGTTTCCTATAACAGA | 183 |
| AACCACGAGGATCAGTACGAA | 184 |
| ACCTGCCGTCTTACTGAACTA | 185 |
| ACCACGAGGATCAGTACGAAA | 186 |
| ACAGCTTGTGATGACTGAATA | 187 |
| AGGATCAGTACGAAAGTTCTA | 188 |
| AACCCGCTGTTTCCTATAACA | 189 |
| CAGTACGAAAGTTCTACAGAA | 190 |
| TACGCGAGTGACAATTTCTCA | 191 |
| ACGAAAGTTCTACAGAAGCAA | 192 |
| CAGGCACTTACTACTAATAAA | 193 |
| CACTTGCTGGTGGATGTTCCC | 194 |
| AACGGTCAAAGACATTCACAA | 195 |
| TGCACAAGCTGCACCCTCAGG | 196 |

Preferable IL-7 target gene sequences are recited in Table 19. The sequences in Table 19 are capable of silencing the IL-7 gene in human.

TABLE 19

| IL-7 target gene sequences | SEQ ID NO: |
|---|---|
| TAAGAGAGTCATAAACCTTAA | 197 |
| AACAAGGTCCAAGATACCTAA | 198 |
| AAGATTGAACCTGCAGACCAA | 199 |
| AAGAGATTTCAAGAGATTTAA | 200 |
| AAGCGCAAAGTAGAAACTGAA | 201 |
| TAGCATCATCTGATTGTGATA | 202 |
| TAAGATAATAATATATGTTTA | 203 |
| ATGGTCAGCATCGATCAATTA | 204 |
| TTGCCTGAATAATGAATTTAA | 205 |
| ATCTGTGATGCTAATAAGGAA | 206 |
| AACAAACTATTTCTTATATAT | 207 |
| AACATTTATCAATCAGTATAA | 208 |
| ATCAATCAGTATAATTCTGTA | 209 |
| AAGGTATCAGTTGCAATAATA | 210 |

Additional preferable IL-7 target gene sequences are recited in Table 20. The sequences in Table 20 are capable of silencing the IL-7 gene in mouse.

TABLE 20

| IL-7 target gene sequences | SEQ ID NO: |
|---|---|
| CGGATCCTACGGAAGTTATGG | 211 |
| GACCATGTTCCATGTTTCTTT | 212 |
| AACCTAAATGACCTTTATTAA | 213 |
| CAGGAGACTAGGACCCTATAA | 214 |
| TAGGGTCTTATTCGTATCTAA | 215 |
| ATGAGCCAATATGCTTAATTA | 216 |
| GCCAATATGCTTAATTAGAAA | 217 |
| CAGCATCGATGAATTGGACAA | 218 |
| TTGCCTGAATAATGAATTTAA | 219 |
| CTGATAGTAATTGCCCGAATA | 220 |
| AAGGGTTTGCTTGTACTGAAT | 221 |
| AACATGTATGTGATGATACAA | 222 |
| TTGCAACATGTAATAATTTAA | 223 |
| AAGAGACTACTGAGAGAAATA | 224 |
| AAGAATCTACTGGTTCATATA | 225 |
| TGCCGTCAGCATATACATATA | 226 |
| AGGGCTCACGGTGATGGATAA | 227 |

Additional preferable IL-7 target gene sequences are recited in Table 21. The sequences in Table 21 are cross species sequences as they are capable of silencing the IL-7 gene in human and mouse.

TABLE 21

| IL-7 target gene sequences | SEQ ID NO: |
|---|---|
| CGCCTCCCGCAGACCATGTTC | 228 |
| TCCGTGCTGCTCGCAAGTTGA | 229 |
| GCCTCCCGCAGACCATGTTCC | 230 |
| CCTCCCGCAGACCATGTTCCA | 231 |
| CTCCCGCAGACCATGTTCCAT | 232 |
| TCCCGCAGACCATGTTCCATG | 233 |
| CCCGCAGACCATGTTCCATGT | 234 |
| CCGCAGACCATGTTCCATGTT | 235 |
| CGCAGACCATGTTCCATGTTT | 236 |
| GCAGACCATGTTCCATGTTTC | 237 |
| CAGACCATGTTCCATGTTTCT | 238 |
| AGACCATGTTCCATGTTTCTT | 239 |

Preferable IL-13Ra-1 target gene sequences are recited in Table 22. The sequences in Table 22 are capable of silencing the IL-13Ra-1 gene in human.

TABLE 22

| IL-13Ra-1 target gene sequences | SEQ ID NO: |
| --- | --- |
| AACCTGATCCTCCACATATTA | 240 |
| CCTGATCCTCCACATATTAAA | 241 |
| AGAAATGTTTGGAGACCAGAA | 242 |
| CAAATAATGGTCAAGGATAAT | 243 |
| TTCCTGATCCTGGCAAGATTT | 244 |
| TAAAGAAATGTTTGGAGACCA | 245 |
| ATGTTTGGAGACCAGAATGAT | 246 |
| CTCCAATTCCTGATCCTGGCA | 247 |

Additional preferable IL-13Ra-1 target gene sequences are recited in Table 23. The sequences in Table 23 are capable of silencing the IL-13Ra-1 gene in mouse.

TABLE 23

| IL-13Ra-1 target gene sequences | SEQ ID NO: |
| --- | --- |
| CAAGAAGACTCTAATGATGTA | 248 |
| CACAGTCAGAGTAAGAGTCAA | 249 |
| ACCCAGGGTATCATAGTTCTA | 250 |
| CTGCTTTGAAATTTCCAGAAA | 251 |
| ATCATAGTTCTAAGAATGAAA | 252 |
| AAGGCTTAAGATCATTATATT | 253 |
| AACTACTTATAAGAAAGTAAA | 254 |
| CACAGAACATCTAGCAAACAA | 255 |
| CTCGTTCTTGTTCAATCCTAA | 256 |
| AACTTGTAGGTTCACATATTA | 257 |
| AACCATTTCTGCAAATTTAAA | 258 |
| CTCAGTGTAGTGCCAATGAAA | 259 |
| CAGGCCTTAGGGACTCATAAA | 260 |
| AAGTATGACATCTATGAGAAA | 261 |
| GTGGAGGTCAATAATACTCAA | 262 |
| CAGAGTATAGGTAAGGAGCAA | 263 |

A preferable IL-18 target gene sequence is recited in Table 24. The sequence in Table 24 is capable of silencing the IL-18 gene in human.

TABLE 24

| IL-18 target gene sequences | SEQ ID NO: |
| --- | --- |
| TTGAATGACCAAGTTCTCTTC | 264 |

Additional preferable IL-18 target gene sequences are recited in Table 25. The sequences in Table 25 are capable of silencing the IL-18 gene in mouse.

TABLE 25

| IL-18 target gene sequences | SEQ ID NO: |
| --- | --- |
| CTCTCTGTGAAGGATAGTAAA | 265 |
| CCGCAGTAATACGGAATATAA | 266 |
| CAAGGAAATGATGTTTATTGA | 267 |
| CAGACTGATAATATACATGTA | 268 |
| TTGGCCGACTTCACTGTACAA | 269 |
| CCAGACCAGACTGATAATATA | 270 |
| AAGATGGAGTTTGAATCTTCA | 271 |
| ACGCTTTACTTTATACCTGAA | 272 |
| TACAACCGCAGTAATACGGAA | 273 |
| CTGCATGATTTATAGAGTAAA | 274 |
| CCCGAGGCTGCATGATTTATA | 275 |
| CACGCTTTACTTTATACCTGA | 276 |
| CGCCTGTATTTCCATAACAGA | 277 |
| CGCAGTAATACGGAATATAAA | 278 |
| TACATGTACAAAGACAGTGAA | 279 |
| CAGGCCTGACATCTTCTGCAA | 280 |
| TTCGAGGATATGACTGATATT | 281 |
| CTGTATTTCCATAACAGAATA | 282 |
| GAGGATATGACTGATATTGAT | 283 |
| CAAGTTCTCTTCGTTGACAAA | 284 |
| CACTAACTTACATCAAAGTTA | 285 |
| ACCGCAGTAATACGGAATATA | 286 |
| CTCTCACTAACTTACATCAAA | 287 |

Preferable CCL20 target gene sequences are recited in Table 26. The sequences in Table 26 are capable of silencing the CCL20 gene in human.

TABLE 26

| CCL20 target gene sequences | SEQ ID NO: |
| --- | --- |
| ATCATCTTTCACACAAAGAAA | 288 |
| AACAGACTTGGGTGAAATATA | 289 |
| ATGGAATTGGACATAGCCCAA | 290 |
| GAGGGTTTAGTGCTTATCTAA | 291 |
| CTCACTGGACTTGTCCAATTA | 292 |
| ATCATAGTTTGCTTTGTTTAA | 293 |
| TTGTTTAAGCATCACATTAAA | 294 |
| AAGCATCACATTAAAGTTAAA | 295 |
| CCCAAAGAACTGGGTACTCAA | 296 |
| CACATTAAAGTTAAACTGTAT | 297 |
| CAGATCTGTTCTTTGAGCTAA | 298 |

TABLE 26-continued

| CCL20 target gene sequences | SEQ ID NO: |
|---|---|
| TTGGTTTAGTGCAAAGTATAA | 299 |
| CAGACCGTATTCTTCATCCTA | 300 |
| AACATTAATAAGACAAATATT | 301 |
| GACCGTATTCTTCATCCTAAA | 302 |

Additional referable CCL20 target gene sequences are recited in Table 27. The sequences in Table 27 are capable of silencing the CCL20 gene in mouse.

TABLE 27

| CCL20 target gene sequences | SEQ ID NO: |
|---|---|
| AAGCTTGTGACATTAATGCTA | 303 |
| CAATAAGCTATTGTAAAGATA | 304 |
| ATCATCTTTCACACGAAGAAA | 305 |
| AGCTATTGTAAAGATATTTAA | 306 |
| CAGCCTAAGAGTCAAGAAGAT | 307 |
| CCCAGTGGACTTGTCAATGGA | 308 |
| ATGAAGTTGATTCATATTGCA | 309 |
| AAGTTGATTCATATTGCATCA | 310 |
| TCACATTAGAGTTAAGTTGTA | 311 |
| CACATTAGAGTTAAGTTGTAT | 312 |
| TATGTTATTTATAGATCTGAA | 313 |
| ATGTTTAGCTATTTAATGTTA | 314 |
| TTAGTGGAAGGATTAATATTA | 315 |
| ACCCAGCACTGAGTACATCAA | 316 |
| TATGTTTAAGGGAATAGTTTA | 317 |

Additional preferable CCL20 target gene sequences are recited in Table 28. The sequences in Table 28 are cross-species target sequences as they are capable of silencing the CCL20 gene in human and mouse.

TABLE 28

| CCL20 target gene sequences | SEQ ID NO: |
|---|---|
| ATGAAGTTGATTCATATTGCA | 318 |
| TGAAGTTGATTCATATTGCAT | 319 |
| GAAGTTGATTCATATTGCATC | 320 |
| AAGTTGATTCATATTGCATCA | 321 |
| AGTTGATTCATATTGCATCAT | 322 |
| GTTGATTCATATTGCATCATA | 323 |
| TTGATTCATATTGCATCATAG | 324 |
| TGATTCATATTGCATCATAGT | 325 |
| TCAATGCTATCATCTTTCACA | 326 |

TABLE 28-continued

| CCL20 target gene sequences | SEQ ID NO: |
|---|---|
| CAATGCTATCATCTTTCACAC | 327 |
| TAATGAAGTTGATTCATATTG | 328 |
| AATGAAGTTGATTCATATTGC | 329 |

Preferable CCL20 target gene sequences are recited in Table 29. The sequences in Table 29 are capable of silencing the CCL20 gene in human.

TABLE 29

| Claudin-2 target gene sequences | SEQ ID NO: |
|---|---|
| AGCATGAAATTTGAGATTGGA | 330 |
| TACAGAGCCTCTGAAAGACCA | 331 |
| CACTACAGAGCCTCTGAAAGA | 332 |
| CTGACAGCATGAAATTTGAGA | 333 |
| ATCTCTGTGGTGGGCATGAGA | 334 |
| CATGAAATTTGAGATTGGAGA | 335 |
| TCTGGCTGAGGTTGGCTCTTA | 336 |
| GTGGGCTACATCCTAGGCCTT | 337 |

Additional preferable CCL20 target gene sequences are recited in Table 30. The sequences in Table 30 are capable of silencing the CCL20 gene in mouse.

TABLE 30

| Claudin-2 target gene sequences | SEQ ID NO: |
|---|---|
| CAGCTTCCTGCTAAACCACAA | 338 |
| CAAGAGTGAGTTCAACTCATA | 339 |
| CTGGTTCCTGACAGCATGAAA | 340 |
| TGGCTGGGACTATATATATAA | 341 |
| GAGGGCAATTGCTATATCTTA | 342 |
| CAGCAGCCAAACGACAAGCAA | 343 |
| CAAGGGTTTCCTTAAGGACAA | 344 |
| CAGATACTTGTAAGGAGGAAA | 345 |
| AAGAAATGGATTAGTCAGTAA | 346 |
| AAGGAAAGCACAAGAAGCCAA | 347 |
| CTGGCTGAGGTTGGCTCTTAA | 348 |
| AACCTGGGATCTAAAGAAACA | 349 |
| AAGGGCTTGGGTATCAAAGAA | 350 |
| CAGGCTCCGAAGATACTTCTA | 351 |
| CCCAATATATAAATTGCCTAA | 352 |
| CTGACCCAGCTTCCTGCTAAA | 353 |

Preferable Chitinase-3 target gene sequences are recited in Table 31. The sequences in Table 31 are capable of silencing the Chitinase-3 gene in human.

TABLE 31

| Chitinase-3 target gene sequences | SEQ ID NO: |
|---|---|
| ACCCACATCATCTACAGCTTT | 354 |
| CATCATCTACAGCTTTGCCAA | 355 |
| CAGCTGGTCCCAGTACCGGGA | 356 |
| CACCAAGGAGGCAGGGACCCT | 357 |
| CCGGTTCACCAAGGAGGCAGG | 358 |
| AGCTGGTCCCAGTACCGGGAA | 359 |
| CAGGCCGGTTCACCAAGGAGG | 360 |
| GGCCGGTTCACCAAGGAGGCA | 361 |

Additional preferable Chitinase-3 target gene sequences are recited in Table 32. The sequences in Table 32 are capable of silencing the Chitinase-3 gene in mouse.

TABLE 32

| Chitinase-3 target gene sequences | SEQ ID NO: |
|---|---|
| TAGGTTTGACAGATACAGCAA | 362 |
| AACCCTGTTAAGGAATGCAAA | 363 |
| ATCAAGTAGGCAAATATCTTA | 364 |
| CGCAGCTTTGTCAGCAGGAAA | 365 |
| TTGGATCAAGTAGGCAAATAT | 366 |
| TTGAGGGACCATACTAATTAT | 367 |
| GAGGACAAGGAGAGTGTCAAA | 368 |
| TGCGTACAAGCTGGTCTGCTA | 369 |
| CAGGAGTTTAATCTCTTGCAA | 370 |
| ATCAAGGAACTGAATGCGGAA | 371 |
| CACCCTGATCAAGGAACTGAA | 372 |
| CACTTGGATCAAGTAGGCAAA | 373 |
| CAGGATTGAGGGACCATACTA | 374 |
| AACTATGACAAGCTGAATAAA | 375 |
| ATGCAAATTCTCAGACTCTAA | 376 |
| ATCCTTCCCTTAGGAACTTAA | 377 |

5. Treatment of Diseases and Disorders

The present invention also provides methods of treating or preventing a disease or disorder in a mammal. The methods include regulating the expression of at least one gene in a cell known to cause a disease or disorder by introducing to the cells of the mammal at least one invasive bacterium, or at least one bacterial therapeutic particle (BTP), containing one or more siRNAs or one or more DNA molecules encoding one or more siRNAs, where the expressed siRNAs interfere with the mRNA of the gene known to cause the disease or disorder of interest.

The RNAi methods of the invention, including BMGS and tkRNAi are used to treat any disease or disorder for which gene expression regulation would be beneficial. This method is effected by silencing or knocking down (decreasing) genes involved with one or more diseases and disorders.

The gene to be regulated to treat or prevent a disease or disorder of interest, can be, but is not limited to, ras, β-catenin, one or more HPV oncogenes, APC, HER-2, MDR-1, MRP-2, FATP4, SGLUT-1, GLUT-2, GLUT-5, apobec-1, MTP, IL-6, IL-6R, IL-7, IL-12, IL-13, IL-13 Ra-1, IL-18, p38/JNK MAP kinase, p65/NF-κB, CCL20 (MIP-3α), Claudin-2, Chitinase 3-like 1, apoA-IV, MHC class I and MHC class II. In one aspect of this embodiment, the ras is k-Ras. In another aspect of this embodiment, the HPV oncogene is E6 or E7.

Preferably, the present invention provides methods of treating or preventing cancer or a cell proliferation disorder, viral disease, an inflammatory disease or disorder, a metabolic disease or disorder, an autoimmune disease or disorder, or a disease, disorder or cosmetic concern in the skin or hair in a mammal by regulating the expression of a gene or several genes known to be associated with the onset, propagation or prolongation of the disease or disorder by introducing a bacterium or BTP to the cell. The bacterium or BTP contain one or more siRNAs or one or more DNA molecules encoding one or more siRNAs, where the expressed siRNAs interfere with the mRNA of the gene known to cause, propagate or prolong the disease or disorder of interest.

In some preferred embodiments, the viral disease can be, but is not limited to, hepatitis B, hepatitis C, Human Papilloma Virus (HPV) infection or epithelial dysplasia or cancer caused by HPV infection or HPV induced transformation, including cervical cancer, rectal cancer and pharyngeal cancer.

In some preferred embodiments, the inflammatory disease or disorder can be, but is not limited to, inflammatory bowel disease, Crohn's disease, ulcerative colitis, an allergy, rheumatoid arthritis.

In some preferred embodiments, the autoimmune disease or disorder can be, but is not limited to, celiac disease.

In some preferred embodiments, the disease, disorder or cosmetic concern can be, but is not limited to, psoriasis, eczema, albinism, balding or gray hair.

The mammal can be any mammal including, but not limited to, human, bovine, ovine, porcine, feline, canine, goat, equine, or primate. Preferably, the mammal is a human.

The terms "treating" and "treatment" as used herein refer to the administration of an agent or formulation (e.g., bacterium and/or BTP containing an siRNA or a DNA encoding for an siRNA) to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

6. Pharmaceutical Compositions and Modes of Administration

In a preferred embodiment of the invention, the invasive bacteria or BTPs containing the RNA molecules, and/or DNA encoding such, are introduced into an animal by intravenous, intramuscular, intradermal, intraperitoneally, peroral, intranasal, intraocular, intrarectal, intravaginal, intraosseous, oral, immersion and intraurethral inoculation routes.

The amount of the invasive bacteria or BTPs of the present invention to be administered to a subject will vary depending on the species of the subject, as well as the disease or condition that is being treated. Generally, the dosage employed will be about $10^3$ to $10^{11}$ viable organisms, preferably about $10^5$ to $10^9$ viable organisms per subject.

The invasive bacteria or BTPs of the present invention are generally administered along with a pharmaceutically acceptable carrier and/or diluent. The particular pharmaceutically acceptable carrier an/or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al. J. Clin. Invest., 79:888-902 (1987); and Black et al J. Infect. Dis., 155:1260-1265 (1987)), or bicarbonate buffer (pH 7.0) containing ascorbic acid, lactose, and optionally aspartame (Levine et al. Lancet, II: 467-470 (1988)). Examples of carriers include proteins, e.g., as found in skim milk, sugars, e.g., sucrose, or polyvinylpyrrolidone. Typically these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria or BTPs are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria or BTPs, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the bacteria of the invention are formulated into ointments, salves, gels, or creams as generally known in the art, so long as the bacteria are still invasive upon contact with a target cell.

The compositions may, if desired, be presented in a pack or dispenser device and/or a kit that may contain one or more unit dosage forms containing the active ingredient. The pack may for example comprise metal or plastic foil, such as a blister pack. The pack or dispenser device may be accompanied by instructions for administration.

The invasive bacteria or BTPs containing the RNA or RNA-encoding DNA to be introduced can be used to infect animal cells that are cultured in vitro, such as cells obtained from a subject. These in vitro-infected cells can then be introduced into animals, e.g., the subject from which the cells were obtained initially, intravenously, intramuscularly, intradermally, or intraperitoneally, or by any inoculation route that allows the cells to enter the host tissue. When delivering RNA to individual cells, the dosage of viable organisms administered will be at a multiplicity of infection ranging from about 0.1 to $10^6$, preferably about $10^2$ to $10^4$ bacteria per cell.

In yet another embodiment of the present invention, bacteria can also deliver RNA molecules encoding proteins to cells, e.g., animal cells, from which the proteins can later be harvested or purified. For example, a protein can be produced in a tissue culture cell.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The present invention is further illustrated by the following examples that should not be construed as limiting in any way. The contents of all cited references including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The following non-limiting examples are merely illustrative of the preferred embodiments of the present invention, and are not to be construed as limiting the invention.

EXAMPLES

Example 1

Knockdown of β-catenin and k-Ras

Previous studies have demonstrated the powerful nature of the siRNA knockdown technology disclosed herein. For example, in vitro and in vivo knockdown of beta catenin and k-ras utilizing bacterial delivery is described in PCT Publication No. WO 06/066048, which is incorporated herein by reference in its entirety.

Example 2

TRIP with Multiple shRNA Expression Cassettes

The TRIP described herein, and described in further detail in PCT Publication No. WO 06/066048, can be modified to produce a plasmid which allows targeting of multiple genes simultaneously or multiple sequences within one gene simultaneously. For example, TRIP with multiple hairpin expression cassettes to produce shRNA can target different sequences in a given gene, or target multiple genes through a simultaneous bacterial treatment.

The TRIP plasmid can incorporate multiple (up to ten) cloning sites to express different shRNA constructs (FIG. 1). The purpose of such a plasmid will be to allow silencing of various genes through a single therapeutic bacterium which will be empowered by the Multiple-expression cassette-TRIP (mec-TRIP) to synthesize short hairpin RNA against a variety of targets simultaneously.

These different hairpins can either be expressed competitively at high levels through the use of an identical high level promoter (such as T7 promoter or a different high level bacterial promoter), or they can be expressed at different levels through the use of promoters with different levels of activity, this will depend on the intended use of the plasmid and the desired relative silencing levels of the target gene.

This mec-TRIP could be useful to treat complex diseases as described herein (e.g. inflammatory diseases, or cancer), through the simultaneous silencing (targeting) of multiple targets as described herein (e.g. multiple oncogenes, such as k-ras and beta-catenin in the case of colon cancer, or HER-2 and MDR-1 in breast cancer, or other combinations).

Example 3

Operator Repressor Titration System

The TRIP system (bacteria and plasmid) have been modified to include the ORT (Operator Repressor Titration) system from Cobra Biomanufacturing (Keele, UK). This adaptation helps to maintain the plasmid in suitable strains in the absence of selective antibiotics. The bacterial carrier strain has been modified accordingly to allow for the ORT system to function (deletion of the DAP gene and replacement with an ORT-controlled DAP gene expression system). The plasmid has been modified to remove the antibiotic selection sequences to support the ORT system. Further changes have been introduced to the bacterial genome, including for example, (a) deletion of the aroA gene (in some CEQ strains) to make the bacteria more susceptible to nutrient shortage, particularly in the intracellular compartment where they will die due to lack of nutrients; (b) insertion of T7RNApolymerase gene into the chromosome and or (c) integration of a shRNA expression cassette under T7 promoter into the chromosome.

Figure 2:
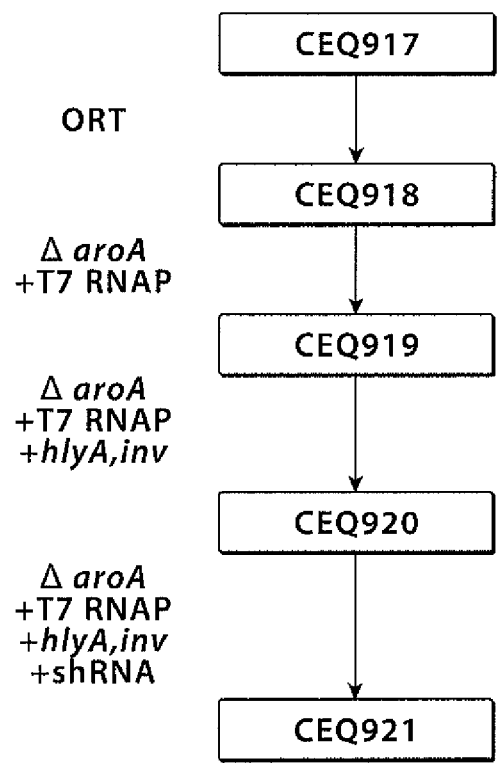
FIG. 2 is a schematic showing the TRIP system (bacteria and plasmid) modified with the Operator Repressor Titration (ORT) system.

FIG. 2 shows development examples of bacterial strains. Further strains developed include, but are not limited to, CEQ922 (CEQ919 without aroA deletion), CEQ923 (CEQ920 without aroA deletion), CEQ924 (CEQ921 without aroA deletion).

Example 4

Intestinal Tract Gene Delivery

S. typhimurium was investigated to determine if it could be used as a vector for RNAi delivery into the epithelial cells lining the intestinal tract. Mice were treated orally with a single dose of $10^8$ SL 7207 and sacrificed at various time points after administration. SL7207 were then stained using the Salmonella specific antibody. 2 h after treatment, numerous SL7207 could be seen invading the intestinal epithelial layer (Salmonella stained red), suggesting that oral administration of SL7207 may be a useful tool to deliver payloads to the intestinal and colonic mucosa. In a follow up experiment, mice were treated with SL7207 harboring a GFP expression plasmid (pEGFPC1, Invitrogen). At 24 h after a single treatment, a small percentage (approximately 1%) of cells was clearly found to express GFP.

Figure 3:
FIG. 3 is a photograph showing cellular staining of the intestinal epithelial layer demonstrating efficient invasion and plasmid delivery by S. typhimurium.

FIG. 3 shows the efficient invasion and plasmid delivery into the intestinal mucosa by S. typhimurium. SL7207 were stained using red fluorescent antibody 6 h after oral administration. Intact SL7207 and fragments of SL7207 were seen in epithelial cells as well as underlying cells of the lamina propria (top left/right). SL7207 successfully deliver expressed DNA into the intestinal mucosa: intestinal mucosal cells expressing GFP after treatment with SL7207 carrying a eukaryotic expression plasmid for GFP (pEGFP-C1)(lower left). For fluorescence microscopy, SL7207 were stained with red fluorescent antibody and nuclei were counterstained with Hoechst 37111.

To test whether SL7207 could be used for the delivery of RNAi to target genes in the intestinal tract, GFP transgenic mice (4 per group) were treated with *S. typhimurium* harboring a shRNA expression plasmid directed against GFP (SL-siGFP) or a shRNA expression plasmid directed against k-RAS (SL-siRAS). $10^8$ c.f.u. was given three times weekly for two weeks by oral gavage. Colonic tissues were subsequently reviewed with fluorescent microscopy (data not shown) and stained analyzed after immunohistochemistry staining for GFP expression using a specific antibody (Living Colors®, Invitrogen). There was a significant reduction in the overall GFP expression level and significant reduction in the number of GFP expressing crypts in the SL-siGFP treated animals compared with the SL-siRAS treated animals (33.9% vs 50%, p<0.05), suggesting that this method could be useful to deliver therapeutic RNAi into the colonic epithelium.

Figure 4:
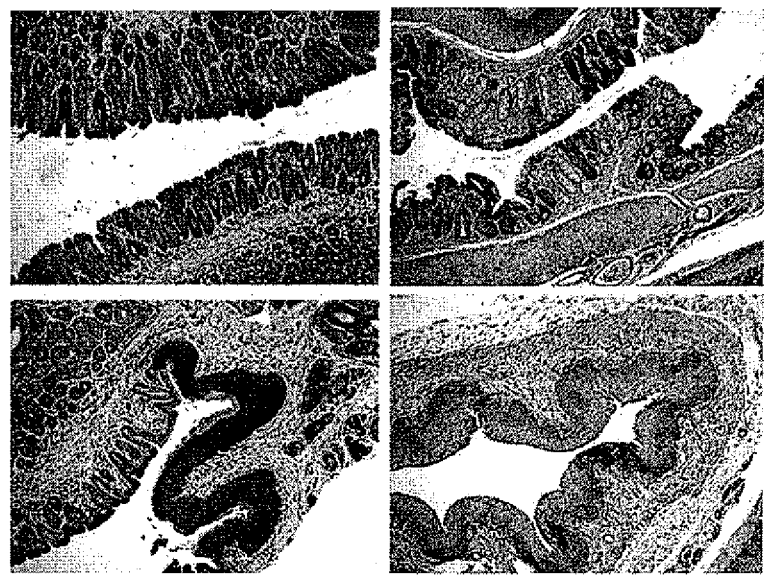
FIG. 4 is a photograph showing that bacteria-mediated RNA interference reduces target gene expression in the gastrointestinal epithelium.

FIG. 4 shows that bacteria-mediated RNA interference reduces target gene expression in the gastrointestinal epithelium. After treatment with SL7207 carrying expression plasmids targeting GFP (SL-siGFP, right bottom panel), colon tissues showed lower levels of GFP expression, and fewer colonic crypts were stained positive for GFP compared with animals treated with SL-siRAS (left bottom panel). Slides were stained with GFP-specific antibody.

Example 5

Construction of CEQ503 Bacterial Strain

Derivation and Description of CEQ 503 (Strain CEQ201 (pNJSZ))

CEQ503 consists of a combination of an attenuated *E. coli* strain (CEQ201) with a specially engineered TRIP plasmid (pNJSZ). The plasmid confers the abilities required to induce tkRNAi (in this case: invasiveness, escape from the entry vesicle, expression of short hairpin RNA). Strain Description of CEQ503 (pNJSZ):

1. Genotype: *Escherichia coli* CEQ201 [glnV44(AS), LAM⁻, rfbC1, endA1, spoT1, thi-1, hsdR17, ($r_k^-$ $m_k^+$), creC510 ΔdapA, ΔrecA].

2. Derivation of CEQ201

MM294 (Meselson and Yuan, Nature 217, 1110, 1968; from CGSC)

| Transformation with plasmid pKD46

MM294 (pKD46)

| Transformation with a ΔdapA::kan cassette generated using PCR with pKD4

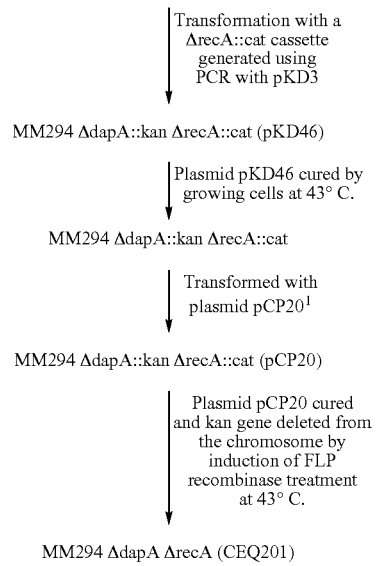

Figure 5:
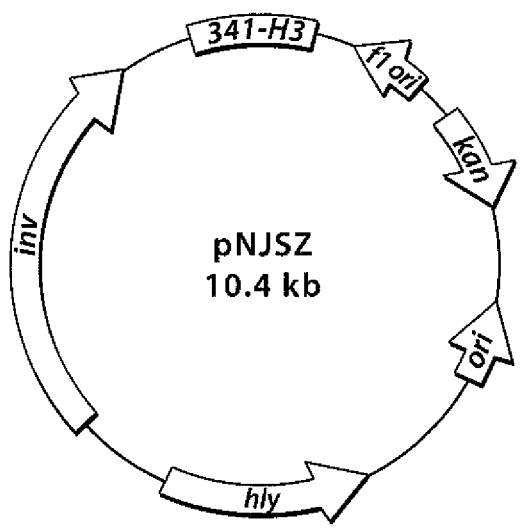
FIG. 5 is a schematic showing pNJSZ plasmid construct.

3. Plasmid: pNJSZ, shown schematically in FIG. 5, is a 10.4 kb plasmid that confers kanamycin resistance to our bacterial strain (CEQ503). This plasmid contains two genes, hly and inv, and the H3 hairpin sequence: ggatccAGGAGTAACAATACAAATGGATTCAA-GAGATCCATTTGTATTGTTACTCCTTTgt cgac (SEQ ID NO:380), which includes BamHI and SalI restriction sites. To verify the presence of this plasmid, PCRs are performed to verify chromosomal deletion of dapA, and minipreps and/or PCR are performed to confirm inv, hly and 341-H3 on the plasmid.

4. Nutritional Requirements: Althea Media Broth or LB, Miller (Luria-Bertani) broth (Amresco; cat. no.: J106-2KG) and 50 µg/ml of DL-Δ; ϵ-Diaminopemilic acid (DAP) (SIGMA; cat. no.: D1377-10G).

5. Growth Conditions: 37° C.

Example 6

BTP Production

BTPs or minicells containing a suitable plasmid such as TRIP have been engineered for delivery of tkRNAi. These cells will express invasin or Opa to enable entry into mammalian cells and listeriolysin will allow lysis of phagosome following minicell degradation/lysis. Additionally, a method for manufacturing minicells has been developed that utilizes a suicide construct for killing intact cells to aid in the purification of minicells. Such suicide plasmids have been described in the literature (Kloos et al., (1994) J. Bacteriol. 176, 7352-61; Jain and Mekalanos, (2000) Infect. Immun 68, 986-989). Summarily, the lambda S and R genes that code for holing and lysozyme are placed under regulation of an inducible promoter on the bacterial chromosome. When induced, they will lyse intact cells but not minicells since minicells lack chromosomes. A number of different types of regulators such as lad, araC, lambda cI857 and rhaS-rhaR can be used for development of an inducible suicide gene construct. Similarly, a number of different types of suicide genes, including *E. coli* autolysis genes and antimicrobial small peptides, can be used in a similar scheme. Purification is enhanced by treatments or mutations that induce filamentation (see, for example, Ward and Lutkenhaus, (1985) Cell 42, 941-949; Bi and Lutkenhaus, 1992). Initial purification involves low speed centrifugation to separate intact cells and retain minicells in the supernatant. This can be followed by density gradient purification or filtration (for example, Shull et al., (1971) J. Bacteriol. 106, 626-633).

Any cell death-triggering gene, also known as a suicide gene, including but not limited to genes encoding antimicrobial proteins, bacteriophage lysins or autolysins can be used in this method for obtaining BTPs from a mixture containing BTPs and bacteria. Suicide genes can kill live bacteria by mechanisms that include but are not limited to cell lysis, or by the destruction, degradation or poisoning of cellular components such as chromosomal DNA or filament components. Any inducible promoter may be used in conjunction with this system. In one embodiment of this invention, the suicide genes are integrated within the chromosome, thereby limiting their presence only in intact bacterial cells as BTPs or minicells will not incorporate these genes because they do not harbor chromosomal DNA.

Figure 6:
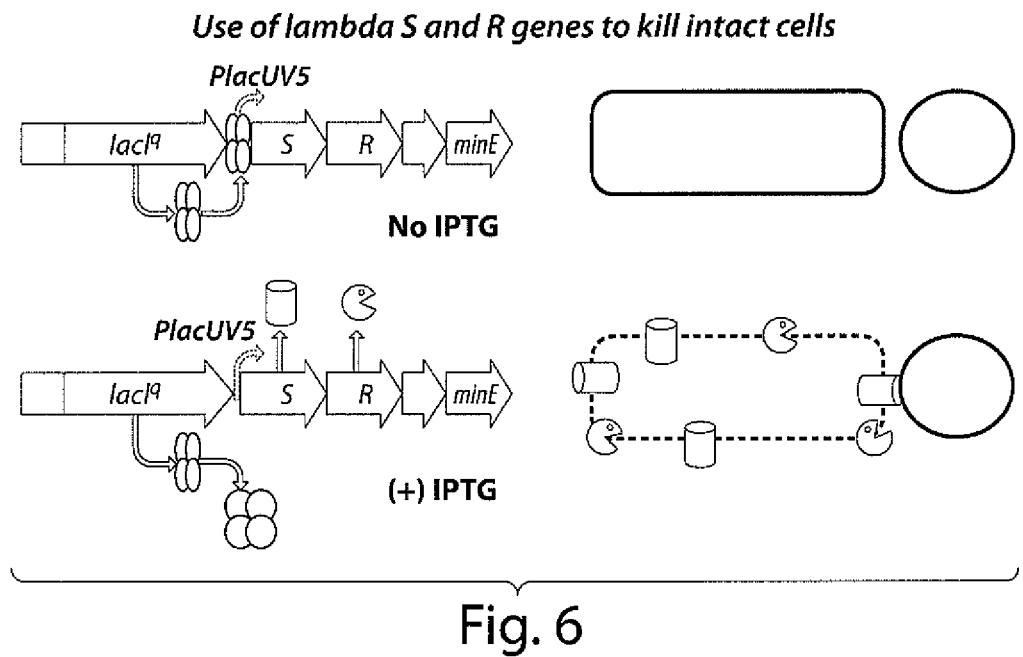
FIG. 6 is a schematic showing the use of lamba S and R genes to kill intact bacteria.

As shown in FIG. 6, induction of suicide genes will lyse intact bacterial cells. The lambda S and R genes (suicide genes) are put under the control of $P_{lacUV5}$ (inducible promoter). The leaky basal activity is repressed by a "super-repressor" coded by $lacI^q$ ene on a $P_{gapA}$ (strong promoter). This cassette is put at the minCD locus.

Example 7 siRNA Inhibition of Human Papillomavirus (HPV) Oncogenes

Experimental Procedures

Cell Culture: Hela cells were cultured in Minimum Essential Medium (MEM, ATCC No. 30-2003) with 10% FBS supplemented with antibiotics: 100 U/ml penicillin G, 10 μg/ml streptomycin (Sigma).

Bacterial Culture: Plasmids were transformed into BL21 (DE3) strain (Invitrogen). Bacteria were grown at 37° C. in LB Broth containing 100 μg/ml ampicillin. Bacterial cell density (in CFU/ml) was calculated using $OD_{600}$ measurement. For cell infection, overnight cultures were inoculated into fresh medium for another 2-3 h growth until the optical density at 600 nm [OD600] reached 0.6.

Invasion Assay: For bacterial invasion, Hela cells were plated in 6-well dishes at 200,000 cells/well and allowed to incubate overnight in 2 ml complete growth medium. The bacterial cells were grown to mid-exponential phase with optical density at 600 nm [OD600] 0.6 in LB Broth with Ampicillin, and then centrifuged at 3,400 rpm for 10 minutes at 4° C. Bacterial pellets were resuspended in MEM without serum or the antibiotics and the bacteria were added to the cells at an MOI of 1:1000, 1:500, 1:250, 1:125, or 1:62.5 and allowed to invade the Hela cells for 2 hours at 37° C. in 5% CO2. The cells were washed 4 times with MEM containing 10% FBS and penicillin-streptomycin (100 IU of penicillin and 100 μg of streptomycin per ml). Cells were incubated in fresh complete medium for further 48 hours at 37° C. in 5% CO2 and total RNA was then isolated by the Qiagen RNeasy system with on-column DNAse digestion or by TRIZOL extraction method.

siRNA Transfection: One day before the transfection, cells were plated in complete growth medium without antibiotics so that the cells will be 30-50% confluent at the time of transfection. Diluted various concentrations of siRNA from a stock of 20 μM in 175 μl of Opti-MEM. Mixed 4 μl of Oligofectamine separately in 15 μl of Opti-MEM. Mixed gently and incubated for 5-10 min at room temperature. Combined the diluted siRNA with diluted oligofectamine and incubated for 15-20 min at room temperature. While the complexes were being formed, removed the growth medium from the cells and added 800 μl of medium without serum to each well containing cells. Added the 200 μl of siRNA/oligofectamine complexes to the cells and incubated at 37° C. for 4 h. Added 1 ml of growth medium containing 3× the normal concentration of serum without removing the transfection mixture. Gene silencing was assayed at 48 h.

RT-PCR: Quantitative real-time reverse transcription PCR (RT-PCR) was performed with the TaqMan RT-PCR master Mix Reagents Kit (Applied Biosystems) using the following primers and a probe set for detection of HPV18E6E7 transcripts:

```
                                      (SEQ ID NO: 381)
Forward Primer: 5'-CTGATCTGTGCACGGAACTGA-3'
(148-168)

(SEQ ID NO: 382)
Reverse Primer: 5'-TGTCTAAGTTTTTCTGCTGGATTCA-3'
(439-463)

(SEQ ID NO: 383)
Probe: 5'-TTGGAACTTACAGAGGTGCCTGCGC-3'
(219-233 and 416-425)
```

The probe was labeled at the 5' end with a reporter fluorescent dye, FAM and at the 3' end with fluorescent dye quencher TAMRA. GAPDH was used to detect human GAPDH transcripts for the normalization.

HPVsHRNA Sequences:

```
H1 (working sequence)
                                      (SEQ ID NO: 384)
5'- ggATCCTAGGTATTTGAATTTGCATTTCAAGAGAATGCAAATTCAA
ATACCTTTTgTCgAC (SEQ ID NO: 385)
5'- GTCGACAAAAGGTATTTGAATTTGCATTCTCTTGAAATGCAAATTCA
AATACCTAGGATCC H2 (ineffective sequence)
                                      (SEQ ID NO: 386)
5'-ggATCCTCAGAAAAACTTAGACACCTTCAAGAGAGGTGTCTAAGT
TTTTCTGTTTgTCgAC (SEQ ID NO: 387)
5'- GTCGACAAACAGAAAAACTTAGACACCTCTCTTGAAGGTGTCTAAG
TTTTTCTGAGGATCC
```

Western Blot: Hela cells were lysed using 1× Cell lysis Buffer (Cell Signaling Technology, Cat No. 9803). For electrophoresis, 50 μg of total protein in 2× loading buffer was loaded to each well of a 12% SDS-PAGE gel. After transferring the blot was blocked and probed with primary antibody at 2 h followed by incubation with HRP-conjugated secondary antibody before detection by ECL. All primary antibodies were used at 1/1000 dilution except HPV18E7 antibody at 1/250.
Anti-Human pRb antibody: BD Pharmingen (Cat No. 554136), Sec Ab: HRP-anti Mouse
HPV18E7: Santa Cruz (Cat No. sc-1590), Sec Ab: donkey anti-goat IgG-HRP Cat no. sc 2020
p53: Santa Cruz (Cat No. sc-126), Sec Ab: HRP-anti Mouse
p21: Santa Cruz (Cat No. sc-397), Sec Ab: HRP-anti Rabbit
c-Myc: Cell Signaling Technology (Cat No. 9402), Sec Ab: HRP-anti Rabbit Colony Formation Assay: Hela cells were harvested after bacterial invasion for 2 h. The cells in either control treated or HPV shRNA treated cells were washed 3× times with complete MEM and one time with PBS. The cells were then trypsinized and counted. 500 cells from each treatment were added to a single well of a six well plate containing 2 ml of complete growth medium. The cells were allowed to grow for 10 days following which the colonies were fixed with GEIMSA stain.

MTT Assay: Hela cells were harvested after bacterial invasion for 2 h. The cells in either control treated or HPV shRNA treated cells were washed 3× times with complete MEM and one time with PBS. The cells were then trypsinized and counted. 5000 cells from each treatment were added to a single well of a 96 well plate in 100 µl of complete growth medium in triplicates. The cells were incubated at 37° C. for 48-72 h following which 10 µl of 0.5 mg/ml MTT was added to each well. The plate was further incubated at 37° C. for 3 h, the medium was aspirated off from the wells and after incubation, 100 µl of MTT solubilization solution [10% Triton X-100 in acidic isoproponal (0.1 N HCl)] was added to each well to stop the reaction. The absorbance was read at 570 nm on the plate reader.

Results

In this example, the suppressive effect of a short hairpin RNA directed towards HPV 18 E6 and E7 oncogenes was investigated. The short hairpin RNA was delivered by infecting human cervical cancer cells (Hela) with bacterial strains that produce the short hairpin RNA. The shRNA expression cassette contained 19 nucleotide (nt) of the target sequence followed by the loop sequence (TTCAAGAGA) (SEQ ID NO:388) and the reverse complement to the 19 nt. For the 19 nt, two shRNA sequences published in Cancer Gene Therapy (2006) 13, 1023-1032, were used to measure siRNA delivery and gene silencing efficiency, oligofectamine reagent in a 6 well format was used. Briefly, Hela cells were plated at a cell density of about 40% confluence in antibiotic free medium. On the next day, siRNA was added to 6 well plates at varying concentrations of 50, 100, 200 nM. The control siRNA was added at a single concentration of 100 nM.

Figure 7:
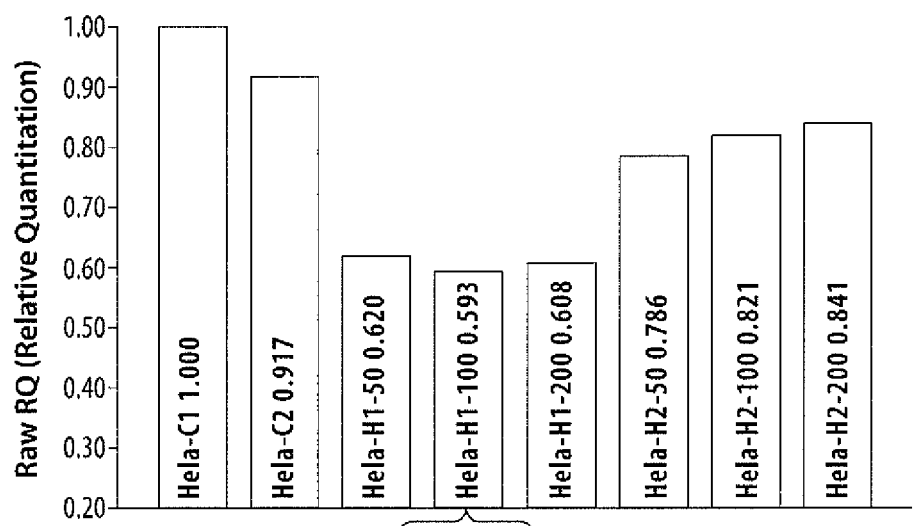
FIG. 7 is a bar graph showing a reduction in HPV oncogene expression with bacterial delivered siRNA.

As shown in FIG. 7, the oligofectamine transfection method resulted in a decrease in E6 mRNA in Hela cells with respect to the control siRNA. The siRNA (H1) showed up to about 40% of reduction in E6 mRNA. The knockdown response was not dose dependent.

Next, the hairpin of the siRNA (H1) was cloned into the TRIP vector. In order to determine if gene silencing could be achieved through the transkingdom system, the shRNA in human cervical cancer cells (Hela) was tested in an invasion assay. Briefly, Hela cells were plated in a six-well plate at 2×10$^5$ cells/well, allowed to grow overnight and incubated the next day for 2 h at different MOIs with bacteria (*E. coli*) engineered to produce the hairpin RNA. The bacteria were washed off with medium containing 10% FBS and Pen Strep four times and the mammalian cells were further incubated for an additional 48 h in the complete medium. RNA or protein was isolated from the bacteria.

Figure 8:
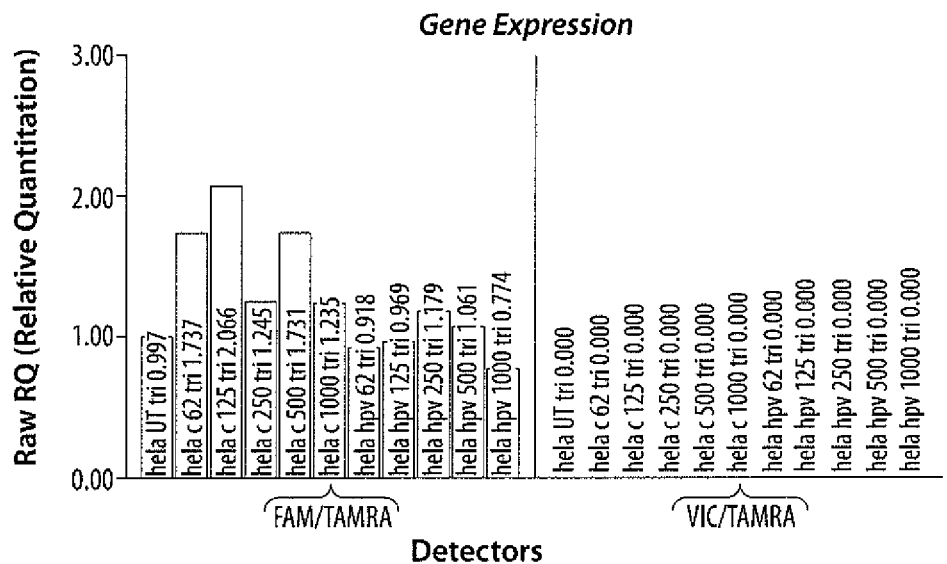
FIG. 8 is a bar graph showing a reduction in HPV oncogene expression with bacterial delivered siRNA.
Figure 9:
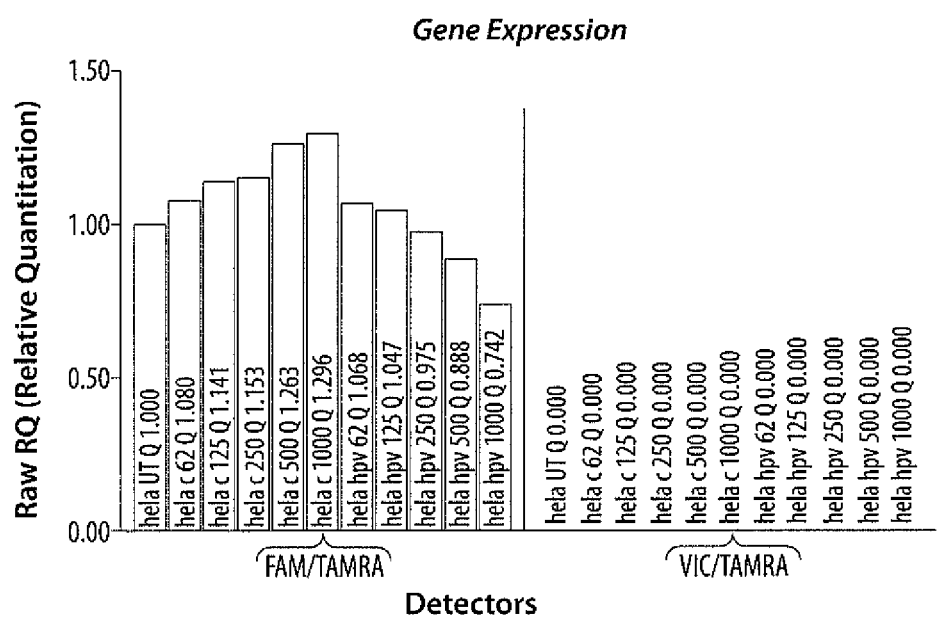
FIG. 9 is a bar graph showing a reduction in HPV oncogene expression with bacterial delivered siRNA.

FIG. 8 and FIG. 9 demonstrate that siRNA downregulates HPV E6 expression in Hela cells. Cells were plated in six well plates and allowed to grow to a confluence of 40% (about 40,000 cells). Oligofectamine/siRNA transfection complexes were prepared in Opti-MEM serum-free medium by mixing 4 µl of oligofectamine with siRNAs (final concentration in 185 µl of medium is 50, 100, 200 nM). 48 hours post-transfection cells were harvested and analyzed by real-time RT-PCR for both target and GAPDH mRNA levels. Data were normalized against the GAPDH signal. Two different negative control siRNAs were used at a single concentration of 200 nM.

Figure 10:
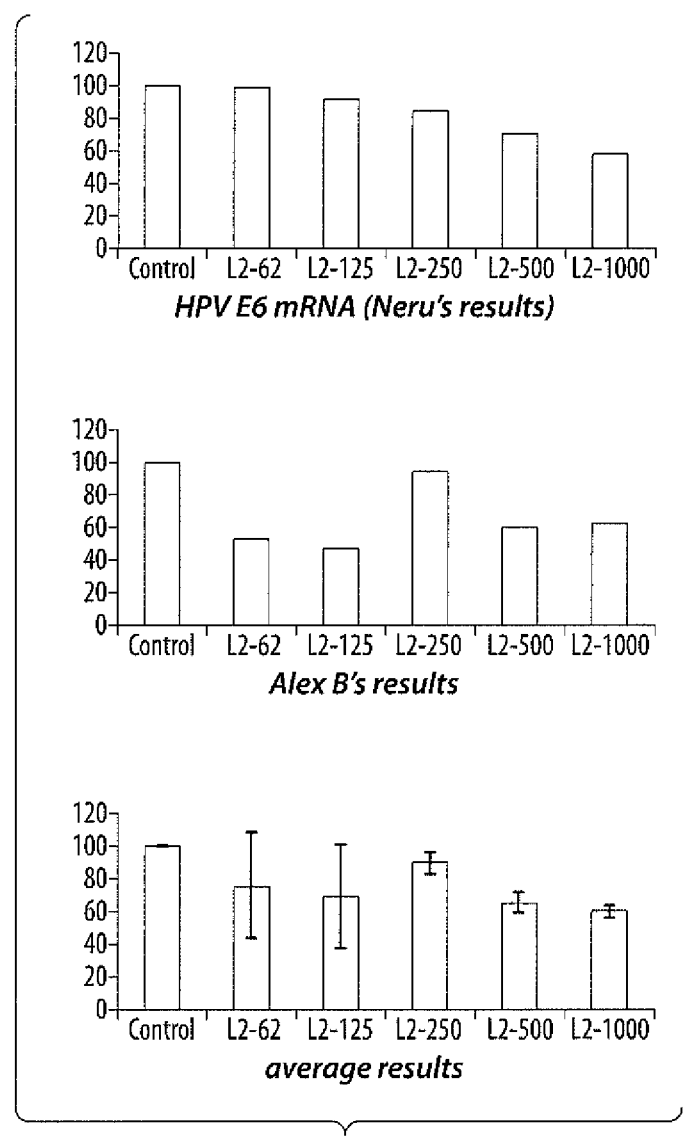
FIG. 10, Panels A-C, are a series of bar graphs showing real time PCR results following invasion of Hela cells with various siRNAs.

FIG. 10, Panels A-C show real time PCR results following invasion assay of Hela cells. Hela cells were incubated for 2 h with shRNA-expressing BL21(DE3) at different multiplicities of infection (MOI). Forty-eight hours post-infection the cells were harvested and analyzed by real-time RT-PCR for both target and GAPDH mRNA levels. Data were normalized against the GAPDH signal. These data were then further normalized to untreated control cells.

Figure 11:
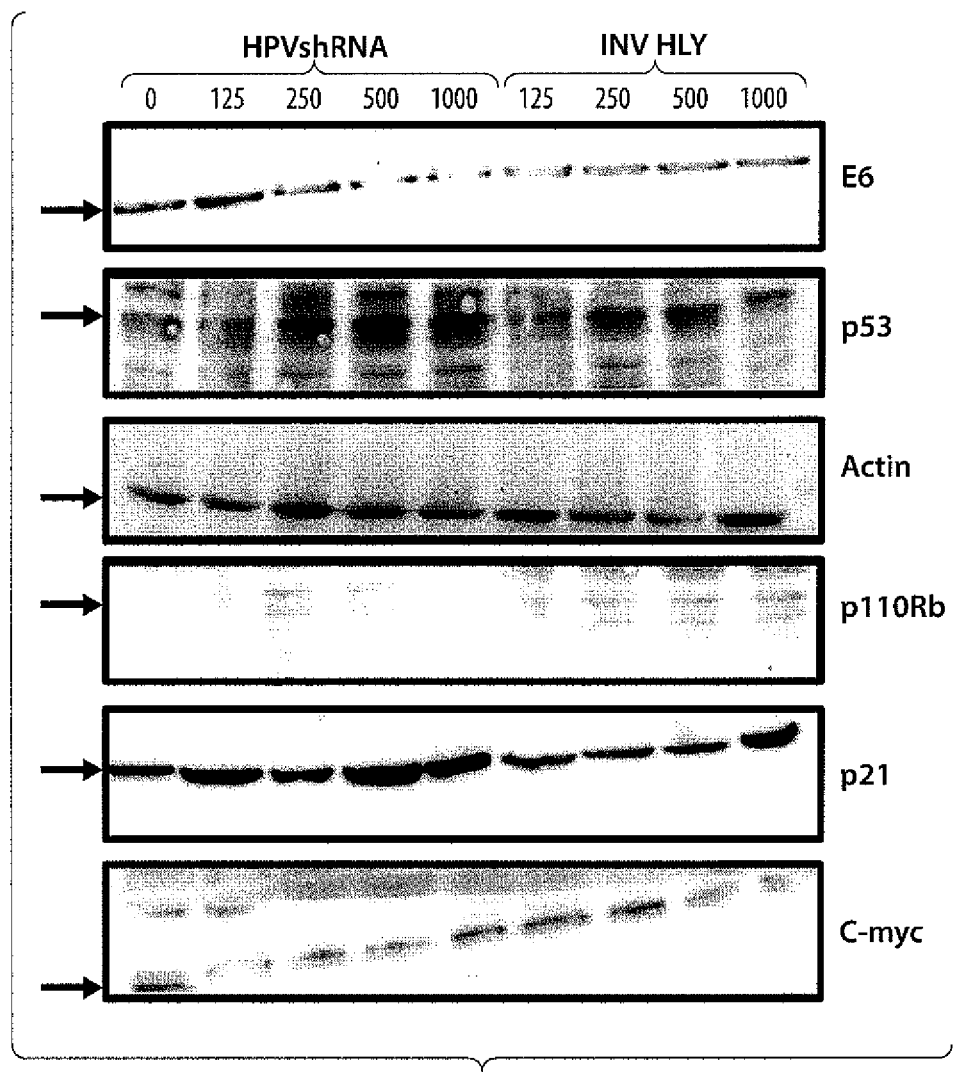
FIG. 11 is a photograph of an immunoblot showing the effects of downregulation of HPV E6 and E7 genes on tumor suppressor pathways and other downstream targets.

FIG. 11 shows the effects of downregulation of HPV E6 and E7 genes on tumor suppressor pathways and other downstream targets. Hela cells were incubated for 2 h with shRNA-expressing BL21(DE3) at different multiplicities of infection (MOI). Forty-eight hours post-infection cells were harvested and analyzed by western blotting. 50 µg of protein was loaded in each lane and resolved by gel electrophoresis, transferred to a membrane and probed with antibodies specific for HPV 18 E7, p53, actin, p110Rb, p21 and c-myc as indicated.

Figure 12:
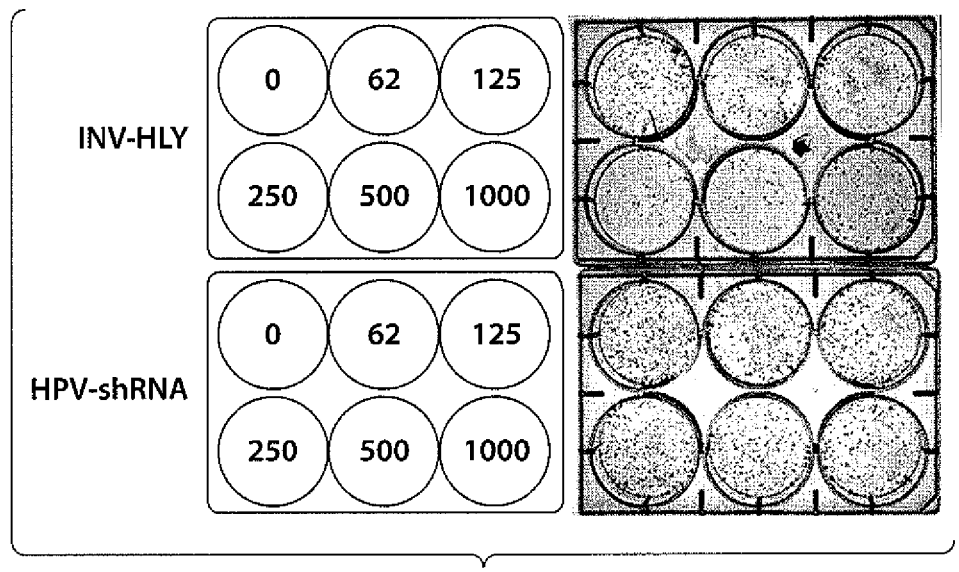
FIG. 12 is a photograph of a colony forming assay showing infection at different multiplicities of infection (MOI).
Figure 13:
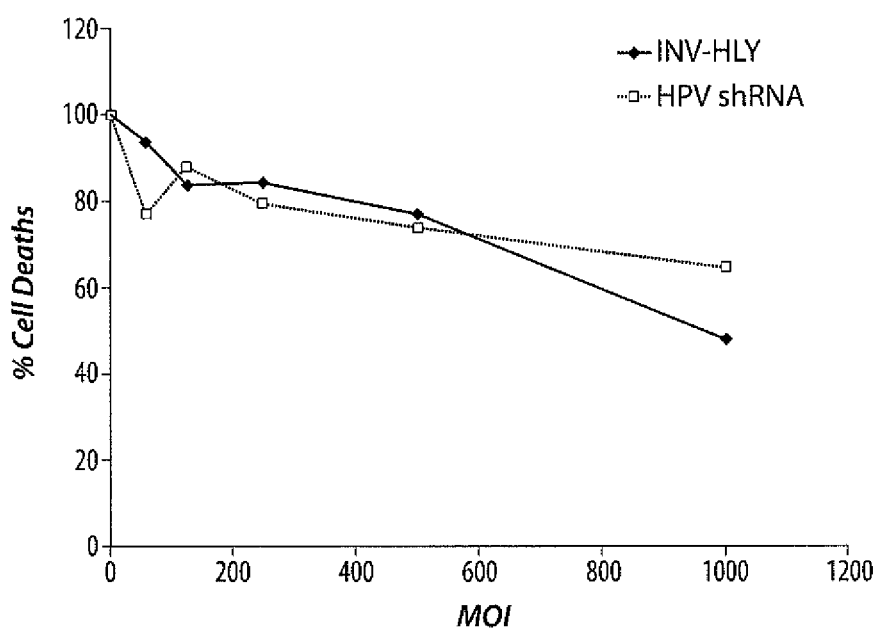
FIG. 13 is a line graph of a MTT assay showing infection at different multiplicities of infection (MOI).

FIGS. 12 and 13 show a colony formation and MTT assay, respectively. Hela cells were incubated for 2 h with shRNA-expressing BL21(DE3) at different multiplicities of infection (MOI). 2 h post-infection cells were washed trypsinized and counted and an equal number of cells for each MOI was added to a well of a six well plate (For CFA: added 500 cells to each well of a 6 well plate, for MTT added 5000 cells in each well of a 96 well plate). For colony formation, the cells were allowed to grow for 10 days and stained with Geimsa, MTT assay was analyzed at 72 h post plating.

Figure 14:
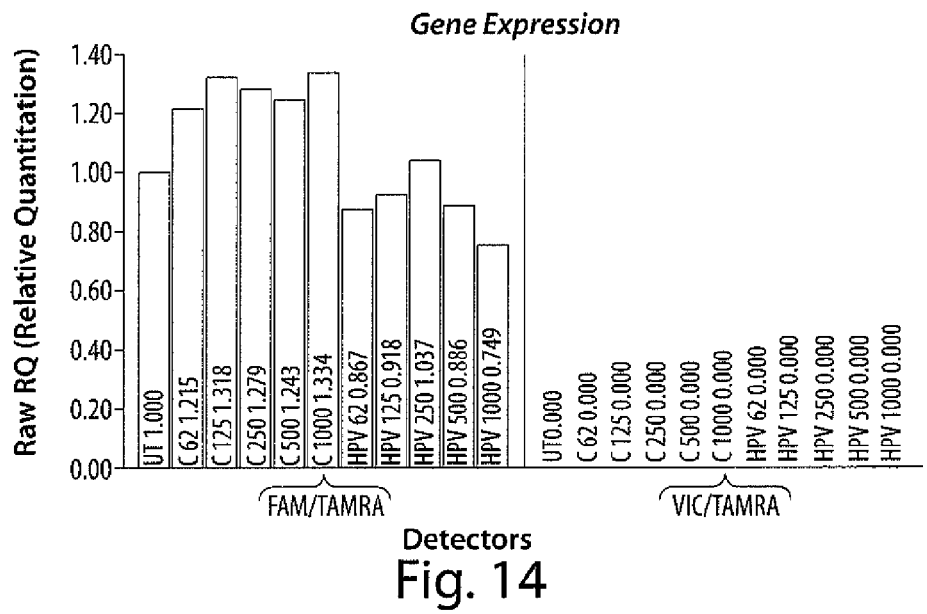
FIG. 14 is a bar graph showing real time PCR results following invasion of Hela cells with various siRNAs FIG. 15, Panels A-C, are a series of bar graphs showing real time PCR results following invasion of Hela cells with various siRNAs.
Figure 15:
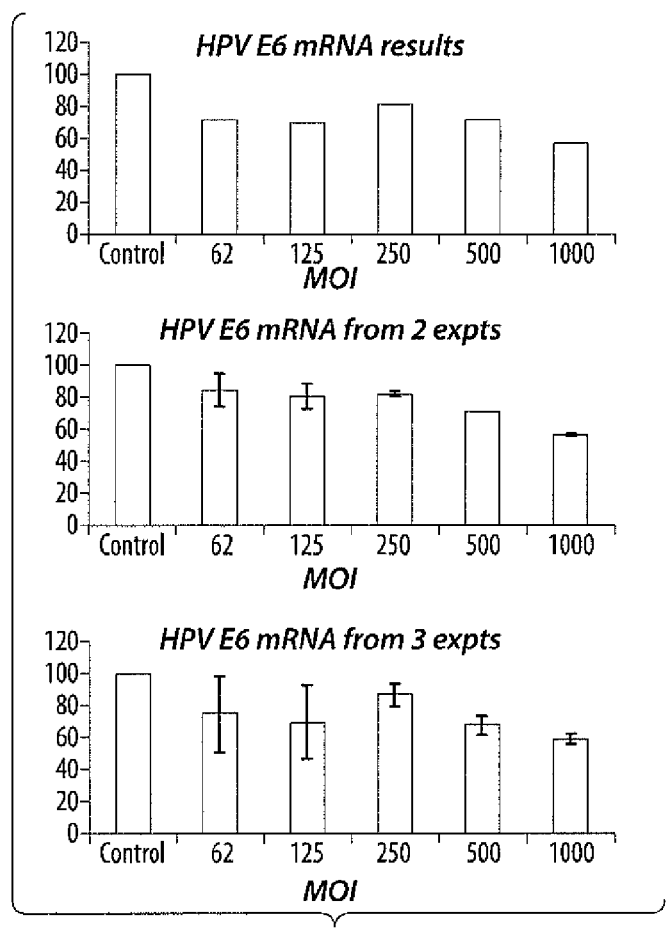

FIGS. 14 and 15 show real time PCR results following invasion assay of Hela cells. Hela cells were incubated for 2 h with shRNA-expressing BL21(DE3) at different multiplicities of infection (MOI). Forty-eight hours post-infection cells were harvested and analyzed by real-time RT-PCR for both target and GAPDH mRNA levels. Data were normalized against the GAPDH signal. These data were then further normalized to untreated control cells.

Figure 16:
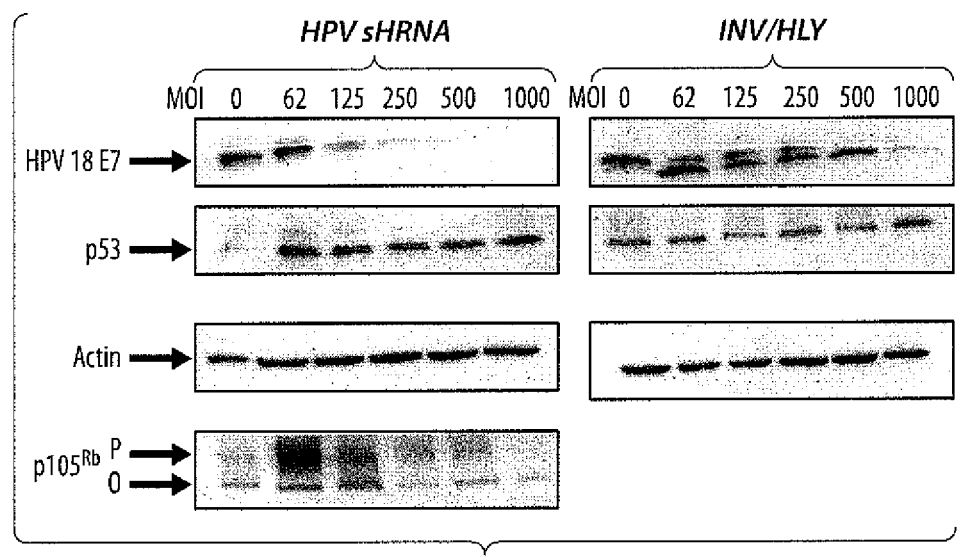
FIG. 16 is a photograph of an immunoblot showing the effects of downregulation of HPV E6 and E7 genes on tumor suppressor pathways and other downstream targets.

FIG. 16 shows the effects of downregulation of HPV E6 and E7 genes on tumor suppressor pathways and other downstream targets. Hela cells were incubated for 2 h with shRNA-expressing BL21(DE3) at different multiplicities of infection (MOI). Forty-eight hours post-infection cells were harvested and analyzed by western blotting. 50 µg of protein was loaded in each lane and resolved by gel electrophoresis, transferred to a membrane and probed with antibodies specific for HPV 18 E7, p53, actin, p110Rb as indicated.

Figure 17:
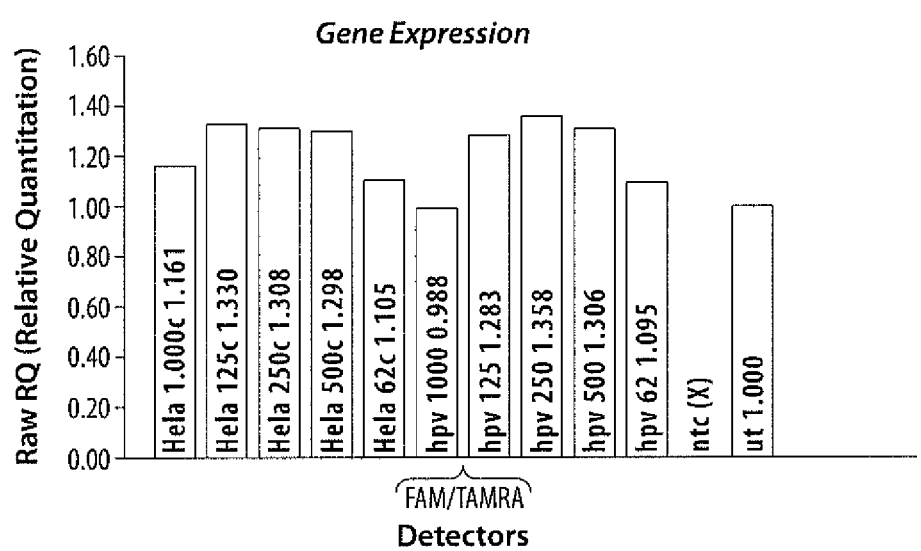
FIG. 17 is a bar graph showing real time PCR results following invasion assay of Hela cells with a frozen aliquot of negative sHRNA control and HPV sHRNA in BL21.

FIG. 17 shows real time PCR results following invasion assay of Hela cells with a frozen aliquot of negative sHRNA control and HPV sHRNA in BL21 (DE3). Hela cells were incubated for 2 h with shRNA-expressing BL21(DE3) at different multiplicities of infection (MOI). Forty-eight hours post-infection cells were harvested and analyzed by real-time RT-PCR for both target and GAPDH mRNA levels. Data were normalized against the GAPDH signal. These data were then further normalized to untreated control cells.

Figure 18:
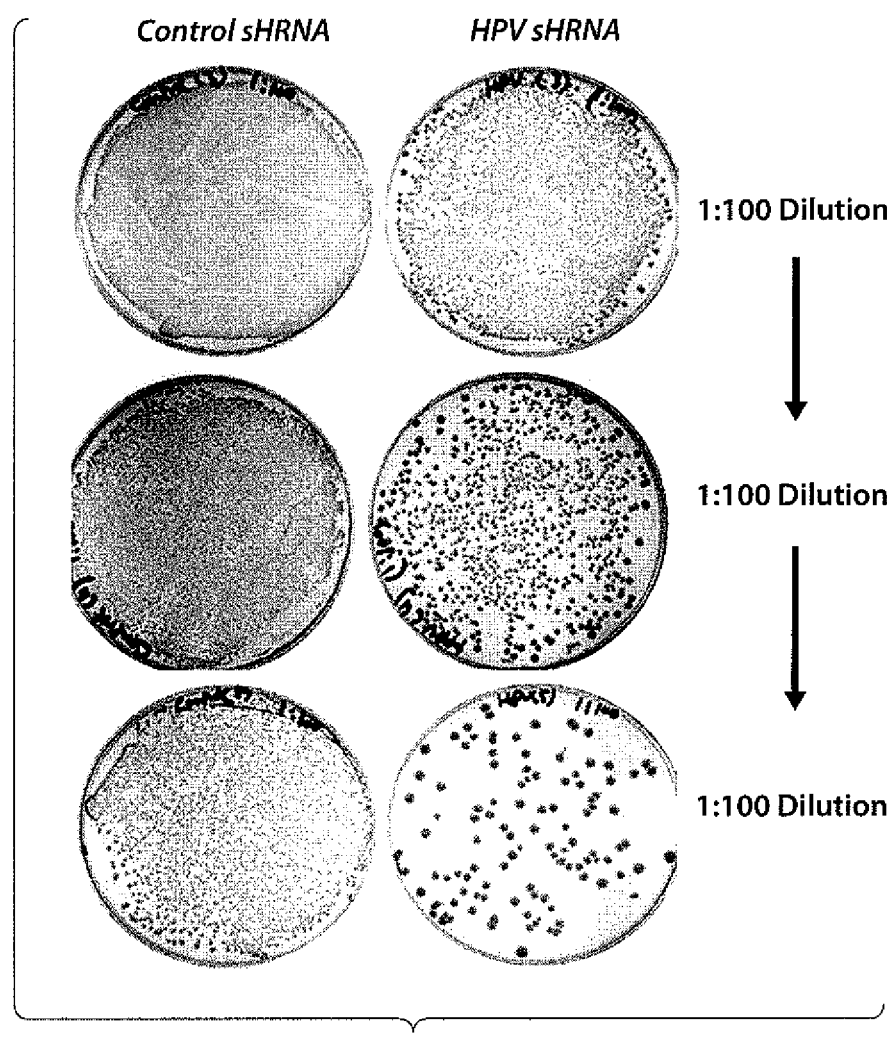
FIG. 18 is a photograph showing the plating efficiency of frozen aliquots of negative sHRNA control and HPV sHRNA in BL21.

FIG. 18 shows the plating efficiency of frozen aliquots of negative sHRNA control and HPV sHRNA in BL21 (DE3). The frozen bacteria were thawed and resuspended to a final concentration of 3.38×10$^8$ cells/ml. Invasion assay was performed with this concentration taking 2 mls of 3.38×10$^8$ cells/ml as an MOI of 1000. Some stock control bacteria or HPV bacteria were serially diluted (1:100) and plated on LB plates to assess for the number and viability of bacteria treated cells at 48 h. Gene silencing was analyzed either by quantitative real-time PCR using the ΔΔCt relative quantitation method or by western blot analysis. HPVE6 mRNA levels were normalized to an endogenous control, GAPDH. The final data were further normalized to the RNA from the untreated cells. For Protein analysis, cell lysates were prepared in Cell Lysis Buffer (Cell Signaling Technology) and the protein concentration was determined using a BCA kit from BioRad. For electrophoresis, the protein expression was normalized to Actin loading control.

Example 8

Knockdown of HPV E6 Gene Assessed by Western Blotting with HPV 18 E7 Antibody

Hela cells were incubated for 2 h with shRNA-expressing BL21(DE3) (HPVH1 construct below) at different multiplicities of infection (MOI). Forty-eight hours post-infection cells were harvested and analyzed by western blotting. The HPV E6 specific knockdown was compared with a negative shRNA control. Briefly, 50 µg of protein was loaded in each lane and resolved by gel electrophoresis, transferred to a membrane and probed with antibodies specific for HPV 18 E7, and actin as indicated.

```
HPVH1
                                       (SEQ ID NO: 389)
5'-GATCC TAGGTATTTGAATTTGCAT TTCAAGAGA
ATGCAAATTCAAATACCTTTT G-3'

(SEQ ID NO: 390)
3'-G ATCCATAAACTTAAACGTA AAGTTCTCT
TACGTTTAAGTTTATGGAAAA CAGCT-5'
```

Figure 19:
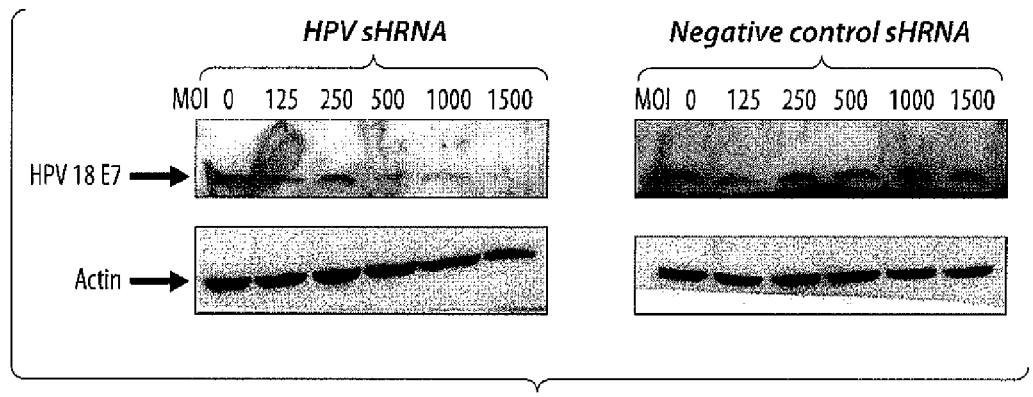
FIG. 19 is a photograph of an immunoblot showing the knockdown of HPV E6 gene assessed by western blotting with HPV 18 E7 antibody.

FIG. 19 shows the knockdown of HPV E6 gene assessed by western blotting with HPV 18 E7 antibody. Hela cells were incubated for 2 h with shRNA-expressing BL21(DE3) at different multiplicities of infection (MOI). Forty-eight hours post-infection cells were harvested and analyzed by western blotting. The HPV E6 specific knockdown was compared with a negative sHRNA control. Briefly, 50 µg of protein was loaded in each lane and resolved by gel electrophoresis, transferred to a membrane and probed with antibodies specific for HPV 18 E7 and actin as indicated.

Example 9

Inhibition of CCL20 Expression in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method.

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) were diluted to 47 uL with serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24 hours at 37 C at which time the media was removed and replaced with 400 uLs of DMEM/10% FCS containing 100 ng/mL of LPS for 2 hours. Following stimulation, the cells were washed and RNA isolated for qRT-PCR according the Qiagen Quantitech method (see manufacturer's protocol) for 50 cycles.

Figure 20:
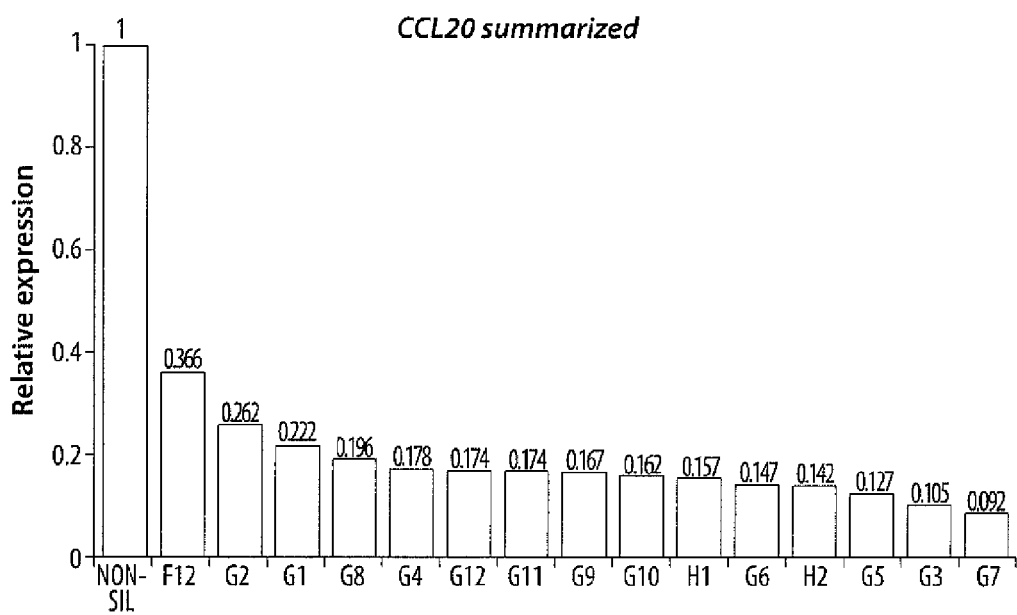
FIG. 20 is a bar graph showing the knockdown of CCL20 expression with the various siRNA sequences in CMT93 cells.

FIG. 20 shows the knockdown of CCL20 expression with the various siRNA sequences in CMT93 cells. The siRNA sequences tested are listed below:

| Well | siRNA sense 5'→3' | SEQ ID NO: | siRNA antisense 5'→3' | SEQ ID NO: |
|---|---|---|---|---|
| G1 | GCUUGUGACAUUAAUGCUAtt | 391 | UAGCAUUAAUGUCACAAGCtt | 392 |
| H1 | AUAAGCUAUUGUAAAGAUAtt | 393 | UAUCUUUACAAUAGCUUAUtg | 394 |
| G2 | CAUCUUUCACACGAAGAAAtt | 395 | UUUCUUCGUGUGAAAGAUGat | 396 |
| H2 | CUAUUGUAAAGAUAUUUAAtt | 397 | UUAAAUAUCUUUACAAUAGct | 398 |
| G3 | GCCUAAGAGUCAAGAAGAUtt | 399 | AUCUUCUUGACUCUUAGGCtg | 400 |
| G4 | CAGUGGACUUGUCAAUGGAtt | 401 | UCCAUUGACAAGUCCACUGgg | 402 |
| G5 | GAAGUUGAUUCAUAUUGCAtt | 403 | UGCAAUAUGAAUCAACUUCat | 404 |
| G6 | GUUGAUUCAUAUUGCAUCAtt | 405 | UGAUGCAAUAUGAAUCAACtt | 406 |
| G7 | ACAUUAGAGUUAAGUUGUAtt | 407 | UACAACUUAACUCUAAUGUga | 408 |
| G8 | CAUUAGAGUUAAGUUGUAUtt | 409 | AUACAACUUAACUCUAAUGtg | 410 |
| G9 | UGUUAUUUAUAGAUCUGAAtt | 411 | UUCAGAUCUAUAAAUAACAta | 412 |
| G10 | GUUUAGCUAUUUAAUGUUAtt | 413 | UAACAUUAAAUAGCUAAACat | 414 |
| G11 | AGUGGAAGGAUUAAUAUUAtt | 415 | UAAUAUUAAUCCUUCCACUaa | 416 |

| Well | siRNA sense 5'→3' | SEQ ID NO: | siRNA antisense 5'→3' | SEQ ID NO: |
|---|---|---|---|---|
| F12 | CCAGCACUGAGUACAUCAAtt | 417 | UUGAUGUACUCAGUGCUGGgt | 418 |
| G12 | UGUUUAAGGGAAUAGUUUAtt | 419 | UAAACUAUUCCCUUAAACAta | 420 |

Example 10

Inhibition of Expression of Claudin-2 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uL added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24 or 48 hours at 37 C at which time the cells were washed and RNA isolated for qRT-PCR according the Qiagen Quantitech method (see manufacturer's protocol) for 50 cycles.

Figure 21:
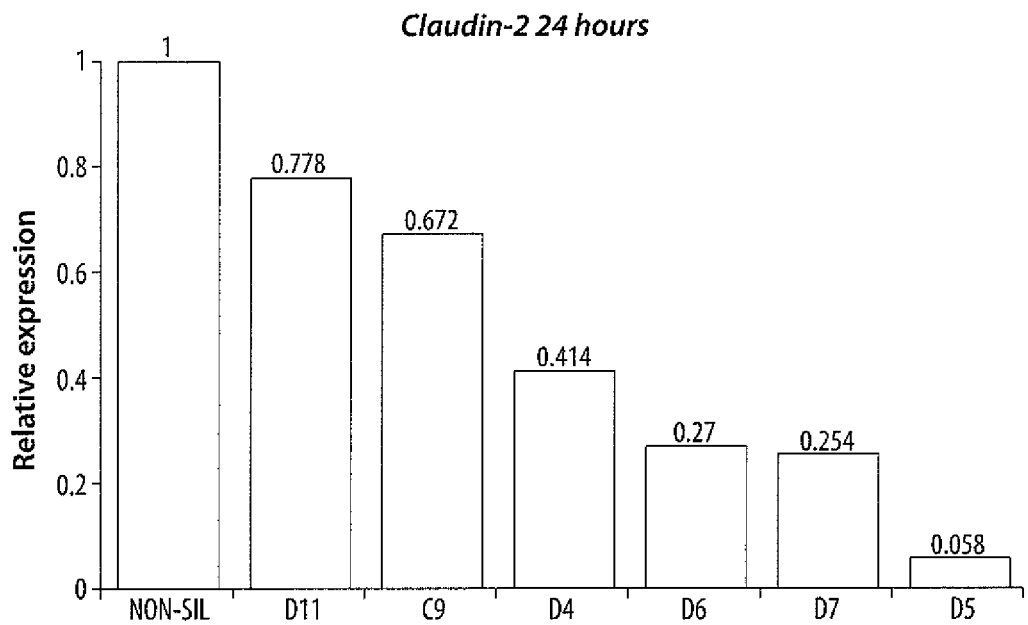
FIG. 21 is a bar graph showing the knockdown of Claudin-2 expression with the various siRNA sequences in CMT93 cells post 24 hr transfection.

FIG. 21 shows the knockdown of Claudin-2 expression with the various siRNA sequences in CMT93 cells post 24 hr transfection. The siRNA sequences tested are listed below:

Example 11

Inhibition of Expression of IL6-Ra in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24, 48 or 72 hours at 37 C at which time the cells were washed and RNA isolated for qRT-PCR according the Qiagen Quantitech method (see manufacturer's protocol) for 40 cycles.

Figure 22:
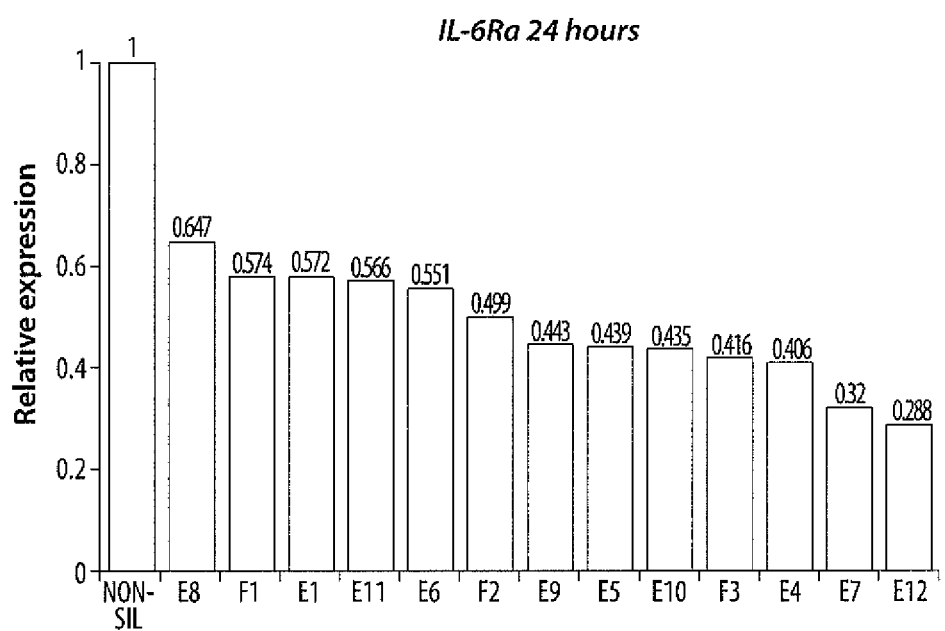
FIG. 22 is a bar graph showing the knockdown of IL6-RA expression with the various siRNA sequences in CMT93 cells post 24 hr transfection.

FIG. 22 shows the knockdown of IL6-RA expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| D4 | GCUGGGACUAUAUAUAUAAtt | 421 | UUAUAUAUAUAGUCCCAGCca | 422 |
| D5 | GGGCAAUUGCUAUAUCUUAtt | 423 | UAAGAUAUAGCAAUUGCCCtc | 424 |
| D6 | GCAGCCAAACGACAAGCAAtt | 425 | UUGCUUGUCGUUUGGCUGCtg | 426 |
| D7 | AGGGUUUCCUUAAGGACAAtt | 427 | UUGUCCUUAAGGAAACCCUtg | 428 |
| C9 | GAAAUGGAUUAGUCAGUAAtt | 429 | UUACUGACUAAUCCAUUUCtt | 430 |
| D11 | GGCUCCGAAGAUACUUCUAtt | 431 | UAGAAGUAUCUUCGGAGCCtg | 432 |

| Well | siRNA sense 5'→3' | SEQ ID NO: | siRNA antisense 5'→3' | SEQ ID NO: |
|---|---|---|---|---|
| E1 | CCUGGAGGGUGACAAAGUAtt | 433 | UACUUUGUCACCCUCCAGGat | 434 |
| F1 | GGUCUGACAAUACCGUAAAtt | 435 | UUUACGGUAUUGUCAGACCca | 436 |
| F2 | GCUGUUUCCUAUAACAGAAtt | 437 | UUCUGUUAUAGGAAACAGCgg | 438 |
| F3 | GCUGUGAAAGGGAAAUUUAtt | 439 | UAAAUUUCCCUUUCACAGCag | 440 |
| E4 | CCUUGUGGUAUCAGCCAUAtt | 441 | UAUGGCUGAUACCACAAGGtt | 442 |
| E5 | GCUUCGAUACCGACCUGUAtt | 443 | UACAGGUCGGUAUCGAAGCtg | 444 |
| E6 | CGGCAGGAAUCCUCUGGAAtt | 445 | UUCCAGAGGAUUCCUGCCGgg | 446 |
| E7 | CCACGAGGAUCAGUACGAAtt | 447 | UUCGUACUGAUCCUCGUGGtt | 448 |
| E8 | CACGAGGAUCAGUACGAAAtt | 449 | UUUCGUACUGAUCCUCGUGgt | 450 |
| E9 | GAUCAGUACGAAAGUUCUAtt | 451 | UAGAACUUUCGUACUGAUCct | 452 |
| E10 | GUACGAAAGUUCUACAGAAtt | 453 | UUCUGUAGAACUUUCGUACtg | 454 |
| E11 | GAAAGUUCUACAGAAGCAAtt | 455 | UUGCUUCUGUAGAACUUUCgt | 456 |
| E12 | GGGUCUGACAAUACCGUAAtt | 457 | UUACGGUAUUGUCAGACCCag | 458 |

Example 12

Inhibition of Expression of IL13-Ra1 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24 or 72 hours at 37 C at which time the cells were washed and RNA isolated for qRT-PCR according the Qiagen Quantitech method (see manufacturer's protocol) for 40 cycles.

Figure 23:
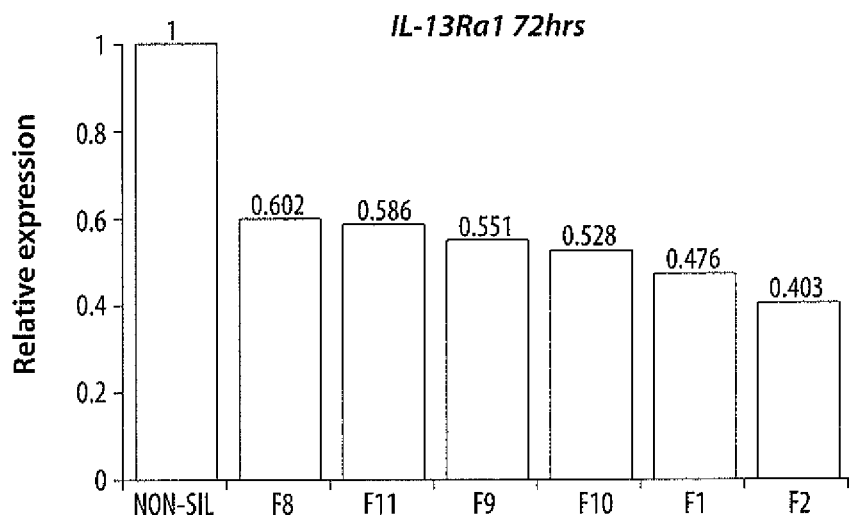
FIG. 23 is a bar graph showing the knockdown of IL13-RA1 expression with the various siRNA sequences in CMT93 cells post 24 hr transfection.

FIG. 23 shows the knockdown of IL13-RA1 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| F1 | AGAAGACUCUAAUGAUGUAtt | 459 | UACAUCAUUAGAGUCUUCUtg | 460 |
| F2 | CAGUCAGAGUAAGAGUCAAtt | 461 | UUGACUCUUACUCUGACUGtg | 462 |
| F8 | CAGAACAUCUAGCAAACAAtt | 463 | UUGUUUGCUAGAUGUUCUGtg | 464 |
| F9 | CUUGUAGGUUCACAUAUUAtt | 465 | UAAUAUGUGAACCUACAAGtt | 466 |
| F10 | CAGUGUAGUGCCAAUGAAAtt | 467 | UUUCAUUGGCACUACACUGag | 468 |
| F11 | GUAUGACAUCUAUGAGAAAtt | 469 | UUUCUCAUAGAUGUCAUACtt | 470 |

Example 13

Inhibition of Expression of IL-18 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of Lipofectamine RNAiMAX transfection reagent (Invitrogen) followed by brief vortexing and incubation at room temperature for 20 minutes. 50 uLs of the complex containing mixture was added to each of 3 wells in a 48 well plate containing CMT93 cells. Transfection was for 24 hours at 37 C at which time the cells were washed and RNA isolated for qRT-PCR according the Qiagen Quantitech method (see manufacturer's protocol) for 40 cycles.

Figure 24:
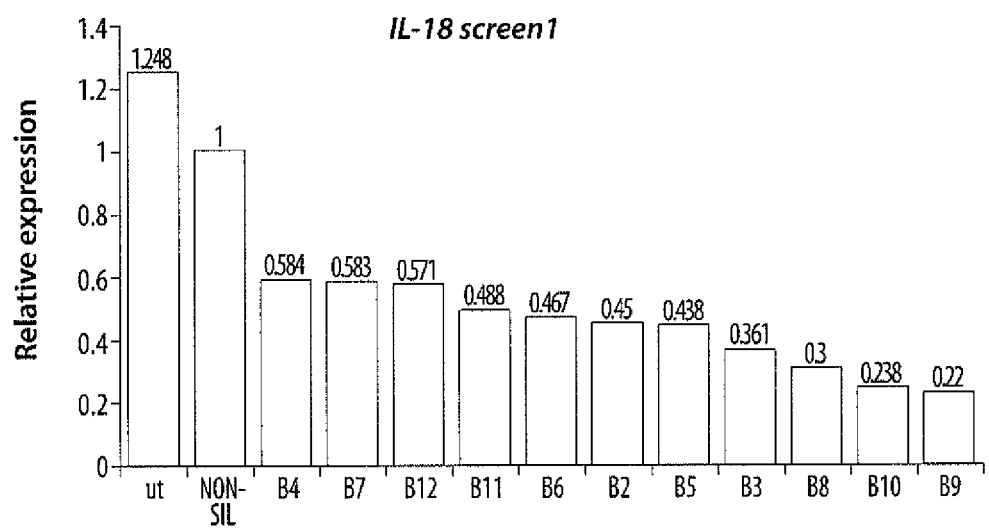
FIG. 24 is a bar graph showing the knockdown of IL18 expression with the various siRNA sequences in CMT93 cells post 24 hr transfection.

FIG. 24 shows the knockdown of IL18 expression with the various siRNA sequences in CMT93 cells post 24 hr transfection. The siRNA sequences tested are listed below:

Example 14

Inhibition of Expression of IL-7 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of Lipofectamine RNAiMAX transfection reagent (Invitrogen) followed by brief vortexing and incubation at room temperature for 20 minutes. 50 uLs of the complex containing mixture was added to each of 3 wells in a 48 well plate containing CMT93 cells. Transfection was for 24 hours at 37 C at which time the cells were washed and RNA isolated for qRT-PCR according the Qiagen Quantitech method (see manufacturer's protocol) for 40 cycles.

Figure 25:
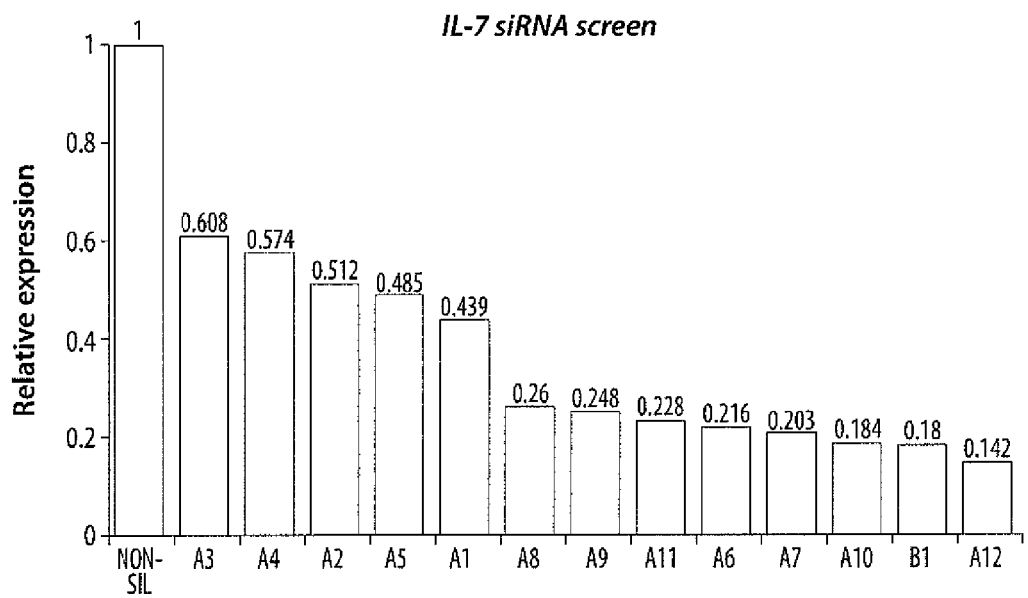
FIG. 25 is a bar graph showing the knockdown of IL-7 expression with the various siRNA sequences in CMT93 cells post 24 hr transfection.

FIG. 25 shows the knockdown of IL-7 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| B2  | AGGAAAUGAUGUUUAUUGAtt | 471 | UCAAUAAACAUCAUUUCCUtg | 472 |
| B3  | GGCCGACUUCACUGUACAAtt | 473 | UUGUACAGUGAAGUCGGCCaa | 474 |
| B4  | GAUGGAGUUUGAAUCUUCAtt | 475 | UGAAGAUUCAAACUCCAUCtt | 476 |
| B5  | CAACCGCAGUAAUACGGAAtt | 477 | UUCCGUAUUACUGCGGUUGta | 478 |
| B6  | CGAGGCUGCAUGAUUUAUAtt | 479 | UAUAAAUCAUGCAGCCUCGgg | 480 |
| B7  | CCUGUAUUUCCAUAACAGAtt | 481 | UCUGUUAUGGAAAUACAGGcg | 482 |
| B8  | CAUGUACAAAGACAGUGAAtt | 483 | UUCACUGUCUUUGUACAUGta | 484 |
| B9  | CGAGGAUAUGACUGAUAUUtt | 485 | AAUAUCAGUCAUAUCCUCGaa | 486 |
| B10 | GGAUAUGACUGAUAUUGAUtt | 487 | AUCAAUAUCAGUCAUAUCCtc | 488 |
| B11 | CUAACUUACAUCAAAGUUAtt | 489 | UAACUUUGAUGUAAGUUAGtg | 490 |
| B12 | CUCACUAACUUACAUCAAAtt | 491 | UUUGAUGUAAGUUAGUGAGag | 492 |

| Well | siRNA sense 5'→3' | SEQ ID NO: | siRNA antisense 5'→3' | SEQ ID NO: |
|---|---|---|---|---|
| A1 | GAUCCUACGGAAGUUAUGGtt | 493 | CCAUAACUUCCGUAGGAUCcg | 494 |
| B1 | CCAUGUUCCAUGUUUCUUUtt | 495 | AAAGAAACAUGGAACAUGGtc | 496 |
| A2 | CCUCCCGCAGACCAUGUUCtt | 497 | GAACAUGGUCUGCGGGAGGcg | 498 |
| A3 | CUCCCGCAGACCAUGUUCCtt | 499 | GGAACAUGGUCUGCGGGAGgc | 500 |
| A4 | UCCCGCAGACCAUGUUCCAtt | 501 | UGGAACAUGGUCUGCGGGAgg | 502 |
| A5 | CCCGCAGACCAUGUUCCAUtt | 503 | AUGGAACAUGGUCUGCGGGag | 504 |
| A6 | CCGCAGACCAUGUUCCAUGtt | 505 | CAUGGAACAUGGUCUGCGGga | 506 |
| A7 | CGCAGACCAUGUUCCAUGUtt | 507 | ACAUGGAACAUGGUCUGCGgg | 508 |
| A10 | AGACCAUGUUCCAUGUUUCtt | 509 | GAAACAUGGAACAUGGUCUgc | 510 |
| A12 | ACCAUGUUCCAUGUUUCUUtt | 511 | AAGAAACAUGGAACAUGGUct | 512 |

Example 15

Inhibition of Expression of Chitinase3-Like-1 (CH13L1) Expression in CMT93 Cells In a 1.7 ml microcentrifuge tube, 2.4 μl of 20 μM double-stranded RNA solution (from Qiagen) was diluted into 394 μl Opti-MEM serum-free medium (Invitrogen) containing 1 μl Lipofectamine RNAiMAX (Invitrogen), mixed, and incubated 10 min at room temperature to enable the formation of transfection complexes. 100 μl of this mixture was added to each of three wells of a 24-well tissue culture dish, on top of which CMT-93 cells were plated in a 500 μl volume, resulting in a final volume of 600 μl per well and a final RNA concentration of 20 nM. After 24 h transfection, 0.1 μg/ml lipopolysaccharide (LPS) (Sigma) was added to each well and cells were incubated for a further 24 h to stimulate CHI3L1 production, after which cells were washed in PBS and harvested for RNA extraction. CMT-93 cells were prepared for transfection as follows. 1 confluent T-175 flask of CMT-93 cells was trypsinized in 10 mls until the cells detached. Trypsin was inactivated by addition of 30 mls of DMEM (10% FBS) and the cells thoroughly mixed by pipetting. From this solution, 10 mls was transferred into a sterile 50 ml tube and 40 mLs of DMEM 10% FBS added. Cells were well mixed and 500 μLs added to each well of a 24-well plate. This concentration of cells resulted in approximately 70% confluency after 24 h of growth.

Figure 26:
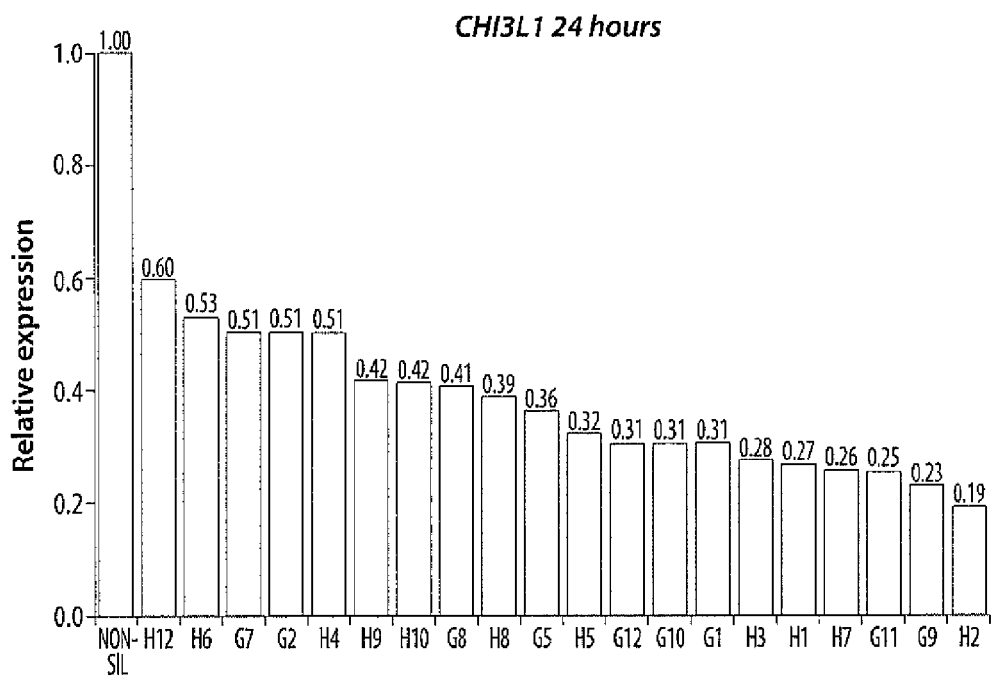
FIG. 26 is a bar graph showing the knockdown of CH13L1 expression with the various siRNA sequences in CMT93 cells post 24 hr transfection.

FIG. 26 shows the knockdown of CH13L1 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| G1 | CCACAUCAUCUACAGCUUUtt | 513 | AAAGCUGUAGAUGAUGUGGgt | 514 |
| H1 | GGUUUGACAGAUACAGCAAtt | 515 | UUGCUGUAUCUGUCAAACCta | 516 |
| G2 | UCAUCUACAGCUUUGCCAAtt | 517 | UUGGCAAAGCUGUAGAUGAtg | 518 |
| H2 | CCCUGUUAAGGAAUGCAAAtt | 519 | UUUGCAUUCCUUAACAGGGtt | 520 |
| H3 | CAAGUAGGCAAAUAUCUUAtt | 521 | UAAGAUAUUUGCCUACUUGat | 522 |
| H4 | CAGCUUUGUCAGCAGGAAAtt | 523 | UUUCCUGCUGACAAAGCUGcg | 524 |
| G5 | GGUUCACCAAGGAGGCAGGtt | 525 | CCUGCCUCCUUGGUGAACCgg | 526 |
| H5 | GGAUCAAGUAGGCAAAUAUtt | 527 | AUAUUUGCCUACUUGAUCCaa | 528 |
| H6 | GAGGGACCAUACUAAUUAUtt | 529 | AUAAUUAGUAUGGUCCCUCaa | 530 |
| G7 | GGCCGGUUCACCAAGGAGGtt | 531 | CCUCCUUGGUGAACCGGCCtg | 532 |
| H7 | GGACAAGGAGAGUGUCAAAtt | 533 | UUUGACACUCUCCUUGUCCtc | 534 |
| G8 | CCGGUUCACCAAGGAGGCAtt | 535 | UGCCUCCUUGGUGAACCGGcc | 536 |
| H8 | CGUACAAGCUGGUCUGCUAtt | 537 | UAGCAGACCAGCUUGUACGca | 538 |
| G9 | GGAGUUUAAUCUCUUGCAAtt | 539 | UUGCAAGAGAUUAAACUCCtg | 540 |

| Well | siRNA sense 5'→3' | SEQ ID NO: | siRNA antisense 5'→3' | SEQ ID NO: |
|---|---|---|---|---|
| H9 | CAAGGAACUGAAUGCGGAAtt | 541 | UUCCGCAUUCAGUUCCUUGat | 542 |
| G10 | CCCUGAUCAAGGAACUGAAtt | 543 | UUCAGUUCCUUGAUCAGGGtg | 544 |
| H10 | CUUGGAUCAAGUAGGCAAAtt | 545 | UUUGCCUACUUGAUCCAAGtg | 546 |
| G11 | GGAUUGAGGGACCAUACUAtt | 547 | UAGUAUGGUCCCUCAAUCCtg | 548 |
| G12 | GCAAAUUCUCAGACUCUAAtt | 549 | UUAGAGUCUGAGAAUUUGCat | 550 |
| H12 | CCUUCCCUUAGGAACUUAAtt | 551 | UUAAGUUCCUAAGGGAAGGat | 552 |

Example 16

Construction of CEQ200

CEQ200 has the following genotype: glnV44(AS), LAM⁻, rfbC1, endA1, spoT1, thi-1, hsdR17, ($r_k^- m_k^+$), creC510 ΔdapA. The MM294 has the following genotype: glnV44 (AS), LAM⁻, rfbC1, endA1, spoT1, thi-1, hsdR17, ($r_k^- m_k^+$), creC510. We purchased the plasmids from CGSC (see Datsenko et al., (2000) Proc. Natl. Acad. Sci. USA 97, 6640-6645).

Derivation of CEQ200

MM294
↓ (from CGSC) Transformation with plasmid pKD46

MM294 (pKD46)
↓ Transformation with a ΔdapA::kan cassette generated using PCR using pKD4

MM294 ΔdapA::kan (pKD46)
↓ Plasmid pKD46 cured by growing cells at 43° C.

MM294 ΔdapA::kan
↓ Transformation with plasmid pCP20

MM294 ΔdapA::kan (pCP20)
↓ Plasmid pCP20 cured and kan gene was deleted by induction of FLP recombinase treatment at 43° C.

CEQ200

Example 17

Construction of CEQ201

CEQ201 has the following genotype: CEQ200 [glnV44 (AS), LAM⁻, rfbC1, endA1, spoT1, thi-1, hsdR17, ($r_k^- m_k^+$), creC510 ΔdapA ΔrecA. The MM294 has the following genotype: glnV44(AS), LAM⁻, rfbC1, endA1, spoT1, thi-1, hsdR17, ($r_k^- m_k^+$), creC510. We purchased the plasmids from CGSC (see Datsenko et al., (2000) Proc. Natl. Acad. Sci. USA 97, 6640-6645).

Derivation of CEQ200

MM294 (from CGSC)
↓ Transformation with plasmid pKD46

MM294 (pKD46)
↓ Transformation with a ΔdapA::kan cassette generated using PCR using pKD4

MM294 ΔdapA::kan (pKD46)
↓ Transformation with a ΔrecA::cat cassette generated using PCR using pKD3

MM294 ΔdapA::kan ΔrecA::cat (pKD46)
↓ Plasmid pKD46 cured by growing cells at 43° C.

-continued

MM294 ΔdapA::kan ΔrecA::cat

↓ Transformed with plasmid pCP20

MM294 ΔdapA::kan ΔrecA::cat (pCD20)

↓ Plasmid pCP20 cured and kan and cat gene was deleted by induction of FLP recombinase treatment at 43° C.

CEQ201

Example 18

Construction of BTPs (CEQ210) by Deletion of minC and/or minD Genes from MM294

MM294 (from CGSC)

↓ Transformation with plasmid pKD46

MM294 (pKD46)

↓ Transformation with a ΔdapA::kan cassette generated using PCR using pKD4

-continued

MM294 ΔminCD::kan (pKD46)

↓ Plasmid pKD46 cured by growing cells at 43° C.

MM294 ΔminCD::kan

↓ Transformed with plasmid pCP20

MM294 ΔminCD::kan (pCP20)

↓ Plasmid pCP20 cured and kan gene was deleted by induction of FLP recombinase treatment at 43° C.

CEQ210

Example 19

Illustration of the pMBV40, pMBV43 and pMBV44 Plasmids

The pMBV40, pMBV43 and pMBV44 plasmids may be used as final or intermediary plasmid in the tkRNA system and may be constructed as follows: pUC19 digested with restriction enzyme PvuII. Resultant ~2.4 kb fragment was ligated with a ~200 bp DNA fragment generated by annealing 5 oligonucleotides with each other. The oligonucleotides have the following names and sequences:

```
                                                         (SEQ ID NO: 553)
OHTOP1: GACTTCATATACCCAAGCTTGGAAAATTTTTTTAAAAAATCTTGACACTTTATGCTTCCGGCTCGTATAATGG
ATCCAGGAGTAACAATACAAATGGA (SEQ ID NO: 554)
OHTOP2: TTCAAGAGATCCATTTGTATTGTTACTCCTTTTTTTTTTTGTCGACGATCCTTAGCGAAAGCTAAGGATTTTTTT
TTTACTCGAGCGGATTACTACATAC (SEQ ID NO: 555)
OHBOT1: GTATGTAGTAATCCGCTCGAGTAAAAAAAAAATCCTTAGCTTTCGCTAAGGATCGTCGACAAAAAAAAAA (SEQ ID NO: 556)
OHBOT2: AGGAGTAACAATACAAATGGATCTCTTGAATCCATTTGTATTGTTACTCCTGGATCCATT (SEQ ID NO: 557)
OHBOT3: ATACGAGCCGGAAGCATAAAGTGTCAAGACTTTTTTAAAAAAAATTTTCCAAGCTTGGGTATATGAAGTC
```

Ligation mix was transformed in E. coli and Ampicillin resistant transformants were selected. Plasmid DNA from a transformant that had the expected DNA sequence of the insert and restriction map was named pMBV38.

pMBV38 was digested with NdeI and blunt end ligated with a ~6 kb fragment generated by BamHI-SalI digestion of the plasmid pKSII-inv-hly The predicted sequence of pKSII-inv-hly is as follows:

```
                                                              (SEQ ID NO: 558)
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGATGTGCTGCAAGGCGATTAAGTTGGGTTACGCCAGGGTTTT
CCCAGTCACGACGTTGTAAAACGACGGCCAGTGAGCGCGCGTAATACGACTCACTATAGGGCGAATTGGAGCT
CCACCGCGGTGGCGGCCGCTCTAGAACTAGRGGATCCCCCGGGCTGCAGCTGGGCCGTAAGATCGGCATTTAA
TCGCGACAATCCTTTTAAAAAAACAGCGCCGCGCAATTAACCTGAGCGGCGTTGTTCTTCTGGACGTTTGCTA
CTTATGGGGCGAGTCTAGGATTGCCGGACTCCCATTCGCGCCCCAAATAATCAGCTCATTAAACTGTTCTTAT
TGCTATCTGTTATCTGGTTATATTGACAGCGCACAGAGCGGGAACGCCAAGTATGCAGGCCCTGGTTGCAGTG
CGCCTGTGTCCATATTCATGGTTTCAAAATCCGTGCTGGTCTTTTTGACCCAATATTCACCAGATTGCCAATC
AGAACTATACGCGGTCAAGCTCCCCCACTCGCCCCACAATGTCCCGTCAGGCGCACGCGTTCCGTTGGTTGCA
CGTGAGGATTCAAGAACCGCAGACATATCTGAACCTTGGCATTGTCTGCTGGCCTCGAGACTGGATACCAGCG
ATCTGCCGCCATCGTATATCCACCGATTTGGGTAGAACCGATAACTCACCGAATAACTTGGGAATTTTTTACT
TTTCGCCGTCACAGCCCACTTCGCTATAGGTTTGGTAGGTAATCGTCACCTGACCCTGATCGTTAACCGATACA
TTGGGTGTGAATGACGACGACCACTCATACTGAGTATTATTAGCAACATCGTTATCCATCTGTAACTGGAATG
TGGCGTTTTTAAAGATCGTTTTCGGGAACCCTTTATCCGTAGCGAAATTTTGCCCGTTAACCAGAATACCGGT
CAGCGTAGGTACCGGGAATAGGGATATTTTTTTCTGCAATGTACTCAGTATCAGGGTATCAACCTGCGGCGTG
ATTGTGACATCACCGACACTATTCCCAACCACCGTCGCGGTATAGCTATCTGGCTGCTCGGTAATGGGGCTAA
TACTCACCGGCACACCGTTTTGAGTAAAACTCAAGCCCTGCATCCCACTGATAAAATGGCCATTCTTATCGAC
AGGGACAAAGGATAATGTGGAACTCATCGTGCCATCAGCCAAGATATCCGGTGTGGGAGACGGTGAAACTGGAG
CGGCCAGCATCTGGAATAGGATCTGCCGTGAAATTAACCGTCACACTCGGCACACTGAACGCAGCCCCATCCA
CTTTCACCGTTACTGTTGCTACCCCCAACGTGGTACTGGTCAATGGTGCGCTATAAGTGCCTACATTGTGATC
CGTGATAACGCCCATATTGCCTAAGGTTGTGTCAAAAGCCACATTCGCGCCAGCCTGCGGGTCCCCATAGGTA
TCCTTCAACTCCAACGTAGATGGTTGAAGCCATTAGACCATCAGCGATATAGATGTCGGTACCGCAGCCAGAG
TGGATTTATCCGCCGCGATAGTACCCTTAACAAAGTGGGTATCAACACTTTGCCGTTGCCCCTCCACTTCTGC
TGTGACTACCGTCACGCCATCTGTCGTATTGGTTAATGCAATGCGCGCGACGCCATTTGCATCTGTCTTTTCC
GTGATTTTATTCGGTAGCGCACCATTATTGGTGGTTATCACCACCTCCTGCCCGGCTAAGGGTTTCCCCTCAA

AATCAGCAACGGTGAACTCAACGGTGATTGCAGTTTTCCCATTAGCCGGTGCGCCATCACCAATGACGGCCGC
CGTTAATGTCAACTGAGGCTGCTGAACGGTGACGCTCAATGTGAATGAGTTAGATCGGTTTCCTTGGTGATCA
ACCGCGAGCGCACTAAGCGAATAAAAGTTGGCTGTCAGGTCGTCCGRRACCCGACTCACTTGTCTGTGCGTT
TATAAGGCGGTAAAACCAAGTTGAATTGTGGTGGTACTCATGGTGTTAATGTGCCGCCAGCGGCAATCAGTTC
GGCATCACTCCAGACAATTTCCCTTACAGCAGATGCCCCTTGTACTTGTGCGTTCACCTGATAAACCTGACCC
GGCAGGCCGGAGATAGTTGCTGGCGATAATGTCAGTTTAACCACCTGCTGTTTCTGATACTCCAACACGATAT
TATTGTTACGATCGACAAGGTTATAGCGGCTCTCCGCCAGTAGACGTGTTCCTGCCACCGCTGAAGGGCTAAG
TTGCGACTGAAAACTCTCGCCCAGGCGATAGTTCATTTGGAGGTTCCACTGTGTTTCATGCTTACTGCTTTTC
CCCATACGCTGATCTACCCCGACAGTGAGTAGAGGCACGGGGGTGTAATTGATCCCGGCAGTCACGGCATAAG
GGTTGCGTTGCAGATTATCTTTACCAAATAAAGCAACACGCTCACCGGTGTATTGCTCATACATCAACTTCCC
CCCCAGTTGTGGGAGTGCAGGTAAATAAGCATTCGCGCGCAAATCCCCCCCAGTGGCTGGGCGCTCTTTATAG
TCGGAGAAATCACGCGACGAGTGCCATCCATTGAGGCGAAAATACCCATTGGCAGCCAACTGTAAATAATCGG
TCCAGGCCTCGGCACCAAGACCGATACGGTGGTTGTGGCCGGTCAAATCATTATCATAAAAAGTATTAAGTCC
GTACAGCCAACCGTTCTCCAATGTACGTATCCCGACGCCAAGGTTAAGTGTGTTGCGGCTGTCTTTATTGCGA
ATACCTAACTGACTAAAAAAGAGGAATGAAGCAGAGTCATACCAAGGAGCCAGCAATCAAGAGAGCTTTCTT
TTAGCGAAAAATTTTTGTCAAAATTCAGATTAACTTGAGCCGTACCGAATCGATTTAACCACTGTTTGATTTC
TTGATTAACCGCATCGCCCACCATTGAGTGAGCAACATCAGATGCCCTGCCTGATGCAGCTAACCTGGCCCCG
GTGCTTATCATCTTATTCACCGCTTCAGTCTCCTGCTCCTTATTGGCGCGATCTATTATTGCAGCATTTCTTT
CTGTATCCGATGCGGAAAAGGGATTGATTGAACTCTCCATTTCATTATTAGGATGGAGATTTTCAAATGCAGA
TGAAGAGACAGAATAAGGCTGGACCTGTGGCGGTGCGTTAGCATCATATTTTTCTGAAGCCCCAGCCATGAAC
ATTCCACATACAAAAAGATACAAATAACTATTCGTGAAATAATATTAAAATGAAATTATTTTATTAAAATACA
TAGACATTCCCGCATTCCTTATCAAGAGAAACTCACTGATTGGCTGGAAAACCATCATAATTTAAATGAAATA
AAGCATACCTGTCATACGTCAAACTGCATGTGCGTTGGCTGTGCTCAACAACTTGAGTTATTTGAGGTATAAC
TGGCCACAAACGAGCATTTGAAATCACCTTGACCATTAATTAAAGATGCAATAGTTGAAAGTGAAACTTGTTT
TCTAATTTAGTAAAGACATTAAGAGGATAGCACTTTTTTAAAAAACCAGACTGGGCAGATTAAAAATATTCAA
AATATATAATAAAACAGTCTATACCATACAGCGATAGAATTGATTTATTGTAACTAAGCAGGTGAGAATACTA
AAAAAAACAAAAATACAAAATGAACTATTATCATATAAATAATATCAATTAGAATAAGCCCCCTTCATTTGAT
GTTGTCAGTTGTCTGCTGCGGTTTTTATTTCTACTTTCAGTCTGAAGTGTTACTCCGCAATATCCGCATTAAT
CCTGATGGTTGCCTTGATGACTGCAGGAATTCGATCCCTCCTTTGATTAGTATATTCCTATCTTAAAGTGACT
TTTATGTTGAGGCATTAACATTTGTTAACGACGATAAAGGGACAGCAGGACTAGAATAAAGCTATAAAGCAAG
CATATAATATTGCGTTTCATCTTTAGAAGCGAATTTCGCCAATATTATAATTATCAAAAGAGAGGGGTGGCAA
```

-continued

```
ACGGTATTTGGCATTATTAGGTTAAAAAATGTAGAAGGAGAGTGAAACCCATGAAAAAAATAATGCTAGTTTT
TATTACACTTATATTAGTTAGTCTACCAATTTCGCAACAAACTGAAGCAAAGGATGCATCTGCATTCAATAAA
GAAAATTCAATTTCATCCATGGCACCACCAGCATCTCCGCCTGCAAGTCCTAAGACGCCAATCGAAAAGAAAC
ACGCGGATGAAATCGATAAGTATATACAAGGATTGGATTACAATAAAAACAATGTATTAGTATACCACGGAGA
TGCAGTGACAAATGTGCCGCCAAGAAAAGGTTACAAAGATGGAAATGAATGTGTTGTTGTGGAGAAAAAGAAG
AAATCCATCAATCAAAATAATGCAGACATTCAAGTTGTGAATGCAATTTCGAGCCTAACCTATCCAGGTGCTC
TCGTAAAAGCGAATTCGGAATTAGTAGAAAATCAACCAGATGTTCTCCCTGTAAAACGTGATTCATTAACACT
CAGCATTGATTTGCCAGGTATGACTAATCAAGACAATAAAATCGTTGTAAAAAATGCCACTAAATCAAACGTT
AACAACGCAGTAAATACATTAGTGGAAAGATGGAATGAAAAATATGCTCAAGCTTATCCAAATGTAAGTGCAA
AAATTGATTATGATGACGAAATGGCTTACAGTGAATCACAATTAATTGCGAAATTTGGTACAGCATTTAAAGC
TGTAAATAATAGCTTGAATGTAAACTTCGGCGCAATCAGTGAAGGGAAAATGCAAGAAGAAGTCATTAGTTTT
AAACAAATTTACTATAACGTGAATGTTAATGAACCTACAAGACCTTCCAGATTTTTCGGCAAAGCTGTTACTA
AAGAGCAGTTGCAAGCGCTTGGAGTGAATGCAGAAAATCCTCCTGCATATATCTCAAGTGTGGCGTATGGCCG
TCAAGTTTATTTGAAATTATCAACTAATTCCCATAGTACTAAAGTAAAAGCTGCTTTTGATGCTGCCGTAAGC
GGAAAATCTGTCTCAGGTGATGTAGAACTAACAAATATCATCAAAAATTCTTCCTTCAAAGCCGTAATTTACG
GAGGTTCCGCAAAAGATGAAGTTCAAATCATCGACGGCAACCTCGGAGACTTACGCGATATTTTGAAAAAAGG
CGCTACTTTTAATCGAGAAACACCAGGAGTTCCCATTGCTTATACAACAAACTTCCTAAAAGACAATGAATTA
GCTGTTATTAAAACAACTCAGAATATATTGAAACAACTTCAAAAGCTTATACAGATGGAAAAATTAACATCG
ATCACTCTGGAGGATACGTTGCTCAATTCAACATTTCTTGGGATGAAGTAAATTATGATCCTGAAGGTAACGA
AATTGTTCAACATAAAAACTGGAGCGAAAACAATAAAAGCAAGCTAGCTCATTTCACATCGTCCATCTATTTG
CCAGGTAACGCGAGAAATATTAATGTTTACGCTAAAGAATGCACTGGTTTAGCTTGGGAATGGTGGAGAACGG
TAATTGATGACCGGAACTTACCACTTGTGAAAAATAGAAATATCTCCATCTGGGGCACCACGCTTTATCCGAA
ATATAGTAATAAAGTAGATAATCCAATCGAATAATTGTAAAAGTAATAAAAAATTAAGAATAAAACCGCTTAA
CACACACGAAAAATAAGCTTGTTTTGCACTCTTCGTAAATTATTTTGTGAAGAATGTAGAAACAGGCTTATT
TTTTAATTTTTTAGAAGAATTAACAAATGTAAAAGAATATCTGACTGTTTATCCATATAATATAAGCATATC
CCAAAGTTTAAGCCACCTATAGTTTCTACTGCAAAACGTATAATTTAGTTCCCACATATACTAAAAAACGTGT
CCTTAACTCTCTCTGTCAGATTAGTTGTAGGTGGCTTAAACTTAGTTTTACGAATTAAAAAGGAGCGGTGAAA
TGAAAAGTAAACTTATTTGTATCATCATGGTAATAGCTTTTCAGGCTCATTTCACTATGACGGTAAAAGCAGA
TTCTGTCGGGGAAGAAAAACTTCAAAATAATACACAAGCCAAAAAGACCCCTGCTGATTTAAAAGCTTATCAA
GCTTATCGATACCGTCGACCTCGAGGGGGGCCCGGTACCCAGCTTTTGTTCCCTTTAGTGAGGGTTAATTGC
GCGCTTGGCGTAATCATGGTCATAGCTGTTTCCTGTGTGAATTGTTATCCGCTCACAATTCCACACAACATA

CGAGCCGGAAGCATAAAGTGTAAAGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGAATCGGCCAACGCGCGGGGAGAGG
CGGTTTGCGTATTGGGCGCTCTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGGACAGTATTTGGTAT
CTGCGCTCTGCTGAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATGAGATTATCAAA

AAGGATCTTCACCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCGGGAAGCTAGAGTAAGTAGTTCGC
CAGTTAATAGTTTGCGCAACGTTCTTGCCATTGCTACAGGCATCGTGGTGTCACGCTCGTCGTTTGGTATGGC
TTCATTCAGCTCCGGTTCCCAACGATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATCACTCATGGTTATGGCAGCACTGC
ATAATTCTCTTACTGTCATGCCATCCGTAAGATGCTTTTCTGTGACTGGTGAGTACTCAACCAAGTCATTCTG
AGAATAGTGTATGCGGCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTACTTTCACCAGCGTTTCTGGGTG
AGCAAAAACAGGAAGGCAAAATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCAC
```

Ligation mix was transformed in *E. coli* and Ampicillin resistant transformants were selected. Plasmid DNA from a transformant that had insertion of inv and hly genes was named pMBV40.

pMBV40 was digested with BspHI and the resultant 7.4 kb DNA fragment was ligated with a PCR fragment containing kan gene generated using plasmid pKD4 (purchased from CGSC (see Datsenko et al., (2000) *Proc. Natl. Acad. Sci. USA* 97, 6640-6645) as the template.

Figure 27:
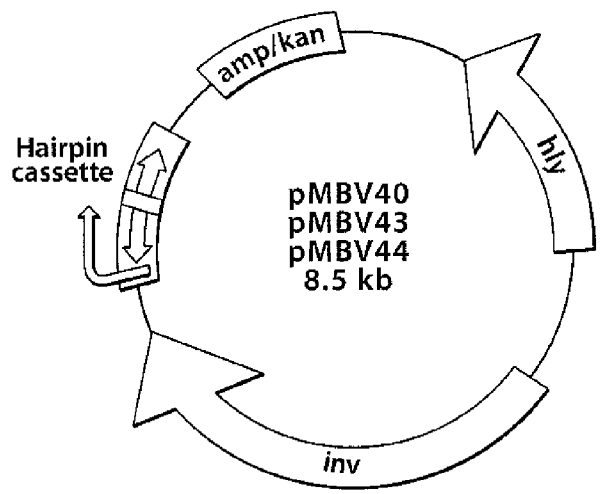
FIG. 27 is a schematic of the pMBV40 or pMBV43 or pMBV44 plasmids.

Ligation mix was transformed in *E. coli* and Kanamycin resistant transformants were selected. They were screened restriction mapping. They two different orientation of kan gene. The plasmids having clockwise and anticlockwise orientation of open reading frame of kan gene were called pMBV43 and pMBV44, respectively As shown in FIG. 27, the pMBV40 (amp selected having H3 hairpin) or pMBV43 and pMBV44 (kan selected having H3 hairpin) plasmids, are followed by the respective sequences.

```
pMBV40
                                                            (SEQ ID NO: 559)
TCGCGCGTTTCGGTGATGACGGTGAAAACCTCTGACACATGCAGCTCCCGGAGACGGTCACAGCTTGTCTGTAAG
CGGATGCCGGGAGCAGACAAGCCCGTCAGGGCGCGTCAGCGGGTGTTGGCGGGTGTCGGGGCTGGCTTAACTATG
CGGCATCAGAGCAGATTGTACTGAGAGTGCACCATATCGACGGTATCGATAAGCTTGATAAGCTTTTAAATCAGC
AGGGGTCTTTTTGGCTTGTGTATTATTTTGAAGTTTTTCTTCCCCGACAGAATCTGCTTTTACCGTCATAGTGAA
ATGAGCCTGAAAAGCTATTACCATGATGATACAAATAAGTTTACTTTTCATTTCACCGCTCCTTTTTAATTCGTA
AAACTAAGTTTAAGCCACCTACAACTAATCTGACAGAGAGAGTTAAGGACACGTTTTTTAGTATATGTGGGAACT
AAATTATACGTTTTGCAGTAGAAACTATAGGTGGCTTAAACTTTGGGATATGCTTATATTATATGGATAAACAGT
CAGATATTCTTTTACATTTGTTAATTCTTCTAAAAAAATTAAAAAATAAGCCTGTTTCTACATTCTTCACAAAAT
AATTTACGAAGAGTGCAAAACAAGCTTATTTTTCGTGTGTGTTAAGCGGTTTTATTCTTAATTTTTTATTACTT
TTACAATTATTCGATTGGATTATCTACTTTATTACTATATTTCGGATAAAGCGTGGTGCCCCAGATGGAGATATT
TCTATTTTTCACAAGTGGTAAGTTCCGGTCATCAATTACCGTTCTCCACCATTCCCAAGCTAAACCAGTGCATTC
TTTAGCGTAAACATTAATATTTCTCGCGTTACCTGGCAAATAGATGGACGATGTGAAATGAGCTAGCTTGCTTTT
ATTGTTTTCGCTCCAGTTTTTATGTTGAACAATTTCGTTACCTTCAGGATCATAATTTACTTCATCCCAAGAAAT
GTTGAATTGAGCAACGTATCCTCCAGAGTGATCGATGTTAATTTTTCCATCTGTATAAGCTTTTGAAGTTGTTTC
AATATATTCTGAGTTGTTTTTAATAACAGCTAATTCATTGTCTTTTAGGAAGTTTGTTGTATAAGCAATGGGAAC
TCCTGGTGTTTCTCGATTAAAAGTAGCGCCTTTTTTCAAAATATCGCGTAAGTCTCCGAGGTTGCCGTCGATGAT
TTGAACTTCATCTTTTGCGGAACCTCCGTAAATTACGGCTTTGAAGGAAGAATTTTTGATGATATTTGTTAGTTC
TACATCACCTGAGACAGATTTTCCGCTTACGGCAGCATCAAAAGCAGCTTTTACTTTAGTACTATGGGAATTAGT
TGATAATTTCAAATAAACTTGACGGCCATACGCCACACTTGAGATATATGCAGGAGGATTTTCTGCATTCACTCC
AAGCGCTTGCAACTGCTCTTTAGTAACAGCTTTGCCGAAAAATCTGGAAGGTCTTGTAGGTTCATTAACATTCAC
GTTATAGTAAATTTGTTTAAAACTAATGACTTCTTCTTGCATTTTCCCTTCACTGATTGCGCCGAAGTTTACATT
CAAGCTATTATTTACAGCTTTAAATGCTGTACCAAATTTCGCAATTAATTGTGATTCACTGTAAGCCATTTCGTC
ATCATAATCAATTTTTGCACTTACATTTGGATAAGCTTGAGCATATTTTTCATTCCATCTTTCCACTAATGTATT
TACTGCGTTGTTAACGTTTGATTTAGTGGCATTTTTTACAACGATTTTATTGTCTTGATTAGTCATACCTGGCAA
ATCAATGCTGAGTGTTAATGAATCACGTTTTACAGGGAGAACATCTGGTTGATTTTCTACTAATTCCGAATTCGC
TTTTACGAGAGCACCTGGATAGGTTAGGCTCGAAATTGCATTCACAACTTGAATGTCTGCATTATTTTGATTGAT
GGATTTCTTCTTTTTCTCCACAACAATATATTCATTTCCATCTTTGTAACCTTTTCTTGGCGGCACATTTGTCAC
TGCATCTCCGTGGTATACTAATACATTGTTTTATTGTAATCCAATCCTTGTATATACTTATCGATTTCATCCGC
GTGTTTCTTTTCGATTGGCGTCTTAGGACTTGCAGGCGGAGATGCTGGTGGTGCCATGGATGAAATTGAATTTTC
TTTATTGAATGCAGATGCATCCTTTGCTTCAGTTTGTTGCGCAATTGGTAGACTAACTAATATAAGTGTAATAAA
AACTAGCATTATTTTTTTCATGGGTTTCACTCTCCTTCTACATTTTTTAACCTAATAATGCCAAATACCGTTTGC
CACCCCTCTCTTTTGATAATTATAATATTGGCGAAATTCGCTTCTAAAGATGAAACGCAATATTATATGCTTGCT
TTATAGCTTTATTCTAGTCCTGCTGTCCCTTTATCGTCGTTAACAAATGTTAATGCCTCAACATAAAAGTCACTT
TAAGATAGGAATATACTAATCAAAGGAGGGATCGAATTCCTGCAGTCATCAAGGCAACCATCAGGATTAATGCGG
ATATTGCGGAGTAACACTTCGACTGAAAGTAGAAATAAAAACCGCAGCAGACAACTGACAACATCAAATGAAGG
GGGCTTATTCTAATTGATATTATTTATATGATAATAGTTCATTTTGTATTTTGTTTTTTTGATATTCTCACCT
GCTTAGTTACAATAAATCAATTCTATCGCTGTATGGTATAGACTGTTTTATTATATATTTTGAATATTTTTAATC
TGCCCAGTCTGGTTTTTTAAAAAAGTGCTATCCTCTTAATGTCTTTACTAAATTAGAAAACAAGTTTCACTTTCA
```

-continued
```
ACTATTGCATCTTTAATTAATGGTCAAGGTGATTTCAAATGCTCGTTTGTGGCCAGTTATACCTCAAATAACTCA

AGTTGTTGAGCACAGCCAACGCACATGCAGTTTGACGTATGACAGGTATGCTTTATTTCATTTAAATTATGATGG

TTTTCCAGCCAATCAGTGAGTTTCTCTTGATAAGGAATGCGGGAATGTCTATGTATTTTAATAAAATAATTTCAT

TTAATATTATTTCACGAATAGTTATTTGTATCTTTTTGATATGTGGAATGTTCATGGCTGGGGCTTCAGAAAAAT

ATGATGCTAACGCACCGCAACAGGTCCAGCCTTATTCTGTCTCTTCATCTGCATTTGAAAATCTCCATCCTAATA

ATGAAATGGAGAGTTCAATCAATCCCTTTTCCGCATCGGATACAGAAAGAAATGCTGCAATAATAGATCGCGCCA

ATAAGGAGCAGGAGACTGAAGCGGTGAATAAGATGATAAGCACCGGGGCCAGGTTAGCTGCATCAGGCAGGGCAT

CTGATGTTGCTCACTCAATGGTGGGCGATGCGGTTAATCAAGAAATCAAACAGTGGTTAAATCGATTCGGTACGG

CTCAAGTTAATCTGAATTTTGACAAAAATTTTTCGCTAAAAGAAAGCTCTCTTGATTGGCTGGCTCCTTGGTATG

ACTCTGCTTCATTCCTCTTTTTTAGTCAGTTAGGTATTCGCAATAAAGACAGCCGCAACACACTTAACCTTGGCG

TCGGGATACGTACATTGGAGAACGGTTGGCTGTACGGACTTAATACTTTTTATGATAATGATTTGACCGGCCACA

ACCACCGTATCGGTCTTGGTGCCGAGGCCTGGACCGATTATTTACAGTTGGCTGCCAATGGGTATTTTCGCCTCA

ATGGATGGCACTCGTCGCGTGATTTCTCCGACTATAAAGAGCGCCCAGCCACTGGGGGGATTTGCGCGCGAATG

CTTATTTACCTGCACTCCCACAACTGGGGGGAAGTTGATGTATGAGCAATACACCGGTGAGCGTGTTGCTTTAT

TTGGTAAAGATAATCTGCAACGCAACCCTTATGCCGTGACTGCCGGGATCAATTACACCCCCGTGCCTCTACTCA

CTGTCGGGGTAGATCAGCGTATGGGGAAAAGCAGTAAGCATGAAACACAGTGGAACCTCCAAATGAACTATCGCC

TGGGCGAGAGTTTTCAGTCGCAACTTAGCCCTTCAGCGGTGGCAGGAACACGTCTACTGGCGGAGAGCCGCTATA

ACCTTGTCGATCGTAACAATAATATCGTGTTGGAGTATCAGAAACAGCAGGTGGTTAAACTGACATTATCGCCAG

CAACTATCTCCGGCCTGCCGGGTCAGGTTTATCAGGTGAACGCACAAGTACAAGGGGCATCTGCTGTAAGGGAAA

TTGTCTGGAGTGATGCCGAACTGATTGCCGCTGGCGGCACATTAACACCACTGAGTACCACACAATTCAACTTGG

TTTTACCGCCTTATAAACGCACAGCACAAGTGAGTCGGGTAACGGACGACCTGACAGCCAACTTTTATTCGCTTA

GTGCGCTCGCGGTTGATCACCAAGGAAACCGATCTAACTCATTCACATTGAGCGTCACCGTTCAGCAGCCTCAGT

TGACATTAACGGCGGCCGTCATTGGTGATGGCGCACCGGCTAATGGGAAAACTGCAATCACCGTTGAGTTCACCG

TTGCTGATTTTGAGGGGAAACCCTTAGCCGGGCAGGAGGTGGTGATAACCACCAATAATGGTGCGCTACCGAATA

AAATCACGGAAAAGACAGATGCAAATGGCGTCGCGCGCATTGCATTAACCAATACGACAGATGGCGTGACGGTAG

TCACAGCAGAAGTGGAGGGGCAACGGCAAAGTGTTGATACCCACTTTGTTAAGGGTACTATCGCGGCGGATAAAT

CCACTCTGGCTGCGGTACCGACATCTATCATCGCTGATGGTCTAATGGCTTCAACCATCACGTTGGAGTTGAAGG

ATACCTATGGGACCCGCAGGCTGGCGCGAATGTGGCTTTTGACACAACCTTAGGCAATATGGGCGTTATCACGG

ATCACAATGACGGCACTTATAGCGCACCATTGACCAGTACCACGTTGGGGGTAGCAACAGTAACGGTGAAAGTGG

ATGGGCTGCGTTCAGTGTGCCGAGTGTGACGGTTAATTTCACGGCAGATCCTATTCCAGATGCTGGCCGCTCCA

GTTTCACCGTCTCCACACCGGATATCTTGGCTGATGGCACGATGAGTTCCACATTATCCTTTGTCCCTGTCGATA

AGAATGGCCATTTTATCAGTGGGATGCAGGGCTTGAGTTTTACTCAAAACGGTGTGCCGGTGAGTATTAGCCCCA

TTACCGAGCAGCCAGATAGCTATACCGCGACGGTGGTTGGGAATAGTGTCGGTGATGTCACAATCACGCCGCAGG

TTGATACCCTGATACTGAGTACATTGCAGAAAAAAATATCCCTATTCCCGGTACCTACGCTGACCGGTATTCTGG

TTAACGGGCAAAATTTCGCTACGGATAAAGGGTTCCCGAAAACGATCTTTAAAAACGCCACATTCCAGTTACAGA

TGGATAACGATGTTGCTAATAATACTCAGTATGAGTGGTCGTCGTCATTCACACCCAATGTATCGGTTAACGATC

AGGGTCAGGTGACGATTACCTACCAAACCTATAGCGAAGTGGCTGTGACGGCGAAAGTAAAAAATTCCCAAGTT

ATTCGGTGAGTTATCGGTTCTACCCAAATCGGTGGATATACGATGGCGGCAGATCGCTGGTATCCAGTCTCGAGG

CCAGCAGACAATGCCAAGGTTCAGATATGTCTGCGGTTCTTGAATCCTCACGTGCAACCAACGGAACGCGTGCGC

CTGACGGGACATTGTGGGCGAGTGGGGGAGCTTGACCGCGTATAGTTCTGATTGGCAATCTGGTGAATATTGGG

TCAAAAAGACCAGCACGGATTTTGAAACCATGAATATGGACACAGGCGCACTGCAACCAGGGCCTGCATACTTGG
```

-continued

CGTTCCCGCTCTGTGCGCTGTCAATATAACCAGATAACAGATAGCAATAAGAACAGTTTAATGAGCTGATTATTT

GGGGCGCGAATGGGAGTCCGGCAATCCTAGACTCGCCCCATAAGTAGCAAACGTCCAGAAGAACAACGCCGCTCA

GGTTAATTGAGCGGCGCTGTTTTTTTAAAAGGATTGTCGCGATTAAATGCCGATCTTACGGCCCAGCTGCAGCCC

GGGGGATCTATGCGGTGTGAAATACCGCACAGATGCGTAAGGAGAAAATACCGCATCAGGCGCCATTCGCCATTC

AGGCTGCGCAACTGTTGGGAAGGGCGATCGGTGCGGGCCTCTTCGCTATTACGCCAGGACTTCATATACCCAAGC

TTGGAAAATTTTTTTTAAAAAAGTCTTGACACTTTATGCTTCCGGCTCGTATAATGGATCCAGGAGTAACAATAC

AAATGGATTCAAGAGATCCATTTGTATTGTTACTCCTTTTTTTTTTGTCGACGATCCTTAGCGAAAGCTAAGGA

TTTTTTTTTACTCGAGCGGATTACTACATACCTGCATTAATGAATCGGCCAACGCGCGGGGAGAGGCGGTTTGC

GTATTGGGCGCTCTTCCGCTTCCTCGCTCACTGACTCGCTGCGCTCGGTCGTTCGGCTGCGGCGAGCGGTATCAG

CTCACTCAAAGGCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTCCCTTCGGGAAGCG

TGGCGCTTTCTCATAGCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTCTGCTGAAGCCAGTTACCT

TCGGAAAAAGAGTTGGTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGTCTGACGCTCAGTGGA

ACGAAAACTCACGTTAAGGGATTTTGGTCATGAGATTATCAAAAAGGATCTTCACCTAGATCCTTTTAAATTAAA

AATGAAGTTTTAAATCAATCTAAAGTATATATGAGTAAACTTGGTCTGACAGTTACCAATGCTTAATCAGTGAGG

CACCTATCTCAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTCCAGATTTATCAG

CAATAAACCAGCCAGCCGGAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTGTTGCCATTGCTACAGGCA

TCGTGGTGTCACGCTCGTCGTTTGGTATGGCTTCATTCAGCTCCGGTTCCCAACGATCAAGGCGAGTTACATGAT

CCCCCATGTTGTGCAAAAAAGCGGTTAGCTCCTTCGGTCCTCCGATCGTTGTCAGAAGTAAGTTGGCCGCAGTGT

TATCACTCATGGTTATGGCAGCACTGCATAATTCTCTTACTGTCATGCCATCCGTAAGATGCTTTTCTGTGACTG

GTGAGTACTCAACCAAGTCATTCTGAGAATAGTGTATGCGGCGACCGAGTTGCTCTTGCCCGGCGTCAATACGGG

ATAATACCGCGCCACATAGCAGAACTTTAAAAGTGCTCATCATTGGAAAACGTTCTTCGGGGCGAAAACTCTCAA

GGATCTTACCGCTGTTGAGATCCAGTTCGATGTAACCCACTCGTGCACCCAACTGATCTTCAGCATCTTTTACTT

TCACCAGCGTTTCTGGGTGAGCAAAAACAGGAAGGCAAAATGCCGCAAAAAAGGGAATAAGGGCGACACGGAAAT

GTTGAATACTCATACTCTTCCTTTTTCAATATTATTGAAGCATTTATCAGGGTTATTGTCTCATGAGCGGATACA

TATTTGAATGTATTTAGAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTTCGTC pMBV43

(SEQ ID NO: 560)

TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATCGACGGTATCGATAAGCTTGATAAGCTTTTAAATCAGC

AGGGGTCTTTTTGGCTTGTGTATTATTTTGAAGTTTTTCTTCCCCGACAGAATCTGCTTTTACCGTCATAGTGAA

-continued

```
ATGAGCCTGAAAAGCTATTACCATGATGATACAAATAAGTTTACTTTTCATTTCACCGCTCCTTTTTAATTCGTA
AAACTAAGTTTAAGCCACCTACAACTAATCTGACAGAGAGAGTTAAGGACACGTTTTTTAGTATATGTGGGAACT
AAATTATACGTTTTGCAGTAGAAACTATAGGTGGCTTAAACTTTGGGATATGCTTATATTATATGGATAAACAGT
CAGATATTCTTTTACATTTGTTAATTCTTCTAAAAAAATTAAAAAATAAGCCTGTTTCTACATTCTTCACAAAAT
AATTTACGAAGAGTGCAAAACAAGCTTATTTTTTCGTGTGTGTTAAGCGGTTTTATTCTTAATTTTTTATTACTT
TTACAATTATTCGATTGGATTATCTACTTTATTACTATATTTCGGATAAAGCGTGGTGCCCCAGATGGAGATATT
TCTATTTTTCACAAGTGGTAAGTTCCGGTCATCAATTACCGTTCTCCACCATTCCCAAGCTAAACCAGTGCATTC
TTTAGCGTAAACATTAATATTTCTCGCGTTACCTGGCAAATAGATGGACGATGTGAAATGAGCTAGCTTGCTTTT
ATTGTTTTCGCTCCAGTTTTTATGTTGAACAATTTCGTTACCTTCAGGATCATAATTTACTTCATCCCAAGAAAT
GTTGAATTGAGCAACGTATCCTCCAGAGTGATCGATGTTAATTTTTCCATCTGTATAAGCTTTTGAAGTTGTTTC
AATATATTCTGAGTTGTTTTTAATAACAGCTAATTCATTGTCTTTTAGGAAGTTTGTTGTATAAGCAATGGGAAC
TCCTGGTGTTTCTCGATTAAAAGTAGCGCCTTTTTTCAAAATATCGCGTAAGTCTCCGAGGTTGCCGTCGATGAT
TTGAACTTCATCTTTTGCGGAACCTCCGTAAATTACGGCTTTGAAGGAAGAATTTTTGATGATATTTGTTAGTTC
TACATCACCTGAGACAGATTTTCCGCTTACGGCAGCATCAAAAGCAGCTTTTACTTTAGTACTATGGGAATTAGT
TGATAATTTCAAATAAACTTGACGGCCATACGCCACACTTGATATATGCAGGAGGATTTTCTGCATTCACTCC
AAGCGCTTGCAACTGCTCTTTAGTAACAGCTTTGCCGAAAAATCTGGAAGGTCTTGTAGGTTCATTAACATTCAC
GTTATAGTAAATTTGTTTAAAACTAATGACTTCTTCTTGCATTTTCCCTTCACTGATTGCGCCGAAGTTTACATT
CAAGCTATTATTTACAGCTTTAAATGCTGTACCAAATTTCGCAATTAATTGTGATTCACTGTAAGCCATTTCGTC
ATCATAATCAATTTTTGCACTTACATTTGGATAAGCTTGAGCATATTTTTCATTCCATCTTTCCACTAATGTATT
TACTGCGTTGTTAACGTTTGATTTAGTGGCATTTTTTACAACGATTTTATTGTCTTGATTAGTCATACCTGGCAA
ATCAATGCTGAGTGTTAATGAATCACGTTTTACAGGGAGAACATCTGGTTGATTTTCTACTAATTCCGAATTCGC
TTTTACGAGAGCACCTGGATAGGTTAGGCTCGAAATTGCATTCACAACTTGAATGTCTGCATTATTTTGATTGAT
GGATTTCTTCTTTTCTCCACAACAATATATTCATTTCCATCTTTGTAACCTTTTCTTGGCGGCACATTTGTCAC
TGCATCTCCGTGGTATACTAATACATTGTTTTATTGTAATCCAATCCTTGTATATACTTATCGATTTCATCCGC
GTGTTTCTTTTCGATTGGCGTCTTAGGACTTGCAGGCGGAGATGCTGGTGGTGCCATGGATGAAATTGAATTTTC
TTTATTGAATGCAGATGCATCCTTTGCTTCAGTTTGTTGCGCAATTGGTAGACTAACTAATATAAGTGTAATAAA
AACTAGCATTATTTTTTTCATGGGTTTCACTCTCCTTCTACATTTTTTAACCTAATAATGCCAAATACCGTTTGC
CACCCCTCTCTTTTGATAATTATAATATTGGCGAAATTCGCTTCTAAAGATGAAACGCAATATTATATGCTTGCT
TTATAGCTTTATTCTAGTCCTGCTGTCCCTTTATCGTCGTTAACAAATGTTAATGCCTCAACATAAAAGTCACTT
TAAGATAGGAATATACTAATCAAAGGAGGGATCGAATTCCTGCAGTCATCAAGGCAACCATCAGGATTAATGCGG
ATATTGCGGAGTAACACTTCAGACTGAAAGTAGAAATAAAACCGCAGCAGACAACTGACAACATCAAATGAAGG
GGGCTTATTCTAATTGATATTATTTATATGATAATAGTTCATTTTGTATTTTGTTTTTTTGATATTCTCACCT
GCTTAGTTACAATAAATCAATTCTATCGCTGTATGGTATAGACTGTTTTATTATATATTTTGAATATTTTTAATC
TGCCCAGTCTGGTTTTTTAAAAAAGTGCTATCCTCTTAATGTCTTTACTAAATTAGAAAACAAGTTTCACTTTCA
ACTATTGCATCTTTAATTAATGGTCAAGGTGATTTCAAATGCTCGTTTGTGGCCAGTTATACCTCAAATAACTCA
AGTTGTTGAGCACAGCCAACGCACATGCGAGTTTGACGTATGACAGGTATGCTTTATTTCATTTAAATTATGATGG
TTTTCCAGCCAATCAGTGAGTTTCTCTTGATAAGGAATGCGGGAATGTCTATGTATTTTAATAAAATAATTTCAT
TTAATATTATTTCACGAATAGTTATTTGTATCTTTTTGATATGTGGAATGTTCATGGCTGGGGCTTCAGAAAAAT
ATGATGCTAACGCACCGCAACAGGTCCAGCCTTATTCTGTCTCTTCATCTGCATTTGAAAATCTCCATCCTAATA
ATGAAATGGAGAGTTCAATCAATCCCTTTTCCGCATCGGATACAGAAAGAAATGCTGCAATAATAGATCGCGCCA
ATAAGGAGCAGGAGACTGAAGCGGTGAATAAGATGATAAGCACCGGGGCCAGGTTAGCTGCATCAGGCAGGGCAT
```

-continued

CTGATGTTGCTCACTCAATGGTGGGCGATGCGGTTAATCAAGAAATCAAACAGTGGTTAAATCGATTCGGTACGG

CTCAAGTTAATCTGAATTTTGACAAAAATTTTTCGCTAAAAGAAAGCTCTCTTGATTGGCTGGCTCCTTGGTATG

ACTCTGCTTCATTCCTCTTTTTTAGTCAGTTAGGTATTCGCAATAAAGACAGCCGCAACACACTTAACCTTGGCG

TCGGGATACGTACATTGGAGAACGGTTGGCTGTACGGACTTAATACTTTTTATGATAATGATTTGACCGGCCACA

ACCACCGTATCGGTCTTGGTGCCGAGGCCTGGACCGATTATTTACAGTTGGCTGCCAATGGGTATTTTCGCCTCA

ATGGATGGCACTCGTCGCGTGATTTCTCCGACTATAAAGAGCGCCCAGCCACTGGGGGGATTTGCGCGCGAATG

CTTATTTACCTGCACTCCCACAACTGGGGGGGAAGTTGATGTATGAGCAATACACCGGTGAGCGTGTTGCTTTAT

TTGGTAAAGATAATCTGCAACGCAACCCTTATGCCGTGACTGCCGGGATCAATTACACCCCGTGCCTCTACTCA

CTGTCGGGGTAGATCAGCGTATGGGAAAAGCAGTAAGCATGAAACACAGTGGAACCTCCAAATGAACTATCGCC

TGGGCGAGAGTTTTCAGTCGCAACTTAGCCCTTCAGCGGTGGCAGGAACACGTCTACTGGCGGAGAGCCGCTATA

ACCTTGTCGATCGTAACAATAATATCGTGTTGGAGTATCAGAAACAGCAGGTGGTTAAACTGACATTATCGCCAG

CAACTATCTCCGGCCTGCCGGGTCAGGTTTATCAGGTGAACGCACAAGTACAAGGGGCATCTGCTGTAAGGGAAA

TTGTCTGGAGTGATGCCGAACTGATTGCCGCTGGCGGCACATTAACACCACTGAGTACCACACAATTCAACTTGG

TTTTACCGCCTTATAAACGCACAGCACAAGTGAGTCGGGTAACGGACGACCTGACAGCCAACTTTTATTCGCTTA

GTGCGCTCGCGGTTGATCACCAAGGAAACCGATCTAACTCATTCACATTGAGCGTCACCGTTCAGCAGCCTCAGT

TGACATTAACGGCGGCCGTCATTGGTGATGGCGCACCGGCTAATGGGAAAACTGCAATCACCGTTGAGTTCACCG

TTGCTGATTTTGAGGGGAAACCCTTAGCCGGGCAGGAGGTGGTGATAACCACCAATAATGGTGCGCTACCGAATA

AAATCACGGAAAAGACAGATGCAAATGGCGTCGCGCGCATTGCATTAACCAATACGACAGATGGCGTGACGGTAG

TCACAGCAGAAGTGGAGGGGCAACGGCAAAGTGTTGATACCCACTTTGTTAAGGGTACTATCGCGGCGGATAAAT

CCACTCTGGCTGCGGTACCGACATCTATCATCGCTGATGGTCTAATGGCTTCAACCATCACGTTGGAGTTGAAGG

ATACCTATGGGACCCGCAGGCTGGCGCGAATGTGGCTTTTGACACAACCTTAGGCAATATGGGCGTTATCACGG

ATCACAATGACGGCACTTATAGCGCACCATTGACCAGTACCACGTTGGGGGTAGCAACAGTAACGGTGAAAGTGG

ATGGGCTGCGTTCAGTGTGCCGAGTGTGACGGTTAATTTCACGGCAGATCCTATTCCAGATGCTGGCCGCTCCA

GTTTCACCGTCTCCACACCGGATATCTTGGCTGATGGCACGATGAGTTCCACATTATCCTTTGTCCCTGTCGATA

AGAATGGCCATTTTATCAGTGGGATGCAGGGCTTGAGTTTTACTCAAAACGGTGTGCCGGTGAGTATTAGCCCCA

TTACCGAGCAGCCAGATAGCTATACCGCGACGGTGGTTGGGAATAGTGTCGGTGATGTCACAATCACGCCGCAGG

TTGATACCCTGATACTGAGTACATTGCAGAAAAAAATATCCCTATTCCCGGTACCTACGCTGACCGGTATTCTGG

TTAACGGGCAAAATTTCGCTACGGATAAAGGGTTCCCGAAAACGATCTTTAAAAACGCCACATTCCAGTTACAGA

TGGATAACGATGTTGCTAATAATACTCAGTATGAGTGGTCGTCGTCATTCACACCCAATGTATCGGTTAACGATC

AGGGTCAGGTGACGATTACCTACCAAACCTATAGCGAAGTGGCTGTGACGGCGAAAAGTAAAAAATTCCCAAGTT

ATTCGGTGAGTTATCGGTTCTACCCAAATCGGTGGATATACGATGGCGGCAGATCGCTGGTATCCAGTCTCGAGG

CCAGCAGACAATGCCAAGGTTCAGATATGTCTGCGGTTCTTGAATCCTCACGTGCAACCAACGGAACGCGTGCGC

CTGACGGGACATTGTGGGGCGAGTGGGGAGCTTGACCGCGTATAGTTCTGATTGGCAATCTGGTGAATATTGGG

TCAAAAAGACCAGCACGGATTTTGAAACCATGAATATGGACACAGGCGCACTGCAACCAGGGCCTGCATACTTGG

CGTTCCCGCTCTGTGCGCTGTCAATATAACCAGATAACAGATAGCAATAAGAACAGTTTAATGAGCTGATTATTT

GGGGCGCGAATGGGAGTCCGGCAATCCTAGACTCGCCCCATAAGTAGCAAACGTCCAGAAGAACAACGCCGCTCA

GGTTAATTGAGCGGCGCTGTTTTTTAAAAGGATTGTCGCGATTAAATGCCGATCTTACGGCCCAGCTGCAGCCC

GGGGGATCTATGCGGTGTGAAATACCGCACAGATGCGTAAGGAGAAAATACCGCATCAGGCGCCATTCGCCATTC

AGGCTGCGCAACTGTTGGGAAGGGCGATCGGTGCGGGCCTCTTCGCTATTACGCCAGGACTTCATATACCCAAGC

TTGGAAAATTTTTTTTAAAAAAGTCTTGACACTTTATGCTTCCGGCTCGTATAATGGATCCAGGAGTAACAATAC

-continued

AAATGGATTCAAGAGATCCATTTGTATTGTTACTCCTTTTTTTTTTGTCGACGATCCTTAGCGAAAGCTAAGGA

TTTTTTTTTTACTCGAGCGGATTACTACATACCTGCATTAATGAATCGGCCAACGCGCGGGGAGAGGCGGTTTGC

GTATTGGGCGCTCTTCCGCTTCCTCGCTCACTGACTCGCTGCGCTCGGTCGTTCGGCTGCGGCGAGCGGTATCAG

CTCACTCAAAGGCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTCCCTTCGGGAAGCG

TGGCGCTTTCTCATAGCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTCTGCTGAAGCCAGTTACCT

TCGGAAAAAGAGTTGGTAGCTCTTGATCCGGCAAACAAACCACCGCTGGTAGCGGTGGTTTTTTGTTTGCAAGC

AGCAGATTACGCGCAGAAAAAAAGGATCTCAAGAAGATCCTTTGATCTTTTCTACGGGGTCTGACGCTCAGTGGA

ACGAAAACTCACGTTAAGGGATTTTGGTCATGATCTGGTAAGGTTGGGAAGCCCTGCAAAGTAAACTGGATGGCT

TTCTTGCCGCCAAGGATCTGATGGCGCAGGGGATCAAGATCTGATCAAGAGACAGGATGAGGATCGTTTCGCATG

ATTGAACAAGATGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTTTTGTCAAGACC

GACCTGTCCGGTGCCCTGAATGAACTGCAGGACGAGGCAGCGCGGCTATCGTGGCTGGCCACGACGGGCGTTCCT

TGCGCAGCTGTGCTCGACGTTGTCACTGAAGCGGGAAGGGACTGGCTGCTATTGGGCGAAGTGCCGGGGCAGGAT

CTCCTGTCATCTCACCTTGCTCCTGCCGAGAAAGTATCCATCATGGCTGATGCAATGCGGCGGCTGCATACGCTT

GATCCGGCTACCTGCCCATTCGACCACCAAGCGAAACATCGCATCGAGCGAGCACGTACTCGGATGGAAGCCGGT

CTTGTCGATCAGGATGATCTGGACGAAGAGCATCAGGGGCTCGCGCCAGCCGAACTGTTCGCCAGGCTCAAGGCG

CGCATGCCCGACGGCGAGGATCTCGTCGTGACCCATGGCGATGCCTGCTTGCCGAATATCATGGTGGAAAATGGC

CGCTTTTCTGGATTCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGCCGCTCCCGATTCG

CAGCGCATCGCCTTCTATCGCCTTCTTGACGAGTTCTTCTGAGCGGGACTCTGGGGTTCGAAATGACCGACCAAG

CGACGCCCAACCTGCCATCACGAGATTTCGATTCCACCGCCGCCTTCTATGAAATCATGACATTAACCTATAAAA

ATAGGCGTATCACGAGGCCCTTTCGTC pMBV44

(SEQ ID NO: 561)

TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATCGACGGTATCGATAAGCTTGATAAGCTTTTAAATCAGC

AGGGGTCTTTTTGGCTTGTGTATTATTTTGAAGTTTTTCTTCCCCGACAGAATCTGCTTTTACCGTCATAGTGAA

ATGAGCCTGAAAAGCTATTACCATGATGATACAAATAAGTTTACTTTTCATTTCACCGCTCCTTTTTAATTCGTA

AAACTAAGTTTAAGCCACCTACAACTAATCTGACAGAGAGAGTTAAGGACACGTTTTTTAGTATATGTGGGAACT

AAATTATACGTTTTGCAGTAGAAACTATAGGTGGCTTAAACTTTGGGATATGCTTATATTATATGGATAAACAGT

CAGATATTCTTTTACATTTGTTAATTCTTCTAAAAAAATTAAAAAATAAGCCTGTTTCTACATTCTTCACAAAAT

AATTTACGAAGAGTGCAAAACAAGCTTATTTTTTCGTGTGTGTTAAGCGGTTTTATTCTTAATTTTTTATTACTT

TTACAATTATTCGATTGGATTATCTACTTTATTACTATATTTCGGATAAAGCGTGGTGCCCCAGATGGAGATATT

TCTATTTTTCACAAGTGGTAAGTTCCGGTCATCAATTACCGTTCTCCACCATTCCCAAGCTAAACCAGTGCATTC

TTTAGCGTAAACATTAATATTTCTCGCGTTACCTGGCAAATAGATGGACGATGTGAAATGAGCTAGCTTGCTTTT

-continued

```
ATTGTTTTCGCTCCAGTTTTTATGTTGAACAATTTCGTTACCTTCAGGATCATAATTTACTTCATCCCAAGAAAT
GTTGAATTGAGCAACGTATCCTCCAGAGTGATCGATGTTAATTTTTCCATCTGTATAAGCTTTTGAAGTTGTTTC
AATATATTCTGAGTTGTTTTTAATAACAGCTAATTCATTGTCTTTTAGGAAGTTTGTTGTATAAGCAATGGGAAC
TCCTGGTGTTTCTCGATTAAAAGTAGCGCCTTTTTTCAAAATATCGCGTAAGTCTCCGAGGTTGCCGTCGATGAT
TTGAACTTCATCTTTTGCGGAACCTCCGTAAATTACGGCTTTGAAGGAAGAATTTTTGATGATATTTGTTAGTTC
TACATCACCTGAGACAGATTTTCCGCTTACGGCAGCATCAAAAGCAGCTTTTACTTTAGTACTATGGGAATTAGT
TGATAATTTCAAATAAACTTGACGGCCATACGCCACACTTGAGATATATGCAGGAGGATTTTCTGCATTCACTCC
AAGCGCTTGCAACTGCTCTTTAGTAACAGCTTTGCCGAAAAATCTGGAAGGTCTTGTAGGTTCATTAACATTCAC
GTTATAGTAAATTTGTTTAAAACTAATGACTTCTTCTTGCATTTTCCCTTCACTGATTGCGCCGAAGTTTACATT
CAAGCTATTATTTACAGCTTTAAATGCTGTACCAAATTTCGCAATTAATTGTGATTCACTGTAAGCCATTTCGTC
ATCATAATCAATTTTTGCACTTACATTTGGATAAGCTTGAGCATATTTTCATTCCATCTTTCCACTAATGTATT
TACTGCGTTGTTAACGTTTGATTTAGTGGCATTTTTTACAACGATTTTATTGTCTTGATTAGTCATACCTGGCAA
ATCAATGCTGAGTGTTAATGAATCACGTTTTACAGGGAGAACATCTGGTTGATTTTCTACTAATTCCGAATTCGC
TTTTACGAGAGCACCTGGATAGGTTAGGCTCGAAATTGCATTCACAACTTGAATGTCTGCATTATTTTGATTGAT
GGATTTCTTCTTTTTCTCCACAACAATATATTCATTTCCATCTTTGTAACCTTTTCTTGGCGGCACATTTGTCAC
TGCATCTCCGTGGTATACTAATACATTGTTTTTATTGTAATCCAATCCTTGTATATACTTATCGATTTCATCCGC
GTGTTTCTTTTCGATTGGCGTCTTAGGACTTGCAGGCGGAGATGCTGGTGGTGCCATGGATGAAATTGAATTTTC
TTTATTGAATGCAGATGCATCCTTTGCTTCAGTTTGTTGCGCAATTGGTAGACTAACTAATATAAGTGTAATAAA
AACTAGCATTATTTTTTCATGGGTTTCACTCTCCTTCTACATTTTTTAACCTAATAATGCCAAATACCGTTTGC
CACCCCTCTCTTTTGATAATTATAATATTGGCGAAATTCGCTTCTAAAGATGAAACGCAATATTATATGCTTGCT
TTATAGCTTTATTCTAGTCCTGCTGTCCCTTTATCGTCGTTAACAAATGTTAATGCCTCAACATAAAAGTCACTT
TAAGATAGGAATATACTAATCAAAGGAGGGATCGAATTCCTGCAGTCATCAAGGCAACCATCAGGATTAATGCGG
ATATTGCGGAGTAACACTTCAGACTGAAAGTAGAAATAAAAACCGCAGCAGACAACTGACAACATCAAATGAAGG
GGGCTTATTCTAATTGATATTATTTATATGATAATAGTTCATTTTGTATTTTTGTTTTTTTGATATTCTCACCT
GCTTAGTTACAATAAATCAATTCTATCGCTGTATGGTATAGACTGTTTTATTATATATTTTGAATATTTTTAATC
TGCCCAGTCTGGTTTTTTAAAAAAGTGCTATCCTCTTAATGTCTTTACTAAATTAGAAAACAAGTTTCACTTTCA
ACTATTGCATCTTTAATTAATGGTCAAGGTGATTTCAAATGCTCGTTTGTGGCCAGTTATACCTCAAATAACTCA
AGTTGTTGAGCACAGCCAACGCACATGCAGTTTGACGTATGACAGGTATGCTTTATTTCATTTAAATTATGATGG
TTTTCCAGCCAATCAGTGAGTTTCTCTTGATAAGGAATGCGGGAATGTCTATGTATTTTAATAAAATAATTTCAT
TTAATATTATTTCACGAATAGTTATTTGTATCTTTTTGATATGTGGAATGTTCATGGCTGGGCTTCAGAAAAAT
ATGATGCTAACGCACCGCAACAGGTCCAGCCTTATTCTGTCTCTTCATCTGCATTTGAAAATCTCCATCCTAATA
ATGAAATGGAGAGTTCAATCAATCCCTTTTCCGCATCGGATACAGAAAGAAATGCTGCAATAATAGATCGCGCCA
ATAAGGAGCAGGAGACTGAAGCGGTGAATAAGATGATAAGCACCGGGGCCAGGTTAGCTGCATCAGGCAGGGCAT
CTGATGTTGCTCACTCAATGGTGGGCGATGCGGTTAATCAAGAAATCAAACAGTGGTTAAATCGATTCGGTACGG
CTCAAGTTAATCTGAATTTTGACAAAAATTTTTCGCTAAAAGAAAGCTCTCTTGATTGGCTGGCTCCTTGGTATG
ACTCTGCTTCATTCCTCTTTTTTAGTCAGTTAGGTATTCGCAATAAAGACAGCCGCAACACACTTAACCTTGGCG
TCGGGATACGTACATTGGAGAACGGTTGGCTGTACGGACTTAATACTTTTTATGATAATGATTTGACCGGCCACA
ACCACCGTATCGGTCTTGGTGCCGAGGCCTGGACCGATTATTTACAGTTGGCTGCCAATGGGTATTTTCGCCTCA
ATGGATGGCACTCGTCGCGTGATTTCTCCGACTATAAAGAGCGCCCAGCCACTGGGGGGATTTGCGCGCGAATG
CTTATTTACCTGCACTCCCACAACTGGGGGGGAAGTTGATGTATGAGCAATACACCGGTGAGCGTGTTGCTTTAT
```

-continued

```
TTGGTAAAGATAATCTGCAACGCAACCCTTATGCCGTGACTGCCGGGATCAATTACACCCCGTGCCTCTACTCA
CTGTCGGGGTAGATCAGCGTATGGGGAAAAGCAGTAAGCATGAAACACAGTGGAACCTCCAAATGAACTATCGCC
TGGGCGAGAGTTTTCAGTCGCAACTTAGCCCTTCAGCGGTGGCAGGAACACGTCTACTGGCGAGAGCCGCTATA
ACCTTGTCGATCGTAACAATAATATCGTGTTGGAGTATCAGAAACAGCAGGTGGTTAAACTGACATTATCGCCAG
CAACTATCTCCGGCCTGCCGGGTCAGGTTTATCAGGTGAACGCACAAGTACAAGGGGCATCTGCTGTAAGGGAAA
TTGTCTGGAGTGATGCCGAACTGATTGCCGCTGGCGGCACATTAACACCACTGAGTACCACACAATTCAACTTGG
TTTTACCGCCTTATAAACGCACAGCACAAGTGAGTCGGGTAACGGACGACCTGACAGCCAACTTTTATTCGCTTA
GTGCGCTCGCGGTTGATCACCAAGGAAACCGATCTAACTCATTCACATTGAGCGTCACCGTTCAGCAGCCTCAGT
TGACATTAACGGCGGCCGTCATTGGTGATGGCGCACCGGCTAATGGGAAACTGCAATCACCGTTGAGTTCACCG
TTGCTGATTTTGAGGGGAAACCCTTAGCCGGGCAGGAGGTGGTGATAACCACCAATAATGGTGCGCTACCGAATA
AAATCACGGAAAAGACAGATGCAAATGGCGTCGCGCGCATTGCATTAACCAATACGACAGATGGCGTGACGGTAG
TCACAGCAGAAGTGGAGGGGCAACGGCAAAGTGTTGATACCCACTTTGTTAAGGGTACTATCGCGGCGGATAAAT
CCACTCTGGCTGCGGTACCGACATCTATCATCGCTGATGGTCTAATGGCTTCAACCATCACGTTGGAGTTGAAGG
ATACCTATGGGGACCCGCAGGCTGGCGCGAATGTGGCTTTTGACACAACCTTAGGCAATATGGGCGTTATCACGG
ATCACAATGACGGCACTTATAGCGCACCATTGACCAGTACCACGTTGGGGGTAGCAACAGTAACGGTGAAAGTGG
ATGGGGCTGCGTTCAGTGTGCCGAGTGTGACGGTTAATTTCACGGCAGATCCTATTCCAGATGCTGGCCGCTCCA
GTTTCACCGTCTCCACACCGGATATCTTGGCTGATGGCACGATGAGTTCCACATTATCCTTTGTCCCTGTCGATA
AGAATGGCCATTTTATCAGTGGGATGCAGGGCTTGAGTTTTACTCAAAACGGTGTGCCGGTGAGTATTAGCCCCA
TTACCGAGCAGCCAGATAGCTATACCGCGACGGTGGTTGGGAATAGTGTCGGTGATGTCACAATCACGCCGCAGG
TTGATACCCTGATACTGAGTACATTGCAGAAAAAAATATCCCTATTCCCGGTACCTACGCTGACCGGTATTCTGG
TTAACGGGCAAAATTTCGCTACGGATAAAGGGTTCCCGAAAACGATCTTTAAAAACGCCACATTCCAGTTACAGA
TGGATAACGATGTTGCTAATAATACTCAGTATGAGTGGTCGTCGTCATTCACACCCAATGTATCGGTTAACGATC
AGGGTCAGGTGACGATTACCTACCAAACCTATAGCGAAGTGGCTGTGACGGCGAAAAGTAAAAAATTCCCAAGTT
ATTCGGTGAGTTATCGGTTCTACCCAAATCGGTGGATATACGATGGCGGCAGATCGCTGGTATCCAGTCTCGAGG
CCAGCAGACAATGCCAAGGTTCAGATATGTCTGCGGTTCTTGAATCCTCACGTGCAACCAACGGAACGCGTGCGC
CTGACGGGACATTGTGGGGCGAGTGGGGGAGCTTGACCGCGTATAGTTCTGATTGGCAATCTGGTGAATATTGGG
TCAAAAAGACCAGCACGGATTTTGAAACCATGAATATGGACACAGGCGCACTGCAACCAGGGCCTGCATACTTGG
CGTTCCCGCTCTGTGCGCTGTCAATATAACCAGATAACAGATAGCAATAAGAACAGTTTAATGAGCTGATTATTT
GGGGCGCGAATGGGAGTCCGGCAATCCTAGACTCGCCCCATAAGTAGCAAACGTCCAGAAGAACAACGCCGCTCA
GGTTAATTGAGCGGCGCTGTTTTTTAAAAGGATTGTCGCGATTAAATGCCGATCTTACGGCCCAGCTGCAGCCC
GGGGGATCTATGCGGTGTGAAATACCGCACAGATGCGTAAGGAGAAAATACCGCATCAGGCGCCATTCGCCATTC
AGGCTGCGCAACTGTTGGGAAGGGCGATCGGTGCGGGCCTCTTCGCTATTACGCCAGGACTTCATATACCCAAGC
TTGGAAAATTTTTTTAAAAAAGTCTTGACACTTTATGCTTCCGGCTCGTATAATGGATCCAGGAGTAACAATAC
AAATGGATTCAAGAGATCCATTTGTATTGTTACTCCTTTTTTTTTTGTCGACGATCCTTAGCGAAAGCTAAGGA
TTTTTTTTTTACTCGAGCGGATTACTACATACCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCCAAGCTGGGCTGTGTGC
```

-continued

```
ACGAACCCCCCGTTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTCTGCTGAAGCCAGTTACCT

TCGGAAAAAGAGTTGGTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGTCTGACGCTCAGTGGA

ACGAAAACTCACGTTAAGGGATTTTGGTCATGATTTCATAGAAGGCGGCGGTGGAATCGAAATCTCGTGATGGCA

GGTTGGGCGTCGCTTGGTCGGTCATTTCGAACCCCAGAGTCCCGCTCAGAAGAACTCGTCAAGAAGGCGATAGAA

GGCGATGCGCTGCGAATCGGGAGCGGCGATACCGTAAAGCACGAGGAAGCGGTCAGCCCATTCGCCGCCAAGCTC

TTCAGCAATATCACGGGTAGCCAACGCTATGTCCTGATAGCGGTCCGCCACACCCAGCCGGCCACAGTCGATGAA

TCCAGAAAAGCGGCCATTTTCCACCATGATATTCGGCAAGCAGGCATCGCCATGGGTCACGACGAGATCCTCGCC

GTCGGGCATGCGCGCCTTGAGCCTGGCGAACAGTTCGGCTGGCGCGAGCCCCTGATGCTCTTCGTCCAGATCATC

CTGATCGACAAGACCGGCTTCCATCCGAGTACGTGCTCGCTCGATGCGATGTTTCGCTTGGTGGTCGAATGGGCA

GGTAGCCGGATCAAGCGTATGCAGCCGCCGCATTGCATCAGCCATGATGGATACTTTCTCGGCAGGAGCAAGGTG

AGATGACAGGAGATCCTGCCCCGGCACTTCGCCCAATAGCAGCCAGTCCCTTCCCGCTTCAGTGACAACGTCGAG

CACAGCTGCGCAAGGAACGCCCGTCGTGGCCAGCCACGATAGCCGCGCTGCCTCGTCCTGCAGTTCATTCAGGGC

ACCGGACAGGTCGGTCTTGACAAAAAGAACCGGGCGCCCCTGCGCTGACAGCCGGAACACGGCGGCATCAGAGCA

GCCGATTGTCTGTTGTGCCCAGTCATAGCCGAATAGCCTCTCCACCCAAGCGGCCGGAGAACCTGCGTGCAATCC

ATCTTGTTCAATCATGCGAAACGATCCTCATCCTGTCTCTTGATCAGATCTTGATCCCCTGCGCCATCAGATCCT

TGGCGGCAAGAAAGCCATCCAGTTTACTTTGCAGGGCTTCCCAACCTTACCAGATCATGACATTAACCTATAAAA

ATAGGCGTATCACGAGGCCCTTTCGTC
```

Example 23

Construction of pNJSZc Plasmid pNJSZ is a 10.4 kb plasmid that confers the abilities required to induce tkRNAi. It contains two genes, inv and hly, that allows bacteria to invade mammalian cells and to escape from the entry vacuole. Expression of the short hairpin RNA is different between the original Trip plasmid and pNJSZ. In pNJSZ, expression of shRNA is under the control of a constitutive bacterial promoter which allows for continuous expression. This is different from the original Trip plasmid, which has an ITPG inducible promoter, which controls the expression of the shRNA. Moreover, pNJSZ and the original Trip plasmid contain different antibiotic resistant genes. pNJSZ has the kanamycin resistance gene, whereas the original Trip plasmid has the ampicillin resistance gene. pNJSZc was constructed from pNJSZ by removing any regions of pNJSZ that were not required for its maintenance or abilities to induce tkRNAi.

Figure 28:
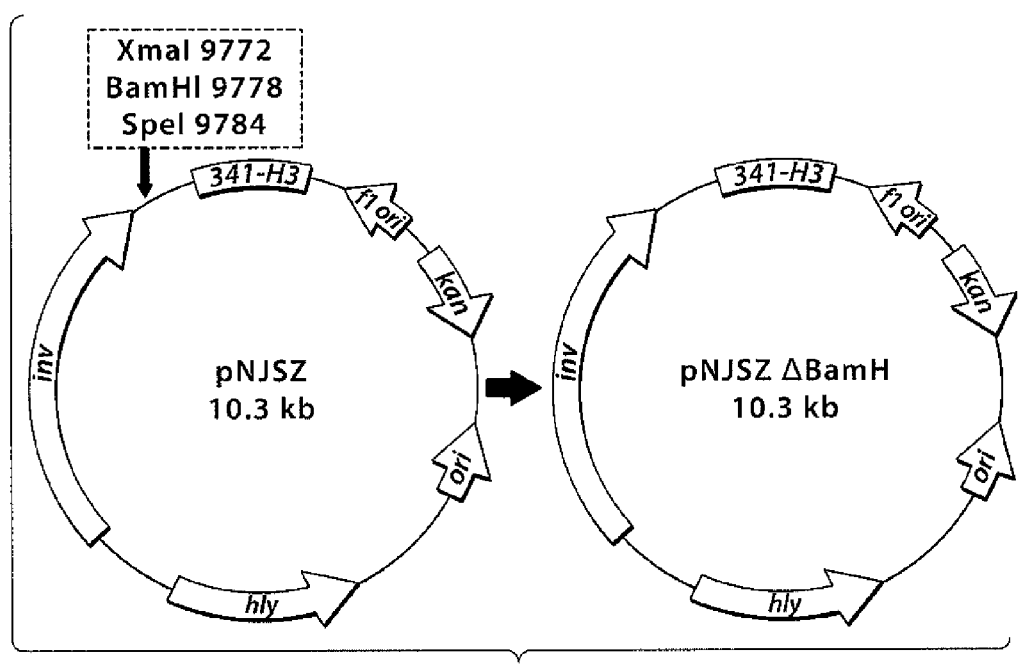
FIG. 28 is a schematic of the pNJSZ ΔBamH1 plasmid.

Step 1 as shown in FIG. 28: Removed an extra BamH1 site at 9778 by digesting pNJSZ with both SpeI (9784) and XmaI (9772), T4 DNA polymerase filled-in these two sites and then allowed the plasmid to self ligate, creating pNJSZ ΔBamH1.

Figure 29:
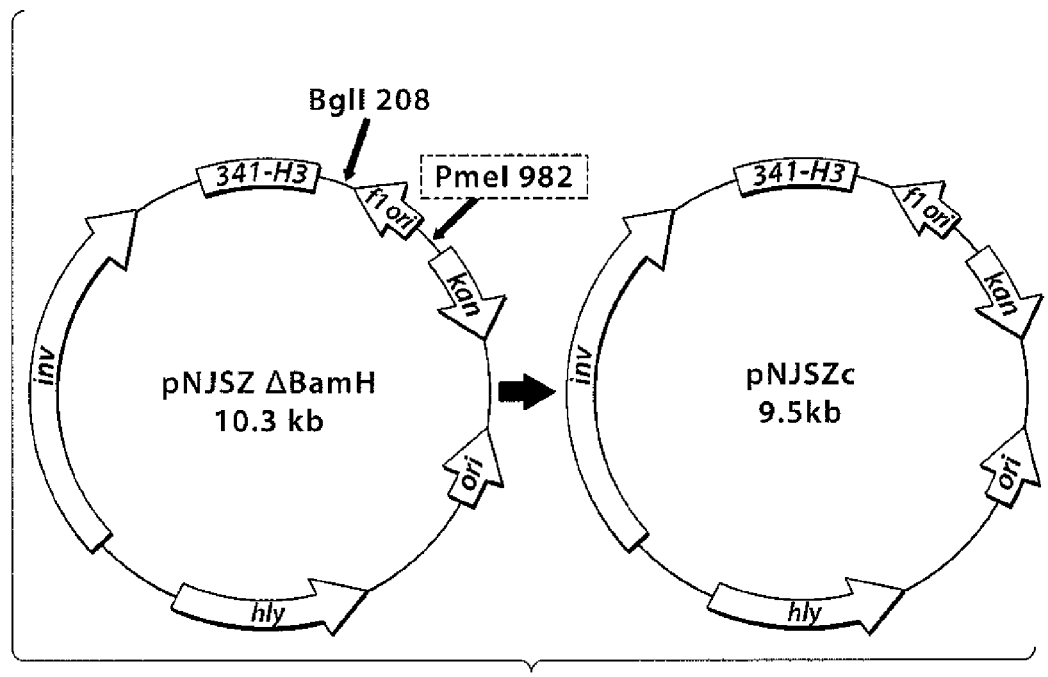
FIG. 29 is a schematic of the pNJSZ pNJSZc plasmid.

Step 2 as shown in FIG. 29: Removed both an extra SalI site at 972 and the f1 origin of replication by digesting pNJSZ ΔBamH1 with BglI (208) and PmeI (982), T4 DNA polymerase filled-in these two sites and allowed the plasmid to self ligate, creating pNJSZc.

The pNJSZc DNA sequence is as follows:

(SEQ ID NO: 562)
```
GGCCGCTCGAGCATGCATCTAGAGGGCCCAATTCGCCCTATAGTGAGTCGTATTACAATTCACTGGCCGTCGTTT

TACAACGTCGTGACTGGGAAAACCCTGGCGTTACCCAACTTAATCGCCTTGCAGCACATCCCCCTTTCGCCAGCT

GGCGTAATAGCGAAGAGGCCCGCACCGATCGCCCTTCCCAACAGTTGCGCAGCCTGAAAAACCGCGCCATGGTGT

GTAGGCTGGAGCTGCTTCGAAGTTCCTATACTTTCTAGAGAATAGGAACTTCGGAATAGGAACTTCAAGATCCCC

CACGCTGCCGCAAGCACTCAGGGCGCAAGGGCTGCTAAAGGAAACGGAACACGTAGAAAGCCAGTCCGCAGAAAC

GGTGCTGACCCCGGATGAATGTCAGCTACTGGGCTATCTGGACAAGGGAAAACGCAAGCGCAAAGAGAAAGCAGG

TAGCTTGCAGTGGGCTTACATGGCGATAGCTAGACTGGGCGGTTTTATGGACAGCAAGCGAACCGGAATTGCCAG

CTGGGGCGCCCTCTGGTAAGGTTGGGAAGCCCTGCAAAGTAAACTGGATGGCTTTCTTGCCGCCAAGGATCTGAT

GGCGCAGGGGATCAAGATCTGATCAAGAGACAGGATGAGGATCGTTTCGCATGATTGAACAAGATGGATTGCACG
```

-continued

```
CAGGTTCTCCGGCCGCTTGGGTGGAGAGGCTATTCGGCTATGACTGGGCACAACAGACAATCGGCTGCTCTGATG

CCGCCGTGTTCCGGCTGTCAGCGCAGGGGCGCCCGGTTCTTTTTGTCAAGACCGACCTGTCCGGTGCCCTGAATG

AACTGCAGGACGAGGCAGCGCGGCTATCGTGGCTGGCCACGACGGGCGTTCCTTGCGCAGCTGTGCTCGACGTTG

TCACTGAAGCGGGAAGGGACTGGCTGCTATTGGGCGAAGTGCCGGGGCAGGATCTCCTGTCATCTCACCTTGCTC

CTGCCGAGAAAGTATCCATCATGGCTGATGCAATGCGGCGGCTGCATACGCTTGATCCGGCTACCTGCCCATTCG

ACCACCAAGCGAAACATCGCATCGAGCGAGCACGTACTCGGATGGAAGCCGGTCTTGTCGATCAGGATGATCTGG

ACGAAGAGCATCAGGGGCTCGCGCCAGCCGAACTGTTCGCCAGGCTCAAGGCGCGCATGCCCGACGGCGAGGATC

TCGTCGTGACCCATGGCGATGCCTGCTTGCCGAATATCATGGTGGAAAATGGCCGCTTTTCTGGATTCATCGACT

GTGGCCGGCTGGGTGTGGCGGACCGCTATCAGGACATAGCGTTGGCTACCCGTGATATTGCTGAAGAGCTTGGCG

GCGAGTGGGCTGACCGCTTCCTCGTGCTTTACGGTATCGCCGCTCCCGATTCGCAGCGCATCGCCTTCTATCGCC

TTCTTGACGAGTTCTTCTGAGCGGGACTCTGGGGTTCGAAATGACCGACCAAGCGACGCCCAACCTGCCATCACG

AGATTTCGATTCCACCGCCGCCTTCTATGAAAGGTTGGGCTTCGGAATCGTTTTCCGGGACGCCGGCTGGATGAT

CCTCCAGCGCGGGGATCTCATGCTGGAGTTCTTCGCCCACCCCAGCTTCAAAAGCGCTCTGAAGTTCCTATACTT

TCTAGAGAATAGGAACTTCGGAATAGGAACTAAGGAGGATATTCATATGGACCATGGCGCGGCATGCAAGCTCGG

TATCATTGCAGCACTGGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTAACTGTCAGACCAAGT

TTACTCATATATACTTTAGATTGATTTAAAACTTCATTTTTAATTTAAAAGGATCTAGGTGAAGATCCTTTTTGA

TAATCTCATGACCAAAATCCCTTAACGTGAGTTTTCGTTCCACTGAGCGTCAGACCCCGTAGAAAAGATCAAAGG

ATCTTCTTGAGATCCTTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGCGCAGATACCAAATAC

TGTTCTTCTAGTGTAGCCGTAGTTAGGCCACCACTTCAAGAACTCTGTAGCACCGCCTACATACCTCGCTCTGCT

AATCCTGTTACCAGTGGCTGCTGCCAGTGGCGATAAGTCGTGTCTTACCGGGTTGGACTCAAGACGATAGTTACC

GGATAAGGCGCAGCGGTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGAAACGCCTGGTATCTTTATAGTCCTGT

CGGGTTTCGCCACCTCTGACTTGAGCGTCGATTTTTGTGATGCTCGTCAGGGGGCGGAGCCTATGGAAAAACGC

CAGCAACGCGGCCTTTTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCGAACGACCGAGCGCAG

CGAGTCAGTGAGCGAGGAAGCGGAAGAGCGCCCAATACGCAAACCGCCTCTCCCCGCGCGTTGGCCGATTCATTA

ATGCAGCTGGCACGACAGTATCGATAAGCTTGATAAGCTTTTAAATCAGCAGGGGTCTTTTTGGCTTGTGTATTA

TTTTGAAGTTTTCTTCCCCGACAGAATCTGCTTTTACCGTCATAGTGAAATGAGCCTGAAAAGCTATTACCATG

ATGATACAAATAAGTTTACTTTTCATTTCACCGCTCCTTTTTAATTCGTAAAACTAAGTTTAAGCCACCTACAAC

TAATCTGACAGAGAGAGTTAAGGACACGTTTTTTAGTATATGTGGGAACTAAATTATACGTTTTGCAGTAGAAAC

TATAGGTGGCTTAAACTTTGGGATATGCTTATATTATATGGATAAACAGTCAGATATTCTTTTACATTTGTTAAT

TCTTCTAAAAAATTAAAAAATAAGCCTGTTTCTACATTCTTCACAAAATAATTTACGAAGAGTGCAAAACAAGC

TTATTTTTTCGTGTGTGTTAAGCGGTTTTATTCTTAATTTTTTATTACTTTTACAATTATTCGATTGGATTATCT

ACTTTATTACTATATTTCGGATAAAGCGTGGTGCCCCAGATGGAGATATTTCTATTTTTCACAAGTGGTAAGTTC

CGGTCATCAATTACCGTTCTCCACCATTCCCAAGCTAAACCAGTGCATTCTTTAGCGTAAACATTAATATTTCTC

GCGTTACCTGGCAAATAGATGGACGATGTGAAATGAGCTAGCTTGCTTTTATTGTTTTCGCTCCAGTTTTTATGT

TGAACAATTTCGTTACCTTCAGGATCATAATTTACTTCATCCCAAGAAATGTTGAATTGAGCAACGTATCCTCCA
```

-continued

```
GAGTGATCGATGTTAATTTTTCCATCTGTATAAGCTTTTGAAGTGTGTTTCAATATATTCTGAGTTGTTTTTAATA
ACAGCTAATTCATTGTCTTTTAGGAAGTTTGTTGTATAAGCAATGGGAACTCCTGGTGTTTCTCGATTAAAAGTA
GCGCCTTTTTTCAAAATATCGCGTAAGTCTCCGAGGTTGCCGTCGATGATTTGAACTTCATCTTTTGCGGAACCT
CCGTAAATTACGGCTTTGAAGGAAGAATTTTTGATGATATTTGTTAGTTCTACATCACCTGAGACAGATTTTCCG
CTTACGGCAGCATCAAAAGCAGCTTTTACTTTAGTACTATGGGAATTAGTTGATAATTTCAAATAAACTTGACGG
CCATACGCCACACTTGAGATATATGCAGGAGGATTTTCTGCATTCACTCCAAGCGCTTGCAACTGCTCTTTAGTA
ACAGCTTTGCCGAAAAATCTGGAAGGTCTTGTAGGTTCATTAACATTCACGTTATAGTAAATTTGTTTAAAACTA
ATGACTTCTTCTTGCATTTTCCCTTCACTGATTGCGCCGAAGTTTACATTCAAGCTATTATTTACAGCTTTAAAT
GCTGTACCAAATTTCGCAATTAATTGTGATTCACTGTAAGCCATTTCGTCATCATAATCAATTTTTGCACTTACA
TTTGGATAAGCTTGAGCATATTTTTCATTCCATCTTTCCACTAATGTATTTACTGCGTTGTTAACGTTTGATTTA
GTGGCATTTTTTACAACGATTTTATTGTCTTGATTAGTCATACCTGGCAAATCAATGCTGAGTGTTAATGAATCA
CGTTTTACAGGGAGAACATCTGGTTGATTTTCTACTAATTCCGAATTCGCTTTTACGAGAGCACCTGGATAGGTT
AGGCTCGAAATTGCATTCACAACTTGAATGTCTGCATTATTTTGATTGATGGATTTCTTCTTTTTCTCCACAACA
ATATATTCATTTCCATCTTTGTAACCTTTTCTTGGCGGCACATTTGTCACTGCATCTCCGTGGTATACTAATACA
TTGTTTTTATTGTAATCCAATCCTTGTATATACTTATCGATTTCATCCGCGTGTTTCTTTTCGATTGGCGTCTTA
GGACTTGCAGGCGGAGATGCTGGTGGTGCCATGGATGAAATTGAATTTTCTTTATTGAATGCAGATGCATCCTTT
GCTTCAGTTTGTTGCGCAATTGGTAGACTAACTAATATAAGTGTAATAAAAACTAGCATTATTTTTTTCATGGGT
TTCACTCTCCTTCTACATTTTTTAACCTAATAATGCCAAATACCGTTTGCCACCCCTCTCTTTTGATAATTATAA
TATTGGCGAAATTCGCTTCTAAAGATGAAACGCAATATTATATGCTTGCTTTATAGCTTTATTCTAGTCCTGCTG
TCCCTTTATCGTCGTTAACAAATGTTAATGCCTCAACATAAAAGTCACTTTAAGATAGGAATATACTAATCAAAG
GAGGGATCGAATTCCTGCAGTCATCAAGGCAACCATCAGGATTAATGCGGATATTGCGGAGTAACACTTCAGACT
GAAAGTAGAAATAAAAACCGCAGCAGACAACTGACAACATCAAATGAAGGGGCTTATTCTAATTGATATTATTT
ATATGATAATAGTTCATTTTGTATTTTGTTTTTTTGATATTCTCACCTGCTTAGTTACAATAAATCAATTCTATC
GCTGTATGGTATAGACTGTTTTATTATATATTTTGAATATTTTTAATCTGCCCAGTCTGGTTTTTTAAAAAAGTG
CTATCCTCTTAATGTCTTTACTAAATTAGAAAACAAGTTTCACTTTCAACTATTGCATCTTTAATTAATGGTCAA
GGTGATTTCAAATGCTCGTTTGTGGCCAGTTATACCTCAAATAACTCAAGTTGTTGAGCACAGCCAACGCACATG
CAGTTTGACGTATGACAGGTATGCTTTATTTCATTTAAATTATGATGGTTTTCCAGCCAATCAGTGAGTTTCTCT
TGATAAGGAATGCGGGAATGTCTATGTATTTTAATAAAATAATTTCATTTAATATTATTTCACGAATAGTTATTT
GTATCTTTTTGATATGTGGAATGTTCATGGCTGGGGCTTCAGAAAAATATGATGCTAACGCACCGCAACAGGTCC
AGCCTTATTCTGTCTCTTCATCTGCATTTGAAAATCTCCATCCTAATAATGAAATGGAGAGTTCAATCAATCCCT
TTTCCGCATCGGATACAGAAAGAAATGCTGCAATAATAGATCGCGCCAATAAGGAGCAGGAGACTGAAGCGGTGA
ATAAGATGATAAGCACCGGGCCAGGTTAGCTGCATCAGGCAGGGCATCTGATGTTGCTCACTCAATGGTGGGCG
ATGCGGTTAATCAAGAAATCAAACAGTGGTTAAATCGATTCGGTACGGCTCAAGTTAATCTGAATTTTGACAAAA
ATTTTTCGCTAAAAGAAAGCTCTCTTGATTGGCTGGCTCCTTGGTATGACTCTGCTTCATTCCTCTTTTTTAGTC
AGTTAGGTATTCGCAATAAAGACAGCCGCAACACACTTAACCTTGGCGTCGGGATACGTACATTGGAGAACGGTT
GGCTGTACGGACTTAATACTTTTTATGATAATGATTTGACCGGCCACAACCACCGTATCGGTCTTGGTGCCGAGG
CCTGGACCGATTATTTACAGTTGGCTGCCAATGGGTATTTTCGCCTCAATGGATGGCACTCGTCGCGTGATTTCT
CCGACTATAAAGAGCGCCCAGCCACTGGGGGGATTTGCGCGCGAATGCTTATTTACCTGCACTCCCACAACTGG
GGGGGAAGTTGATGTATGAGCAATACACCGGTGAGCGTGTTGCTTTATTTGGTAAAGATAATCTGCAACGCAACC
CTTATGCCGTGACTGCCGGGATCAATTACACCCCCGTGCCTCTACTCACTGTCGGGGTAGATCAGCGTATGGGA
AAAGCAGTAAGCATGAAACACAGTGGAACCTCCAAATGAACTATCGCCTGGGCGAGAGTTTTCAGTCGCAACTTA
```

-continued

```
GCCCTTCAGCGGTGGCAGGAACACGTCTACTGGCGGAGAGCCGCTATAACCTTGTCGATCGTAACAATAATATCG

TGTTGGAGTATCAGAAACAGCAGGTGGTTAAACTGACATTATCGCCAGCAACTATCTCCGGCCTGCCGGGTCAGG

TTTATCAGGTGAACGCACAAGTACAAGGGGCATCTGCTGTAAGGGAAATTGTCTGGAGTGATGCCGAACTGATTG

CCGCTGGCGGCACATTAACACCACTGAGTACCACACAATTCAACTTGGTTTTACCGCCTTATAAACGCACAGCAC

AAGTGAGTCGGGTAACGGACGACCTGACAGCCAACTTTTATTCGCTTAGTGCGCTCGCGGTTGATCACCAAGGAA

ACCGATCTAACTCATTCACATTGAGCGTCACCGTTCAGCAGCCTCAGTTGACATTAACGGCGGCCGTCATTGGTG

ATGGCGCACCGGCTAATGGGAAAACTGCAATCACCGTTGAGTTCACCGTTGCTGATTTTGAGGGGAAACCCTTAG

CCGGGCAGGAGGTGGTGATAACCACCAATAATGGTGCGCTACCGAATAAAATCACGGAAAAGACAGATGCAAATG

GCGTCGCGCGCATTGCATTAACCAATACGACAGATGGCGTGACGGTAGTCACAGCAGAAGTGGAGGGGCAACGGC

AAAGTGTTGATACCCACTTTGTTAAGGGTACTATCGCGGCGGATAAATCCACTCTGGCTGCGGTACCGACATCTA

TCATCGCTGATGGTCTAATGGCTTCAACCATCACGTTGGAGTTGAAGGATACCTATGGGACCCGCAGGCTGGCG

CGAATGTGGCTTTTGACACAACCTTAGGCAATATGGGCGTTATCACGGATCACAATGACGGCACTTATAGCGCAC

CATTGACCAGTACCACGTTGGGGGTAGCAACAGTAACGGTGAAAGTGGATGGGGCTGCGTTCAGTGTGCCGAGTG

TGACGGTTAATTTCACGGCAGATCCTATTCCAGATGCTGGCCGCTCCAGTTTCACCGTCTCCACACCGGATATCT

TGGCTGATGGCACGATGAGTTCCACATTATCCTTTGTCCCTGTCGATAAGAATGGCCATTTTATCAGTGGGATGC

AGGGCTTGAGTTTTACTCAAAACGGTGTGCCGGTGAGTATTAGCCCCATTACCGAGCAGCCAGATAGCTATACCG

CGACGGTGGTTGGGAATAGTGTCGGTGATGTCACAATCACGCCGCAGGTTGATACCCTGATACTGAGTACATTGC

AGAAAAAAATATCCCTATTCCCGGTACCTACGCTGACCGGTATTCTGGTTAACGGGCAAAATTTCGCTACGGATA

AAGGGTTCCCGAAAACGATCTTTAAAAACGCCACATTCCAGTTACAGATGGATAACGATGTTGCTAATAATACTC

AGTATGAGTGGTCGTCGTCATTCACACCCAATGTATCGGTTAACGATCAGGGTCAGGTGACGATTACCTACCAAA

CCTATAGCGAAGTGGCTGTGACGGCGAAAAGTAAAAAATTCCCAAGTTATTCGGTGAGTTATCGGTTCTACCCAA

ATCGGTGGATATACGATGGCGGCAGATCGCTGGTATCCAGTCTCGAGGCCAGCAGACAATGCCAAGGTTCAGATA

TGTCTGCGGTTCTTGAATCCTCACGTGCAACCAACGGAACGCGTGCGCCTGACGGGACATTGTGGGGCGAGTGGG

GGAGCTTGACCGCGTATAGTTCTGATTGGCAATCTGGTGAATATTGGGTCAAAAAGACCAGCACGGATTTTGAAA

CCATGAATATGGACACAGGCGCACTGCAACCAGGGCCTGCATACTTGGCGTTCCCGCTCTGTGCGCTGTCAATAT

AACCAGATAACAGATAGCAATAAGAACAGTTTAATGAGCTGATTATTTGGGGCGCGAATGGGAGTCCGGCAATCC

TAGACTCGCCCCATAAGTAGCAAACGTCCAGAGAACAACGCCGCTCAGGTTAATTGAGCGGCGTTGTTTTTTTAA

AAGGATTTGTCGCGATAAGCGTGAGCTGGCGTTAAATGCCGATCTTACGGCCCAGCTGCAGCCCGGCTAGTAACG

GCCGCCAGTGTGCTGGAATTCGCCCTTAATCGGCATCATTCACCAAGCTTGCCAGGCGACTGTCTTCAATATTAC

AGCCGCAACTACTGACATGGCGGGTGATGGTGTTCACTATTCCAGGGCGATCGGCACCCAACGCAGTGATCACCA

GATAATGTTGCGATGACAGTGTCAAACTGGTTATTCCTTCAAGGGGTGAGTTGTTCTTAAGCATGCCGGTTTGCT

GTAAAGTTTAGGGAGATTTGATGGCTTACTCTGTTCAAAAGTCGCGCCTGGCAAAGGTTGCGGGTGTTTCGCTTG

TTTTATTACTCGCTGCCTGTAGTTCTGACTCACGCTATAAGCGTCAGGTCAGTGGTGATGAAGCCTACCTGGAAG

CGCCATGGCATGCAAGGGCGAATTCTGCAGATATCCATCACACTGGCGGCCCTAGACCAGGCTTTACACTTTATG

CTTCCGGCTCGTATAATGTGTGGAAGGATCCAGGAGTAACAATACAAATGGATTCAAGAGATCCATTTGTATTGT

TACTCCTTTGTCGACTGGACAGTTCAAGAGACTGTCCATCAATATCAGCTTTGTCACAAACCCCGCCACCGGCGG

GGTTTTTTTCTGCTCTAGGGCCGCTCGAGCATGCATCTAGAGGGCCCAATTCGCCCTATAGTGAGTCGTATTACA

ATTCACTGGCCGTCGTTTTACAACGTCGTGACTGGGAAAACCCTGGCGTTACCCAACTTAATCGCCTTGCAGCAC

ATCCCCCTTTCGCCAGCTGGCGTAATAGCGAAGAGGCCCGCACCGATCGCCCTTCCCAACAGTTGCGCAGCCTGA

AAAACCGCGCCATGGTGTGTAGGCTGGAGCTGCTTCGAAGTTCCTATACTTTCTAGAGAATAGGAACTTCGGAAT
```

-continued
```
AGGAACTTCAAGATCCCCCACGCTGCCGCAAGCACTCAGGGCGCAAGGGCTGCTAAAGGAAACGGAACACGTAGA

AAGCCAGTCCGCAGAAACGGTGCTGACCCCGGATGAATGTCAGCTACTGGGCTATCTGGACAAGGGAAAACGCAA

GCGCAAAGAGAAAGCAGGTAGCTTGCAGTGGGCTTACATGGCGATAGCTAGACTGGGCGGTTTTATGGACAGCAA

GCGAACCGGAATTGCCAGCTGGGGCGCCCTCTGGTAAGGTTGGGAAGCCCTGCAAAGTAAACTGGATGGCTTTCT

TGCCGCCAAGGATCTGATGGCGCAGGGGATCAAGATCTGATCAAGAGACAGGATGAGGATCGTTTCGCATGATTG

AACAAGATGGATTGCACGCAGGTTCTCCGGCCGCTTGGGTGGAGAGGCTATTCGGCTATGACTGGGCACAACAGA

CAATCGGCTGCTCTGATGCCGCCGTGTTCCGGCTGTCAGCGCAGGGGCGCCCGGTTCTTTTGTCAAGACCGACC

TGTCCGGTGCCCTGAATGAACTGCAGGACGAGGCAGCGCGGCTATCGTGGCTGGCCACGACGGGCGTTCCTTGCG

CAGCTGTGCTCGACGTTGTCACTGAAGCGGGAAGGGACTGGCTGCTATTGGGCGAAGTGCCGGGGCAGGATCTCC

TGTCATCTCACCTTGCTCCTGCCGAGAAAGTATCCATCATGGCTGATGCAATGCGGCGGCTGCATACGCTTGATC

CGGCTACCTGCCCATTCGACCACCAAGCGAAACATCGCATCGAGCGAGCACGTACTCGGATGGAAGCCGGTCTTG

TCGATCAGGATGATCTGGACGAAGAGCATCAGGGGCTCGCGCCAGCCGAACTGTTCGCCAGGCTCAAGGCGCGCA

TGCCCGACGGCGAGGATCTCGTCGTGACCCATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGCTACCCGTGATA

TTGCTGAAGAGCTTGGCGGCGAGTGGGCTGACCGCTTCCTCGTGCTTTACGGTATCGCCGCTCCCGATTCGCAGC

GCATCGCCTTCTATCGCCTTCTTGACGAGTTCTTCTGAGCGGGACTCTGGGGTTCGAAATGACCGACCAAGCGAC

GCCCAACCTGCCATCACGAGATTTCGATTCCACCGCCGCCTTCTATGAAAGGTTGGGCTTCGGAATCGTTTTCCG

GGACGCCGGCTGGATGATCCTCCAGCGCGGGATCTCATGCTGGAGTTCTTCGCCCACCCCAGCTTCAAAAGCGC

TCTGAAGTTCCTATACTTTCTAGAGAATAGGAACTTCGGAATAGGAACTAAGGAGGATATTCATATGGACCATGG

CGCGGCATGCAAGCTCGGTATCATTGCAGCACTGGGGCCAGATGGTAAGCCCTCCCGTATCGTAGTTATCTACAC

GACGGGGAGTCAGGCAACTATGGATGAACGAAATAGACAGATCGCTGAGATAGGTGCCTCACTGATTAAGCATTG

GTAACTGTCAGACCAAGTTTACTCATATATACTTTAGATTGATTTAAAACTTCATTTTTAATTTAAAAGGATCTA

GGTGAAGATCCTTTTTGATAATCTCATGACCAAAATCCCTTAACGTGAGTTTTCGTTCCACTGAGCGTCAGACCC

CGTAGAAAAGATCAAAGGATCTTCTTGAGATCCTTTTTTTCTGCGCGTAATCTGCTGCTTGCAAACAAAAAAACC

ACCGCTACCAGCGGTGGTTTGTTTGCCGGATCAAGAGCTACCAACTCTTTTTCCGAAGGTAACTGGCTTCAGCAG

AGCGCAGATACCAAATACTGTTCTTCTAGTGTAGCCGTAGTTAGGCCACCACTTCAAGAACTCTGTAGCACCGCC

TACATACCTCGCTCTGCTAATCCTGTTACCAGTGGCTGCTGCCAGTGGCGATAAGTCGTGTCTTACCGGGTTGGA

CTCAAGACGATAGTTACCGGATAAGGCGCAGCGGTCGGGCTGAACGGGGGGTTCGTGCACACAGCCCAGCTTGGA

GCGAACGACCTACACCGAACTGAGATACCTACAGCGTGAGCTATGAGAAAGCGCCACGCTTCCCGAAGGGAGAAA

GGCGGACAGGTATCCGGTAAGCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGATGCTCGTCAGGGGGCG

GAGCCTATGGAAAAACGCCAGCAACGCGGCCTTTTTACGGTTCCTGGCCTTTTGCTGGCCTTTTGCTCACATGTT

CTTTCCTGCGTTATCCCCTGATTCTGTGGATAACCGTATTACCGCCTTTGAGTGAGCTGATACCGCTCGCCGCAG

CCGAACGACCGAGCGCAGCGAGTCAGTGAGCGAGGAAGCGGAAGAGCGCCCAATACGCAAACCGCCTCTCCCCGC

GCGTTGGCCGATTCATTAATGCAGCTGGCACGACAGTATCGATAAGCTTGATAAGCTTTAAATCAGCAGGGGTC

TTTTTGGCTTGTGTATTATTTTGAAGTTTTTCTTCCCCGACAGAATCTGCTTTTACCGTCATAGTGAAATGAGCC

TGAAAAGCTATTACCATGATGATACAAATAAGTTTACTTTTCATTTCACCGCTCCTTTTTAATTCGTAAAACTAA

GTTTAAGCCACCTACAACTAATCTGACAGAGAGAGTTAAGGACACGTTTTTTAGTATATGTGGGAACTAAATTAT

ACGTTTTGCAGTAGAAACTATAGGTGGCTTAAACTTTGGGATATGCTTATATTATATGGATAAACAGTCAGATAT

TCTTTTACATTTGTTAATTCTTCTAAAAAAATTAAAAAATAAGCCTGTTTCTACATTCTTCACAAAATAATTTAC

GAAGAGTGCAAAACAAGCTTATTTTTTCGTGTGTGTTAAGCGGTTTTATTCTTAATTTTTTATTACTTTTACAAT
```

-continued

```
TATTCGATTGGATTATCTACTTTATTACTATATTTCGGATAAAGCGTGGTGCCCCAGATGGAGATATTTCTATTT
TTCACAAGTGGTAAGTTCCGGTCATCAATTACCGTTCTCCACCATTCCCAAGCTAAACCAGTGCATTCTTTAGCG
TAAACATTAATATTTCTCGCGTTACCTGGCAAATAGATGGACGATGTGAAATGAGCTAGCTTGCTTTTATTGTTT
TCGCTCCAGTTTTTATGTTGAACAATTTCGTTACCTTCAGGATCATAATTTACTTCATCCCAAGAAATGTTGAAT
TGAGCAACGTATCCTCCAGAGTGATCGATGTTAATTTTTCCATCTGTATAAGCTTTTGAAGTTGTTTCAATATAT
TCTGAGTTGTTTTAATAACAGCTAATTCATTGTCTTTTAGGAAGTTTGTTGTATAAGCAATGGGAACTCCTGGT
GTTTCTCGATTAAAAGTAGCGCCTTTTTTCAAAATATCGCGTAAGTCTCCGAGGTTGCCGTCGATGATTTGAACT
TCATCTTTTGCGGAACCTCCGTAAATTACGGCTTTGAAGGAAGAATTTTTGATGATATTTGTTAGTTCTACATCA
CCTGAGACAGATTTTCCGCTTACGGCAGCATCAAAAGCAGCTTTTACTTTAGTACTATGGGAATTAGTTGATAAT
TTCAAATAAACTTGACGGCCATACGCCACACTTGAGATATATGCAGGAGGATTTTCTGCATTCACTCCAAGCGCT
TGCAACTGCTCTTTAGTAACAGCTTTGCCGAAAAATCTGGAAGGTCTTGTAGGTTCATTAACATTCACGTTATAG
TAAATTTGTTTAAAACTAATGACTTCTTCTTGCATTTTCCCTTCACTGATTGCGCCGAAGTTTACATTCAAGCTA
TTATTTACAGCTTTAAATGCTGTACCAAATTTCGCAATTAATTGTGATTCACTGTAAGCCATTTCGTCATCATAA
TCAATTTTTGCACTTACATTTGGATAAGCTTGAGCATATTTTTCATTCCATCTTTCCACTAATGTATTTACTGCG
TTGTTAACGTTTGATTTAGTGGCATTTTTTACAACGATTTTATTGTCTTGATTAGTCATACCTGGCAAATCAATG
CTGAGTGTTAATGAATCACGTTTTACAGGGAGAACATCTGGTTGATTTTCTACTAATTCCGAATTCGCTTTTACG
AGAGCACCTGGATAGGTTAGGCTCGAAATTGCATTCACAACTTGAATGTCTGCATTATTTTGATTGATGGATTTC
TTCTTTTCTCCACAACAATATATTCATTTCCATCTTTGTAACCTTTTCTTGGCGGCACATTTGTCACTGCATCT
CCGTGGTATACTAATACATTGTTTTTATTGTAATCCAATCCTTGTATATACTTATCGATTTCATCCGCGTGTTTC
TTTTCGATTGGCGTCTTAGGACTTGCAGGCGGAGATGCTGGTGGTGCCATGGATGAAATTGAATTTTCTTTATTG
AATGCAGATGCATCCTTTGCTTCAGTTTGTTGCGCAATTGGTAGACTAACTAATATAAGTGTAATAAAAACTAGC
ATTATTTTTTCATGGGTTTCACTCTCCTTCTACATTTTTTAACCTAATAATGCCAAATACCGTTTGCCACCCCT
CTCTTTTGATAATTATAATATTGGCGAAATTCGCTTCTAAAGATGAAACGCAATATTATATGCTTGCTTTATAGC
TTTATTCTAGTCCTGCTGTCCCTTTATCGTCGTTAACAAATGTTAATGCCTCAACATAAAAGTCACTTTAAGATA
GGAATATACTAATCAAAGGAGGGATCGAATTCCTGCAGTCATCAAGGCAACCATCAGGATTAATGCGGATATTGC
GGAGTAACACTTCAGACTGAAAGTAGAAATAAAAACCGCAGCAGACAACTGACAACATCAAATGAAGGGGCTTA
TTCTAATTGATATTATTTATATGATAATAGTTCATTTTGTATTTGTTTTTTGATATTCTCACCTGCTTAGTTA
CAATAAATCAATTCTATCGCTGTATGGTATAGACTGTTTTATTATATATTTTGAATATTTTTAATCTGCCCAGTC
TGGTTTTTTAAAAAAGTGCTATCCTCTTAATGTCTTTACTAAATTAGAAAACAAGTTTCACTTTCAACTATTGCA
TCTTTAATTAATGGTCAAGGTGATTTCAAATGCTCGTTTGTGGCCAGTTATACCTCAAATAACTCAAGTTGTTGA
GCACAGCCAACGCACATGCAGTTTGACGTATGACAGGTATGCTTTATTTCATTTAAATTATGATGGTTTTCCAGC
CAATCAGTGAGTTTCTCTTGATAAGGAATGCGGGAATGTCTATGTATTTAATAAAATAATTTCATTTAATATTA
TTTCACGAATAGTTATTTGTATCTTTTTGATATGTGGAATGTTCATGGCTGGGCTTCAGAAAAATATGATGCTA
ACGCACCGCAACAGGTCCAGCCTTATTCTGTCTCTTCATCTGCATTTGAAAATCTCCATCCTAATAATGAAATGG
AGAGTTCAATCAATCCCTTTTCCGCATCGGATACAGAAAGAAATGCTGCAATAATAGATCGCGCCAATAAGGAGC
AGGAGACTGAAGCGGTGAATAAGATGATAAGCACCGGGGCCAGGTTAGCTGCATCAGGCAGGGCATCTGATGTTG
CTCACTCAATGGTGGGCGATGCGGTTAATCAAGAAATCAAACAGTGGTTAAATCGATTCGGTACGGCTCAAGTTA
ATCTGAATTTTGACAAAAATTTTTCGCTAAAAGAAAGCTCTCTTGATTGGCTGGCTCCTTGGTATGACTCTGCTT
CATTCCTCTTTTTTAGTCAGTTAGGTATTCGCAATAAAGACAGCCGCAACACACTTAACCTTGGCGTCGGGATAC
GTACATTGGAGAACGGTTGGCTGTACGGACTTAATACTTTTTATGATAATGATTTGACCGGCCACAACCACCGTA
```

-continued

```
TCGGTCTTGGTGCCGAGGCCTGGACCGATTATTTACAGTTGGCTGCCAATGGGTATTTTCGCCTCAATGGATGGC
ACTCGTCGCGTGATTTCTCCGACTATAAAGAGCGCCCAGCCACTGGGGGGGATTTGCGCGCGAATGCTTATTTAC
CTGCACTCCCACAACTGGGGGGGAAGTTGATGTATGAGCAATACACCGGTGAGCGTGTTGCTTTATTTGGTAAAG
ATAATCTGCAACGCAACCCTTATGCCGTGACTGCCGGGATCAATTACACCCCCGTGCCTCTACTCACTGTCGGGG
TAGATCAGCGTATGGGGAAAAGCAGTAAGCATGAAACACAGTGGAACCTCCAAATGAACTATCGCCTGGGCGAGA
GTTTTCAGTCGCAACTTAGCCCTTCAGCGGTGGCAGGAACACGTCTACTGGCGGAGAGCCGCTATAACCTTGTCG
ATCGTAACAATAATATCGTGTTGGAGTATCAGAAACAGCAGGTGGTTAAACTGACATTATCGCCAGCAACTATCT
CCGGCCTGCCGGGTCAGGTTTATCAGGTGAACGCACAAGTACAAGGGGCATCTGCTGTAAGGGAAATTGTCTGGA
GTGATGCCGAACTGATTGCCGCTGGCGGCACATTAACACCACTGAGTACCACACAATTCAACTTGGTTTTACCGC
CTTATAAACGCACAGCACAAGTGAGTCGGGTAACGGACGACCTGACAGCCAACTTTTATTCGCTTAGTGCGCTCG
CGGTTGATCACCAAGGAAACCGATCTAACTCATTCACATTGAGCGTCACCGTTCAGCAGCCTCAGTTGACATTAA
CGGCGGCCGTCATTGGTGATGGCGCACCGGCTAATGGGAAAACTGCAATCACCGTTGAGTTCACCGTTGCTGATT
TTGAGGGGAAACCCTTAGCCGGGCAGGAGGTGGTGATAACCACCAATAATGGTGCGCTACCGAATAAAATCACGG
AAAAGACAGATGCAAATGGCGTCGCGCGCATTGCATTAACCAATACGACAGATGGCGTGACGGTAGTCACAGCAG
AAGTGGAGGGGCAACGGCAAAGTGTTGATACCCACTTTGTTAAGGGTACTATCGCGGCGGATAAATCCACTCTGG
CTGCGGTACCGACATCTATCATCGCTGATGGTCTAATGGCTTCAACCATCACGTTGGAGTTGAAGGATACCTATG
GGGACCCGCAGGCTGGCGCGAATGTGGCTTTTGACACAACCTTAGGCAATATGGGCGTTATCACGGATCACAATG
ACGGCACTTATAGCGCACCATTGACCAGTACCACGTTGGGGGTAGCAACAGTAACGGTGAAAGTGGATGGGGCTG
CGTTCAGTGTGCCGAGTGTGACGGTTAATTTCACGGCAGATCCTATTCCAGATGCTGGCCGCTCCAGTTTCACCG
TCTCCACACCGGATATCTTGGCTGATGGCACGATGAGTTCCACATTATCCTTTGTCCCTGTCGATAAGAATGGCC
ATTTTATCAGTGGGATGCAGGGCTTGAGTTTTACTCAAAACGGTGTGCCGGTGAGTATTAGCCCCATTACCGAGC
AGCCAGATAGCTATACCGCGACGGTGGTTGGGAATAGTGTCGGTGATGTCACAATCACGCCGCAGGTTGATACCC
TGATACTGAGTACATTGCAGAAAAAAATATCCCTATTCCCGGTACCTACGCTGACCGGTATTCTGGTTAACGGGC
AAAATTTCGCTACGGATAAAGGGTTCCCGAAAACGATCTTTAAAAACGCCACATTCCAGTTACAGATGGATAACG
ATGTTGCTAATAATACTCAGTATGAGTGGTCGTCGTCATTCACACCCAATGTATCGGTTAACGATCAGGGTCAGG
TGACGATTACCTACCAAACCTATAGCGAAGTGGCTGTGACGGCGAAAAGTAAAAAATTCCCAAGTTATTCGGTGA
GTTATCGGTTCTACCCAAATCGGTGGATATACGATGGCGGCAGATCGCTGGTATCCAGTCTCGAGGCCAGCAGAC
AATGCCAAGGTTCAGATATGTCTGCGGTTCTTGAATCCTCACGTGCAACCAACGGAACGCGTGCGCCTGACGGGA
CATTGTGGGGCGAGTGGGGAGCTTGACCGCGTATAGTTCTGATTGGCAATCTGGTGAATATTGGGTCAAAAGA
CCAGCACGGATTTTGAAACCATGAATATGGACACAGGCGCACTGCAACCAGGGCCTGCATACTTGGCGTTCCCGC
TCTGTGCGCTGTCAATATAACCAGATAACAGATAGCAATAAGAACAGTTTAATGAGCTGATTATTTGGGCGCGA
ATGGGAGTCCGGCAATCCTAGACTCGCCCCATAAGTAGCAAACGTCCAGAGAACAACGCCGCTCAGGTTAATTGA
GCGGCGTTGTTTTTTAAAAGGATTTGTCGCGATAAGCGTGAGCTGGCGTTAAATGCCGATCTTACGGCCCAGCT
GCAGCCCGGCTAGTAACGGCCGCCAGTGTGCTGGAATTCGCCCTTAATCGGCATCATTCACCAAGCTTGCCAGGC
GACTGTCTTCAATATTACAGCCGCAACTACTGACATGGCGGGTGATGGTGTTCACTATTCCAGGGCGATCGGCAC
CCAACGCAGTGATCACCAGATAATGTTGCGATGACAGTGTCAAACTGGTTATTCCTTCAAGGGGTGAGTTGTTCT
TAAGCATGCCGGTTTGCTGTAAAGTTTAGGGAGATTTGATGGCTTACTCTGTTCAAAAGTCGCGCCTGGCAAAGG
TTGCGGGTGTTTCGCTTGTTTTATTACTCGCTGCCTGTAGTTCTGACTCACGCTATAAGCGTCAGGTCAGTGGTG
ATGAAGCCTACCTGGAAGCGCCATGGCATGCAAGGGCGAATTCTGCAGATATCCATCACACTGGCGGCCCTAGAC
CAGGCTTTACACTTTATGCTTCCGGCTCGTATAATGTGTGGAAGGATCCAGGAGTAACAATACAAATGGATTCAA
```

GAGATCCATTTGTATTGTTACTCCTTTGTCGACTGGACAGTTCAAGAGACTGTCCATCAATATCAGCTTTGTCAC

AAACCCCGCCACCGGCGGGGTTTTTTTCTGCTCTAG

---

What is claimed is:

1. A plasmid comprising a prokaryotic promoter and one or more DNA molecules, wherein the prokaryotic promoter comprises the promoter sequence of SEQ ID NO: 378, and the one or more DNA molecules encode for one or more short hairpin RNAs (shRNAs).

2. The plasmid of claim 1 further comprising terminator sequences.

3. The plasmid of claim 1 further comprising a rrnC terminator.

4. The plasmid of claim 1 further comprising invasion factor sequences.

5. The plasmid of claim 1 further comprising an Inv gene.

6. The plasmid of claim 1 further comprising lysis regulation sequences.

7. The plasmid of claim 1 further comprising a HylA gene.

8. The plasmid of claim 1, wherein the target gene for the one or more shRNAs is selected from the group consisting of RAS, β-catenin, one or more HPV oncogenes, APC, HER-2, MDR-1, MRP-2, FATP4, SGLUT-1, GLUT-2, GLUT-5, APOBEC-1, MTP, IL-6, IL-6R, IL-7, IL-12, IL-13, IL-13 Ra-1, IL-18, p38/JNK MAP Kinase, p65/NF-κB, CCL20 (or MIP-3α), Claudin-2, Chitinase 3-like 1, APOA-IV, MHC class I and MHC class II.

9. The plasmid of claim 1, wherein the target sequence for the one or more shRNA's is selected from the group consisting of SEQ ID NOs: 52-377.

10. The plasmid of claim 1, wherein the nucleotide sequence of the plasmid is SEQ ID NO:560.

11. A bacterium comprising a plasmid comprising a prokaryotic promoter and one or more DNA molecules, wherein the prokaryotic promoter comprises the promoter sequence of SEQ ID NO: 378, and the one or more DNA molecules encode for one or more short hairpin RNAs (shRNAs).

12. The bacterium of claim 11, wherein the bacterium is a non-pathogenic or non-virulent bacterium.

13. The bacterium of claim 11, wherein the bacterium is an invasive bacterium.

14. The bacterium of claim 11, wherein the bacterium is attenuated.

15. The bacterium of claim 11, wherein the nucleotide sequence of the plasmid is SEQ ID NO:560.

16. The bacterium of claim 11, wherein the target gene for the one or more shRNAs is selected from the group consisting of RAS, β-catenin, one or more HPV oncogenes, APC, HER-2, MDR-1, MRP-2, FATP4, SGLUT-1, GLUT-2, GLUT-5, APOBEC-1, MTP, IL-6, IL-6R, IL-7, IL-12, IL-13, IL-13 Ra-1, IL-18, p38/JNK MAP Kinase, p65/NF-κB, CCL20 (or MIP-3α), Claudin-2, Chitinase 3-like 1, APOA-IV, MHC class I and MHC class II.

17. The bacterium of claim 11, wherein the target sequence for the one or more shRNA's is selected from the group consisting of SEQ ID NOs: 52-377.

18. A composition comprising the bacterium of claim 11 and a pharmaceutically acceptable carrier.

19. A eukaryotic cell comprising a plasmid comprising a prokaryotic promoter and one or more DNA molecules, wherein the prokaryotic promoter comprises the promoter sequence of SEQ ID NO: 378, and the one or more DNA molecules encode for one or more short hairpin RNAs (shRNAs).

20. The eukaryotic cell of claim 19, wherein the eukaryotic cell is an animal cell or plant cell.

21. The eukaryotic cell of claim 19, wherein the eukaryotic cell is a human cell.

22. The eukaryotic cell of claim 19, wherein the eukaryotic cell is selected from the group consisting of gastrointestinal epithelial cells, macrophages, cervical epithelial cells, rectal epithelial cells and pharyngeal epithelial cells.

23. The eukaryotic cell of claim 19, wherein the eukaryotic cell is selected from the group consisting of a cervical epithelial cell, a rectal epithelial cell, a macrophage, a skin cell, a melanocyte, a keratinocyte, a hair follicle cell, colon cancer cell, an ovarian cancer cell, a bladder cancer cell, a pharyngeal cancer cell, a rectal cancer cell, a prostate cancer cell, a breast cancer cell, a lung cancer cell, a renal cancer cell, a pancreatic cancer cell, and a hematologic cancer cell.

* * * * *